US008084449B2

(12) United States Patent
Callahan et al.

(10) Patent No.: US 8,084,449 B2
(45) Date of Patent: Dec. 27, 2011

(54) DUAL PHARMACOPHORES—PDE4-MUSCARINIC ANTAGONISTICS

(75) Inventors: James Francis Callahan, King of Prussia, PA (US); Guoliang Lin, King of Prussia, PA (US); Zehong Wan, Shanghai (CN); Hongxing Yan, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 249 days.

(21) Appl. No.: 12/365,930

(22) Filed: Feb. 5, 2009

(65) Prior Publication Data

US 2009/0203657 A1 Aug. 13, 2009

Related U.S. Application Data

(60) Provisional application No. 61/026,563, filed on Feb. 6, 2008.

(51) Int. Cl.
*A61K 31/496* (2006.01)
*A61K 31/551* (2006.01)
*A61K 31/437* (2006.01)
*C07D 487/04* (2006.01)

(52) U.S. Cl. .................. 514/218; 514/253.04; 514/303; 540/575; 544/362; 546/119

(58) Field of Classification Search .................. None
See application file for complete search history.

(56) References Cited

U.S. PATENT DOCUMENTS

| 3,755,340 | A | 8/1973 | Hoehn et al. | |
| 3,833,594 | A | 9/1974 | Hoehn et al. | |
| 3,840,546 | A | 10/1974 | Hoehn et al. | |
| 3,856,799 | A | 12/1974 | Hoehn et al. | |
| 3,925,388 | A | 12/1975 | Hoehn et al. | |
| 3,966,746 | A | 6/1976 | Hoehn et al. | |
| 3,979,399 | A | 9/1976 | Hoehn et al. | |
| 6,825,184 | B2 | 11/2004 | Cirillo et al. | 514/183 |
| 2007/0167485 | A1 | 7/2007 | Coe et al. | 514/303 |
| 2007/0254913 | A1 | 11/2007 | Dunn et al. | 514/303 |

FOREIGN PATENT DOCUMENTS

| CA | 1003419 | 1/1977 |
| EP | 0076035 B1 | 12/1985 |
| WO | 00/15222 A1 | 3/2000 |
| WO | WO 02/060900 A2 | 8/2002 |
| WO | 03/87064 A1 | 10/2003 |
| WO | 2004/012684 A2 | 2/2004 |
| WO | 2004/024728 A2 | 3/2004 |
| WO | 2004/056823 A1 | 7/2004 |
| WO | 2004/091482 A2 | 10/2004 |
| WO | 2005/009362 A2 | 2/2005 |
| WO | 2005/009439 A1 | 2/2005 |
| WO | 2005/009440 A1 | 2/2005 |
| WO | 2005/037224 A2 | 4/2005 |
| WO | 2005/037280 A1 | 4/2005 |
| WO | 2005/046586 A2 | 5/2005 |
| WO | 2005/055940 A2 | 6/2005 |
| WO | 2005/055941 A2 | 6/2005 |
| WO | 2005/058892 A1 | 6/2005 |
| WO | 2005/067537 A2 | 7/2005 |
| WO | 2005/086873 A2 | 9/2005 |
| WO | 2005/087236 A1 | 9/2005 |
| WO | 2005/090348 A1 | 9/2005 |
| WO | 2005/090352 A1 | 9/2005 |
| WO | 2005/090353 A1 | 9/2005 |
| WO | 2005/090354 A1 | 9/2005 |
| WO | 02/081463 A1 | 10/2005 |
| WO | 2005/094251 A2 | 10/2005 |
| WO | 2005/094834 A1 | 10/2005 |
| WO | 2005/094835 A1 | 10/2005 |
| WO | 2005/099706 A2 | 10/2005 |
| WO | 2005/104745 A2 | 11/2005 |
| WO | 2005/112644 A2 | 12/2005 |
| WO | 2005/118594 A1 | 12/2005 |
| WO | 2006/005057 A2 | 1/2006 |
| WO | 2006/017767 A2 | 2/2006 |
| WO | 2006/017768 A2 | 2/2006 |
| WO | 2006/050239 A2 | 5/2006 |
| WO | 2006/055503 A2 | 5/2006 |
| WO | 2006/055553 A2 | 5/2006 |
| WO | 2006/062883 A2 | 6/2006 |
| WO | 2006/062931 A2 | 6/2006 |
| WO | 2006/065755 A2 | 6/2006 |
| WO | 2006/065788 A2 | 6/2006 |

(Continued)

OTHER PUBLICATIONS

Naganuma et al. Bioorganic & Medicinal Chemistry Letters, vol. 19, pp. 3174-3176 (2009).*
Peretto et al. Medicinal Research Reviews, vol. 29, pp. 867-902 (2009) (Abstract).*
Laine Expert Review of Clinical Pharmacology, vol. 3, pp. 43-53 (2010) (Abstract).*
Fryer and Jacoby, "Muscarinic Receptors and Control of Airway Smooth Muscle" Am J. Respir Crit Care Med; 1998; vol. 158 (5); pp. S154-S160).
Fryer, et al. "Effects of inflammatory cells on neuronal M2 muscarinic receptor function in the lung" Life Sciences;1999; vol. 64(6-7); pp. 449-455 (Abstract provided).

(Continued)

*Primary Examiner* — Emily Bernhardt
(74) *Attorney, Agent, or Firm* — Robert J. Smith

(57) ABSTRACT

The present invention is directed to novel compounds of Formula (I) and pharmaceutically acceptable salts thereof,

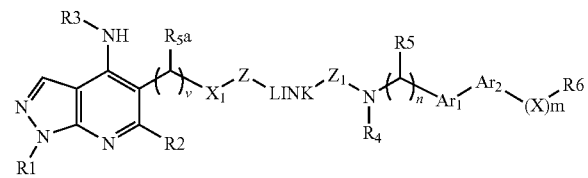

pharmaceutical compositions and their use as dual chromaphores having inhibitory activity against PDE4 and muscarinic acetylcholine receptors (mAChRs), and thus being useful for treating respiratory diseases.

13 Claims, No Drawings

FOREIGN PATENT DOCUMENTS

| | | |
|---|---|---|
| WO | 2007/016639 A2 | 2/2007 |
| WO | 2007/016650 A2 | 2/2007 |
| WO | 2007/018508 A1 | 2/2007 |
| WO | 2007/018514 A1 | 2/2007 |
| WO | 2007/022351 A2 | 2/2007 |
| WO | WO 2008/009735 A1 | 1/2008 |
| WO | 2005/095407 A1 | 6/2011 |

OTHER PUBLICATIONS

Pauwels, et al., "Global Strategy for the Diagnosis, Management, and Prevention of Chronic Obstructive Pulmonary Disease" Am J. Respir Crit Care Med; 2001; vol. 163; pp. 1256-1276 .

Gwilt, et al., "The non-neuronal cholinergic system in the airways: An unappreciated regulatory role in pulmonary inflammation?" Pharmacology & Therapeutics; 2007; pp. 208-222.

Kummer and Lips, "Non-neuronal acetylcholine release and its contribution to COPD pathology" Drug Discovery Today: Disease Mechanisms; 2006; vol. 3; pp. 47-52.

Hohn, et al., "1H-Pyrazolo[3,4-b] pyridines" Journal of Heterocyclic Chemistry; 1972; vol. 9(2); pp. 235-253.

Patel and Malick, "Pharmacological Properties of Tracazolate: A New Non-Benzodiazepine Anxiolytic Agent" European Journal of Pharmacology; 1982; vol. 78; pp. 323-333.

Bare, et al., "Synthesis and Structure-Activity Relationships of a Series of Anxioselective Pyrazolopyridine Ester and Amide Anxiolytic Agents" J. Med. Chem; 1989; vol. 32; pp. 2561-2573.

Denzel, "Neue Synthese 1-unsubstituierter 1H-Pyrazolo [3,4-b] pyridin-5-carbon-saureeser" Archiv der Pharmazie; 1974; vol. 307(3); pp. 177-186.

Ochiai, et al., "New orally active PDE4 inhibitors with therapeutic potential" Bioorganic & Medicinal Chemistry; 2004; vol. 12; pp. 4089-4100.

Ochiai, et al., "Discovery of New Orally Active Phosphodiesterase (PDE4) Inhibitors" Chem. Pharm. Bull.; 2004; vol. 52(9); pp. 1098-1104.

Shi, et al., "Pyrazolopyridines: Effect of Structural Alterations on Activity at Adenosine- and GABAa-Receptors" Drug Development Research; 1997; vol. 42; pp. 41-56.

Schenone, et al., "Synthesis and Biological Data of 4-Amino-1-(2-chloro-2-phenylethyl)-1H-pyrazolo[3,4-b] pyridine-5-carboxylic Acid Ethyl Esters, a New Series of Al-Adenosine Receptor (A1AR) Ligands" Bioorganic & Medicinal Chemistry Letters; 2001; vol. 11; pp. 2529-2531.

Bondavalli, et al., "Synthesis, Molecular Modeling Studies, and Pharmacological Activity of Selective A1 Receptor Antagonists" 2002; vol. 45; pp. 4875-4887.

De Mello, et al., "Antileishmanial Pyrazolopyridine Derivatives: Synthesis and Structure-Activity Relationship Analysis" J. Med. Chem; 2004; vol. 47; pp. 5427-5432.

Provins, et al., "First dual M3 antagonists-PDE4 inhibitors: Synthesis and SAR of 4,6-diaminopyrimidine derivatives" Bioorganic & Medicinal Chemistry Letters; 2006; vol. 16; pp. 1834-1839.

Provins, et al., "Dual M3 antagonists-PDE4 inhibitors. Part 2: Synthesis and SAR of 3-substituted azetidinyl derivatives" Bioorganic & Medicinal Chemistry Letters; 2007; vol. 17; pp. 3077-3080.

Ochiai, et al., "New orally active PDE4 inhibitors with therapeutic potential" Bioorganic & Medicinal Chemistry Letters; 2004; vol. 14; pp. 29-32.

Daly J. W. et al.; 1-methyl-4-substituted-1H-pyrazolo [3, 4-b] pyridine-5-carboxylic acid derivatives: effect of structural alterations on activity at A1 and A2 adenosine receptors; Medicinal Chemistry Research; 1994; 4(5); pp. 293-306; Birkhaeuser; Boston US.

* cited by examiner

DUAL PHARMACOPHORES—PDE4-MUSCARINIC ANTAGONISTICS

CROSS REFERENCE TO PRIOR APPLICATIONS

This application claims the benefit of U.S. Provisional application 61/026,563 filed 6 Feb. 2008.

FIELD OF THE INVENTION

The present invention relates to novel compounds of Formula (I), or salts thereof, processes for their preparation, intermediates usable in these processes, and pharmaceutical compositions containing the compounds or salts. The invention also relates to the use of these compounds or salts thereof in therapy, for example as inhibitors of phosphodiesterase type IV (PDE4) and as antagonists of muscarinic acetylcholine receptors (mAChRs), and useful in the treatment of, and/or prophylaxis of respiratory diseases, including anti-inflammatory and allergic diseases such as chronic obstructive pulmonary disease (COPD), asthma, rhinitis (e.g. allergic rhinitis), atopic dermatitis or psoriasis.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors having seven transmembrane domains. There are five subtypes of mAChRs, termed M1-M5, and each is the product of a distinct gene. Each of these five subtypes displays unique pharmacological properties. Muscarinic acetylcholine receptors are widely distributed in vertebrate organs, and these receptors can mediate both inhibitory and excitatory actions. For example, in smooth muscle found in the airways, M3 mAChRs mediate contractile responses. For a review, see Caulfield (1993 Pharmac. Ther. 58:319-79).

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 Am J Respir Crit Care Med 158(5, pt 3) S 154-60).

Three subtypes of mAChRs have been identified as important in the lungs, M1, M2 and M3 mAChRs. The M3 mAChRs, located on airway smooth muscle, mediate muscle contraction. Stimulation of M3 mAChRs activates the enzyme phospholipase C via binding of the stimulatory G protein Gq/11 (Gs), leading to liberation of phosphatidyl inositol-4,5-bisphosphate, resulting in phosphorylation of contractile proteins. M3 mAChRs are also found on pulmonary submucosal glands. Stimulation of this population of M3 mAChRs results in mucus secretion.

M2 mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal M2 mAChRs are located on postganglionic parasympathetic nerves. Under normal physiologic conditions, neuronal M2 mAChRs provide tight control of acetylcholine release from parasympathetic nerves. Inhibitory M2 mAChRs have also been demonstrated on sympathetic nerves in the lungs of some species. These receptors inhibit release of noradrenaline, thus decreasing sympathetic input to the lungs.

M1 mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory M2 muscarinic acetylcholine autoreceptor function on parasympathetic nerves supplying the pulmonary smooth muscle, causing increased acetylcholine release following vagal nerve stimulation (Fryer et al. 1999 Life Sci 64 (6-7) 449-55). This mAChR dysfunction results in airway hyperreactivity and hyperresponsiveness mediated by increased stimulation of M3 mAChRs.

Recent literature has focused on the non-neuronal cholinergic system in the lungs where there is an emerging literature supporting a role for muscarinic receptors in mediating immunomodulatory and inflammatory functions in respiratory diseases such as asthma and COPD. Many of the components for cholinergic signaling have been reported to be contained within inflammatory and resident cells of the lungs, including muscarinic receptor expression on lymphocytes, alveolar macrophages, mast cells and epithelial cells. The view that acetylcholine is solely a neurotransmitter of the parasympathetic nervous system is currently being challenged as there is mounting evidence to suggest it has an integral role in host defense and airway inflammation. For a full review see Gwilt et al., 2007 (Gwilt C R. et al., The non-neuronal cholinergic system in the airways: An unappreciated regulatory role in pulmonary inflammation? Pharmacol. Ther. 2007; 115: 208-222) and Kummer & Lips 2006 (Kummer W and Lips K S. Non-neuronal acetylcholine release and its contribution to COPD pathology. Drug Discovery Today: Disease Mechanisms 2006; 3:47-52). A consequence of this emerging science is the implication that anti-cholinergic antagonists may have a much broader therapeutic potential for respiratory diseases with anti-inflammatory and disease modifying activity as well as the their well established utility as bronchodilator agents.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 Am. J. Respir. Crit. Care Med. 163:1256-1276).

Despite the large body of evidence supporting the use of anti-cholinergic therapy for the treatment of airway hyperreactive diseases, relatively few anti-cholinergic compounds are available for use in the clinic for pulmonary indications. Ipratropium Bromide (Atrovent©; and Combivent©, in combination with albuterol) is one of the few inhaled anti-cholinergic marketed for the treatment of airway hyperreactive diseases. While this compound is a potent anti-muscarinic agent, it is short acting, and thus must be administered as many as four times daily in order to provide relief for the COPD patient. The long-acting anti-cholinergic Tiotropium Bromide (Spiriva©) has recently been approved in a number of countries.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anti-cholinergic use.

WO 2004/091482 describes a dimeric bicyclic amine derivative having anti-muscarinic receptor activity:

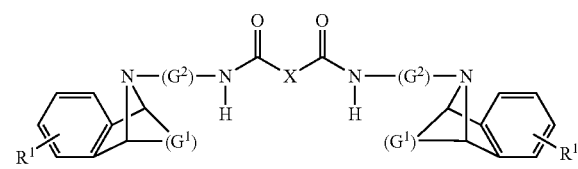

wherein, inter alia, X represents a group of the formula (d) or (e):

—Y—Ar—Y— (d)

—Y-L-Y— (e)

Y is selected from the group consisting of a bond, $OR^2$, $SR^2$, $NR^2R^3$, and $C_{1-4}$ alkyl; and L represents a bond, $C_{1-4}$ alkyl or $C_{3-8}$ cycloalkyl.

WO 2005/095407 also discloses a similar dimeric bicyclic amine derivative to that above having anti-muscarinic receptor activity wherein inter alia, X is a group of the formula (d), (e) and (f):

—Y—Ar—Y— (d)

—Y-L-Y— (e)

Y—Ar$^1$—Z—Ar$^2$—Y (f)

Y is, independently, selected from the group consisting of a bond, O, S, $NR^2$, —$NR^2C_{1-4}$ alkyl-, and $C_{1-4}$ alkyl-; each of the alkyl groups may contain a heteroatom selected from O, $NR^2$, or S; and Z represents a bond, O, $NR^2$, S, $C_{1-4}$ alkylidene or $C_{1-4}$ alkyl.

Other mAChR antagonists, non-dimeric in structure, may be found in WO 2004/012684; WO 2005/009439; WO 2005/09362; WO 2005/09440; WO 2005/037280; WO 2005/037224; WO 2005/046586; WO 2005/055940; WO 2005/055941; WO 2005/067537; WO 2005/087236; WO 2005/086873; WO 2005/094835; WO 2005/094834; WO 2005/094251; WO 2005/099706; WO 2005/104745; WO 2005/112644; WO 2005/118594; WO 2006/005057; WO 2006/017767; WO 2006/017768; WO 2006/050239; WO 2006/055503; WO 2006/055553; WO 2006/062931; WO 2006/062883; WO 2006/065788; WO 2006/065755; WO 2007/018514; WO 2007/018508; WO 2007/016639; WO 2007/016650; and WO 2007/022351.

NVA237 (glycopyrrolate) glycopyrrolate or glycopyrronium bromide, a quaternary ammonium derivative with anti-cholinergic and antimuscarinic properties. It is being developed by Novartis for once daily treatment of COPD.

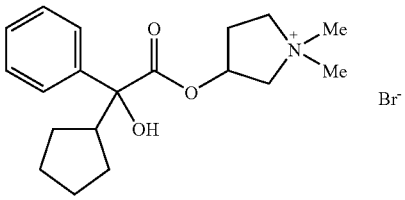

LAS-34273, also known as aclidinium bromide, is a quaternary ammonium anticholinergic muscarinic M3 antagonist originated by Almirall and believed to be in phase 3 development for treating COPD.

LAS-34273

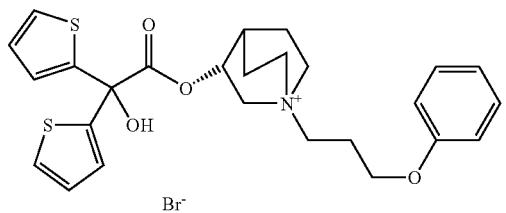

With respect to the PDE4 moieties: U.S. Pat. No. 3,979,399, U.S. Pat. No. 3,840,546, and U.S. Pat. No. 3,966,746 (E.R. Squibb & Sons) disclose 4-amino derivatives of pyrazolo[3,4-b]pyridine-5-carboxamides wherein the 4-amino group $NR_3R_4$ can be an acyclic amino group wherein $R_3$ and $R_4$ may each be hydrogen, lower alkyl (e.g. butyl), phenyl, etc.; $NR_3R_4$ can alternatively be a 3-6-membered heterocyclic group such as pyrrolidino, piperidino and piperazino. The compounds are disclosed as central nervous system depressants useful as ataractic, analgesic and hypotensive agents.

U.S. Pat. No. 3,925,388, U.S. Pat. No. 3,856,799, U.S. Pat. No. 3,833,594 and U.S. Pat. No. 3,755,340 (E.R. Squibb & Sons) disclose 4-amino derivatives of pyrazolo[3,4-b]pyridine-5-carboxylic acids and esters. The compounds are mentioned as being central nervous system depressants useful as ataractic agents or tranquilizers, as having anti-inflammatory and analgesic properties. The compounds are mentioned as increasing the intracellular concentration of adenosine-3',5'-cyclic monophosphate and for alleviating the symptoms of asthma.

H. Hoehn et al., *J. Heterocycl. Chem.*, 1972, 9(2), 235-253 discloses a series of 1H-pyrazolo[3,4-b]pyridine-5-carboxylic acid derivatives with 4-hydroxy, 4-chloro, 4-alkoxy, 4-hydrazino, and 4-amino substituents. Ethyl 4-(n-butylamino)-1-ethyl-1H-pyrazolo[3,4-b]-pyridine-5-carboxylate is disclosed therein; this compound is cartazolate.

The compound tracazolate, ethyl 4-(n-butylamino)-1-ethyl-6-methyl-1H-pyrazolo[3,4-b]-pyridine-5-carboxylate, is known as an anxiolytic agent (e.g. see J. B. Patel et al., *Eur. J. Pharmacol.*, 1982, 78, 323). Other 1-substituted 4-($NH_2$ or NH-alkyl)-1H-pyrazolo[3,4-b]-pyridine-5-carboxylic acid esters and amides are disclosed as potential anxiolytic agents in T. M. Bare et al., *J. Med. Chem.*, 1989, 32, 2561-2573.

CA 1003419, CH 553 799 and T. Denzel, *Archiv der Pharmazie*, 1974, 307(3), 177-186 disclose 4,5-disubstituted 1H-pyrazolo[3,4-b]pyridines unsubstituted at the 1-position.

Japanese laid-open patent application JP-2002-20386-A (Ono Yakuhin Kogyo K K) published on 23 Jan. 2002 discloses pyrazolopyridine compounds of the following inter alia formula:

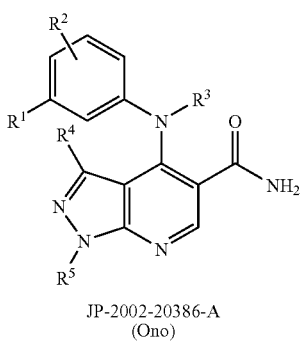

JP-2002-20386-A
(Ono)

The compounds of JP-2002-20386-A are stated as having PDE4 inhibitory activity and as being useful in the prevention and/or treatment of inflammatory diseases and many other diseases.

1,3-Dimethyl-4-(arylamino)-pyrazolo[3,4-b]pyridines with a 5-C(O)NH$_2$ substituent similar or identical to those in JP-2002-20386-A were disclosed as orally active PDE4 inhibitors by authors from Ono Pharmaceutical Co. in: H. Ochiai et al., *Bioorg. Med. Chem. Lett.*, 2004, vol. 14(1), pp. 29-32. Full papers on these and similar compounds as orally active PDE4 inhibitors are: H. Ochiai et al., *Bioorg. Med. Chem.*, 2004, 12(15), 4089-4100, and H. Ochiai et al., *Chem. Pharm. Bull.*, 2004, 52(9), 1098-1104.

EP 0 076 035 A1 (ICI Americas) discloses pyrazolo[3,4-b]pyridine derivatives as central nervous system depressants useful as tranquilizers or ataractic agents for the relief of anxiety and tension states.

J. W. Daly et al., *Med. Chem. Res.*, 1994, 4, 293-306 and D. Shi et al., *Drug Development Research*, 1997, 42, 41-56 disclose a series of 4-(amino) substituted 1H-pyrazolo[3,4-b]pyridine-5-carboxylic acid derivatives, including ethyl 4-cyclopentylamino-1-methyl-1H-pyrazolo[3,4-b]pyridine-5-carboxylate, and their affinities and antagonist activities at A$_1$- and A$_{2A}$-adenosine receptors, and the latter paper discloses their affinities at various binding sites of the GABA$_A$-receptor channel. S. Schenone et al., *Bioorg. Med. Chem. Lett.*, 2001, 11, 2529-2531, and F. Bondavalli et al., *J. Med. Chem.*, 2002, 45(22), pp. 4875-4887 disclose a series of 4-amino-1-(2-chloro-2-phenylethyl)-1H-pyrazolo[3,4-b]pyridine-5-carboxylic acid ethyl esters as A$_1$-adenosine receptor ligands.

WO 02/060900 A2 appears to disclose, as MCP-1 antagonists for treatment of allergic, inflammatory or autoimmune disorders or diseases, a series of bicyclic heterocyclic compounds with a —C(O)—NR$^4$—C(O)—NR$^5$R$^6$ substituent, including isoxazolo[5,4-b]pyridines and 1H-pyrazolo[3,4-b]pyridines (named as pyrazolo[5,4-b]pyridines) with the —C(O)—NR$^4$—C(O)—NR$^5$R$^6$ group as the 5-substituent and optionally substituted at the 1-, 3-, 4-, and/or 6-positions. Bicyclic heterocyclic compounds with a —C(O)NH$_2$ substituent instead of the —C(O)—NR$^4$—C(O)—NR$^5$R$^6$ substituent are alleged to be disclosed in WO 02/060900 as intermediates in the synthesis of the —C(O)—NR$^4$—C(O)—NR$^5$R$^6$ substituted compounds. See also WO 02/081463 A1 for similar MCP-1 antagonists.

WO 00/15222 (Bristol-Myers Squibb) discloses inter alia pyrazolo[3,4-b]pyridines having inter alia a C(O)—X$_1$ group at the 5-position and a group E$_1$ at the 4-position of the ring system. Amongst other things, X$_1$ can for example be —OR$_9$, —N(R$_9$)(R$_{10}$) or —N(R$_5$)(-A$_2$-R$_2$), and E$_1$ can for example be —NH-A$_1$-cycloalkyl, —NH-A$_1$-substituted cycloalkyl, or —NH-A$_1$-heterocyclo; wherein A$_1$ is an alkylene or substituted alkylene bridge of 1 to 10 carbons and A$_2$ can for example be a direct bond or an alkylene or substituted alkylene bridge of 1 to 10 carbons. The compounds are disclosed as being useful as inhibitors of cGMP phosphodiesterase, especially PDE type V, and in the treatment of various cGMP-associated conditions such as erectile dysfunction.

H. de Mello, A. Echevarria, et al., *J. Med. Chem.*, 2004, 47(22), 5427-5432, discloses 3-methyl or 3-phenyl 4-anilino-1H-pyrazolo[3,4-b]pyridine 5-carboxylic esters as potential anti-*Leishmania* drugs.

WO 2004/056823 A1 (PCT/EP2003/014867, filed on 19 Dec. 2003, published on 8 Jul. 2004, Glaxo Group Limited), and incorporated herein by reference in its entirety as though fully set forth, discloses and claims pyrazolo[3,4-b]pyridine compounds or salts thereof with a 4-NR$^3$R$^{3a}$ group (R$^{3a}$ is preferably H) and with a group Het at the 5-position of the pyrazolo[3,4-b]pyridine, wherein Het is usually a 5-membered optionally substituted heteroaryl group.

WO 2004/056823 A1 also discloses the use of these compounds as PDE4 inhibitors and for the treatment and/or prophylaxis of inter alia COPD, asthma or allergic rhinitis.

WO 2004/024728 A2 (PCT/EP2003/011814, filed on 12 Sep. 2003, published on 25 Mar. 2004, Glaxo Group Limited), discloses pyrazolo[3,4-b]pyridine having the following generic formula.

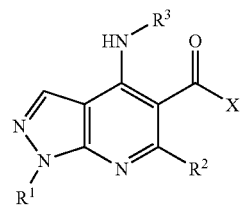

In WO 2004/024728 A2, pyrazolo[3,4-b]pyridine compounds are disclosed as being inhibitors of PDE4. WO 2004/024728 and WO 2004/056823 are noted in *Expert Opin. Ther. Patents*, 2005 (January edition), 15(1), 111-114.

WO 2005/058892 A1 (PCT/EP2004/014490, filed on 17 Dec. 2004, published on 30 Jun. 2005, Glaxo Group Limited), discloses pyrazolo[3,4-b]pyridine compounds for use as PDE4 inhibitors for treating inflammatory or allergic diseases such as COPD, asthma, rheumatoid arthritis, allergic rhinitis or atopic dermatitis.

Further pyrazolo[3,4-b]pyridine compounds and their use as PDE4 inhibitors, are disclosed in patent applications WO 2005/090353 A1 (PCT/GB2005/000976), WO 2005/090348 A1 (PCT/GB2005/000983), WO 2005/090354 A1 (PCT/GB2005/000987), and WO 2005/090352 A1 (PCT/EP2005/003038) (all Glaxo Group Limited). PCT/EP2005/003038, PCT/GB2005/000987 and PCT/GB2005/000983, were all filed 15 Mar. 2005.

WO 03/087064 is directed to compounds having both antagonism of the M3 muscarinic receptor and inhibition of PDE4, having the formula:

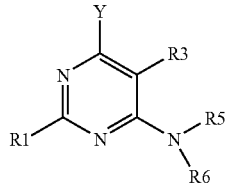

(I)

wherein, inter alia, Y is —NH—R2 or

Two subsequent papers describe in vitro profiles of the lead compounds and in vivo activity after intranasal dosing. Provins, L., et al., Bioorganic & Medicinal Chemistry Letters, 16: 1834-1839 (2006), and Provins, L. et al., Bioorganic & Medicinal Chemistry Letters, 17:3007-3080 (2007). Although promising the data demonstrates that the compounds do not display the in vitro profile that will deliver an in vivo profile displayed by compounds optimized for each molecular target.

Therefore, there is still a need for compounds which contain both the strength and benefit of a combination of PDE4 inhibitory activity and the muscarinic antagonist activity for the treatment of and/or prophylaxis of respiratory diseases, such as chronic obstructive pulmonary disease (COPD), asthma, or inflammatory or allergic diseases such as rhinitis (e.g. allergic rhinitis), atopic dermatitis or psoriasis. The present invention is directed to the novel concept of providing a dual pharmacophore which has both activities.

SUMMARY OF THE INVENTION

The present invention provides for the novel compounds of Formula (I), and pharmaceutical compositions comprising a compound of Formula (I) and a pharmaceutically acceptable carrier or diluent.

Compounds of formula (I) are represented by the structure:

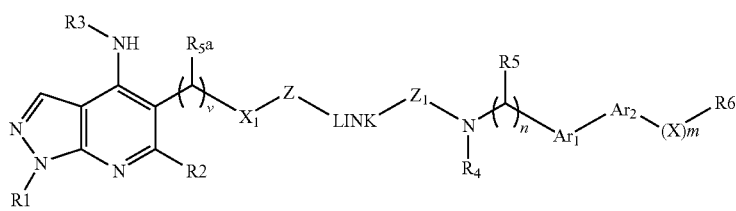

(I)

wherein
LINK is ((CReRe)s3-(CRf=CRf)v1-(CRgRg))s4-$X_3$—((CReRe)t2-(CRf=CRf)v2-(CRgRg))t3;
$X_1$ is oxygen, or N($R_{4a}$);
$X_3$ is an optionally substituted heteroaryl ring;
$R_{4a}$ is hydrogen, methyl or ethyl;
$R_{5a}$ is hydrogen, methyl or ethyl;
Z is selected from the group consisting of C(O), S(O)q, C(O)NH, and C(O)O;
Z1 is selected from the group consisting of C(O), S(O)q, HNC(O), and OC(O);
n is an integer having a value of 1, 2 or 3;
m is 0 or an integer having a value of 1, or 2;
q is 0 or an integer having a value of 1 or 2;
v is an integer having a value of 1 to 5;
v1 is 0 or an integer of 1 to 5;
v2 is 0 or an integer of 1 to 5;
s3 is 0 or an integer 1 to 5;
s4 is 0 or an integer of 1 to 5;
t2 is 0 or an integer of 1 to 5;
t3 is 0 or an integer of 1 to 5;

Re, Rf, and Rg are each independently selected at each occurrence from hydrogen, or $C_{1-4}$alkyl;
$R^1$ is selected from the group consisting of $C_{1-3}$alkyl, —$CH_2$—$C_{1-2}$fluoroalkyl, and —$CH_2CH_2OH$;
$R^2$ is selected from the group consisting of a hydrogen atom, $C_{1-4}$alkyl, $C_{1-2}$fluoroalkyl, cyclopropyl, cyclobutyl, and (cyclopropyl)methyl-;
$R^3$ is selected from the group consisting of an optionally substituted $C_{4-7}$cycloalkyl, an optionally substituted mono-unsaturated-$C_{5-7}$cycloalkenyl, an optionally substituted heterocyclic group of sub-formula (aa), (bb) or (cc), and a bicyclic group of sub-formula (dd), and (ee);

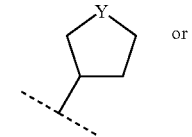

(aa)

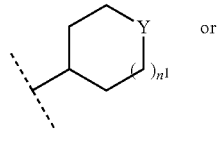

(bb)

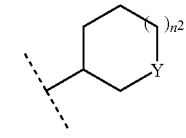

(cc)

-continued

(dd)

(ee)

$n^1$ is an integer having a value of 1 or 2;
$n^2$ is an integer having a value of 1 or 2;
Y is O, S, $SO_2$, or $NR^{10a}$;
$R^{10a}$ is a hydrogen atom (H), methyl, C(O)$NH_2$, C(O)-methyl, or C(O)—$C_1$fluoroalkyl;
$Y^1, Y^2$ and $Y^3$ are independently $CH_2$ or oxygen, provided that no more than one of $Y^1, Y^2$ and $Y^3$ are oxygen;

and wherein when $R^3$ is $C_{4-7}$cycloalkyl it is optionally substituted on a ring carbon with one or two substituents independently selected from oxo (=O); OH; methoxy; $C_1$fluoroalkoxy; $NH_2$; $C_{1-2}$alkyl; $C_1$fluoroalkyl; —$CH_2OH$; —CH(Me)OH; —$CH_2CH_2OH$; —$CH_2NH_2$; —C(O)OH; —C(O)NHR$^{24}$ wherein $R^{24}$ is H or methyl; —C(O)methyl; fluoro; hydroxyimino (=N—OH); or ($C_{1-2}$alkoxy)imino (=N—OR$^{26}$ where $R^{26}$ is $C_{1-2}$alkyl);

and wherein any OH, methoxy, fluoroalkoxy or $NH_2$ substituent is not bonded to the $R^3$ ring carbon bonded to the —NH— group of formula (I); and any OH, methoxy, fluoroalkoxy, —$CH_2OH$, —CH(Me)OH, —$CH_2CH_2OH$, —$CH_2NH_2$, or —C(O)OH substituent on a ring carbon of the $C_{4-7}$cycloalkyl is at the 3-position of a $R^3$ cyclobutyl ring; or at the 3- or 4-position of a $R^3$ cyclopentyl ring; or at the 3-, 4- or 5-position of a $R^3$ cyclohexyl ring; or at the 3-, 4-, 5- or 6-position of a $R^3$ cycloheptyl ring;

and if the $C_{4-7}$cycloalkyl is substituted by —C(O)NHR$^{24}$ or —C(O)methyl substituent on a ring carbon it is at the 3-position of the $R^3$ cyclobutyl ring; or at the 3- or 4-position of the $R^3$ cyclopentyl ring; or at the 4-position of a $R^3$ cyclohexyl ring; or at the 3-, 4-, 5- or 6-position of a $R^3$ cycloheptyl ring (wherein, in this connection, the 1-position of the $R^3$ cycloalkyl ring is deemed to be the connection point to the —NH— in formula (I), that is the ring atom connecting to the —NH— in formula (I));

and wherein, when $R^3$ is the optionally substituted heterocyclic group of sub-formula (aa), (bb) or (cc), then $R^3$ is the heterocyclic group of sub-formula (aa), (bb) or (cc) optionally substituted on a ring carbon with one or two oxo (=O) substituents;

and wherein, when $R^3$ is optionally substituted mono-unsaturated-$C_{5-7}$cycloalkenyl, then the cycloalkenyl is optionally substituted on a ring carbon with one substituent being fluoro or methyl, and the $R^3$ ring carbon bonded to the —NH— group of formula (I) does not partake in the cycloalkenyl double bond;

$Ar_1$ and $Ar_2$ are independently selected from the group consisting of an optionally substituted phenyl and an optionally substituted monocyclic heteroaryl;

$R_6$ is $NR_7R_8$, or is a heterocyclic group of the subformula (ff), (gg), (hh), (ii), (jj), (kk), (ll), (mm) or (nn):

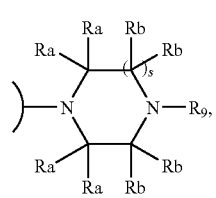
(ff)

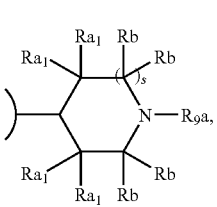
(gg)

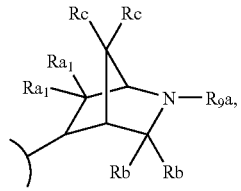
(hh)

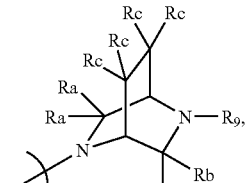
(ii)

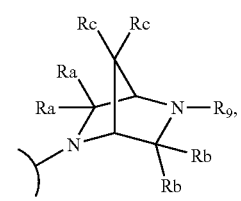
(jj)

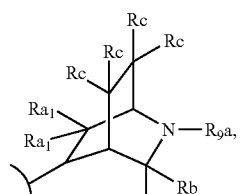
(kk)

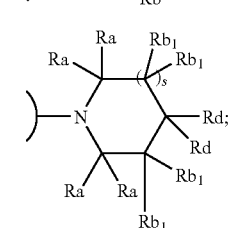
(ll)

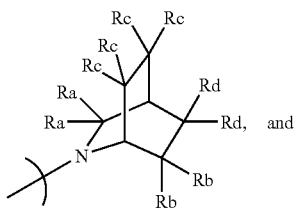
(mm)

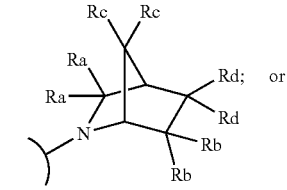
(nn)

$R_6$ is an optionally substituted C5-C7 membered ring containing one or two nitrogens, or a corresponding bicyclic ring containing one or two nitrogens;

$R_9$ is selected from the group consisting of hydrogen, optionally substituted $C_{1-6}$ alkyl, optionally substituted aryl, optionally substituted aryl$C_{1-2}$alkyl, optionally substituted heteroaryl, optionally substituted heteroaryl $C_{1-2}$alkyl, optionally substituted heterocyclic, optionally substituted heterocyclic $C_{1-2}$alkyl, and $C(O)C_{1-2}$alkyl;

$R_{9a}$ is selected from the group consisting of hydrogen, optionally substituted $C_{1-6}$ alkyl, optionally substituted aryl, optionally substituted aryl$C_{1-2}$alkyl, optionally substituted heteroaryl, optionally substituted heteroaryl $C_{1-2}$alkyl, optionally substituted heterocyclic, optionally substituted heterocyclic $C_{1-2}$alkyl, and $C(O)C_{1-2}$alkyl;

Rd is independently selected at each occurrence from the group consisting of hydrogen, hydroxy, optionally substituted $C_{1-6}$ alkyl, amino, optionally substituted aryl, optionally substituted aryl$C_{1-2}$alkyl, optionally substituted heterocyclic, optionally substituted heterocyclic$C_{1-2}$alkyl, optionally substituted heteroaryl, optionally substituted heteroaryl $C_{1-2}$alkyl, $=O$, $C(O)C_{1-2}$alkyl, $OC(O)R_{17}$, and $C(O)N(R_{10})_2$;

$R_{15}$ and $R_{16}$ are each independently selected at each occurrence from hydrogen, or $C_{1-4}$ alkyl;

$R_{17}$ is independently selected at each occurrence from the group consisting of optionally substituted $C_{1-4}$ alkyl, optionally substituted $C_{3-7}$ cycloalkyl, optionally substituted $C_{3-7}$ cycloalkyl$C_{1-4}$alkyl, optionally substituted aryl, optionally substituted aryl$C_{1-4}$alkyl, heterocyclic, optionally substituted heterocyclic, optionally substituted heterocyclic$C_{1-4}$alkyl, optionally substituted heteroaryl, and optionally substituted heteroaryl $C_{1-4}$alkyl;

$R_a$ is independently selected at each occurrence from the group consisting of hydrogen, optionally substituted $C_{1-4}$ alkyl, optionally substituted $C_{3-7}$ cycloalkyl, optionally substituted $C_{3-7}$ cycloalkyl-$C_{1-4}$alkyl, $C_{1-4}$ alkoxy, $NR_{15}R_{16}C_{1-4}$alkyl, $S(O)_qC_{1-4}$ alkyl, $=O$, $-CH(O)$, $C(O)_2C_{1-4}$ alkyl, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl;

$R_{a1}$ is independently selected at each occurrence from the group consisting of hydrogen, halogen, optionally substituted $C_{1-4}$ alkyl, optionally substituted $C_{3-7}$ cycloalkyl, optionally substituted $C_{3-7}$ cycloalkyl$C_{1-4}$ alkyl, $C_{1-4}$ alkoxy, $NR_{15}R_{16}$, $NR_{15}R_{16}C_{1-4}$alkyl, $S(O)_qC_{1-4}$ alkyl, hydroxy, $=O$, $-CH(O)$, $C(O)_2C_{1-4}$ alkyl, $OC(O)R_{17}$, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl;

$R_b$ is independently selected at each occurrence from the group consisting of hydrogen, optionally substituted $C_{1-4}$ alkyl, optionally substituted $C_{3-7}$ cycloalkyl, optionally substituted $C_{3-7}$ cycloalkyl$C_{1-4}$ alkyl, $C_{1-4}$ alkoxy, $NR_{15}R_{16}C_{1-4}$alkyl, $S(O)_qC_{1-4}$ alkyl, $=O$, $-CH(O)$, $C(O)_2C_{1-4}$ alkyl, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl;

$R_{b1}$ is independently selected at each occurrence from the group consisting of hydrogen, halogen, optionally substituted $C_{1-4}$ alkyl, optionally substituted $C_{3-7}$ cycloalkyl, optionally substituted $C_{3-7}$ cycloalkyl$C_{1-4}$ alkyl, $C_{1-4}$ alkoxy, $NR_{15}R_{16}$, $NR_{15}R_{16}C_{1-4}$alkyl, $S(O)_qC_{1-4}$ alkyl, hydroxy, $=O$, $-CH(O)$, $C(O)_2C_{1-4}$ alkyl, $OC(O)R_{17}$, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl;

$R_c$ is independently selected at each occurrence from hydrogen or $C_{1-4}$ alkyl;

$R_{10}$ is independently selected at each occurrence from hydrogen or $C_{1-4}$ alkyl;

$R_{13a}$ is selected from hydrogen, or $C_{1-2}$ alkyl;

$R_{13}$ is independently selected from the group consisting of hydrogen, $C_{1-2}$ alkyl, $-CH_2OH$, $-CH(CH_3)OH$, $-CH_2CH_2OH$, OH, and $=O$;

X is $(C(R_{13}))_p$, or $(CR_eR_e)_{s1}-X_2-(CR_fR_f)_{s2}$;

$X_2$ is $NR_{13a}$, O, $S(O)m$, or $C(O)$;

s is 0, or is an integer having a value of 1 or 2;

s1 is 0 or an integer having a value of 1 to 2;

s2 is 0 or an integer having a value of 1 to 2, provided that when $R_6$ is a heterocyclic group of the subformulas (ff), (ii), (jj) and (ll), and $X_2$ is $NR_{13a}$, O, or $S(O)m$ and m is 0 or 1, then s2 is 1 or 2, or X is $(CH(R_{13}))p$;

p is an integer having a value of 1 or 2;

t is an integer having a value of 1 to 4;

t1 is 0 or an integer having a value of 1 to 4;

$R_{11}$ and $R_{12}$ are independently selected from hydrogen, or $C_{1-4}$ alkyl;

$R_4$ and $R_5$ are each independently selected from the group consisting of hydrogen, optionally substituted $C_{1-4}$ alkyl, optionally substituted $C_3$-$C_7$ cycloalkyl, optionally substituted $C_3$-$C_7$ cycloalkyl $C_{1-4}$ alkyl, optionally substituted heterocyclic, optionally substituted heterocyclic $C_{1-4}$ alkyl, optionally substituted alkenyl, optionally substituted aryl, optionally substituted aryl$C_{1-4}$ alkyl optionally substituted heteroaryl, and optionally substituted heteroaryl $C_{1-4}$ alkyl;

$R_7$ is selected from hydrogen, or an optionally substituted $C_{1-4}$ alkyl;

$R_8$ is $(CR_{d1}R_{d1})_t-NR_{11}R_{12}$ or $(CR_{d1}R_{d1})_{t1}-R_{14}$;

$R_{d1}$ is independently at each occurrence selected from the group consisting of hydrogen, optionally substituted $C_{1-4}$ alkyl, optionally substituted aryl, optionally substituted heteroaryl, and optionally substituted heterocyclic; and $R_{14}$ is selected from the group consisting of $C_{1-4}$ alkyl, $C_3$-$C_6$ cycloalkyl, optionally substituted heterocyclic, and optionally substituted heteroaryl moiety;

or a pharmaceutically acceptable salt thereof.

This invention provides for a method of treating both a muscarinic acetylcholine receptor (mAChR) mediated disease, wherein acetylcholine binds to an $M_3$ mAChR and a phosphodiesterase type IV (PDE4) mediated disease, whereby the compound also binds to the PDE4 isotype, which comprises administering an effective amount of a compound of Formula (I) or a pharmaceutically acceptable salt thereof to a mammal in need thereof.

One use of compounds of Formula (I), or pharmaceutically acceptable salt thereof are in the treatment and/or prophylaxis of an inflammatory and/or allergic disease in a mammal.

One or more specific compounds within the presently invented compounds may be suitable for use as dual PDE4/mAChR inhibitors via an inhaled route of administration.

Compounds of the present invention provide for a single compound which has the attributes of each pharmacophore optimized for each molecular target in a balanced fashion. This resulting in vivo profile allows for efficacy and duration of action at both targets, e.g. inhibition of PDE-IV and antagonism of the mAChR, in a defined dose range. It is now possible to produce a compound which is developable to treat at least two aspects of complex disease etiology, for example bronchoconstriction and inflammation found in diseases such as COPD and asthma.

The present invention is directed to a novel concept of having dual pharmacophores in one molecule that retains potency across both pharmacological groups. Another aspect of the invention is that in addition to retaining dual pharmacological activity the compounds are developable for commercial activities.

In one embodiment of the invention the compound may be administered to a mammal in needed thereof, suitably one to four times daily, and preferably either a once or a twice daily treatment. Suitably, the compound is administered topically or by inhalation (via nose or mouth) for use in the treatment and/or prophylaxis of a disease for which either pharmacophore has previously been associated with treatment of. For purposes herein topical administration includes both skin and lung tissue. In this particular instance, a PDE4 or an M3 mediated disease. Generally this will be an inflammatory and/or allergic disease, such as the treatment of COPD, asthma, adult respiratory distress syndrome, rhinitis, allergic rhinitis, atopic dermatitis, urticaria, allergic conjunctivitis, psoriasis, ulcerative colitis, or Crohn's disease.

One or more specific compounds within the presently invented compounds may be suitable for use as dual PDE4/mAChR inhibitors via an inhaled route of administration.

One or more specific compounds within the presently invented compounds may be suitable for use as dual PDE4/mAChR inhibitors via an intranasal route of administration.

One or more specific compounds within the presently invented compounds may be suitable for use as dual PDE4/mAChR inhibitors via a topical route of administration.

In compounds of formula (I), $R^1$ is suitably selected from $C_{1-3}$alkyl, —$CH_2$—$C_{1-2}$fluoroalkyl, or —$CH_2CH_2OH$. In one embodiment of the invention, $R^1$ is suitably selected from $C_{1-3}$alkyl, such as methyl, ethyl, n-propyl, or isopropyl. In another embodiment $R^1$ is ethyl.

Suitably, $R^2$ is hydrogen, $C_{1-4}$alkyl, such as methyl, ethyl, n-propyl, isopropyl, or n-butyl, a $C_{1-2}$fluoroalkyl, cyclopropyl, cyclobutyl, or (cyclopropyl)methyl-. In one embodiment of the invention, $R^2$ is methyl, ethyl, n-propyl, isopropyl, or n-butyl. In another embodiment of the invention, $R^2$ is ethyl.

Suitably, $R^3$ is optionally substituted $C_{4-7}$cycloalkyl, or optionally substituted mono-unsaturated-$C_{5-7}$cycloalkenyl, or an optionally substituted heterocyclic group of sub-formula (aa), (bb) or (cc), or a bicyclic group of sub-formula (dd), or (ee);

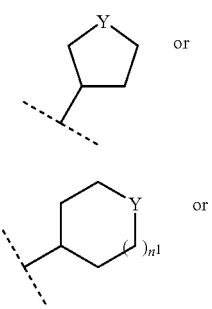

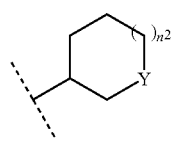

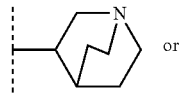

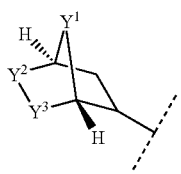

Suitably, $n^1$ and $n^2$ are independently selected from an integer having a value of 1 or 2.

Suitably, Y is O, S, $SO_2$, or $NR^{10a}$. In one embodiment of the invention Y is O.

Suitably, $R^{10a}$ is a hydrogen atom (H), methyl, $C(O)NH_2$, C(O)-methyl, or C(O)—$C_1$fluoroalkyl.

Suitably, $Y^1$, $Y^2$ and $Y^3$ are each independently selected from $CH_2$ or oxygen, provided that no more than one of $Y^1$, $Y^2$ and $Y^3$ are oxygen.

When $R^3$ is an optionally substituted $C_{4-7}$cycloalkyl, then the $C_{4-7}$cycloalkyl ring is optionally substituted on a ring carbon with one or two substituents independently selected from oxo (=O); OH; methoxy; $C_1$fluoroalkoxy; $NH_2$; $C_{1-2}$alkyl; $C_1$fluoroalkyl; —$CH_2OH$; —CH(Me)OH; —$CH_2CH_2OH$; —$CH_2NH_2$; —C(O)OH; —C(O)NHR$^{24}$ wherein R$^{24}$ is H or methyl; —C(O)methyl; fluoro; hydroxyimino (=N—OH); or ($C_{1-2}$alkoxy)imino (=N—OR$^{26}$ where R$^{26}$ is $C_{1-2}$alkyl); and wherein any OH, methoxy, fluoroalkoxy or $NH_2$ substituent is not bonded to the $R^3$ ring carbon bonded to the —NH— group of formula (I).

When $R^3$ is the optionally substituted heterocyclic group of sub-formula (aa), (bb) or (cc), then $R^3$ is the heterocyclic group of sub-formula (aa), (bb) or (cc) optionally substituted on a ring carbon with one or two oxo (=O) substituents.

When $R^3$ is optionally substituted mono-unsaturated-$C_{5-7}$ cycloalkenyl, then the cycloalkenyl is optionally substituted on a ring carbon with one substituent being fluoro or methyl, and the $R^3$ ring carbon bonded to the —NH— group of formula (I) does not partake in the cycloalkenyl double bond.

In one embodiment of the invention when $R^3$ is the heterocyclic group of sub-formula (aa) and Y is NR$^{10}$, then R$^{10}$ is not C(O)-methyl, or C(O)—$C_1$fluoroalkyl; and when $R^3$ is the heterocyclic group of sub-formula (bb) and Y is NR$^{10}$, then R$^{10}$ is not methyl; and when $R^3$ is the heterocyclic group of sub-formula (cc), then Y is O, S, $SO_2$ or NR$^{10}$ wherein R$^{10}$ is H or methyl.

When $R^3$ is optionally substituted $C_{4-7}$cycloalkyl, then any —C(O)NHR$^{24}$ or —C(O)R$^{25}$ substituent on a ring carbon is: at the 3-position of a $R^3$ cyclobutyl ring; or at the 3- or 4-position of a $R^3$ cyclopentyl ring; or at the 4-position of a $R^3$ cyclohexyl ring; or at the 3-, 4-, 5- or 6-position of a $R^3$ cycloheptyl ring (wherein, in this connection, the 1-position of the $R^3$ cycloalkyl ring is deemed to be the connection point to the —NH— in formula (I), that is the ring atom connecting to the —NH— in formula (I)).

When $R^3$ is optionally substituted $C_{4-7}$cycloalkyl, then any OH, methoxy, fluoroalkoxy, —$CH_2OH$, —CH(Me)OH, —CH$_2$CH$_2$OH, —CH$_2$NH$_2$, or —C(O)OH substituent on a ring carbon is: at the 3-position of a R$^3$ cyclobutyl ring; or at the 3- or 4-position of a R$^3$ cyclopentyl ring; or at the 3-, 4- or 5-position of a R$^3$ cyclohexyl ring; or at the 3-, 4-, 5- or 6-position of a R$^3$ cycloheptyl ring.

In one embodiment of the invention, R$^3$ is the sub-formula (bb) and (cc). In another embodiment of the invention R$^3$ is the sub-formula (bb) and (cc), and n1 and n$^2$ independently are 1 or 2. In another embodiment, Y is O, and n1 and n$^2$ are 1.

In one embodiment of the invention, R$^3$ is the sub-formula (bb). In another embodiment R$^3$ is the sub-formula (bb), and Y is O. In yet another embodiment R$^3$ is the sub-formula (bb), Y is O, and n$^1$ is 1.

Suitably, X$_1$ is oxygen, or N(R$_{4a}$). In one embodiment of the invention X is N(R$_{4a}$).

Suitably, R$_{4a}$ is hydrogen, methyl or ethyl. In one embodiment of the invention R$_{4a}$ is hydrogen or methyl. In another embodiment of the invention R$_{4a}$ is hydrogen.

Suitably, LINK is ((CReRe)s3-(CRf═CRf)v1-(CRgRg))s 4-X$_3$—((CReRe)t2-(CRf═CRf)v2-(CRgRg))t3.

Suitably, X$_3$ is an optionally substituted heteroaryl ring. The heteroaryl ring is suitably selected from an optionally substituted C5-C7 mono heteroaryl ring or an optionally substituted C8-C12 fused bicyclic heteroaryl ring. It is recognized that only one of the fused rings may be aromatic, and the other partially unsaturated or saturated and contain one or more additional heteroatoms, suitably one or two heteroatoms selected from oxygen, nitrogen or sulfur. It is also recognized that in a non-aromatic system the ring nitrogen may be optionally substituted with a C1-6 alkyl or a C(O)R18 moiety, wherein R18 is hydrogen, C1-6 alkyl, C3-7 cycloalkyl, cycloalkylC1-4 alkyl, aryl or aryl C1-4 alkyl. The ring sulfur atom in a non-aromatic ring system may also be oxidized to a sulfinyl or sulfonyl derivative.

The terms "heteroaryl ring", "heteroaryl moiety", and "heteroaryl" which appear herein may be used interchangeably. Suitable examples of a LINK heteroaryl ring include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil.

Suitable examples of a LINK bicyclic fused aromatic ring includes, but is not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

Suitable examples of a LINK bicyclic fused ring system which contains a nonaromatic ring includes, but is not limited to, an indoline, indanyl, 1,4-dioxino[2,3-c]pyrrole, 1,4-dioxino[2,3-c]furan, or 1,4-dioxino[2,3-c]thiophene.

In one embodiment of the invention the LINK heteroaryl is selected from pyridine (e.g. 2-pyridyl, 3-pyridyl, or 4-pyridyl), pyrimidine, furan, thienyl, pyrrole, 1,4-dioxino[2,3-c] pyrrole, or benzimidazole.

The LINK heteroaryl ring may be optionally substituted by the moiety (Y$_4$)n3, wherein Y$_4$ is independently selected at each occurrence from hydrogen, halogen, hydroxy, C$_{1-4}$ alkyl or C$_{1-4}$ alkoxy. It should be noted that the Y$_4$ moieties may be substituted on either ring of the fused bicyclic ring system.

Suitably, n$_3$ is an integer having a value of 1 to 4.

Suitably, Re, Rf, and Rg are independently selected at each occurrence from hydrogen, or C$_{1-4}$alkyl. In one embodiment of the invention Re, Rf, and Rg are all hydrogen.

Suitably, v1 is 0 or an integer of 1 to 5. In one embodiment of the invention, v1 is 0.

Suitably, v2 is 0 or an integer of 1 to 5. In one embodiment of the invention, v2 is 0.

Suitably, s3 is 0 or an integer 1 to 5. In one embodiment of the invention, s3 is 0.

Suitably, s4 is 0 or an integer of 1 to 5. In one embodiment of the invention, s4 is 0.

Suitably, t2 is 0 or an integer of 1 to 5. In one embodiment of the invention, t2 is 0.

Suitably, t3 is 0 or an integer of 1 to 5. In one embodiment of the invention, t3 is 0.

In one embodiment of the invention, v1, v2, s3, s4, t2, and t3 are all zero.

Suitably, Z is selected from C(O), S(O)q, C(O)NH, or C(O)O.

Suitably, Z1 is selected from C(O), S(O)q, HNC(O), or OC(O).

In one embodiment of the invention, Z and Z1 are both C(O). In another embodiment of the invention Z is C(O) and Z1 is S(O)q. In another embodiment of the invention Z is C(O) and Z1 is HNC(O). In another embodiment of the invention Z is C(O) and Z1 is OC(O). In one embodiment of the invention, Z and Z1 are both S(O)q. In another embodiment of the invention Z is S(O)q, and Z1 is C(O). In another embodiment Z is S(O)q, and Z1 is HNC(O). In another embodiment Z is S(O)q, and Z1 is OC(O). In another embodiment Z is C(O)NH and Z1 is C(O). In another embodiment Z is C(O) NH and Z1 is S(O)q. In another embodiment Z is C(O)NH and Z1 is S(O)q. In another embodiment Z is C(O)NH and Z1 is OC(O). In another embodiment Z is C(O)O and Z1 is HNC(O). In another embodiment Z is C(O)O and Z1 is C(O). In another embodiment Z is C(O)O and Z1 is S(O)q. In another embodiment Z is C(O)O and Z1 is HNC(O). In another embodiment Z is C(O)O and Z1 is OC(O). Suitably, when either Z or Z1 is S(O)q, q is 2.

Suitably, q is independently selected at each occurrence from 0 or an integer having a value of 1 or 2. In one embodiment of the invention q is 2 when Z is S(O)q. In another embodiment of the invention q is 2 when Z1 is S(O)q. In another embodiment of the invention q is 2 when Z and Z1 are both S(O)q.

Suitably, R$_{5a}$ is hydrogen, methyl or ethyl. In one embodiment of the invention R$_{5a}$ is hydrogen.

Suitably, v is an integer having a value of 1 to 5. In one embodiment of the invention v is 1.

Suitably, Ar$_1$ and Ar$_2$ are independently selected from the group consisting of an optionally substituted phenyl and an optionally substituted monocyclic heteroaryl. In one embodiment, Ar$_1$ and Ar$_2$ are independently selected from an optionally substituted aryl. In another embodiment both Ar$_1$ and Ar$_2$ are independently selected from an optionally substituted phenyl.

Ar$_1$ and Ar$_2$ are independently substituted one or more times, suitably 1 to 4 times, at each occurrence by halogen, such as fluorine, chlorine, bromine or iodine; cyano; hydroxy; hydroxy substituted C$_{1-4}$alkyl; C$_{1-4}$ alkoxy, such as methoxy or ethoxy; S(O)$_m$C$_{1-10}$ alkyl, wherein m' is 0, 1 or 2, such as methyl thio, methyl sulfinyl or methyl sulfonyl; amino, a mono or di-substituted C$_{1-2}$alkyl amino; C$_{1-4}$alkyl, such as methyl, ethyl, propyl, isopropyl, or t-butyl; C$_{2-4}$alkyl alkenyl, such as ethenyl, 1-propenyl, 2-propenyl, or 2-methyl-1-propenyl; or a halosubstituted C$_{1-4}$ alkyl, such CH$_2$F, CH$_2$CH$_2$F, or CF$_3$. In one embodiment of the invention the optional substituents are independently selected from halogen, alkyl, alkoxy, or cyano. In another embodiment the optional substituents are independently selected from fluorine, chlorine, methyl, methoxy or cyano.

Examples of suitable heteroaryl rings for $Ar_1$ and $Ar_2$ include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, and triazinyl. In one embodiment of the invention the heteroaryl ring is a pyridine.

In one embodiment of the invention, $Ar_1$ and $Ar_2$ are both independently selected from an optionally substituted aryl, preferably an optionally substituted phenyl. In one embodiment of the invention both $Ar_1$ and $Ar_2$ are independently selected from optionally substituted phenyls.

In one embodiment of the invention, the Ar2 ring is phenyl.

In one embodiment of the invention, the Ar1 ring is a heteroaryl ring. In another embodiment the Ar1 ring is a pyridine ring.

In another embodiment of the invention, the Ar1 ring is a phenyl optionally substituted one or more times independently by halogen, alkyl, alkoxy, or cyano. In another embodiment the Ar1 ring is a phenyl optionally substituted one or more times independently by fluorine, chlorine, methyl, methoxy or cyano.

In another embodiment of the invention, the Ar2 ring is phenyl, and the Ar1 ring is a phenyl optionally substituted one or more times independently by halogen, alkyl, alkoxy, or cyano.

For purposes herein the ring position numbering on the $Ar_1$ moiety, when $Ar_1$ is a phenyl ring, is as shown below:

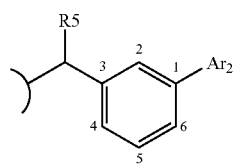

In one embodiment the $Ar_1$ ring is mono-substituted in the 5- or in the 6-position. In another embodiment if the $Ar_1$ ring is di-substituted it is substituted in both the 5 and 6-position.

In one embodiment, the $Ar_1$ 1 ring is an optionally substituted phenyl ring. In another embodiment the phenyl ring is substituted one or more times, suitably 1 to 2 times, by halogen, cyano, or $C_{1-4}$ alkoxy. In another embodiment, the $Ar_1$ ring is a phenyl, or an optionally substituted phenyl in the 6-position, such as by fluorine, or methoxy.

Suitably, $R_6$ is $NR_7R_8$, or is a heterocyclic group of the subformula (ff), (gg), (hh), (ii), (jj), (kk), (ll), (mm) or (nn):

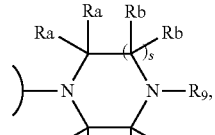
(ff)

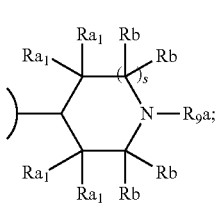
(gg)

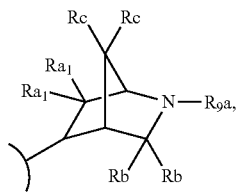
(hh)

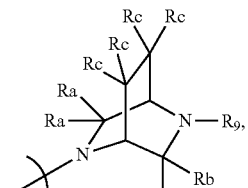
(ii)

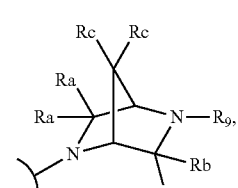
(jj)

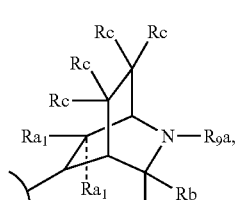
(kk)

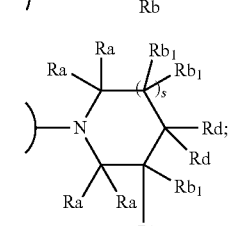
(ll)

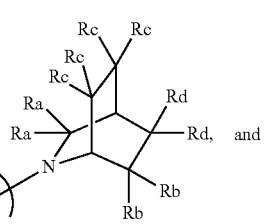
(mm)

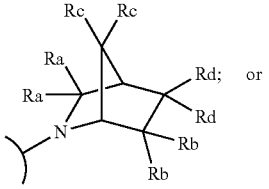
(nn)

$R_6$ is an optionally substituted C5-C7 membered ring containing one or two nitrogens, or a corresponding bicyclic ring containing one or two nitrogens.

Suitably, when $R_6$ is an optionally substituted C5-C7 membered ring containing one or two nitrogens, or a corresponding bicyclic ring containing one or two nitrogens the rings include variations of the ring nitrogen positions from subformulas (ff) to (nn). For instance, in formula (ff) the nitrogens are at the 1-4 position, other options include 1-3, or 1-2 nitrogens with similarly substituted Ra, Rb, Rb1, R9, etc. substituents. Some of these exemplified ring systems are shown below:

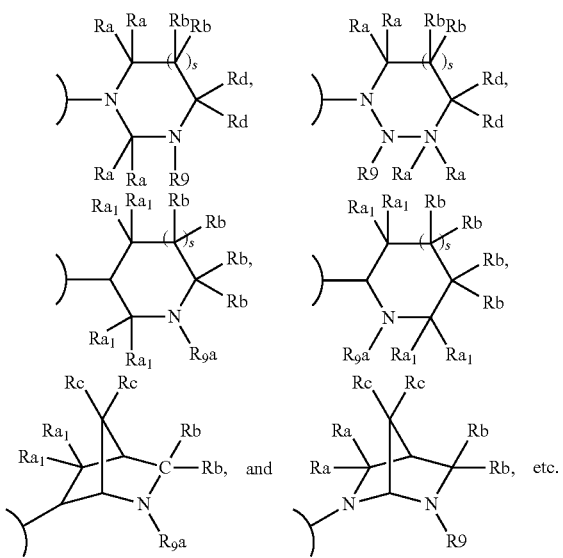

Suitably s is 0, or is an integer having a value of 1 or 2. In one embodiment of the invention s is 1 or 2. In another embodiment of the invention s is 1.

In one embodiment of the invention, $R_6$ is a heterocyclic group of the subformula (ff), and s is 1 or 2. In another embodiment, $R_6$ is a heterocyclic group of the subformula (ff), s is 1 or 2, and Rb is independently selected from hydrogen, or methyl.

In another embodiment, $R_6$ is a heterocyclic group of the subformula (jj).

Suitably, $R_7$ is selected from hydrogen, or an optionally substituted $C_{1-4}$ alkyl. In one embodiment of the invention $R_7$ is hydrogen or methyl.

Suitably, $R_8$ is $(CR_{d1}R_{d1})_t$—$NR_{11}R_{12}$ or $(CR_{d1}R_{d1})_{t1}$—$R_{14}$.

Suitably, t1 is 0 or an integer having a value of 1 to 4.

Suitably, $R_{d1}$ is independently at each occurrence selected from the group consisting of hydrogen, optionally substituted $C_{1-4}$ alkyl, optionally substituted aryl, optionally substituted heteroaryl, optionally substituted heterocyclic.

Suitably, $R_{14}$ is selected from $C_{1-4}$ alkyl, $C_3$-$C_6$ cycloalkyl, optionally substituted aryl, optionally substituted heterocyclic, or optionally substituted heteroaryl moiety. When R14 is a heterocyclic group of the subformula (ff), (ii), (jj), (ll), (mm) and (nn), then t1 is other than 0.

Suitably, when $R_{14}$ is a heteroaryl it is a monocyclic five- to seven-membered unsaturated hydrocarbon ring containing at least one heteroatom selected from oxygen, nitrogen and sulfur; or a fused C8-C12 aromatic ring comprising at least one heteroatom selected from oxygen, nitrogen and sulfur.

Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, uracil, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl. In one embodiment when $R_{14}$ is an optionally substituted heteroaryl it is selected from an optionally substituted thiophenyl, optionally substituted pyridinyl, or an optionally substituted pyrimidinyl.

Suitably, when $R_{14}$ is a heterocyclic it is a C3-C7 monocyclic non-aromatic hydrocarbon ring containing at least one heteroatom selected from nitrogen, oxygen, sulphur or oxidized sulphur moieties, such as S(O)m, and m is 0 or an integer having a value of 1 or 2, or the heterocyclic is a fused, C8-C12 saturated or partially unsaturated ring system wherein one of the rings may be aromatic, or heteroaromatic. Each of the fused rings may have from four to seven ring atoms. Examples of suitable heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety). In one embodiment when $R_{14}$ is an optionally substituted heterocyclic ring, the ring is an optionally substituted piperidinyl, piperazinyl, optionally substituted oxohexahydro-1H-azepine, or an optionally substituted 3'-[(1-Azabicyclo-[2.2.2]oct-3-yl.

In one embodiment when $R_{14}$ is a $C_3$-$C_6$ cycloalkyl it is suitably selected from cyclopropyl, cyclopentyl, or cyclohexyl. In another embodiment when $R_{14}$ is a $C_{1-4}$ alkyl it is ethyl, isopropyl, n-propyl, n-butyl, sec-butyl, or t-butyl.

Suitably, t is an integer having a value of 1 to 4. In one embodiment, t is 1 or 2.

Suitably, t1 is 0 or an integer having a value of 1 to 4. In one embodiment, t1 is 0, or 1. In another embodiment, t1 is 0.

Suitably, $R_{11}$ and $R_{12}$ are independently selected from hydrogen, or $C_{1-4}$ alkyl.

Suitably, Rd is independently at each occurrence selected from the group consisting of hydrogen, optionally substituted $C_{1-4}$ alkyl, optionally substituted aryl, optionally substituted heteroaryl, and an optionally substituted heterocyclic moiety. When Rd is an optionally substituted moiety, excluding hydrogen, the moiety may be substituted one or more times, suitably 1 to 4 times, independently by halogen, such as fluorine or chlorine, or a $C_{1-2}$alkyl. In one embodiment of the invention Rd is independently hydrogen or methyl.

Suitably, $R_9$ is hydrogen, optionally substituted $C_{1-6}$ alkyl, optionally substituted aryl, optionally substituted aryl$C_{1-2}$ alkyl, optionally substituted heteroaryl, optionally substituted heteroaryl $C_{1-2}$alkyl, optionally substituted heterocyclic, optionally substituted heterocyclic $C_{1-2}$alkyl, or C(O) $C_{1-2}$alkyl. When $R_9$ is an optionally substituted $C_{1-6}$ alkyl, the alkyl is substituted one or more times, suitably 1 or 2 times independently by halogen, hydroxy, NR15R16, $C_{1-4}$ alkoxy, S(O)q$C_{1-4}$ alkyl. In one embodiment of the invention, $R_9$ is hydrogen or methyl.

Suitably, $R_{9a}$ is hydrogen, optionally substituted $C_{1-6}$ alkyl, optionally substituted aryl, optionally substituted aryl$C_{1-2}$ alkyl, optionally substituted heteroaryl, optionally substituted heteroaryl $C_{1-2}$alkyl, optionally substituted heterocyclic, optionally substituted heterocyclic $C_{1-2}$alkyl, C(O)$C_{1-2}$ alkyl. In one embodiment of the invention, $R_{9a}$ is hydrogen or optionally substituted $C_{1-3}$ alkyl.

Suitably, $R_a$ is independently selected at each occurrence from hydrogen, $C_{1-4}$ alkyl, $C_{3-7}$cycloalkyl, $C_{3-7}$cycloalkyl$C_{1-4}$ alkyl, $C_{1-4}$ alkoxy, $NR_{15}R_{16}C_{1-4}$alkyl, $S(O)_q$ $C_{1-4}$alkyl, =O, —CH(O), $C(O)_2C_{1-4}$alkyl, $OC(O)C_{1-4}$alkyl, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl. In one embodiment, $R_a$ is independently hydrogen, or methyl.

Suitably, $R_{a1}$ is independently selected at each occurrence from hydrogen, halogen, optionally substituted $C_{1-4}$ alkyl, optionally substituted $C_{3-7}$ cycloalkyl, optionally substituted $C_{3-7}$ cycloalkyl$C_{1-4}$ alkyl, $C_{1-4}$ alkoxy, $NR_{15}R_{16}$, $NR_{15}R_{16}$ $C_{1-4}$alkyl, $S(O)_qC_{1-4}$ alkyl, hydroxy, =O, —CH(O), $C(O)_2$ $C_{1-4}$ alkyl, $OC(O)R_{17}$, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl. In one embodiment, $R_a$ is independently hydrogen, or methyl.

Suitably, $R_b$ is independently selected at each occurrence from hydrogen, optionally substituted $C_{1-4}$ alkyl, optionally substituted $C_{3-7}$ cycloalkyl, optionally substituted $C_{3-7}$ cycloalkyl$C_{1-4}$ alkyl, $C_{1-4}$ alkoxy, $NR_{15}R_{16}C_{1-4}$alkyl, $S(O)_q$ $C_{1-4}$ alkyl, =O, —CH(O), $C(O)_2C_{1-4}$ alkyl, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl. In one embodiment of the invention, $R_b$ is independently selected from hydrogen or methyl.

Suitably, $R_{b1}$ is independently selected at each occurrence from hydrogen, halogen, optionally substituted $C_{1-4}$ alkyl, optionally substituted $C_{3-7}$ cycloalkyl, optionally substituted $C_{3-7}$ cycloalkyl$C_{1-4}$ alkyl, $C_{1-4}$ alkoxy, $NR_{15}R_{16}$, $NR_{15}R_{16}$ $C_{1-4}$alkyl, $S(O)_qC_{1-4}$ alkyl, hydroxy, =O, —CH(O), $C(O)_2$ $C_{1-4}$ alkyl, $OC(O)R_{17}$, $C(O)N(R_{10})_2$, optionally substituted aryl, optionally substituted aryl$C_{1-4}$ alkyl, optionally substituted heterocyclic, optionally substituted heterocyclic $C_{1-4}$ alkyl, optionally substituted heteroaryl, and optionally substituted heteroaryl$C_{1-4}$ alkyl. In one embodiment of the invention, $R_{b1}$ is independently selected from hydrogen or methyl.

Suitably, Rd is independently selected at each occurrence from hydrogen, hydroxy, optionally substituted $C_{1-6}$ alkyl, amino, optionally substituted aryl, optionally substituted aryl$C_{1-2}$alkyl, optionally substituted heterocyclic, optionally substituted heterocyclic$C_{1-2}$alkyl, optionally substituted heteroaryl, optionally substituted heteroaryl $C_{1-2}$alkyl, =O, $C(O)C_{1-2}$alkyl, $OC(O)R_{17}$, or $C(O)N(R_{10})_2$. When $R_d$ is an optionally substituted $C_{1-6}$ alkyl, the alkyl is substituted one or more times, suitably 1 or 2 times independently by halogen, hydroxy, $NR15R16$, $C_{1-4}$ alkoxy, $S(O)qC_{1-4}$alkyl. In one embodiment of the invention, $R_d$ is hydrogen or methyl.

Suitably, $R_c$ is independently selected at each occurrence from hydrogen or $C_{1-4}$ alkyl.

Suitably, $R_{10}$ is independently selected from hydrogen or $C_{1-4}$ alkyl.

Suitably, $R_{15}$ and $R_{16}$ are independently selected from hydrogen, or $C_{1-4}$ alkyl. In one embodiment of the invention $R_{15}$ and $R_{16}$ are hydrogen or methyl.

Suitably, $R_{17}$ is selected from optionally substituted $C_{1-4}$ alkyl, optionally substituted C3-7 cycloalkyl, optionally substituted $C_{3-7}$ cycloalkyl$C_{1-4}$alkyl, optionally substituted aryl, optionally substituted aryl$C_{1-4}$alkyl, heterocyclic, optionally substituted heterocyclic, optionally substituted heterocyclic$C_{1-4}$alkyl, optionally substituted heteroaryl, and optionally substituted heteroaryl $C_{1-4}$alkyl.

Suitably, X is $(C(R_{13}))p$, or $(CR_eR_e)_{s1}$—$X_2$—$(CR_fR_f)_{s2}$.

Suitably, $X_2$ is $NR_{13a}$, O, S(O)m, or C(O).

Suitably, $R_{13}$ is selected from hydrogen, $C_{1-2}$ alkyl, —CH$_2$OH, —CH(CH$_3$)OH, —CH$_2$CH$_2$OH, OH, or =O. In one embodiment of the invention $R_{13}$ is hydrogen.

Suitably, $R_{13a}$ is selected from hydrogen, $C_{1-2}$ alkyl. In one embodiment of the invention $R_{13}$ is hydrogen.

Suitably, s1 is 0 or an integer having a value of 1 to 2. In one embodiment of the invention s1 is 0.

Suitably, s2 is 0 or an integer having a value of 1 to 2. However, when $R_6$ is a heterocyclic group of the subformulas (ff), (ii), (jj) and (ll), and $X_2$ is $NR_{13a}$, O, or S(O)m (and m is 0 or 1) then s2 is 1 or 2, or X is the group $(CH(R_{13}))p$.

Suitably, p is an integer having a value of 1 or 2.

Suitably, q is 0 or an integer having a value of 1 or 2.

Suitably, n is an integer having a value of 1, 2 or 3.

Suitably, $n_3$ is an integer having a value of 1 to 3.

Suitably, m is 0 or an integer having a value of 1, or 2.

Suitably, $Y_4$ is independently selected at each occurrence from hydrogen, halogen, or $C_{1-4}$ alkyl, $C_3$-$C_7$ cycloalkyl, or $C_3$-$C_7$ cycloalkyl $C_{1-4}$ alkyl. In one embodiment of the invention $Y_4$ is hydrogen, and $n_3$ is 1.

Suitably, $R_4$ and $R_5$ are independently selected from the group consisting of hydrogen, optionally substituted $C_{1-4}$alkyl, optionally substituted $C_3$-$C_7$ cycloalkyl, optionally substituted $C_3$-$C_7$ cycloalkyl $C_{1-4}$alkyl, optionally substituted heterocyclic, optionally substituted heterocyclic $C_{1-4}$alkyl, optionally substituted $C_{2-4}$ alkenyl, optionally substituted aryl, optionally substituted aryl $C_{1-4}$alkyl optionally substituted heteroaryl, and optionally substituted heteroaryl $C_{1-4}$alkyl.

In one embodiment $R_5$ is hydrogen, and n is 1. In one embodiment $R_4$ is hydrogen, or $C_{1-4}$alkyl. In another embodiment, $R_4$ and $R_5$ are both hydrogen, and n is 1.

In one embodiment of the invention, R3 is morpholino, X1 is $N(R_{4a})$, Z is C(O), Z1 is C(O), n is 1, v is 1, R5 is hydrogen, Ar1 and Ar2 are optionally substituted phenyl rings, X is (C(R13))p, R13 is hydrogen, m is 1, s3, v1, s4, t2, v2 and t3 are all zero.

In another embodiment, $R^1$ is $C_{1-4}$alkyl, $R^2$ is a $C_{1-4}$alkyl, R3 is morpholino, X1 is $N(R_{4a})$, Z is C(O), Z1 is C(O), n is 1, v is 1, R5 is hydrogen, Ar1 and Ar2 are optionally substituted phenyl rings, (C(R13))p, R13 is hydrogen, m is 1, s3, v1, s4, t2, v2 and t3 are all zero.

In another embodiment, $R^1$ is $C_{1-4}$alkyl, $R^2$ is a $C_{1-4}$alkyl, R3 is morpholino, X1 is $N(R_{4a})$, Z is C(O), Z1 is C(O), n is 1, v is 1, R5 is hydrogen, Ar1 and Ar2 are optionally substituted phenyl rings, (C(R13))p, R13 is hydrogen, m is 1, s3, v1, s4, t2, v2 and t3 are all zero, and R6 is NR7R8.

In another embodiment, $R^1$ is $C_{1-4}$alkyl, $R^2$ is a $C_{1-4}$alkyl, R3 is morpholino, X1 is $N(R_{4a})$, Z is C(O), Z1 is C(O), n is 1, v is 1, R5 is hydrogen, Ar1 and Ar2 are optionally substituted phenyl rings, (C(R13))p, R13 is hydrogen, m is 1, s3, v1, s4, t2, v2 and t3 are all zero, and R6 is an optionally substituted C5-C7 membered ring containing one or two nitrogens, or a corresponding bicyclic ring containing one or two nitrogens, or is a heterocyclic group of the subformula (ff), (gg), (hh), (ii), (jj), (kk), (ll), (mm) or (nn).

In another embodiment, $R^1$ is $C_{1-4}$alkyl, $R^2$ is a $C_{1-4}$alkyl, R3 is morpholino, X1 is $N(R_{4a})$, Z is C(O), Z1 is C(O), n is 1, v is 1, R5 is hydrogen, Ar1 and Ar2 are optionally substituted phenyl rings, (C(R13))p, R13 is hydrogen, m is 1, s3, v1, s4, t2, v2 and t3 are all zero, and LINK is an optionally substituted pyridine.

Another embodiment of the invention are compounds of formulas (Ia), (Ib) and (Ic), subsets of compounds of Formula (I) shown above:

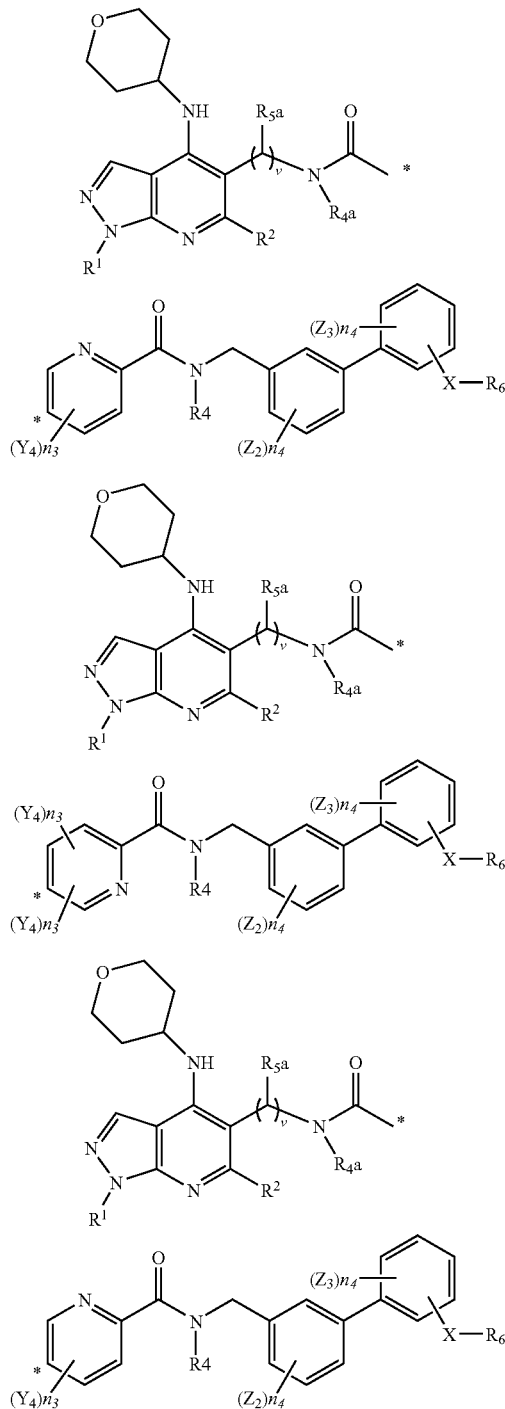

wherein, $R^1$ is $C_{1-4}$alkyl;

$R^2$ is a $C_{1-4}$alkyl;

$R_{4a}$ is selected from hydrogen, methyl or ethyl;

$R_{5a}$ is selected from hydrogen, methyl or ethyl;

$Z_2$ and $Z_3$ are independently at each occurrence selected from the group consisting of hydrogen, halogen, cyano and $C_{1-4}$alkoxy;

$n_3$ is an integer having a value of 1 to 4;

$n_4$ is independently selected at each occurrence from 0 or an integer having a value of 1 or 2;

$Y_4$ is independently selected at each occurrence from the group consisting of hydrogen, halogen, $C_{1-4}$ alkyl and $C_{1-4}$ alkoxy; and two of the $Y_4$ moieties together with the carbons to which they are attached form a 5-6 membered saturated, partially unsaturated or fully unsaturated C5-C6 ring;

$R_6$ is $NR_7R_8$, or is a heterocyclic group of the subformula (ff), (gg), (hh), (ii), (jj), (kk), (ll), (mm) or (nn):

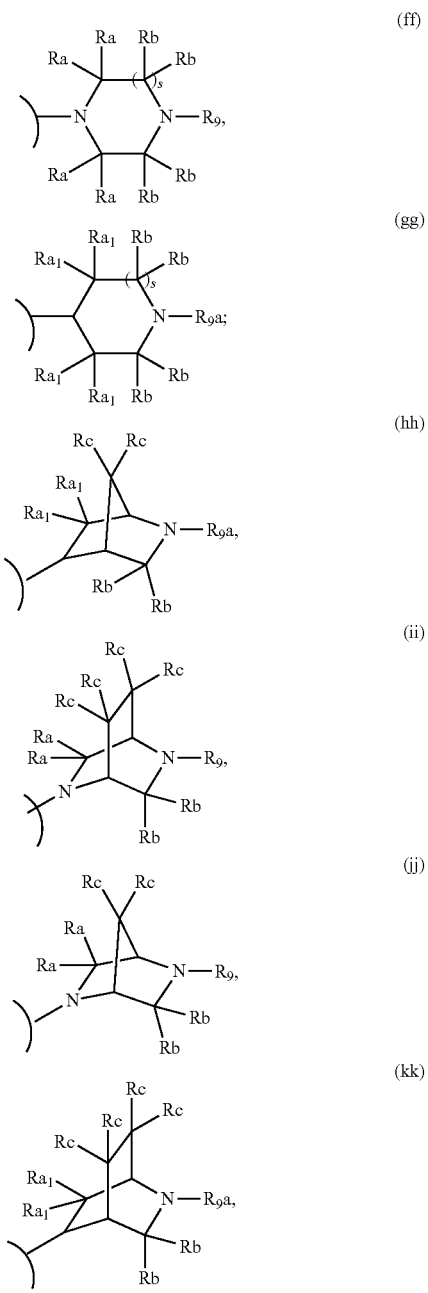

-continued

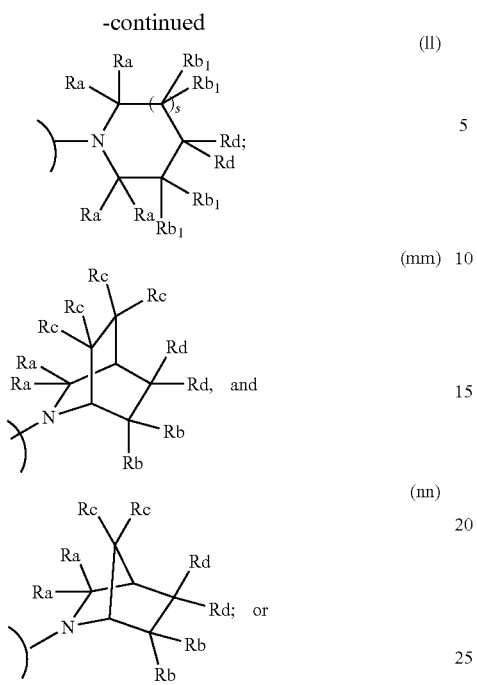

R$_6$ is an optionally substituted C5-C7 membered ring containing one or two nitrogens, or a corresponding bicyclic ring containing one or two nitrogens;

R$_9$ is selected from the group consisting of hydrogen, optionally substituted C$_{1-6}$ alkyl, optionally substituted aryl, optionally substituted arylC$_{1-2}$alkyl, optionally substituted heteroaryl, optionally substituted heteroaryl C$_{1-2}$alkyl, optionally substituted heterocyclic, optionally substituted heterocyclic C$_{1-2}$alkyl, and C(O)C$_{1-2}$alkyl;

R$_{9a}$ is selected from the group consisting of hydrogen, optionally substituted C$_{1-6}$ alkyl, optionally substituted aryl, optionally substituted arylC$_{1-2}$alkyl, optionally substituted heteroaryl, optionally substituted heteroaryl C$_{1-2}$alkyl, optionally substituted heterocyclic, optionally substituted heterocyclic C$_{1-2}$alkyl, and C(O)C$_{1-2}$alkyl;

Rd is independently selected at each occurrence from the group consisting of hydrogen, hydroxy, optionally substituted C$_{1-6}$ alkyl, amino, optionally substituted aryl, optionally substituted arylC$_{1-2}$alkyl, optionally substituted heterocyclic, optionally substituted heterocyclicC$_{1-2}$alkyl, optionally substituted heteroaryl, optionally substituted heteroaryl C$_{1-2}$alkyl, =O, C(O)C$_{1-2}$alkyl, OC(O)R$_{17}$, and C(O)N(R$_{10}$)$_2$;

R$_{15}$ and R$_{16}$ are each independently selected at each occurrence from hydrogen, or C$_{1-4}$ alkyl;

R$_{17}$ is independently, at each occurrence, selected from the group consisting of optionally substituted C$_{1-4}$ alkyl, optionally substituted C3-7 cycloalkyl, optionally substituted C$_{3-7}$ cycloalkylC$_{1-4}$alkyl, optionally substituted aryl, optionally substituted arylC$_{1-4}$alkyl, heterocyclic, optionally substituted heterocyclic, optionally substituted heterocyclicC$_{1-4}$alkyl, optionally substituted heteroaryl, and optionally substituted heteroaryl C$_{1-4}$alkyl;

R$_a$ is independently selected at each occurrence from the group consisting of hydrogen, optionally substituted C$_{1-4}$ alkyl, optionally substituted C$_{3-7}$ cycloalkyl, optionally substituted C$_{3-7}$ cycloalkyl-C$_{1-4}$alkyl, C$_{1-4}$ alkoxy, NR$_{15}$R$_{16}$C$_{1-4}$alkyl, S(O)$_q$C$_{1-4}$alkyl, =O, —CH(O), C(O)$_2$C$_{1-4}$ alkyl, C(O)N(R$_{10}$)$_2$, optionally substituted aryl, optionally substituted arylC$_{1-4}$ alkyl, optionally substituted heterocyclic, optionally substituted heterocyclic C$_{1-4}$ alkyl, optionally substituted heteroaryl, and optionally substituted heteroarylC$_{1-4}$ alkyl;

R$_{a1}$ is independently selected at each occurrence from the group consisting of hydrogen, halogen, optionally substituted C$_{1-4}$ alkyl, optionally substituted C$_{3-7}$ cycloalkyl, optionally substituted C$_{3-7}$ cycloalkylC$_{1-4}$ alkyl, C$_{1-4}$ alkoxy, NR$_{15}$R$_{16}$, NR$_{15}$R$_{16}$C$_{1-4}$alkyl, S(O)$_q$C$_{1-4}$ alkyl, hydroxy, =O, —CH(O), C(O)$_2$C$_{1-4}$ alkyl, OC(O)R$_{17}$, C(O)N(R$_{10}$)$_2$, optionally substituted aryl, optionally substituted arylC$_{1-4}$ alkyl, optionally substituted heterocyclic, optionally substituted heterocyclic C$_{1-4}$ alkyl, optionally substituted heteroaryl, and optionally substituted heteroarylC$_{1-4}$ alkyl;

R$_b$ is independently selected at each occurrence from hydrogen, optionally substituted C$_{1-4}$ alkyl, optionally substituted C$_{3-7}$ cycloalkyl, optionally substituted C$_{3-7}$ cycloalkylC$_{1-4}$ alkyl, C$_{1-4}$ alkoxy, NR$_{15}$R$_{16}$C$_{1-4}$alkyl, S(O)$_q$C$_{1-4}$ alkyl, =O, —CH(O), C(O)$_2$C$_{1-4}$ alkyl, C(O)N(R$_{10}$)$_2$, optionally substituted aryl, optionally substituted arylC$_{1-4}$ alkyl, optionally substituted heterocyclic, optionally substituted heterocyclic C$_{1-4}$ alkyl, optionally substituted heteroaryl, and optionally substituted heteroarylC$_{1-4}$ alkyl;

R$_{b1}$ is independently selected at each occurrence from hydrogen, halogen, optionally substituted C$_{1-4}$ alkyl, optionally substituted C$_{3-7}$ cycloalkyl, optionally substituted C$_{3-7}$ cycloalkylC$_{1-4}$ alkyl, C$_{1-4}$ alkoxy, NR$_{15}$R$_{16}$, NR$_{15}$R$_{16}$C$_{1-4}$ alkyl, S(O)$_q$C$_{1-4}$ alkyl, hydroxy, =O, —CH(O), C(O)$_2$C$_{1-4}$ alkyl, OC(O)R$_{17}$, C(O)N(R$_{10}$)$_2$, optionally substituted aryl, optionally substituted arylC$_{1-4}$ alkyl, optionally substituted heterocyclic, optionally substituted heterocyclic C$_{1-4}$ alkyl, optionally substituted heteroaryl, and optionally substituted heteroarylC$_{1-4}$ alkyl;

R$_c$ is independently selected at each occurrence from hydrogen or C$_{1-4}$ alkyl;

R$_{10}$ is independently selected at each occurrence from hydrogen or C$_{1-4}$ alkyl;

R$_{13a}$ is selected from hydrogen, C$_{1-2}$ alkyl;

R$_{13}$ is independently selected from the group consisting of hydrogen, C$_{1-2}$ alkyl, —CH$_2$OH, —CH(CH$_3$)OH, —CH$_2$CH$_2$OH, OH, and =O;

X is (C(R$_{13}$))$_p$, or (CR$_e$R$_e$)$_{s1}$—X$_2$—(CR$_f$R$_f$)$_{s2}$;

X$_2$ is NR$_{13a}$, O, S(O)$_m$, or C(O);

Re, and Rf are each independently selected at each occurrence from hydrogen, or C$_{1-4}$alkyl;

s is 0, or is an integer having a value of 1 or 2;

s1 is 0 or an integer having a value of 1 to 2;

s2 is 0 or an integer having a value of 1 to 2, provided that when R$_6$ is a heterocyclic group of the subformulas (ff), (ii), (jj) and (ll), and X$_2$ is NR$_{13a}$, O, or S(O)m and m is 0 or 1, then s2 is 1 or 2, or X is (CH(R$_{13}$))p;

p is an integer having a value of 1 or 2;

q is 0 or an integer having a value of 1 or 2;

R$_4$ is selected from the group consisting of hydrogen, optionally substituted C$_{1-4}$ alkyl, optionally substituted C$_3$-C$_7$ cycloalkyl, optionally substituted C$_3$-C$_7$ cycloalkyl C$_{1-4}$ alkyl, optionally substituted heterocyclic, optionally substituted heterocyclic C$_{1-4}$ alkyl, optionally substituted alkenyl, optionally substituted aryl, optionally substituted arylC$_{1-4}$ alkyl optionally substituted heteroaryl, and optionally substituted heteroaryl C$_{1-4}$ alkyl;

R$_7$ is selected from hydrogen, or an optionally substituted C$_{1-4}$ alkyl;

R$_8$ is (CR$_{d1}$R$_{d1}$)$_t$—NR$_{11}$R$_{12}$ or (CR$_{d1}$R$_{d1}$)$_{t1}$—R$_{14}$;

R$_{d1}$ is independently at each occurrence selected from the group consisting of hydrogen, optionally substituted C$_{1-4}$ alkyl, optionally substituted aryl, optionally substituted heteroaryl, and optionally substituted heterocyclic;

$R_{14}$ is selected from the group consisting of $C_{1-4}$ alkyl, $C_3$-$C_6$ cycloalkyl, optionally substituted heterocyclic, and optionally substituted heteroaryl moiety;

t is an integer having a value of 1 to 4;

t1 is 0 or an integer having a value of 1 to 4;

$R_{11}$ and $R_{12}$ are independently selected from hydrogen, or $C_{1-4}$ alkyl; and the asterix indicates the point of attachment to the pyridine ring;

or a pharmaceutically acceptable salt thereof.

The asterix in the formulas indicates a point of attachment of the Z term, or the carbonyl moiety as noted in the formulas above to the heteroaryl ring. In the formulas above this is portrayed as a pyridine ring, and can be attached in the 1-3, 1-4 or the 1,-5 position of the pyridine ring [shown from the point of view of the left hand side of the molecule].

For purposes herein, all substituents for Formula (Ia), (Ib) and (Ic) are as defined above for Formula (I) unless specifically indicated otherwise.

It is to be understood that the present invention covers all combinations of particular and preferred groups described hereinabove. It is also to be understood that the present invention encompasses compounds in which a particular group or parameter, e.g. S(O)m, etc. may occur more than once. In such compounds it will be appreciated that each group or parameter is independently selected from the values listed. When any variable occurs more than one time in a formula, its definition on each occurrence is independent of its definition at every other occurrence.

Particular compounds according to the invention include those mentioned in the examples and their pharmaceutically acceptable derivatives.

As used herein, the term "pharmaceutically acceptable" means a compound which is suitable for pharmaceutical and veterinary usage. Salts and solvates of compounds of the invention which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives. In one embodiment pharmaceutically acceptable derivatives are salts, solvates, esters, carbamates and phosphate esters. In another embodiment pharmaceutically acceptable derivatives are salts, solvates and esters. In yet another embodiment of the invention pharmaceutically acceptable derivatives are salts and esters, in particular salts.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Salts of the compounds of the present invention may, for example, comprise acid addition salts resulting from reaction of an acid with a nitrogen atom present in a compound of formula (I). Salts encompassed within the term "pharmaceutically acceptable salts" refer to non-toxic salts of the compounds of this invention. Suitable addition salts are formed from acids which form non-toxic salts and examples are acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanesulphonate, formate, fumarate, gluceptate, gluconate, glutamate, glycollylarsanilate, hexylresorcinate, hydrabamine, hydrobromide, hydrochloride, hydrogen phosphate, hydroiodide, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmitate, pantothenate, phosphate/diphosphate, piruvate, polygalacturonate, saccharate, salicylate, stearate, subacetate, succinate, sulphate, tannate, tartrate, teoclate, tosylate, triethiodide, trifluoroacetate and valerate.

Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of Formula (I), or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water. A complex with water is known as a "hydrate". Solvates of the compound of the invention are within the scope of the invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series; Edward B. Roche, ed., Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy or amine groups are bonded to any group that, when administered to a patient, cleaves to form the hydroxy or amine groups. Thus, representative examples of prodrugs include (but are not limited to) acetate, formate and benzoate derivatives of alcohol and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halo-substituted $C_{1-10}$ alkoxy; S(O)m alkyl, such as methyl thio, methylsulfinyl or methyl sulfonyl; a ketone (—C(O)), or an aldehyde (—C(O)$R_{6'}$), such as C(O)$C_{1-10}$ alkyl or C(O)aryl, wherein $R_{6'}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl (and wherein the $R_{6'}$ moieties, excluding hydrogen, may themselves be optionally substituted 1 or 2 times, independently by halogen; hydroxy; hydroxy substituted alkyl; $C_{1-4}$ alkoxy; S(O)$_m C_{1-4}$ alkyl; amino, mono & di-substituted $C_{1-4}$ alkyl amino; $C_{1-4}$ alkyl, or $CF_3$); C(O)O$R_{6'}$; N$R_4 R_{14'}$, wherein $R_{4'}$ and $R_{14'}$ are each independently hydrogen or $C_{1-4}$ alkyl, such as amino or mono or -disubstituted $C_{1-4}$ alkyl or wherein the $R_4 R_{14'}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-4}$ alkoxy; S(O)$_m C_{1-4}$ alkyl; amino, mono & di-substituted $C_{1-4}$ alkyl amino; $C_{1-4}$ alkyl, or $CF_3$.

The term "halo" or "halogens" is used herein to mean the halogens, chloro, fluoro, bromo and iodo.

As used herein, the term "$C_{1-10}$alkyl" or "alkyl" or "alkyl$_{1-10}$" is used herein to mean both straight and branched hydrocarbon chain containing the specified number of carbon atoms, e.g. $C_{1-10}$alkyl means a straight of branched alkyl chain of at least 1, and at most 10, carbon atoms, unless the chain length is otherwise limited. Examples of "alkyl" as used herein include, but are not limited to, methyl, ethyl, n-propyl, n-butyl, n-pentyl, isobutyl, isopropyl, sec-butyl, tert-butyl or t-butyl and hexyl and the like.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl, 2-propenyl, 3-butenyl, 2-butenyl, 2-pentenyl, 3-pentenyl, 3-methyl-2-butenyl, 3-methylbut-2-enyl, 3-hexenyl, 1,1-dimethylbut-2-enyl and the like.

As used herein, the term "alkoxy" refers to straight or branched chain alkoxy groups containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

As used herein, the term "cycloalkyl" refers to cyclic radicals, such as a non-aromatic hydrocarbon ring containing a specified number of carbon atoms. For example, $C_{3-7}$cycloalkyl means a non-aromatic ring containing at least three, and at most seven, ring carbon atoms. Representative examples of "cycloalkyl" as used herein include, but are not limited to, cyclopropyl, cyclobutyl, cyclopentyl, cyclohexyl and cycloheptyl and the like.

The term "cycloalkenyl" is used herein to mean cyclic radicals, such as a non-aromatic hydrocarbon ring containing a specified number of carbon atoms preferably of 5 to 7 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl, naphthyl, and indene.

The terms "heteroaryl ring", "heteroaryl moiety", and "heteroaryl" are used herein to mean a monocyclic five- to seven-membered unsaturated hydrocarbon ring containing at least one heteroatom selected from oxygen, nitrogen and sulfur. Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil. The terms "heteroaryl ring", "heteroaryl moiety", and "heteroaryl" shall also used herein to refer to fused aromatic rings comprising at least one heteroatom selected from oxygen, nitrogen and sulfur. Each of the fused rings may contain five or six ring atoms. Examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

The terms "heterocyclic rings", "heterocyclic moieties", and "heterocyclyl" is used herein to mean a monocyclic three- to seven-membered saturated or non-aromatic, unsaturated hydrocarbon ring containing at least one heteroatom selected from nitrogen, oxygen, sulphur or oxidized sulphur moieties, such as S(O)m, and m is 0 or an integer having a value of 1 or 2. The terms "heterocyclic rings", "heterocyclic moieties", and "heterocyclyl" shall also refer to fused rings, saturated or partially unsaturated, and wherein one of the rings may be aromatic, or heteroaromatic. Each of the fused rings may have from four to seven ring atoms. Examples of heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

The term "arylalkyl" or "heteroarylalkyl" or "heterocyclicalkyl" is used herein to mean a $C_{1-4}$ alkyl (as defined above)

attached to an aryl, heteroaryl or heterocyclic moiety (as also defined above) unless otherwise indicated.

The term "sulfinyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean $C(O)C_{1-10}$ alkyl wherein the alkyl is as defined above.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

With regard to stereoisomers, the compounds of the Formulas herein may have one or more asymmetric carbon atom and may occur as racemates, racemic mixtures and as individual enantiomers or diastereomers. All such isomeric forms are included within the present invention, including mixtures thereof.

C is (E) and trans (Z) isomerism may also occur. The present invention includes the individual stereoisomers of the compound of the invention and where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. A stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

Furthermore, some of the crystalline forms of the compounds of the Formulas herein may exist as polymorphs, which are included in the present invention.

Exemplified compounds of the compounds of this invention include the racemates, or optically active forms of the compounds of the working examples herein, and pharmaceutically acceptable salts thereof.

Methods of Treatment

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

In one embodiment of the present invention, the agents of the present invention are delivered via oral inhalation or intranasal administration. Appropriate dosage forms for such administration, such as an aerosol formulation or a metered dose inhaler, may be prepared by conventional techniques.

For administration by inhalation the compounds may be delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Dry powder compositions for topical delivery to the lung by inhalation may, for example, be presented in capsules and cartridges of for example gelatine or blisters of for example laminated aluminum foil, for use in an inhaler or insufflator. Powder blend formulations generally contain a powder mix for inhalation of the compound of the invention and a suitable powder base (carrier/diluent/excipient substance) such as mono-, di- or poly-saccharides (e.g. lactose or starch).

Each capsule or cartridge may generally contain between 20 µg-10 mg of the compound of formula (I) optionally in combination with another therapeutically active ingredient. Alternatively, the compound of the invention may be presented without excipients.

Suitably, the packing/medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant an inhaler having a reservoir form pack suitable for comprising multiple (un-metered doses) of medicament in dry powder form and including means for metering medicament dose from the reservoir to a delivery position. The metering means may for example comprise a metering cup, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

In the case of multi-dose delivery, the formulation can be pre-metered (e.g. as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (e.g. as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,656, the disclosures of which are hereby incorporated by reference).

The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of Formula (I) preferably combined with lactose.

Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament there from.

In one aspect, the multi-dose blister pack comprises plural blisters arranged in generally circular fashion on a disc-form blister pack. In another aspect, the multi-dose blister pack is elongate in form, for example comprising a strip or a tape.

In one aspect, the multi-dose blister pack is defined between two members peelably secured to one another. U.S. Pat. Nos. 5,860,419; 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Where the medicament container is an aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 µl, such as 25 µl, 50 µl or 63 µl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined there between and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085. Additionally, intra-nasal delivery of the present compounds is effective.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the medicament must be capable of resisting those forces in the nasal passages that function to remove particles from the nose. Such forces, referred to as 'mucociliary clearance', are recognized as being extremely effective in removing particles from the nose in a rapid manner, for example, within 10-30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors.

A suitable dosing regime for the formulation of the present invention when administered to the nose would be for the patient to inhale deeply subsequent to the nasal cavity being cleared. During inhalation the formulation would be applied to one nostril while the other is manually compressed. This procedure would then be repeated for the other nostril.

In one embodiment, the means for applying a formulation of the present invention to the nasal passages is by use of a pre-compression pump. Most preferably, the pre-compression pump will be a VP7 model manufactured by Valois SA. Such a pump is beneficial as it will ensure that the formulation is not released until a sufficient force has been applied, otherwise smaller doses may be applied. Another advantage of the pre-compression pump is that atomisation of the spray is ensured as it will not release the formulation until the threshold pressure for effectively atomising the spray has been achieved. Typically, the VP7 model may be used with a bottle capable of holding 10-50 ml of a formulation. Each spray will typically deliver 50-100 µl of such a formulation, therefore, the VP7 model is capable of providing at least 100 metered doses.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of Formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants, e.g., oleic acid or lecithin and cosolvents, e.g. ethanol. Pressurized formulations will generally be retained in a canister (e.g. an aluminum canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means e.g., by micronization. The desired fraction may be separated out by air classification or sieving. Suitably, the particles will be crystalline in form. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

For all methods of use disclosed herein for the compounds of Formula (I), the daily topical dosage regimen will preferably be from 0.01 mg to 1000 mg, administered one to four times daily. The daily inhalation dosage regimen will preferably be from about 0.05 microgram/kg to about 1 mg/kg per day, more preferably from about 0.2 microgram/kg to about 20 microgram/kg, administered in one or more daily doses. The daily intranasal dosage regimen will preferably be from about 0.05 microgram/kg to about 1 mg/kg per day, more preferably from about 0.2 microgram/kg to about 20 microgram/kg, administered in one or more daily doses. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of antagonism of a muscarinic receptor or a PDE-IV enzyme. In particular, the treatment, therapeutically or prophylactically, in animals include disease states such as those noted herein in the Methods of Treatment section.

For use herein treatment may include prophylaxis. It may also include reducing the symptoms of, ameliorating the symptoms of, reducing the severity of, reducing the incidence of, or any other change in the condition of the patient, which improves the therapeutic outcome.

It should be understood that in addition to the ingredients particularly mentioned above, the formulations of this invention may include other agents conventional in the art having regard to the type of formulation in question, for example those suitable for oral administration may include flavoring agents, or those for inhalation may include carriers, such as lactose.

The anticipated therapeutic activity for a dual pharmacophore antagonist of muscarinic receptors and an inhibitor of the PDE4 enzyme within a single molecule is both as a bronchodilator (provided by both muscarinic receptor antagonist activity and PDE4 inhibition) and as an anti-inflammatory (by elevation of cytosolic levels of 3',5'-cyclic adenosine monophosphate (cAMP) through inhibition of the PDE4 enzyme and by blockade other pro-inflammatory mechanisms mediated through muscarinic receptors on immune and resident cells) within the lungs. There is also a potential for further positive cooperatively as an anti-inflammatory through simultaneous interaction of downstream signaling pathways via modulation of both targets within the same cell.

Muscarinic receptors are coupled to G-proteins ($M_1$, $M_3$ & $M_5$ via $G_{q/11}$ and $M_2$ & $M_4$ via $G_{i/o}$) which can lead to activation of a number of intracellular targets and signaling cascades. For example, $M_2$ and $M_4$ receptors via $G_{i/o}$ can decrease cellular adenylyl cyclase levels and increase MAP kinase activation whereas $M_1$, $M_3$ & $M_5$ receptors via $G_{q/11}$ can elevate phospholipase Cβ (PLCβ) and increase MAP kinase activation (Nathanson N M. A multiplicity of muscarinic mechanisms: enough signaling pathways to take your breathe away. *Proc. Natl. Acad. Sci. USA.* 2000; 97:6245-6247. Lanzafame AA. Cellular signaling mechanisms for muscarinic acetylcholine receptors. *Recept. Chann.* 2003; 9:241-260).

There is a potential therefore to elevate intracellular levels of cAMP through inhibition of the PDE4 enzyme, the enzyme responsible for breaking down cAMP into 5'-AMP and by increasing adenylyl cyclase activity, the enzyme responsible for conversion of ATP into cAMP, via blockade of $M_2$ receptors on immune cells, thus inhibiting acetylcholine signaling through $G_{i/O}$ and therefore inhibiting decrease of adenylyl cyclase activity. Simultaneous activities of $M_2$ receptor blockade and PDE4 inhibition at the same cell would therefore lead to elevation of intracellular cAMP by two independent mechanisms increasing the overall concentration of cAMP within the cell. Elevated levels of cyclic AMP has been shown to have anti-inflammatory activity in a range of immune cells including T-cells, macrophages and neutrophils as well as resident lung cells such as epithelial and airway smooth muscle cells. Elevated cAMP can also cause airway smooth muscle relaxation and may offer a further mechanism independent of $M_3$ receptor blockade to initiate bronchodilation. For a full review of the potential therapeutic activities of PDE4 inhibitors in respiratory diseases see: Kroegel C & Foerster M. Phophodiesterase-4 inhibitors as a novel approach for the treatment of respiratory disease: cilomilast. *Expert Opin. Investig. Drugs* 2007; 16:109-124. Dastidar S G. et al., Therapeutic benefit of PDE4 inhibitors in inflammatory diseases. *Curr. Opin. Investig. Drugs* 2007; 8:364-372. Krymskaya V P & Panettieri R A. Phosphodiesterases regulate airway smooth muscle function in health and disease *Curr. Top. Dev. Biol.* 2007; 79:61-74. Spina D. The potential of PDE4 inhibitors in respiratory disease. *Curr. Drug Targets Inflamm. Allergy* 2004; 3:231-236.

The disposition within the lungs of a single drug substance which acts at both muscarinic receptors and as a PDE4 inhibitor at the same cell offers the greatest opportunity for cooperative anti-inflammatory or bronchodilator activity through modulation of these independent targets. This approach offers a greater potential to maximize the interaction of these two independent mechanisms compared to co-administration of two pharmacophores directed against each target as co-disposition at the cells of the lungs cannot be guaranteed through the second approach. The novel single dual pharmacophore approach outlined here, therefore offers a significantly greater potential for co-disposition to cells of the lung compared to administration of two separate pharmacophores directed against each target. Further to this such a pharmacophore will also be more amenable to combination with existing or other novel inhaled therapies for the treatment of respiratory diseases.

Therefore, compounds and pharmaceutical formulations according to the invention may be used in combination with or include one or more other therapeutic agents, for example selected from anti-inflammatory agents, other selective anticholinergic agents (particularly an $M_1$, $M_2$, or $M_1/M_2$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, $\beta_2$-adrenoreceptor agonist, an antiinfective agent (e.g. an antibiotic or an antiviral), or an antihistamine. One aspect of the present invention are combinations comprising a compound of Formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimize the activity and/or stability and/or physical characteristics (e.g. solubility) of the therapeutic ingredient. It will be clear also that where appropriate, the therapeutic ingredients may be used in optically pure form.

One suitable combination of the present invention comprises of compound of the invention together with a $\beta_2$-adrenoreceptor agonist. Examples of $\beta_2$-adrenoreceptor agonists include salmeterol (which may be a racemate or a single enantiomer, such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period, such as salmeterol or formoterol.

Suitable long acting $\beta_2$-adrenoreceptor agonists include those described in WO02/66422A, WO02/270490, WO02/076933, WO03/024439, WO03/072539, WO 03/091204, WO04/016578, WO04/022547, WO04/037807, WO04/037773, WO04/037768, WO04/039762, WO04/039766, WO01/42193 and WO03/042160, whose disclosures are incorporated by reference herein.

Preferred long-acting $\beta_2$-adrenoreceptor agonists are:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]foramide, and
N-2{2-[4-(3-phenyl-4-methoxyphenyl)aminophenyl]ethyl}-2-hydroxy-2-(8-hydroxy-2(1H)-quinolinon-5-yl)ethylamine.

Suitable anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16β-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-17α-(1-methylcylopropylcarbonyl)oxy-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester, beclomethasone esters (such as the 17-propionate ester or the 17,21-dipropionate ester), budesonide, flunisolide, mometasone esters (such as the furoate ester), triamcinolone acetonide, rofleponide, ciclesonide, (16α, 17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds having glucocorticoid agonism that may possess selectivity for transrepression over transactivation and that may be useful in combination therapy include those covered in the following patents: WO03/082827, WO01/10143, WO98/54159, WO04/005229, WO04/009016, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277.

Suitable anti-inflammatory agents include non-steroidal anti-inflammatory drugs (NSAID's). Suitable NSAID's include sodium cromoglycate, nedocromil sodium, leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, 5-lipoxygenase inhibitors, p38 inhibitors, and IKK2 inhibitors. Suitable other $\beta_2$-adrenoreceptor agonists include salmeterol (for example, as the xinafoate), salbutamol (for example, as the sulphate or the free base), formoterol (for example, as the fumarate), fenoterol or terbutaline and salts thereof. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are generally represented by three types of antihistamines: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.
Ethylenediamines: pyrilamine maleate, tripelennamine HCl, and tripelennamine citrate.
Alkylamines: chloropheniramine and its salts such as the maleate salt, and acrivastine.
Piperazines: hydroxyzine HCl, hydroxyzine pamoate, cyclizine HCl, cyclizine lactate, meclizine HCl, and cetirizine HCl.
Piperidines: Astemizole, levocabastine HCl, loratadine or its descarboethoxy analogue, and terfenadine and fexofenadine hydrochloride or another pharmaceutically acceptable salt.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The invention will now be described by reference to the following biological examples which are merely illustrative and are not to be construed as a limitation of the scope of the present invention.

BIOLOGICAL EXAMPLES

As compounds of Formula (I) have dual pharmacophores, maximizing both activities is a component of the testing process. There is a desire to balance the antagonism of the muscarinic $M_3$ receptor with the inhibition of the PDE4 enzyme. Although the $M_3$ antagonism is measured in a human receptor expressed in a mammalian cell line as described herein, PDE4 is usually measured on isolated human enzyme, therefore a secondary cell assay is monitored that reflects intracellular PDE4 inhibition. An example of such a cellular assay is the PBMC assay as shown below. Therefore it is desired to optimize PDE4 inhibition in the cell (measured using PBMC assay). Desired attributes of the molecule would be to maintain or improve the $M_3$ pharmacophores potency with no or partial $M_1$ agonism since agonism of the $M_1$ receptor is usually counter-indicated. Another attribute is to decrease the dropoff between the PDE4 enzyme assay and inhibition reflected in the PBMC assay. Since both pharmacophores are in a single molecule, it is desirable to enhance intracellular inhibition of PDE4 reflected in the PBMC assay while retaining significant activity against the transmembrane $M_3$ receptor. In addition, in vivo efficacy and duration of action is not always reflected by in vitro measurements of activity, therefore other physiochemical properties of the molecules may be important for balanced efficacy at both targets. Therefore, one embodiment of the invention are compounds which posses appropriately balanced pharmacology, and have desirable physicochemical properties, such as solubility, dissolution rate, permeability, crystallinity, micronizability, and excipient compatibility. If the compounds are administered by inhalation, then low aqueous solubility is generally not suitable for a nebulized/solution formulation.

One embodiment of the invention is a display of sufficient antagonism at the $M_3$ receptor wherein $pIC50 \geq 8.0$ and a $pA_2 \geq 8.0$, as well as inhibition of the PDE4 enzyme with a $pIC_{50} \geq 8.0$ and cellular activity (as reflected in the PBMC assay) with a $pIC_{50} \geq 7.0$.

In one embodiment of the invention compounds of Formula (I) are generally selective against agonism or partial agonism of the various muscarinic receptors ($M_1$, $M_2$, $M_3$) and PDE4>100-fold vs. other PDEs.

The inhibitory effects of compounds at the mAChR (muscarinic) receptor and the PDE4 enzyme for the present invention are determined by the following in vitro and in vivo functional assays.

maChR (Muscarinic) Receptor Assays

In Vitro Assays
Muscarinic Receptor Radioligand Binding Assays
Radioligand Binding Studies to Determine Interaction at Cloned Human Receptors The human $M_1$-$M_3$ receptors are cloned and stably expressed in Chinese Hamster Ovary (CHO) cell lines. $M_2$ ACh receptor is co-expressed with the chimeric G protein, Gqi5, in CHO cells. Competition for [$^3$H]-N-methyl scopolamine (0.5 nM) binding is performed using crude CHO cell membranes using a Scintillation Proximity Assay (SPA). Atropine is run in every assay as the control.

In the SPA assay membranes are preincubated with wheatgerm agglutinin beads (GE) in 50 mM HEPES buffer (Sigma, St. Louis Mo.) (pH 7.4) at 4° C. for 30 min, and then incubated with 0.5 nM [$^3$H]-N-methyl scopolamine (PerkinElmer) in a 96-well Optiplate (Perkin Elmer), for 2 hr in the presence of vehicle (1% DMSO) or compound (0.01-1000 nM), in 0.2 mL final volume, at room temperature. At the end of the incubation the plates are centrifuged (Beckman CS-6R) for 5 min at 2000 RPM, and counted in a Top Count Microplate Scintillation counter (model A9912 Packard, Meriden Conn.).

Concentration-response curves for each compound are run using duplicate samples in 3 independent experiments. Specific binding is determined by subtracting non-specific binding (defined in the presence of 0.3 μM Atropine) from total binding. $IC_{50}$ values are estimated from concentration-response curves and used to determine the inhibition constant (Ki) of each inhibitor using the Cheng and Prusoff equation [for competitive antagonists: The Kd's utilized for the calculations are: 0.17, 0.28, and 0.16, nM for M1, M2 and M3 respectively.

$$K_i = \rightarrow \frac{IC_{50}}{[L]/K_d + 1}$$

Membrane Preparation

Cells are harvested by centrifugation at 1000×g for 10 min at 4° C. The cell pellet is washed with Phosphate Buffered Saline (PBS) and quick frozen with liquid nitrogen. The pellet is stored at −80° C. until the membrane preparation is made. The frozen pellet is thawed and re-suspended in cold hypotonic membrane buffer (40 mM Tris, pH 7.5, 1 mM MgSO$_4$, 0.5 mM EDTA, 1 mM phenylmethylsulfonyl fluoride, 2.5 mg/L leupeptin, 0.1 mg/mL aprotinin) and incubated on ice for 5 min. The cell suspension is homogenized in a 40 mL Dounce homogenizer and centrifuged at 2000 rpm at 4° C. for 6 min to remove nuclei and cellular debris. The 2000 rpm pellet is resuspended in homogenization buffer and spun again at 2000 rpm for 6 min. This process is repeated two more times. The combined supernatant is collected and cell membranes are pelleted at 100000×g for 1 hr at 4° C. The membrane pellet is resuspended in membrane buffer and aliquots stored at −80° C. Protein concentration is quantified using the Bio-Rad protein assay reagent.

Calcium Mobilization Studies (FLIPR)

Studies to determine the effectiveness of antagonists to cause blockade of functional intracellular calcium fluxes following agonist (ACh) treatment of cloned human receptors. This system is used for characterizations of antagonist-receptor interactions using four distinct variations of the FLIPR methodology: (a) potency: $IC_{50}$ determination, (b) potency: $pA_2$ determination, (c) reversibility of antagonist-receptor interaction, or (d) confirmation of no functional agonist activity.

Cell Source The human M1-M3 receptors are cloned and stably expressed in Chinese Hamster Ovary (CHO) cells. The M2 receptors are co-expressed with the chimeric G protein, Gqi5.

Cell lines: M1 stable: Biocat#1044; M2+Gqi5 stable: Biocat#95663; M3 stable: Biocat#1049

Method of Culture: CHO-M1, CHO-Gqi5-M2 and CHO-M3 cells are cultured to confluence at 37° C. in a humidified incubator with 5% $CO_2$/95% air. CHO-M1 and CHO-M3 are cultured in Alpha MEM with nucleosides and L-glutamine and 10% fetal calf serum. Cells expressing the M2 receptor are cultured in DMEM/F12 media, supplemented with 200 mg/L G418 (geneticin), and 10% fetal calf serum.

Assay Readout: Calcium mobilization, monitored as change in cytosolic calcium concentration, is measured as change in 516 nm emission fluorescence intensity of cytosolic loaded Fluo-4, a green fluorescent calcium indicator which exhibits large (>100-fold) fluorescence intensity increases on binding to calcium, the change in intensity being, therefore, directly related to cytosolic calcium levels. The emitted fluorescence from all 96 wells is measured simultaneously using a cooled CCD camera. Data points are collected every second. Maximal change in emission from each well after simultaneous addition of agonist or compound to each of the 96 wells is then exported to an excel spreadsheet. This data is then transferred to GraphPad Prism Version 4.03 for plotting of response to each treatment condition (ACh or compound).

Experimental Protocols:

Cell plating: A microtiter plate based calcium mobilization FLIPR (Fluorometric Imaging Plate Reader, Molecular Devices, Sunnyvale Calif., [Schroeder K S, Neagle, B D. FLIPR: a new instrument for accurate, high throughput optical screening. *J. Biomol. Screen.* 1996; 1:75.]) assay is used for the functional characterization of compounds against M1, M2 (w/Gqi5) and M3 ACh receptors stably expressed in CHO cells. On the day prior to assay, cells are plated in 96 well, blackwall, clear bottom plates (Packard View) at a concentration of 40000 cells per well and incubated at 37° C. in a humidified incubator with 5% $CO_2$/95% air for 18 to 24 hours.

a) $IC_{50}$ Determination for Antagonists:

Receptor antagonist characterization ($IC_{50}$ determination), compounds tested for potency of inhibition of ACh induced muscarinic receptor activation: To evaluate antagonist potency of compounds against the $M_1$, $M_2$ and $M_3$ receptors, cell culture media is aspirated and replaced with 100 µL of dye load media [Eagles Minimal Essential Medium (EMEM) with Earl's salts and L-Glutamine, 0.1% BSA (Seriologicals Corporation), 4 µM Fluo-4-acetoxymethyl ester fluorescent indicator dye (Fluo-4 AM, Molecular Probes, Eugene, Oreg.) and 2.5 mM probenecid]. Cells are then incubated for 1 hour at 37° C. The dye load media is then aspirated off the cells and replaced with identical media without Fluo-4 AM and with 0.1% Gelatin (BSA removed) and 2.5 mM probenecid. Cells are incubated for 10 minutes at 37° C. and then washed 3 times with KRH assay buffer [Krebs Ringer Henseleit (120 mM NaCl, 4.6 mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES (pH 7.4)) with 0.1% gelatin and 2.5 mM probenecid]. 100 µL KRH assay buffer with 0.1% gelatin and 2.5 mM probenecid is added to wells of dye loaded and washed cells followed by 50 µL of 3× compound ($1\times10^{-8}$-$3.3\times10^{-5}$ M final in the assay) and plate warmed to 37° C. for 10 minutes before being placed in FLIPR where the dye loaded, compound pretreated cells are exposed to excitation light (488 nm) from a 6 watt Argon Laser. The basal emission fluorescence is measured, then the cellular response to an $EC_{80}$ concentration of ACh (3.3 nM against $M_1$, 10 nM against $M_2$ and 1.0 nM against $M_3$) prepared in KRH assay buffer with 0.1% BSA (no gelatin), is monitored in FLIPR for 90 seconds and then 50 µL of 100 µM ATP (assay concentration of 20 µM) is added to check cell viability (H. M. Sarau et al, 1999. *Mol. Pharmacol.* 56, 657-663). Maximal change in emission from each well, vehicle or compound pretreated, after simultaneous addition of ACh to each of the 96 wells is then determined. The $IC_{50}$ is defined as the compound pretreatment concentration which inhibits 50% of the ACh induced response. Compounds are believed to be active in this assay are those having an $IC_{50}$ of about 33 uM to about 10 nM or less.

The $IC_{50}$ is defined as the compound pretreatment concentration which inhibits 50% of the ACh induced response. A compound is believed to be active in this assay if it has an $IC_{50}$ of between 33 uM and 10 nM or less. Exemplary compounds of Formula (I) which have been tested in this assay and found to be the most active can be found in Examples 126-138, 140-144, 146-155, 157, 159-160, 162-192, 194-197, 199-201, and 203-217.

b) $pA_2$ Determination for Antagonists:

Single concentration kinetic characterization of compounds tested for potency of inhibition of ACh induced muscarinic receptor activation: $pA_2$: Compounds which show $IC_{50}$'s of <1.0 µM may be further characterized in a single compound concentration kinetic assay. To confirm antagonist potency of more potent compounds against the M1, M2 and M3 receptors, dye loaded (culture media is aspirated, replaced with 100 µL of dye load media and incubated for 1 hour at 37° C.) and washed cells (washed three times with 100 µL KRH assay buffer) are treated with 150 µL of KRH assay buffer with 0.1% gelatin and 2.5 mM probenecid containing vehicle (0.01% DMSO), for control response, or appropriate concentration of antagonist (single concentration for each column of 12 wells, concentration determined from $IC_{50}$ value) and incubated for 20 minutes at 37° C. Buffer is aspirated off and 150 µL of fresh KRH assay buffer with 0.1% gelatin and 2.5 mM probenecid containing vehicle (0.01% DMSO) or appropriate concentration of compound is added and incubated for 10 minutes at 37° C. Plates are then placed into FLIPR for fluorescent measurements. After determination of basal fluorescence emission, a concentration range of ACh (0.033-100,000 nM for M1/M3 and 0.33-1,000,000 nM for M2) is added to vehicle or compound treated (columns of 12 wells) cells to determine the shift of receptor potency in response to ACh in presence of compound. Compound potency at the receptor is determined using the following formula: $pA_2=\log(DR-1)-\log[B]$ where DR is the dose ratio defined as the ratio of equiactive concentration ($EC_{50}$) of agonist in presence and absence of antagonist and [B] is concentration of antagonist.

c) Determination of Antagonist Reversibility

Evaluation of antagonist-receptor occupancy following antagonist wash-out (reversibility) using FLIPR methodology: After aspirating off growth media the cells are washed 3 times with 100 µl KRH assay buffer containing 0.1% gelatin. Each column (12 wells) is treated with 150 µL of EMEM containing 0.1% gelatin with vehicle (0.01% DMSO) or antagonist at an appropriate concentration: 1.0 nM, 10 nM, 100 nM or 1000 nM, (washout columns), or not treated (no washout columns) and incubated for 60 minutes at 37° C. EMEM is aspirated and KRH assay buffer containing 0.1% gelatin with vehicle (0.01% DMSO) or antagonist is added to washout columns and incubated at 37° C. for 20 minutes. Buffer with vehicle or compound is aspirated and cells retreated and incubated at 37° C. for an additional 10 minutes. Buffer with vehicle or compound is then aspirated and cells washed 3 times with KRH assay buffer containing 0.1% BSA. KRH buffer (100 µL) containing 0.1% BSA is then added and cells incubated for 30 minutes at 37° C. and washed 3 times. Cells are incubated for a further 30 minutes and washed 3 times, followed by a further 30 minute incubation. After this 90 minute washout, all cells are washed 3 times with KRH containing 0.1% gelatin. Cells are loaded with dye using 150 µL dye load media with 0.1% gelatin and 2.5 mM probenecid for washout columns or same dye load media with 0.1% gelatin and 2.5 mM probenecid with vehicle (0.01% DMSO) or appropriate concentration of compound (1.0 nM, 10 nM, 100 nM or 1000 nM) for no washout columns and incubated for 60 minutes at 37° C. Dye load media is aspirated and cells are retreated with 150 µL of KRH assay buffer containing 0.1% gelatin and 2.5 mM probenicid for washout columns or KRH assay buffer containing 0.1% gelatin and 2.5 mM probenicid and vehicle or appropriate concentration of compound for no washout columns. Cells are incubated for 20 minutes at 37° C. Pretreatment buffer is aspirated and 150 µL of fresh KRH assay buffer with 0.1% gelatin and 2.5 mM probenicid is then added to washout columns and the same buffer containing vehicle (0.01% DMSO) or the appropriate concentration of antagonist is added to the no washout columns. Plates are incubated for 10 minutes at 37° C. and plates placed into FLIPR where fluorescence is monitored. Baseline measurements are recorded and acetylcholine concentration response curves are added to each column while continuing to monitor fluorescence. Comparison of ACh concentration response curves is performed between vehicle-treated and antagonist-treated [1.0 nM, 10 nM, 100 nM or 1000 nM] cells following washout to determine if there remained a shift in the $EC_{50}$ value post washout. Fold-shift (fs) values were determined using the following formula: fs=[X]/[V]; wherein X is the concentration of acetylcholine required to elicit a 50% maximum calcium mobilization response following antagonist treatment and washout; V is the concentration of acetylcholine required to elicit a 50% maximum calcium mobilization response following vehicle treatment and washout.

d) Confirmation of No Agonist Activity

Receptor agonist characterization ($EC_{50}$ determination): compounds tested to confirm no agonist potential at muscarinic receptors: To evaluate agonist potential of compounds and ACh potency for the $M_1$, $M_2$ and $M_3$ receptors, culture media is aspirated and replaced with 100 µL of dye load media. Cells are then incubated for 1 hour at 37° C. The dye load media is then aspirated off the cells and replaced with identical media without Fluo-4 AM and with 0.1% Gelatin (BSA removed) and 2.5 mM probenecid. Cells are incubated for 10 minutes at 37° C. and then washed 3 times with 100 µL KRH assay buffer. 100 µL KRH assay buffer with 0.1% gelatin and 2.5 mM probenecid is added to wells of dye loaded and washed cells and plate warmed to 37° C. for 10 minutes before being placed in FLIPR where dye loaded cells are exposed to excitation light (488 nm) from a 6 watt Argon Laser. The basal emission fluorescence is measured, then the cellular response to a concentration range of ACh or compound (50 µL of 3× in assay buffer) is monitored in FLIPR for 90 seconds and then 50 µL of 100 µM ATP (assay concentration of 25 µM) was added to check cell viability. The $EC_{50}$ is the ACh or compound concentration required to obtain 50% the maximal response.

Superfusion Protocols

All procedures were performed in accredited facilities in accordance with Universal Precautions for Handling Human Blood, Body Fluids, and Tissue (BAR #88-06-22-060) and institutional guidelines including the Guide for the Care and Use of Laboratory Animals (DHSS #NIH 85-23) and approved protocol #86-077 (Animal Care and Use Committee, GlaxoSmithKline). Human lungs from organ donors were obtained from the National Disease Research Interchange (NDRI, Philadelphia, Pa., www.ndriresource.org). Sections of bronchus were removed from the lung and cleaned of adherent connective, parenchymal and fatty tissue. Bronchial strips of approximately 3-4 mm in width were prepared and placed into modified Krebs-Henseleit solution. Composition of the solution was (mM): NaCl (113.0), KCl (4.8), $CaCl_2$ (2.5), $KH_2PO_4$ (1.2), $MgSO_4$ (1.2), $NaHCO_3$ (25.0) and dextrose (11.0) and equilibrated with 95% $O_2$: 5% $CO_2$ and maintained at 37° C.; meclofenamic acid (1 µM) was added to block endogenous cycloxygenase activity. Alternatively, trachea was removed from male Hartely guinea pigs (Charles River, Portage, Mich.; weight range 450-650 g). The epithelium of the trachea was removed and strips were cut, approximately 2 cartilage rings in width. Individual tissues were suspended via silk suture in a superfusion chamber (Coleman, 1989; Harvard Apparatus, Inc., Holliston, Mass., www.harvardapparatus.com) and connected to BIOPAC TSD125C transducers. The tissues were then continuously superfused with Krebs-Henseleit solution at 2 mL/min for the duration of the experiment. Stock solutions of agonist and antagonist were infused (0.02 mL/min) via 22-gauge needle inserted into the superfusion tubing. Mechanical responses were recorded isometrically using a commercially-available data acquisition system (MP100WS/Acknowledge; BIOPAC Systems, Goleta, Calif., www.biopac.com) interfaced with a computer.

Duration of PDE4M compound-induced inhibition of the carbachol response was investigated in two ways. The first protocol described was used to assess onset and offset of compound-induced inhibition. The second protocol was used to evaluate inhibition of the carbachol response in the presence of infused compounds as compared to inhibitory activity remaining after overnight washout.

Protocol A: Tissues were suspended under an optimal resting tension of 1.5 g. After a 60 min equilibration period, the tissues were contracted with carbachol (1 µM) for the duration of the experiment. Upon reaching a sustained contraction isoproterenol (10 µM) was administered to maximally relax the tissue, and this change served as a reference. Isoproterenol exposure was halted and the carbachol-induced tension allowed to recover. Compounds and vehicle were infused at a single concentration per tissue until a sustained level of inhibition was attained. Compounds were infused for six hours and upon which the infusion of compounds and vehicle was halted. Carbachol-induced tension in tissues was then allowed to recover for 10 hours. After this recovery period, carbachol was removed from the perfusate and tissues allowed to return to baseline tone. A carbachol concentration-response curve was then generated, whole-log increments from 10 nM to 100 μM, followed by a 1 mM histamine-induced contraction for reference.

The following parameters were determined for each concentration of antagonist, and expressed as the mean±SEM for n individual tissues (n=numbers). Inhibition of the carbachol-induced contraction was expressed as a percent of the isoproterenol reference response. The onset halftime to maximal inhibition of tension (ON $t_{1/2}$) was determined. The offset halftime of tension recovery (OFF $t_{1/2}$), following removal of the compound from the superfusate, was determined by measuring the time required for tension to return to the level used to measure the respective onset halftime. Tension recovery was plotted vs. time as a percentage of the % recovery of maximal inhibition.

Post-recovery concentration-response curves were plotted with data as a percent of the 1 mM post-histamine reference contractions. $EC_{50}$ and fold-shift vs. control values were calculated for each compound tested.

Protocol B: Tissues were suspended under an optimal resting tension of 1.5 g. After an incubation period to reach stable basal tone, histamine (10 μM) was infused to assess tissue contraction response. After tension reached a plateau, histamine infusion was halted and tissues tension allowed to return to baseline. Compounds and vehicle were then infused onto the tissues for 6 hours. A carbachol concentration-response curve was generated, in the presence of infused compounds or vehicle, by infusing carbachol over the tissues in cumulative half-log increments, 10 nM to 100 μM, followed by a 1 μM histamine-induced contraction for reference. Upon completion of this curve, infusion of compounds into the perfusate was halted and tissue tension allowed to return to baseline. The tissues were then washed with perfusate buffer overnight. The following morning, histamine (10 μM) was again infused to contract the tissues and assess tissue response. After tension reached a plateau, histamine infusion was halted and tissues tension allowed to return to baseline. Another carbachol concentration-response curve was generated, this time in the absence of infused compounds other than that remaining after the overnight washout.

Agonist-induced responses for each tissue were expressed as a percentage of the reference histamine (10 uM)-induced contraction obtained at the end of the curve. Geometric mean $EC_{50}$ values were calculated from nonlinear regression analyses of data (Motulsky, 2003). $EC_{50}$ and fold-shift vs. control values were calculated for each compound tested. For tissues where carbachol concentration-response curves were generated in the presence of infused test compounds, antagonist potencies were calculated and expressed as $pK_B$ and $pA_2$ where appropriate (Arunlakshana & Schild, 1958): pKB=−log [antagonist]/X−1, where X is the ratio of agonist concentration required to elicit 50% of the maximal contraction in the presence of the antagonist compared with that in its absence and $pA_2$=−log of the antagonist dissociation constant.

In Vivo Assays:
Inhibition of Acetylcholine-Induced Bronchoconstriction in Conscious Guinea Pigs
a. Method
Procedure for Wet Suspension Intratracheal Dosing.

A stock solution of 5% weight/volume of Tween 80 is made at least one day prior to dosing. The solution is made by dissolving 1 gram of Tween 80 in a total volume of 20 ml sterile saline. On the day of dosing the stock 5% Tween solution is diluted 1:10 in sterile saline for a final concentration of 0.5% Tween. This solution is filtered through a 0.22 micron syringe filter to yield the final wet vehicle. Animals are weighed and the weights averaged for dose calculations:

((animal weight[kg])×(dose in[mg/kg]))/(dose volume [ml])=Dose Concentration[mg/ml]

Drug is weighed and placed into a glass homogenizer with the appropriate amount of vehicle, i.e. if 1.5 mg is weighed, than 1 ml vehicle is be added. The mixture is then homogenized by hand until it appears uniform. For doses lower than 1.0 mg/kg appropriate dilution of the suspension is made immediately after homogenization.

A one ml syringe capped with a 22 ga 2.5 inch rat gavage needle is filled with 200 μl of dosing solution. After an animal is anesthetized with isoflorane they are placed in the supine position and the dosing needle is introduced into the trachea via the mouth. After the drug solution is injected into the trachea the animal is returned to a recovery cage. Recovery from anesthesia is noted within 5 minutes.
Whole Body Plethysmograph Determination of Penh in Conscious Guinea Pigs:

Four and 24 hours (for dose-response experiment) and 4, 24, 48 and 72 hours (for duration of action experiment) after intratracheal drug or vehicle administration, male Dunkin-Hartley guinea pigs (650-750 g) (Charles River Labs, St Constance Canada) are placed into a whole body plethysmograph box (internal volume of approximately 7 liters). A bias air flow of 2 L/minute was applied to the box and flow changes in the box are measured and recorded using a Buxco XA data acquisition and respiratory analysis system (Buxco Electronics, Wilmington, N.C.). Animals are allowed to acclimate to the plethysmograph box for 3 minutes before air flow data is recorded. Recordings are collected for 5 minutes to determine basal airway parameters. Animals are exposed to an aerosol of acetylcholine (ACh) produced by an ultrasonic nebulizer (Delvibiss Pulmosonic 5000D) (3.5 mg/mL, pushed by a trickle flow of 0.6 mL/minute for 36 seconds followed by a 2 minute drying time) that generates an aerosol into a mixing chamber, then directly into the plethysmographic box airstream. Measurements are collected for 10 minutes following the ACh exposure. Collected values are retained and Penh (enhanced pause) is calculated. Penh has previously been shown as an index of airway obstruction and correlates with increased intrapleural pressure (Hamelmann E. et al., Noninvasive measurement of airway responsiveness in allergic mice using barometric plethysmography. *Am. J. Crit. Care Med.* 156:766-75]. The algorithm for the Penh calculation is as follows: Penh=[(expiratory time/relaxation time)−1]×(peak expiratory flow/peak inspiratory flow) where relaxation time is the amount of time required for 70% of the tidal volume to be expired. Animals are returned to caging until the next noted exposure timepoint. Each animal's baseline airway parameter is used as its own control when determining the effect of ACh aerosol exposure.

PDE4 Assays

In Vitro Assays
Inhibition of Phosphodiesterase IVB Enzyme Activity

Human recombinant PDE4B, in particular the 2B splice variant thereof (HSPDE4B2B), is disclosed in WO 94/20079 and also in M. M. McLaughlin et al., "A low Km, rolipram-sensitive, cAMP-specific phosphodiesterase from human brain: cloning and expression of cDNA, biochemical characterization of recombinant protein, and tissue distribution of mRNA", *J. Biol. Chem.*, 1993, 268, 6470-6476. For example, in Example 1 of WO 94/20079, human recombinant PDE4B is described as being expressed in the PDE-deficient yeast *Saccharomyces cerevisiae* strain GL62. PDE4B expression is induced by the addition of 150 μM $CuSO_4$.

For luminescence-coupled assay based screening the supernatant fractions of yeast cell lysates are subjected to Cibacron blue affinity chromatography, dialysis and desalting, to enrich for PDE4B and to remove components, e.g. ATP, able to interfere with the assay. Human recombinant PDE4D (HSPDE4D3A) is disclosed in P. A. Baecker et al., "Isolation of a cDNA encoding a human rolipram-sensitive cyclic AMP phosphodiesterase (PDE $IV_D$)", *Gene*, 1994, 138, 253-256. Expression of human PDE4D in yeast, and subsequent preparation of the recombinant protein for assay was as described for PDE4B.

Inhibition of PDE Activity: Luciferase-Coupled PDE Assay

Inhibition of PDE4B and PDE4D are measured using a luminescence-coupled assay system developed by Cambrex. This assay system couples the formation of AMP, derived from PDE4-catalyzed hydrolysis of cAMP, to the formation of ATP. The ATP is then used as a substrate for Luciferase and results in light as a signal output. When PDE is inhibited or inactive, no AMP is produced, the Luciferase is inactive, and no light signal is produced. This assay is used in a quenched assay format, where PDE4 enzyme (2.5 μL; ~120 pM enzyme in 40 mM Tris-HCl, 10 mM $MgCl_2$, 1 mM CHAPS, 0.01% BSA, pH 7.5) and cAMP substrate (2.5 μL; 2 μM cAMP in 40 mM Tris-HCl, 10 mM $MgCl_2$, 1 mM CHAPS, 0.01% BSA, pH 7.5) are added sequentially to a 384 well assay plate (Greiner 784075) pre-stamped with 12.5-50 nL compound at the desired concentration. The reaction is incubated at room temperature for 1 hr, then is quenched by the addition of enzyme stop solution (1.5 μL; prepared as described by vendor; catalog #LT27-253) and then the light signal is generated by the addition of detection reagent (2.5 μL, prepared as described by vendor, catalog #LT27-250). The luminescence is then measured on a Viewlux imager (Perkin Elmer) using emission filters of 613/55 nm or 618/40 nm and a 5 second exposure. Compounds are prepared in neat DMSO at a concentration of 10 mM. For inhibition curves, compounds are diluted using a three fold serial dilution and tested at 11 concentrations (e.g. 50 μM-0.8 nM or 25 μM-0.42 nM or 2.5 μM to 42 μM). Curves were analyzed using ActivityBase and XL fit, and results are expressed as $pIC_{50}$ values.

Compounds having a $pIC_{50}$ of about 5 or greater are believed to be active in this assay, with the upper limit of resolution being approximately $pIC_{50}$=10.2.

Curves were analyzed using ActivityBase and XL fit, and results are expressed as $pIC_{50}$ values. A compound was believed to be active in this assay if it had a $pIC_{50}$ of about 6 to 10.4 or greater against PDE4B. Compounds of Formula (I) which have been tested in the PDE4B assay and found to be the most active can be found in Examples 126-138, 140-155, 157-189, 191-210, and 212-217.

Other In Vitro Assays:

Inhibition of TNF-α (TNF-Alpha) Production in Human PBMC (Peripheral Blood Mononuclear Cell) Assay A 96-well flat bottom polystyrene tissue culture plate (manufacturer code 167008 Thermo Fisher Scientific, Kamstrupvej 90, Kamstrup, Roskilde DK-4000 Denmark) is prepared by initially adding to column 1 ca. 10 mM of test compound dissolved in DMSO, which is diluted about 7.94 fold in the well with DMSO to give a 1.26 mM solution. For a more potent compound, a more diluted solution in DMSO may be used. The compound is further diluted with DMSO into columns 2 to 9 by 8 successive 3-fold dilutions using the Biomek® 2000 Laboratory Automation Workstation (Beckman Coulter, Inc., 4300 N. Harbor Boulevard, P.O. Box 3100, Fullerton, Calif. 92834-3100 USA). Column 10 is used as a DMSO negative control (High Signal, 0% response), while column 11, which contains 1.26 mM of the PDE4 inhibitor roflumilast, is used as a positive control (Low Signal, 100% response). About 1 μl (about 1 ul) of compound is transferred to the compound plate using a Biomek® FX Laboratory Automation Workstation.

PBMC cells (peripheral blood mononuclear cells) are prepared from heparinised human blood (using 1% v/v Heparin Sodium 1000 IU/ml Endotoxin Free, Leo Laboratories Ltd., Cashel Road, Dublin 12. Ireland, Cat No: PL0043/0149) from normal volunteers using the Accuspin™ System-Histopaque®-1077 essentially (Sigma-Aldrich Company Ltd., The Old Brickyard New Rd, Gillingham Dorset SP8 4XT). About 20 ml of blood is overlaid onto 15 ml Histopaque® in Accuspin™ tubes. The tube is then centrifuged at about 800 g for ca. 20 minutes. The cells are collected from the cell layer, washed by centrifugation (ca. 1300 g, ca. 10 minutes) and resuspended in RPMI1640 medium (Low endotoxin RPMI1640 medium, Cat No: 31870, Invitrogen Corporation Invitrogen Ltd, 3 Fountain Drive, Inchinnan Business Park, Paisley PA4 9RF, UK) containing 10% foetal calf serum, 1% L-glutamine (Invitrogen Corporation, Cat No: 25030) and 1% penicillin/streptomycin (Invitrogen Corporation, Cat No: 15140). Viable cells are counted by trypan blue staining and diluted to $1 \times 10^6$ viable cells/ml. About 50 μl (about 50 ul) of diluted cells and about 75 μl (about 75 ul) of LPS (ca. 1 ng/ml final; Sigma Cat No: L-6386) are added to the compound plate, which is then incubated at 37° C., 5% $CO_2$, for about 20 hours.

The supernatant is removed and the concentrations of TNF-α are determined by electrochemiluminescence assay using the Meso Scale Discovery (MSD) technology (Meso Scale Discovery, 9238 Gaither Road, Gaithersburg, Md. 20877, USA). See the "TNF-α (TNF-alpha) MSD Assay" described below for typical details.

Results can be expressed as pIC50 values for inhibition of TNF-α (TNF-alpha) production in PBMCs, and it should be appreciated that these results can be subject to variability or error.

TNF-α (TNF-Alpha) MSD Assay:

MSD Human Serum Cytokine Assay Diluent, (25 μl) Meso Scale Discovery, 9238 Gaither Road, Gaithersburg, Md. 20877) is added to a 96-well High-Bind MSD plate pre-coated with anti-hTNF alpha capture antibody (MA6000) and then incubated for about 24 hours at 4° C. to prevent non-specific binding. About 20 μl (ul) of supernatant from the PBMC plate are then transferred from columns 1-11 to columns 1-11 of the MSD plate using the Biomek FX. About 20 μl (ul) of TNF-α standard (Cat No. 210-TA; R&D Systems Inc., 614 McKinley Place NE, Minneapolis, Minn. 55413, USA) are added to column 12 of the MSD plate to generate a standard calibration curve (about 0 to 30000 pg/ml final). About 20 μl (ul) of diluted sulfo-TAG antibody (ca. 1 μg/ml working concentration) is added to each well, and the plates/wells are shaken at room temperature for about 2 hours. Finally, about 90 μl (ul) of MSD Read Buffer P (diluted to 2.5 times with distilled water) is added and the plates are read on a MSD Sector 6000.

Data Analysis:

Data analysis is performed with ActivityBase/XC50 module (ID Business Solutions Ltd., 2 Occam Court, Surrey Research Park, Guildford, Surrey, GU2 7QB UK) or with Bioassay (Cambridgesoft 1 Signet Court Swann's Road, Cambridge, CB5 8LA, UK). Data are normalized and expressed as % inhibition using the formula 100*((U−C1)/

$(C_2-C_1))$ where U is the unknown value, C1 is the average of the high signal (0%) control wells (column 10), and C2 is the average of the low signal (100%) control wells (column 11). Curve fitting is performed with the following equation: $y=A+((B-A)/(1+(10^x/10^C)^D))$, where A is the minimum response, B is the maximum response, C is the log 10(IC50), and D is the Hill slope. The XC50 module automatically constrains A, B or A and B if an acceptable unconstrained fit cannot be achieved. QC criteria are applied and fits are rejected where A<−40 or >30, B<80 or >140 or the ratio of upper and lower confidence limits on C>10. The results for each compound are recorded as pIC50 values (−C in the above equation).

Compounds are considered active in this assay if they demonstrated a $pIC_{50}$ of greater than 5 up to a $pIC_{50}$ of 10 or greater, and were screened at concentrations up to 10 uM. Representative compounds of Formula (I) as described in Examples 126-138, 140, 142-144, 146-153, 157-160, 162-168, 173-182, 184, 187-189, 192-197, 199-201, 203, 206-215, and 217 were tested in the above assay and found to be the most active.

In Vivo Biological Assays

The in vitro enzymatic PDE4B inhibition assay(s) described herein, or generally similar or generally analogous assays should be regarded as being the primary test(s) of biological activity. However, additional in vivo biological tests which are not an essential measure of activity, efficacy or side-effects but may be used for further characterization are described below.

LPS-Induced Pulmonary Neutrophilia in Rats: Effect of i.t. Administered PDE4 Inhibitors Pulmonary neutrophil influx is thought to be a significant component to the family of pulmonary diseases like chronic obstructive pulmonary disease (COPD) which can involve chronic bronchitis and/or emphysema (G. F. Filley, Chest. 2000; 117(5); 251s-260s). The purpose of this neutrophilia model is to study the potentially anti-inflammatory effects in vivo of orally administered PDE4 inhibitors on neutrophilia induced by inhalation of aerosolized lipopolysaccharide (LPS), modeling the neutrophil inflammatory component(s) of COPD. See the literature section below for scientific background.

For initial screening purposes, male Lewis rats (Charles River, Raleigh, N.C., USA) weighing approximately 280-400 grams are pretreated with a single intratracheal dose (200 μl) of either 300 μg/kg, or 30 μg/kg, of the test compound suspended in 0.5% Tween 80 (Sigma-Aldrich, St Louis, Mo., USA) in phosphate buffered saline or vehicle only. Secondarily, dose response curves may be generated using intratracheal doses of 300, 30 and 10 μg/kg, again administered in 0.5% Tween 80 (Sigma-Aldrich, St Louis, Mo., USA) in phosphate buffered saline (200 μl per rat, 30 minutes prior to LPS exposure. After a predetermined pretreatment time, the rats are exposed to aerosolized LPS (Serotype *E. Coli* 026:B6 prepared by trichloroacetic acid extraction, Sigma-Aldrich, St Louis, Mo., USA), generated from a nebulizer containing a 100 μg/mL LPS solution. Rats are exposed to the LPS aerosol at a rate of ca. 4 L/min for. 20 minutes. LPS exposure is carried out in a closed chamber with internal dimensions of roughly 45 cm length×24 cm width×20 cm height. The nebulizer and exposure chamber are contained in a certified fume hood. At about 4 hours-post LPS exposure the rats are euthanized by overdose with pentobarbital at 90 mg/kg, administered intraperitoneally. Bronchoalveolar lavage (BAL) is performed through a 14 gauge blunt needle into the exposed trachea. Five, 5 ml washes are performed to collect a total of 25 ml of BAL fluid. Total cell counts and leukocyte differentials are performed on the BAL fluids in order to calculate neutrophil influx into the lung. For single dose experiments, percent inhibition of neutrophil number, neutrophil percent, or both may be calculated and reported for that specific dose. For the secondary dose response studies, percent neutrophil inhibitions of either neutrophil number or neutrophil percent at each dose (cf. vehicle) may be used to calculate a sigmoidal dose-response curve (variable slope) usually using Prism Graph-Pad. The dose-response curve may also be used to calculate an ED50 value (in mg per kg of body weight) for inhibition by the test compounds of the LPS-induced neutrophilia.

Various literature references include, but are not limited to:

Filley G. F. Comparison of the structural and inflammatory features of COPD and asthma. Chest. 2000; 117(5) 251s-260s.

Howell R E, Jenkins L P, Fielding L E, and Grimes D. Inhibition of antigen-induced pulmonary eosinophilia and neutrophilia by selective inhibitors of phosphodiesterase types 3 and 4 in brown Norway rats. Pulmonary Pharmacology. 1995; 8: 83-89.

Spond J, Chapman R, Fine J, Jones H, Kreutner W, Kung T T, Minnicozzi M. Comparison of PDE 4 inhibitors, Rolipram and SB 207499 (Ariflo™), in a rat model of pulmonary neutrophilia. Pulmonary Pharmacology and Therapeutics. 2001; 14: 157-164.

Underwood D C, Osborn R R, Bochnowicz S, Webb E F, Rieman D J, Lee J C, Romanic A M, Adams J L, Hay D W P, and Griswold D E. SB 239063, a p38 MAPK inhibitor, reduces neutrophilia, inflammatory cytokines, MMP-9, and fibrosis in lung. Am J Physiol Lung Cell Mol Physiol. 2000; 279: L895-L902.

Examples are listed as producing "significant" inhibition if the test compound demonstrated significant (p<0.05, using a two tailed distribution and two sample equal variance students T test performed in Microsoft Excel) inhibition of either neutrophil number, neutrophil percent, or both, when dosed at either 300 or 30 μg/kg, 30 minutes prior to LPS aerosol exposure.

For purposes herein:

| $pIC_{50}$ | $IC_{50}$ (nM) | $IC_{50}$ (uM) |
|---|---|---|
| 4.00 | 100,000.0 | 100 |
| 5.00 | 100,000.0 | 10 |
| 6.00 | 1,000.0 | 1 |
| 7.00 | 100.0 | 0.1 |
| 8.00 | 10.0 | 0.01 |
| 9.00 | 1.0 | 0.001 |
| 10.00 | 0.1 | 0.0001 |

Methods of Manufacture

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples. For purposes herein, the compounds in the Schemes are shown generically with the formula terms, and LINK representing an alkyl linker. Where appropriate additional substituent groups as defined within the scheme, e.g. L is a leaving group, P represents a protecting group, etc.

Compounds of formula (IX) shown below, wherein $R^1$, $R^2$ and $R^3$ are as defined herein and $R^4$ represents hydrogen, can be prepared by hydrogenation of an azide compound of formula (XI), wherein $R^1$, $R^2$ and $R^3$ are as defined herein, in the presence of a suitable catalyst such as a palladium catalyst, e.g. palladium on carbon, in a suitable solvent such as ethanol, e.g. at a suitable temperature such as room temperature:

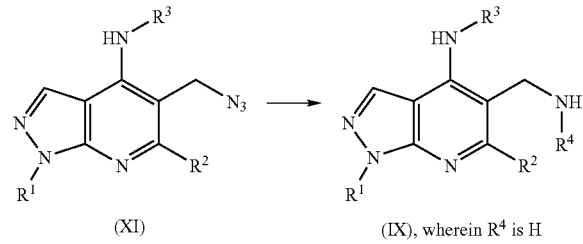

(XI)     (IX), wherein $R^4$ is H

Compounds of formula (XI), wherein $R^1$, $R^2$ and $R^3$ are as defined herein, may be prepared from compounds of formula (XII), wherein $R^1$, $R^2$ and $R^3$ are as defined herein and wherein $X^6$ is a leaving group such as a halogen atom, mesylate (methanesulfonate), tosylate (p-toluenesulfonate), or triflate (trifluoromethanesulfonate) (suitably a halogen atom such as a chlorine atom).

For example the compounds of formula (XII), e.g. wherein $X^6$ is Cl, can be reacted with an azide salt such as sodium, lithium or potassium azide, in a suitable solvent such as dimethylsulfoxide such as dry DMSO, e.g. at a suitable temperature such as room temperature, to give compounds of formula (XI).

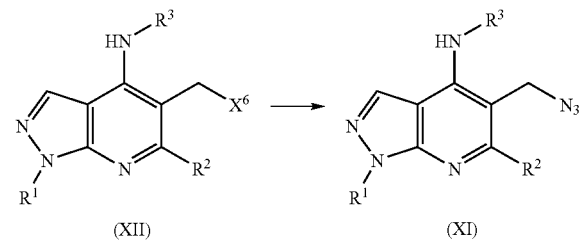

(XII)     (XI)

Compounds of formula (XII), wherein $R^1$, $R^2$ and $R^3$ and $X^6$ are as defined herein, can be prepared by reaction of compounds of formula (XIII), wherein $R^1$, $R^2$ and $R^3$ are as defined herein, with a suitable reagent such as thionyl chloride (for when $X^6$ is Cl), oxalyl chloride (for when $X^6$ is Cl), methanesulfonyl chloride (for when $X^6$ is mesylate), or paratoluenesulfonyl chloride (for when $X^6$ is tosylate), preferably thionyl chloride. Suitable conditions, for when $X^6$ is Cl, include reacting with thionyl chloride in a suitable non-aqueous (e.g. anhydrous) aprotic organic solvent such as toluene, e.g. with heating to ca. 60-90° C. for example ca. 85° C. Alternative conditions include reacting compounds of formula (XIII) with thionyl chloride and methanesulfonic acid in a suitable non-aqueous (e.g. anhydrous) aprotic organic solvent such as dichloromethane, e.g. at a suitable temperature such as room temperature.

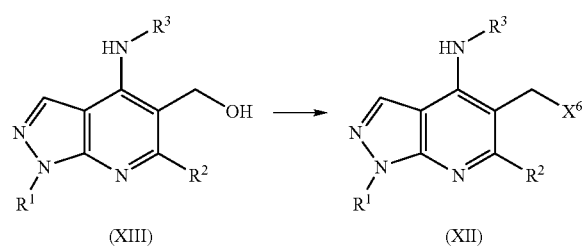

(XIII)     (XII)

Alternatively, compounds of formula (XI) wherein $R^1$, $R^2$ and $R^3$ are as defined herein can be prepared directly from compounds of formula (XIII) wherein $R^1$, $R^2$ and $R^3$ are as defined herein. For example, compounds of formula (XI) may be prepared by reacting compounds of formula (XIII) with an azide salt, e.g. sodium azide, in the presence of a halogenating agent such as carbon tetrabromide and a phosphine such as triphenylphosphine under suitable conditions, such as N,N-dimethylformamide, e.g. at a suitable temperature such as between 0° C. and room temperature (see e.g. Toyota et. al. *Journal of Organic Chemistry* (2000), 65(21), 7110-7113).

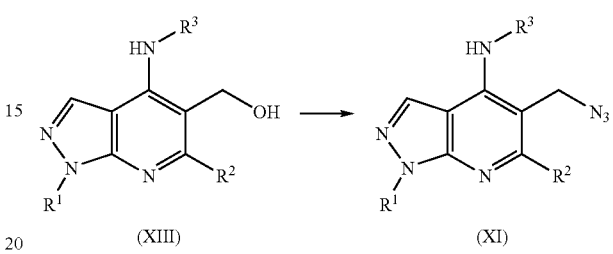

(XIII)     (XI)

This route, (XIII) to (XI) directly, may be suitable for where $R^3$ is a urea-containing group [such as a N-aminocarbonyl-piperidinyl or N-aminocarbonyl-pyrrolidinyl group within sub-formula (bb) or (aa), because it is noted that these $R^3$ urea-containing groups may not be tolerant of thionyl chloride which may be used in converting (XIII) to (XII) wherein $X^6$ is Cl and onward to (XI).

In another alternative embodiment of particular interest, an amine compound of formula (IX) or a salt thereof (e.g. HCl salt thereof), wherein $R^1$, $R^2$ and $R^3$ are as defined herein and $R^4$ is as defined herein (in particular where $R^4$ is a hydrogen atom), may be prepared directly from a compound of formula (XII) or a salt thereof, wherein $R^1$, $R^2$ and $R^3$ and $X^6$ are as defined herein, without first converting to an azide compound of formula (XI). For example, in compound (XII), $X^6$ can in particular be a chlorine atom. When $X^6$ is a chlorine atom, a benzenesulfonate salt of the compound of formula (XII) can for example be used, in particular when $R^1$ and $R^2$ are ethyl and when $R^3$ is, for instance, a tetrahydro-2H-pyran-4-yl.

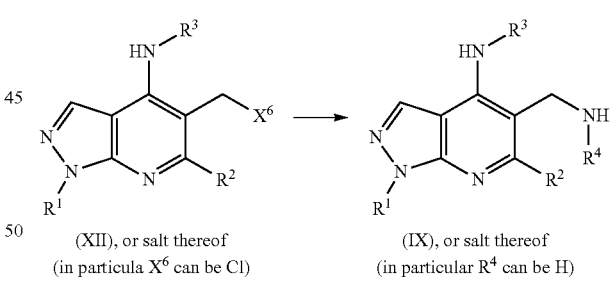

(XII), or salt thereof     (IX), or salt thereof
(in particula $X^6$ can be Cl)     (in particular $R^4$ can be H)

The reaction of the compound (XII) or the salt thereof to the amine compound (IX) or the salt thereof may optionally be carried out under suitable conditions, for example by reaction of a compound of formula (XII) or a salt thereof with an aminating agent. When $R^4$ represents a hydrogen atom, and optionally for example when $X^6$ is a chlorine atom, a suitable aminating agent may be used, e.g. an alkali-metal hexamethyldisilazide such as lithium hexamethyldisilazide, sodium hexamethyldisilazide or potassium hexamethyldisilazide (in particular lithium hexamethyldisilazide, e.g. with slow mixing/addition), in a suitable non-aqueous non-alcohol (aprotic) organic solvent (e.g. anhydrous solvent) such as tetrahydrofuran, for example at a suitable temperature such as about 25 to about 50° C., for example ca. 30-45° C. or ca. 30-40° C. The reaction with the suitable aminating agent (e.g. with the alkali-metal hexamethyldisilazide) is suitably followed by treatment with an aqueous acid such as aqueous hydrochloric acid (e.g. 2-10M, e.g. about 5M), for example at a suitable temperature such as from 0° C. to room temperature, for example at 5-15° C. or ca. 10° C. Optionally, extraction of an organic solution of (IX) or a salt thereof with aqueous base such as conc. (e.g. 32% w/w) NaOH solution, can be used to form the amine compound (IX) as the "free base". Optionally, a mono-acid-addition salt, e.g. monohydrochloride, of the amine (IX) can be formed by converting the "free base" amine compound (IX) with about 1 equivalent (e.g. 1.03 equiv.) of a suitable acid such as HCl (e.g. aqueous hydrochloric acid such as ca. 36% w/w aq. HCl).

In a simplified embodiment of the process from compound (XII) or a salt thereof to an amine compound (IX) or a salt thereof, when $X^6$ is a chlorine atom in the compound of formula (XII) and when $R^4$ is a hydrogen atom in the compound of formula (IX), the precursor alcohol compound of formula (XIII) or a salt thereof is converted into the amine of formula (IX) or a salt thereof, via the compound of formula (XII) or a salt thereof, without substantially purifying and/or without substantially isolating the compound of formula (XII) or the salt thereof wherein $X^6$ is a chlorine atom. In this embodiment, the compound of formula (XII) or the salt thereof wherein $X^6$ is a chlorine atom can for example be in the form of the benzenesulfonate salt, in particular when $R^1$ and $R^2$ are ethyl and when $R^3$ is for instance, a tetrahydro-2H-pyran-4-yl:

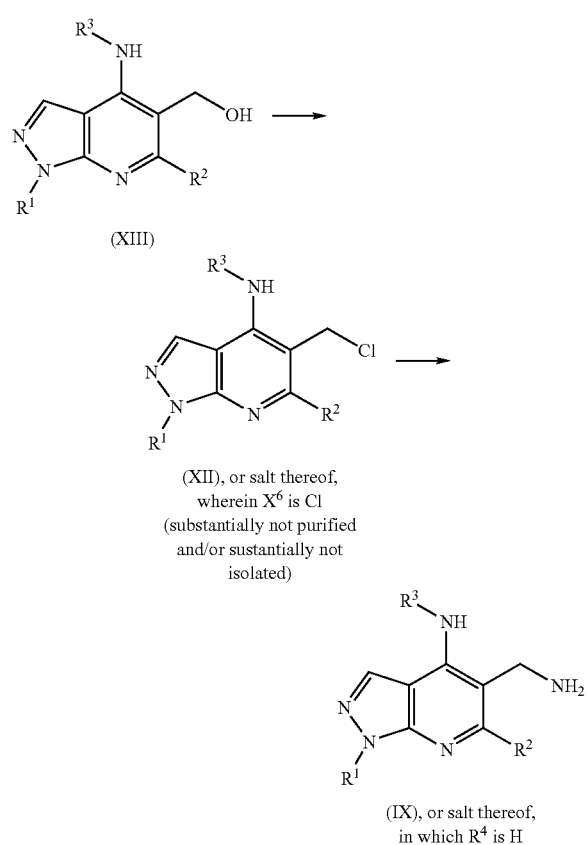

(XII), or salt thereof, wherein $X^6$ is Cl
(substantially not purified and/or sustantially not isolated)

(IX), or salt thereof, in which $R^4$ is H

Compounds of formula (XIII) below, wherein $R^1$, $R^2$ and $R^3$ are as defined herein, can be prepared by reaction of compounds of formula (XIV), wherein $R^1$, $R^2$ and $R^3$ are as defined herein, and wherein $X^7$ is an alkyl group such as a $C_{1-6}$ or $C_{1-4}$ alkyl (e.g. straight-chain alkyl) group e.g. in particular ethyl, with a suitable reducing agent in a suitable solvent, e.g. at a suitable temperature. One suitable reducing agent is lithium borohydride, in which case: a suitable solvent can be a mixture of tetrahydrofuran (e.g. dry) and methanol (e.g. dry) optionally also with toluene (e.g. dry), or THF, or methanol, and/or a suitable reaction temperature can be from room temperature to the reflux temperature, e.g. about 50 to about 75° C., e.g. about 60 to about 70° C., e.g. 63-69° C. or 64-68° C. Another reducing agent is di-iso-butylaluminium hydride (e.g. solution in toluene), in which case: a suitable solvent is dichloromethane and/or toluene, and/or a suitable reaction temperature can be about 0° C.

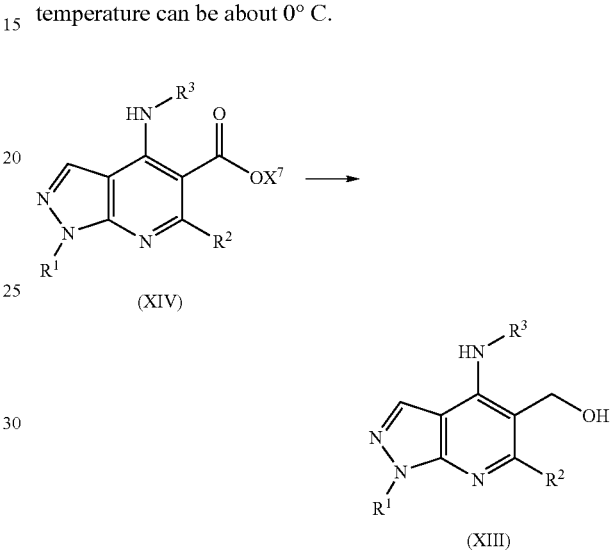

Compounds of formula (XIV), wherein $R^1$, $R^2$ and $R^3$ and $X^7$ are as defined herein, may be prepared by reaction of a compound of formula (XV) with an amine of formula $R^3NH_2$, for example generally according to the method described by Yu et. al. in *J. Med. Chem.*, 2001, 44, 1025-1027. The reaction is preferably carried out in the presence of a base such as triethylamine or N,N-diisopropylethylamine, and/or in an organic solvent such as ethanol, dioxane, 1-methyl-2-pyrrolidinone (NMP) or acetonitrile. The reaction may require heating e.g. to ca. 60-180° C., for example at 115° C.:

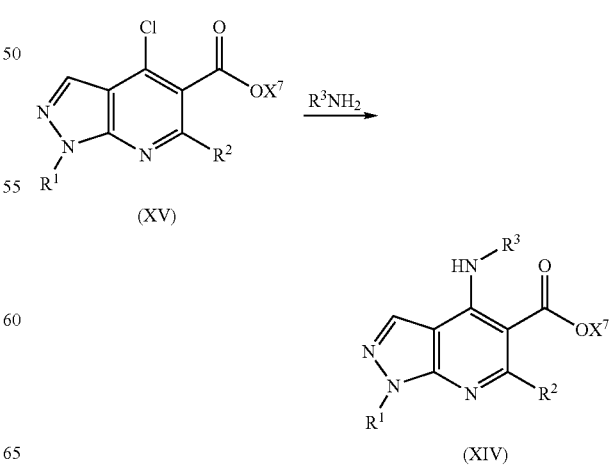

When R³ is a N-aminocarbonyl-piperidinyl or N-aminocarbonyl-pyrrolidinyl group the compound of formula (XIV) can be prepared by reacting a compound of formula (XIVa), below, wherein R¹, R² and X⁷ are as defined herein and n⁴=0 or 1, or a salt thereof (e.g. a hydrochloride salt thereof) with a urea-forming reagent capable of converting the (4-piperidinyl)amino or (3-pyrrolidinyl)amino group in the compound of formula (XIVa) into a [(1-aminocarbonyl)-4-piperidinyl]amino group or [(1-aminocarbonyl)-3-pyrrolidinyl]amino group as in formula (XIV) respectively:

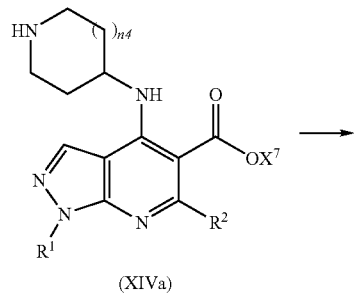

(XIVa)

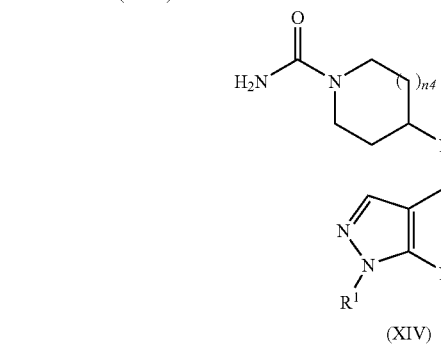

(XIV)

The urea-forming reagent may be benzyl isocyanate (followed later by debenzylation e.g. reductive debenzylation), or preferably the urea-forming reagent is tri($C_{1-4}$alkyl)silyl isocyanate such as a tri($C_{1-2}$alkyl)silyl isocyanate, preferably trimethylsilyl isocyanate. The conversion of the compound (XIVa) or salt thereof to the compound (XIV) may be carried out in the presence of a suitable base such as N,N-diisopropylethylamine, in a suitable solvent such as dichloromethane or chloroform, at a suitable temperature such as at room temperature or at the reflux temperature of the solvent.

Compound (XIVa), wherein R¹, R², X⁷ and n⁴ are as defined herein, or the salt thereof can be prepared from compound (XIVb) below, wherein R¹, R², X⁷ and n⁴ are as defined herein and Prot is a suitable nitrogen protecting group such as (tert-butyloxy)carbonyl, by removal of the nitrogen protecting group. For example, removal of the (tert-butyloxy)carbonyl group can be effected under suitable acidic conditions, such as with hydrogen chloride (e.g. 4M) in a suitable solvent such as 1,4-dioxane:

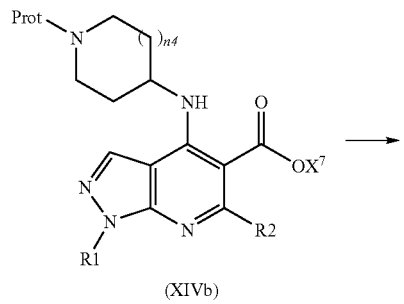

(XIVb)

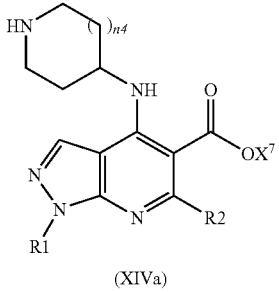

(XIVa)

Compound (XIVb), wherein R¹, R², and n⁴ are as defined herein, X⁷ is ethyl and Prot is (tert-butyloxy)carbonyl, can be prepared by reaction of a compound of formula (XV), wherein R¹ and R² are as defined herein and X⁷=ethyl, with 1,1-dimethylethyl 4-amino-1-piperidinecarboxylate (e.g. commercially available from AstaTech, Philadelphia, USA) or 1,1-dimethylethyl 3-amino-1-pyrrolidinecarboxylate (e.g. commercially available from Aldrich). The reaction is optionally carried out in the presence of a base such as triethylamine or N,N-diisopropylethylamine, optionally in a suitable organic solvent such as acetonitrile, at a suitable temperature such as 60-100° C. (e.g. 80-90° C.).

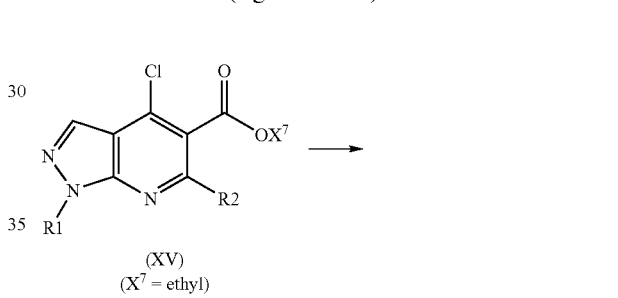

(XV)
(X⁷ = ethyl)

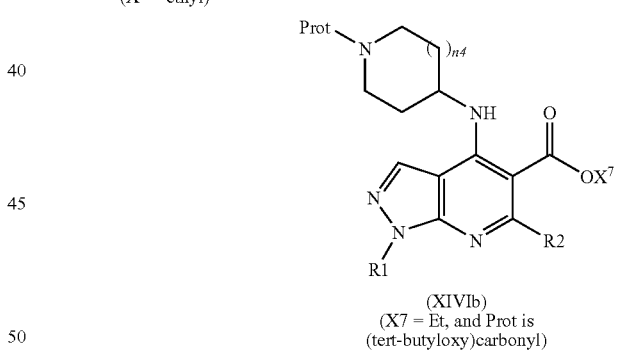

(XIVb)
(X7 = Et, and Prot is (tert-butyloxy)carbonyl)

Compounds of formula (XV), wherein R¹, R², and X⁷ are as defined herein can be prepared by reaction of compounds of formula (XVI), wherein R¹ is as defined herein, with a dialkyl (1-chloroalkylidene)propanedioate, for example a diethyl (1-chloroalkylidene)-propanedioate of formula (XVII) (wherein R² and X⁷ are as defined herein), followed by reaction with phosphorous oxychloride. Suitable conditions for reaction of compounds of formula (XVI) with a dialkyl (1-chloroalkylidene)propanedioate of formula (XVII) include heating in a suitable solvent such as toluene, in the presence of a suitable base such as triethylamine, at a suitable temperature such as the reflux temperature of the solvent. Suitable conditions for the reaction of the intermediate with phosphorous oxychloride include heating at the reflux temperature of phosphorous oxychloride.

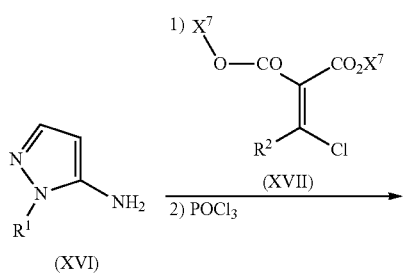

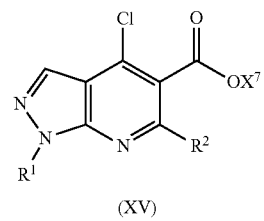

Compounds of formula (XVII), wherein $R^2$ and $X^7$ are as defined herein, may be prepared by reaction of compounds of formula (XVIII), wherein $R^2$ and $X^7$ are as defined herein, with phosphorus oxychloride in the presence of a suitable base such as tributylamine, at a suitable temperature such as 80-130° C., for example ca. 100-120° C.

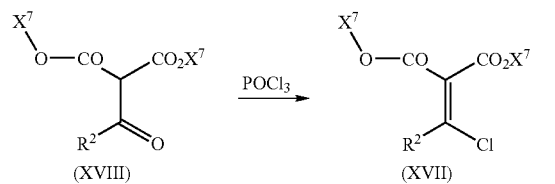

Compounds of formula (XVIII), wherein $R^2$ and $X^7$ are as defined herein, may be prepared by reaction of a dialkyl malonate of formula (XIX), wherein $X^7$ is as defined herein, with magnesium chloride and a suitable base such as triethylamine, in a suitable solvent such as acetonitrile, at a suitable temperature such as 5-10° C., followed by addition of an acid chloride of formula (XX), for example propanoyl chloride, at a suitable temperature such as between 10° C. and room temperature.

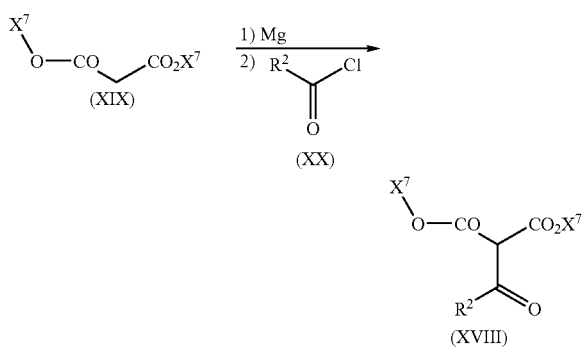

Compounds of formulae (XIX) and (XX) are either known compounds or may be prepared by conventional means. For example compounds of formulae (XIX) and (XX) where $X^7$ and $R^2$ respectively represent ethyl are available from Aldrich.

Compounds of formula (XV), wherein $R^1$, $R^2$ and $X^7$ are as defined herein, may alternatively be prepared by reaction of a compound of formula (XVI), wherein $R^1$ is as defined herein, with compounds of formula (XXI), wherein $R^2$ and $X^7$ are as defined herein, with heating, followed by reaction with phosphorous oxychloride, again with heating (see Yu et. al. in *J. Med. Chem.*, 2001, 44, 1025-1027). Compounds of formula (XXI) can for example be diethyl [(ethyloxy)methylidene]propanedioate (wherein $R^2$ is H and $X^7$ is Et, available from Aldrich) or diethyl[1-(ethyloxy)ethylidene]propanedioate (wherein $R^2$ is Me and $X^7$ is Et, see Eur. Pat. Appl. (1991), EP 413918 A2).

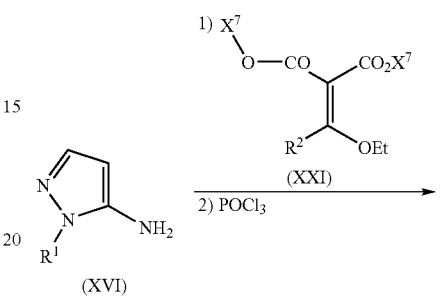

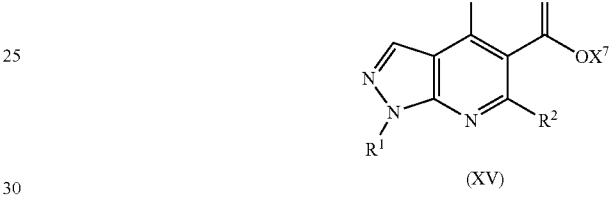

Where the desired amino pyrazole of formula (XVI) is not commercially available, preparation can be achieved using methods described by Dorgan et. al. in *J. Chem. Soc.*, Perkin Trans. 1, (4), 938-42; 1980, by reaction of 3-hydrazinopropanenitrile (available from Lancaster Synthesis) with a suitable aldehyde of formula $R^{40}CHO$ in a suitable solvent such as ethanol, with heating, followed by reduction with, for example sodium in a suitable solvent such as t-butanol. $R^{40}$ should be chosen so as to contain one less carbon atom than $R^1$, for example $R^{40}$=methyl will afford $R^1$=ethyl.

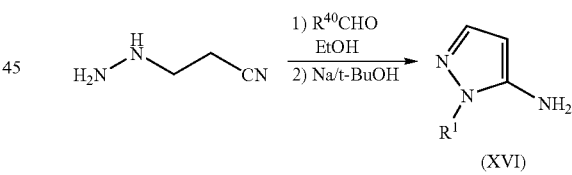

In an alternative embodiment of Process A, the 4-chloro substituent in the compound of formula (XV) can be replaced by another halogen atom, such as a bromine atom, or by another suitable leaving group which is displaceable by an amine of formula $R^3NH_2$. The leaving group can, for example, be an alkoxy group —$OR^{35}$ such as —$OC_{1-4}$alkyl (in particular —OEt) or a group —O—S(O)$_2$—$R^{37}$, wherein $R^{37}$ is methyl, CF$_3$, or phenyl or 4-methyl-phenyl. The reaction may be carried out with or without solvent and may require heating.

Compounds of formula (XI), wherein $R^1$ and $R^2$ are as defined herein and $R^3$ represents the N-aminocarbonyl-piperidinyl or N-aminocarbonyl-pyrrolidinyl group of sub-formula (bb) or (aa), may alternatively be prepared from compounds for formula XXXVIII, wherein $R^1$ and $R^2$ are as defined herein, $n^3$ is 0 or 1, and Proc represents a suitable protecting group such as tert-butoxycarbonyl. Suitable conditions include treatment suitable acidic conditions such as hydrogen chloride in a suitable solvent such as 1,4-dioxane at a suitable temperature such as room temperature.

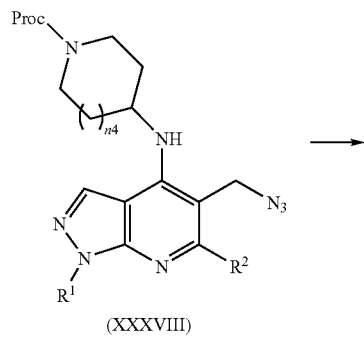

(XXXVIII)

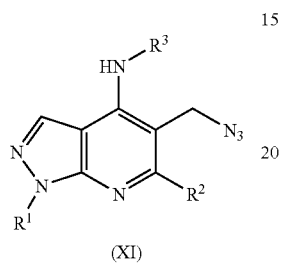

(XI)

Compounds for formula XXXVIII, wherein $R^1$ and $R^2$, $n^4$ and Proc are as defined herein, may be prepared from compounds for formula XXXIX, wherein $R^1$ and $R^2$, $n^3$ and Proc are as defined herein. Suitable conditions include reaction of compounds of formula XXXIX with an azide such as sodium azide and a halogenating agent such as carbon tetrabromide, in the presence of a suitable phosphine such as triphenylphosphine, in a suitable solvent such as N,N,-dimethylformamide, at a suitable temperature such as between 0° C. and room temperature.

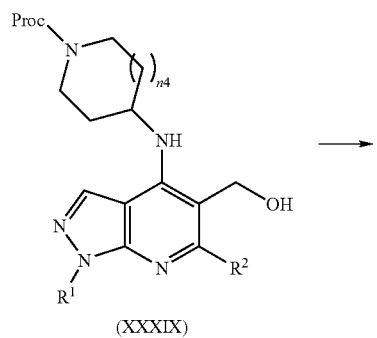

(XXXIX)

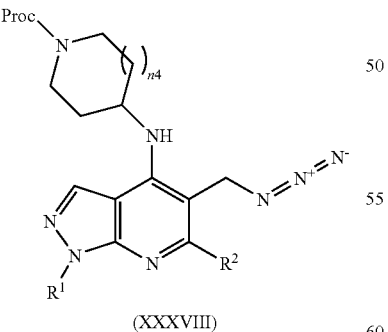

(XXXVIII)

Compounds of formula (XXXIX), wherein $R^1$ and $R^2$, $n^4$ and Proc are as defined herein, may be prepared from compounds of formula (XL), wherein $R^1$ and $R^2$, $n^4$, Proc and $X^7$ are as defined herein, by reduction with a suitable reducing agent such as lithium borohydride, in a suitable solvent such as a mixture of tetrahydrofuran and methanol, at a suitable temperature such as at the reflux temperature of the solvent.

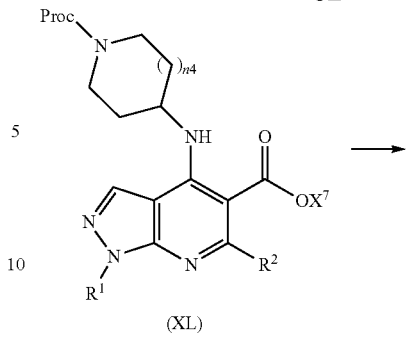

(XL)

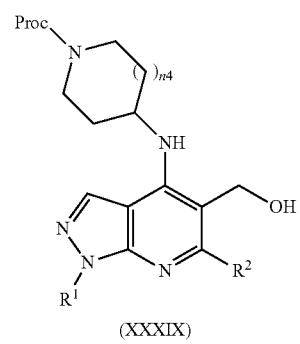

(XXXIX)

Compounds of formula (XL), wherein $R^1$ and $R^2$, $n^4$, Proc and $X^7$ are as defined herein, may be prepared from compounds of formula (XV), wherein $R^1$, $R^2$, and $X^7$ are as defined herein, by reaction of a compound of formula (XV) with an amine of formula (XLI), wherein Proc and $n^4$ are as defined herein. The reaction is preferably carried out in the presence of a base such as triethylamine or N,N-diisopropylethylamine, and/or in an organic solvent such as ethanol, dioxane, 1-methyl-2-pyrrolidinone (NMP) or acetonitrile. The reaction may require heating e.g. to ca. 60-180° C., for example at 120° C.:

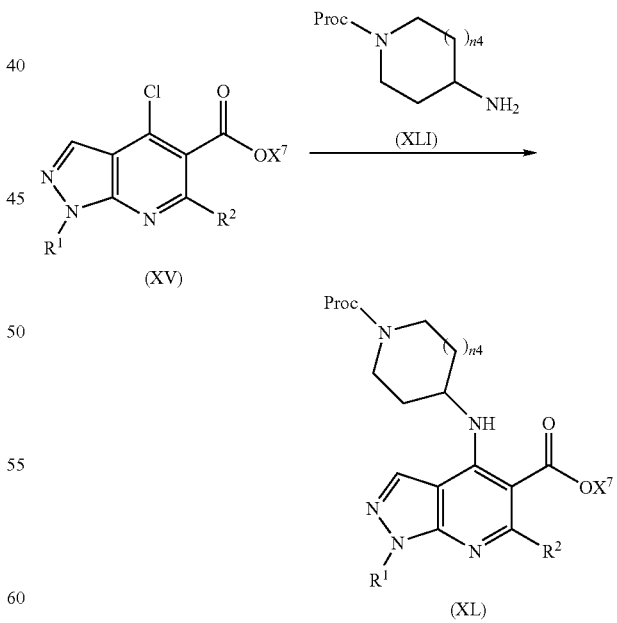

Compounds of formula (XIV) wherein $R^2$ represents fluoroalkyl (for example trifluoromethyl) may be prepared according to the following Scheme A and followed by subsequent steps such as those described in other schemes herein:

Scheme A

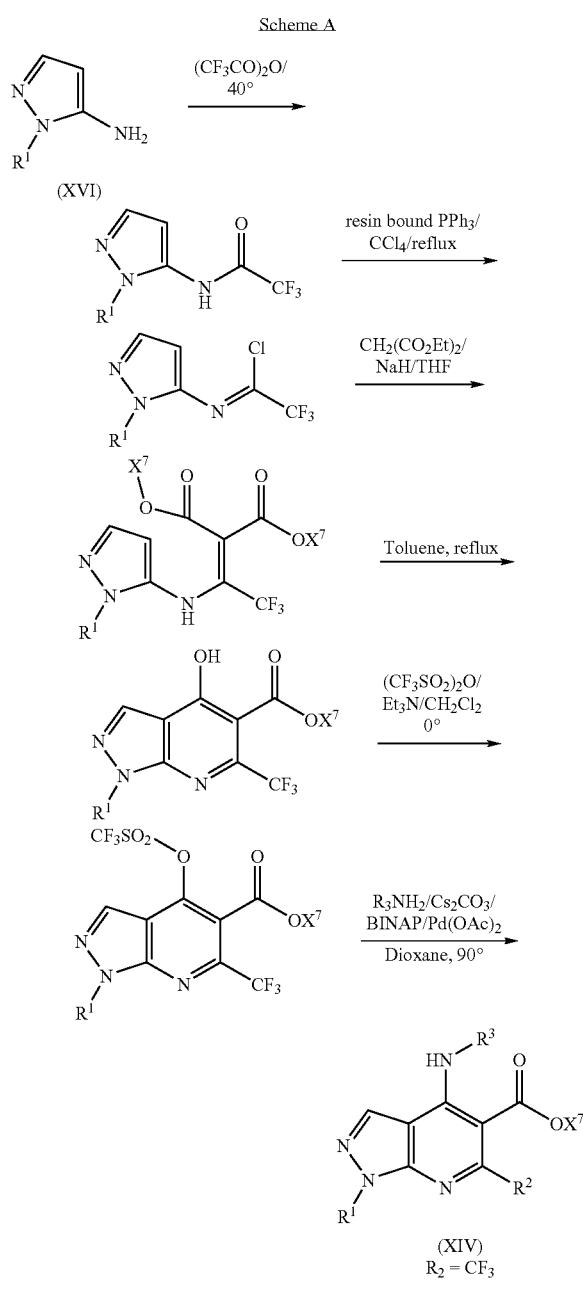

Compounds of formula (IX) wherein $R^4$ represents methyl or ethyl may be prepared according to the following scheme, wherein R″ represents H when $R^4$ is methyl and R″ represents methyl when $R^4$ is ethyl:

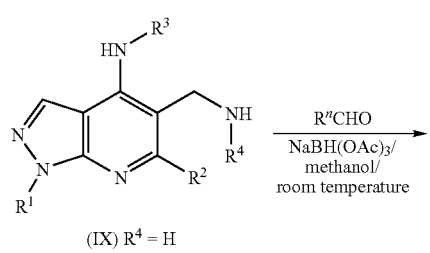

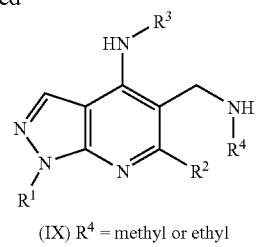

The following schemes are directed to the preparation of preparing compounds of Formula (I) as defined herein.

Scheme 1. General Synthesis of Analogs

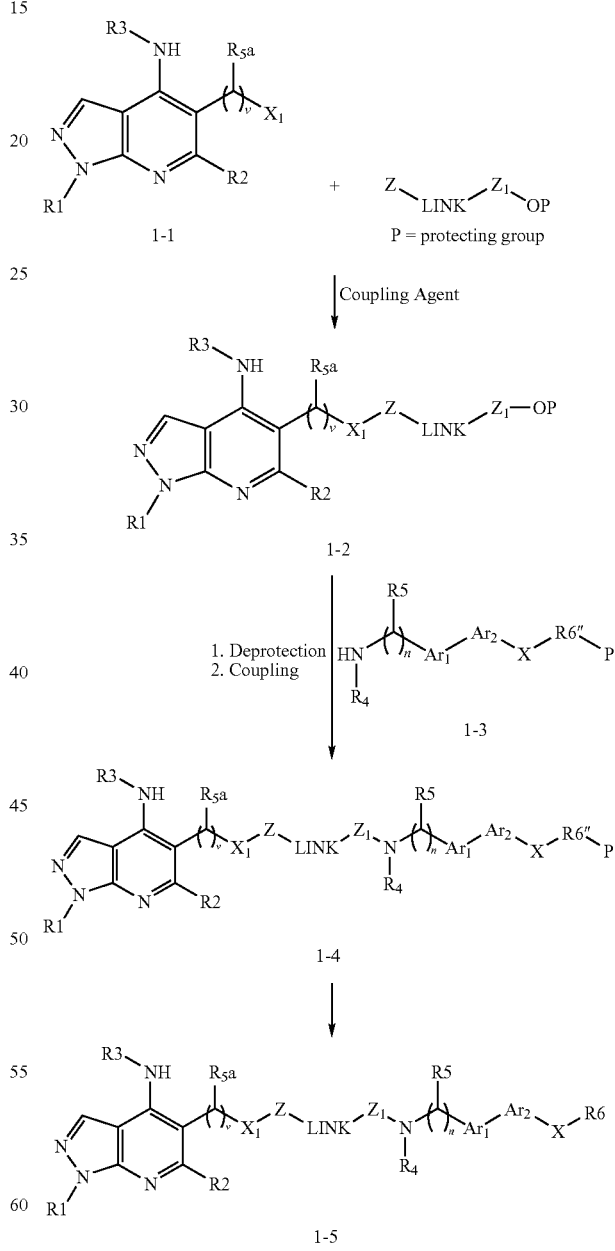

Scheme 1 above describes a general synthesis for compounds of the formula 1-4. Compound 1-1 is coupled to an appropriately protected bis-carboxylic acid ($Z=CO_2H$; $Z_1=CO_2H$), bis-sulfonic acid ($Z=SO_2H$; $Z_1=SO_2H$) or carboxylic, sulfonic acid ($Z=CO_2H$; $Z_1=SO_2H$ or $Z=SO_2H$;

$Z_1$=$CO_2$H) to give 1-2. When Z=$CO_2$H, the suitable protected linker is treated with a coupling agent such as DCC, EDC, HATU, HBTU, with or without the addition of HOBt, in the presence of a tertiary amine such as triethyl amine or diisopropyl ethyl amine in a solvent such as methylene chloride or DMF. When Z=$SO_2$H, the sulfonic acid is first converted to the corresponding sulfonyl chloride with a reagent such as thionylchloride or $POCl_3$. The resulting sulfonyl chloride (Z=$SO_2$Cl) is then added to 1-1 in the presence of a tertiary amine such as triethyl amine or diisopropyl ethyl amine in a solvent such as methylene chloride to give 1-2. Intermediate 1-2 is then de-protected using methods dependent on the nature of the protecting group. For example, when 1-2 is protected as a methyl or ethyl ester ($Z_1$=$CO_2$Me or $Z_1$=$CO_2$Et), 1-2 is treated with solution of an aqueous base, e.g. NaOH, LiOH, in an organic solvent such as methanol, ethanol or dioxane. The resulting carboxylic acid (Z1=$CO_2$H) and a suitable protected, where necessary, $Ar_1$-$Ar_2$ amine 1-3 is treated with a coupling agent such as DCC, EDC, HATU, HBTU, with or without the addition of HOBt, in the presence of a tertiary amine such as triethyl amine or diisopropyl ethyl amine in a solvent such as methylene chloride or DMF. For example, a suitable protecting group is needed when $R_6$ contains a primary or secondary amine. The resulting intermediate 1-4 is then deprotected in a method defined by the nature of the protecting group used. In the case of an acid labile amine protecting group like Boc, deprotection can be achieved using a strong acid such as TFA in a solvent such as dichloromethane to give 1-5.

a coupling agent such as DCC, EDC, HATU, HBTU, with or without the addition of HOBt, in the presence of a tertiary amine such as triethyl amine or diisopropyl ethyl amine in a solvent such as methylene chloride or DMF. For example, a suitable protecting group is needed when $R_6$ contains a primary or secondary amine. The resulting intermediate 2-4 is then deprotected in a method defined by the nature of the protecting group used. In the case of an acid labile amine protecting group like Boc, deprotection can be achieved using a strong acid such as TFA in a solvent such as dichloromethane to give 2-5.

Scheme 2. General Synthesis of Analogs

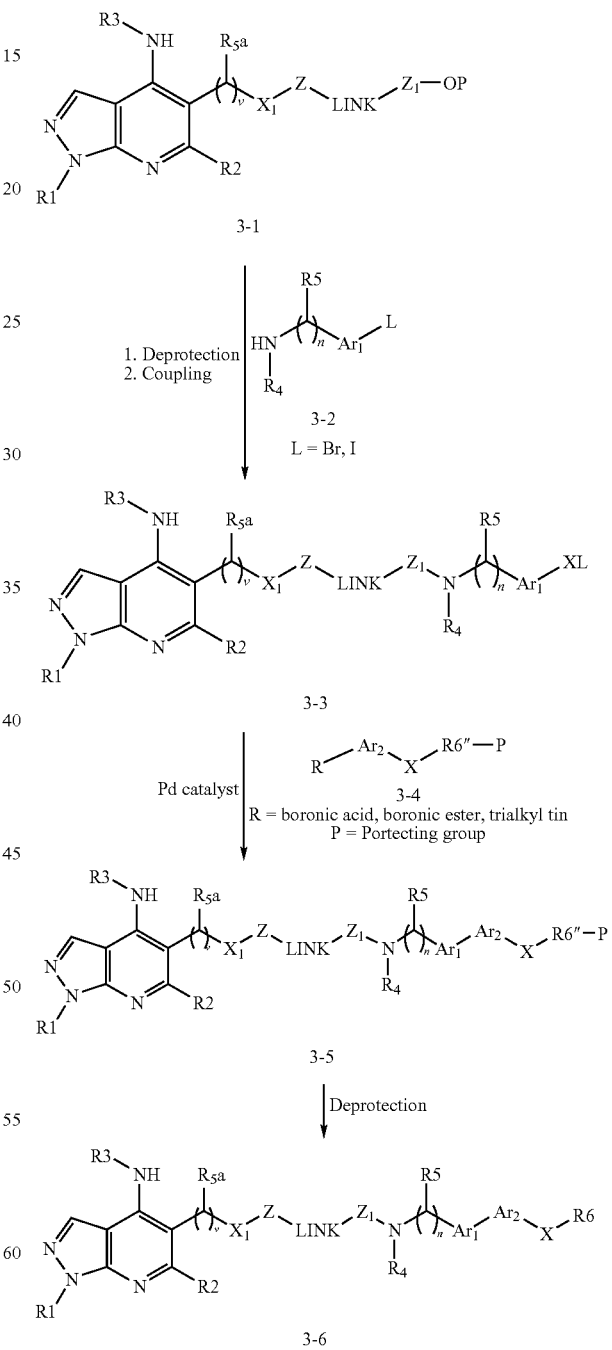

Scheme 3. General Synthesis of Analogs

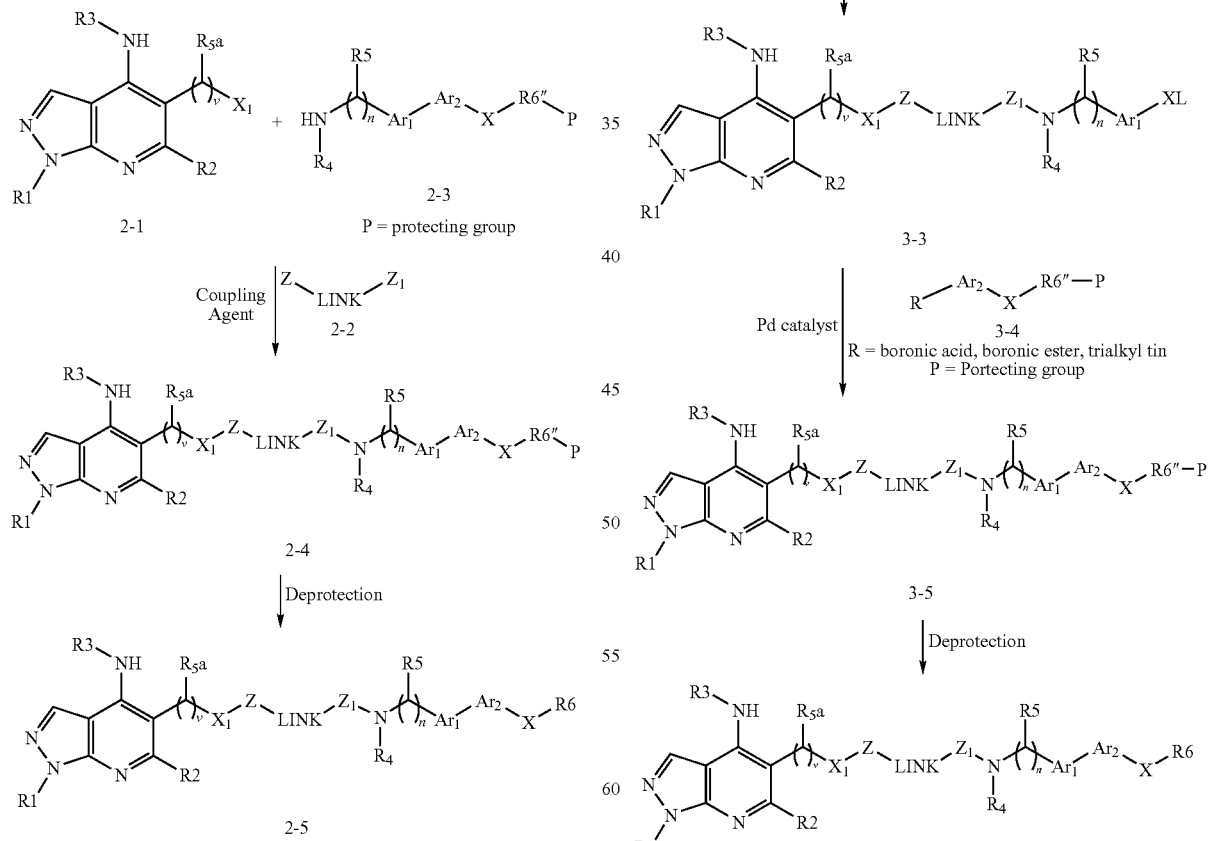

Scheme 2 above describes a synthesis of the compounds where Z and $Z_1$=$CO_2$H. This procedure is particularly amenable to array format. A mixture of compound 2-1, a bis-carboxylic acid 2-2 (Z=$CO_2$H; $Z_1$=$CO_2$H), and a suitable protected, where necessary, $Ar_1$-$Ar_2$ amine 2-3 is treated with Scheme 3 above describes an alternate synthesis for compounds of the formula in compound 3-5 (wherein the P on the $R^6$ designates a protected functionality). Intermediate 3-1 is deprotected using methods dependent on the nature of the protecting group. For example, when 3-1 is protected as a methyl or ethyl ester ($Z_1=CO_2Me$ or $Z_1=CO_2Et$), 3-1 is treated with solution of an aqueous, e.g. NaOH, LiOH in an organic solvent such as methanol, ethanol or dioxane. The resulting carboxylic acid ($Z_1=CO_2H$) and $Ar_1$ amine 3-2 with the $Ar_1$ substituted with a bromine or iodine (XL=Br, I) is treated with a coupling agent such as DCC, EDC, HATU, HBTU, with or without the addition of HOBt, in the presence of a tertiary amine such as triethyl amine or diisopropyl ethyl amine in a solvent such as methylene chloride or DMF to give intermediate 3-3. Suzuki coupling of 3-3 with a suitably protected boronic acid or boronic ester 3-4 (R=boronic acid, boronic ester) in the presence of a palladium catalyst, such as $Pd(PPh_3)_4$, or $Pd(OAc)_2/PPh_3$ gives intermediate 3-5. Alternately, Stille coupling of 3-3 with a suitably protected trialkyl tin 3-4 (R=trialkyl tin) in the presence of a palladium catalyst, such as $Pd(PPh_3)_4$, or $Pd(OAc)_2/PPh_3$ gives intermediate 3-5. The resulting intermediate 3-5 is then deprotected in a method defined by the nature of the protecting group used. In the case of an acid labile amine protecting group like Boc, deprotection can be achieved using a strong acid such as TFA in a solvent such as dichloromethane to give 3-6.

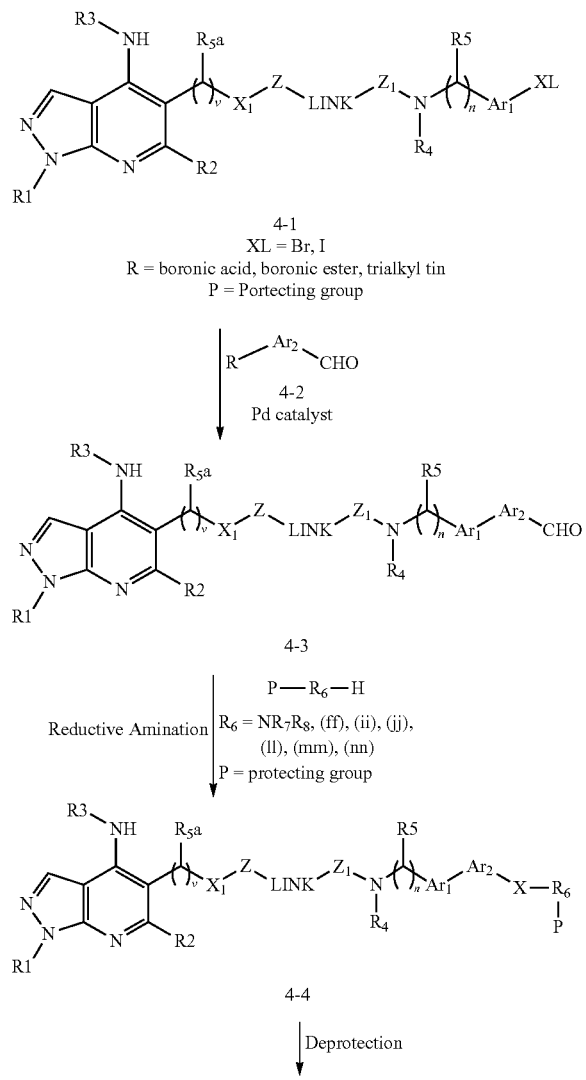

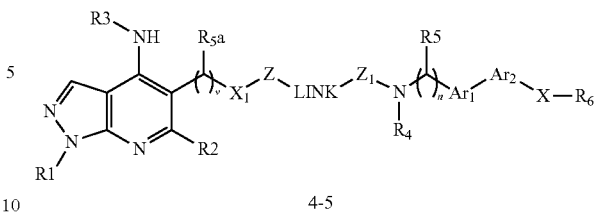

Scheme 4 above describes an alternate synthesis for compounds of the general formula shown in compound 4-5 (wherein the P on the R6 designates a protected functionality). Suzuki coupling of intermediate 4-1 with a boronic acid or boronic ester aldehyde 4-2 (R=boronic acid, boronic ester) in the presence of a palladium catalyst, such as $Pd(PPh_3)_4$, or $Pd(OAc)_2/PPh_3$ gives intermediate 4-3. Alternately, Stille coupling of 4-2 with a trialkyl tin aldehyde (R=trialkyl tin) in the presence of a palladium catalyst, such as $Pd(PPh_3)_4$, or $Pd(OAc)_2/PPh_3$ gives intermediate 4-3. Reductive amination of the resulting intermediate 4-3 with a suitably protected $R_6$—H using a reducing reagent such as $NaBH_3CN$ in methanol or $NaBH(OAc)_3$ in dichloroethane or DMF gives intermediate 4-4. Intermediate 4-4 is then deprotected in a method defined by the nature of the protecting group used. In the case of an acid labile amine protecting group like Boc, deprotection can be achieved using a strong acid such as TFA in a solvent such as dichloromethane to give 4-5.

Experimentals Section

The invention will now be described by reference to the following examples which are merely illustrative and are not to be construed as a limitation of the scope of the present invention.

General Procedures

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash system used for purification in this application was purchased from Isco, Inc. CombiFlash purification was carried out using prepacked silica gel columns, a detector with UV wavelength at 254 nm and a variety of solvents or solvent combinations. Preparative HPLC was performed using a Gilson Preparative System with variable wavelength UV detection or an Agilent Mass Directed AutoPrep (MDAP) system with both mass and variable wavelength UV detection. A variety of reverse phase columns, e.g., Luna 5u C18(2) 100A, SunFire™ C18, XBridge™ C18 were used in the purification with the choice of column support dependent upon the conditions used in the purification. The compounds are eluted using a gradient of acetonitrile and water. Neutral conditions used an acetonitrile and water gradient with no additional modifier, acidic conditions used an acid modifier, usually 0.1% TFA (added to both the acetonitrile and water) and basic conditions used a basic modifier, usually 0.1% $NH_4OH$ (added to the water). Analytical HPLC was run using an Agilent system with variable wavelength UV detection using reverse phase chromatography with an acetonitrile and water gradient with a 0.05 or 0.1% TFA modifier (added to each solvent). LC-MS was determined using either a PE Sciex Single Quadrupole LC/MS API-150 or a Waters. The compound is analyzed using a reverse phase column, e.g., Thermo Aquasil/Aquasil C18, Acquity UPLC C18, Thermo Hypersil Gold eluted using an acetonitrile and water gradient with a low percentage of an acid modifier such as 0.02% TFA or 0.1% formic acid.

Nuclear magnetic resonance spectra were recorded at 400 MHz using a Bruker AC 400 or Brucker DPX400 spectrometer. $CDCl_3$ is deuteriochloroform, DMSO-$D_6$ is hexadeuteriodimethylsulfoxide, and $CD_3OD$ is tetradeuteriomethanol. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Melting points were determined using a Electrothermal 9100 apparatus (Electrothermal Engineering Ltd.).

Heating of reaction mixtures with microwave irradiations was carried out on a Smith Creator (purchased from Personal Chemistry, Forboro, Mass., now owned by Biotage), an Emrys Optimizer (purchased from Personal Chemistry) or an Explorer (purchased from CEM, Matthews, N.C.) microwave.

Cartridges or columns containing polymer based functional groups (acid, base, metal chelators, etc) can be used as part of compound workup. The "amine" columns or cartridges are used to neutralize or basify acidic reaction mixtures or products. These include NH2 Aminopropyl SPE-ed SPE Cartridges available from Applied Separations and diethylamino SPE cartridges available from United Chemical Technologies, Inc.

Abbreviations are listed in the table below. All other abbreviations are as described in the ACS Style Guide (American Chemical Society, Washington, D.C., 1986).

Examples

Intermediate Compounds

Intermediate A N-[(3-Bromophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide

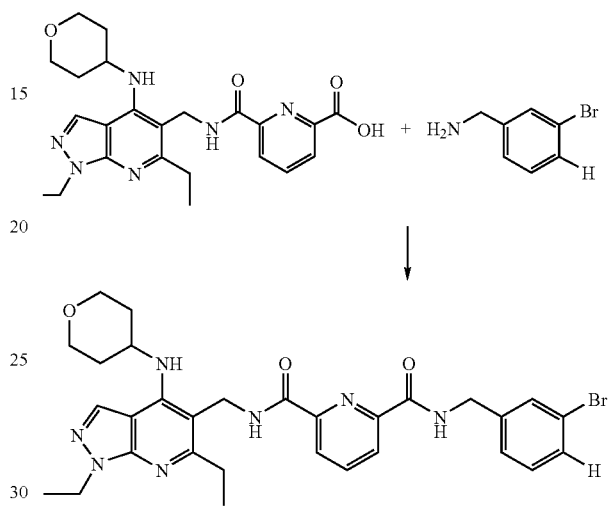

A mixture of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (600 mg, 1.326 mmol), 1-(3-bromophenyl)methanamine (247 mg, 1.326 mmol), HBTU (o-Benzotriazol-1-yl-N,N,N',N'-tetramethyluronium hexafluorophosphate) (603 mg, 1.591 mmol) and $Et_3N$ (0.924 mL, 6.63 mmol) in DCM was stirred at room temperature over the weekend. The reaction was quenched with saturated $NaHCO_3$ and extracted with DCM twice. The combined organic layers were washed with brine and then concentrated

| Table of Abbreviations | |
|---|---|
| DMAP: 4-(Dimethylamino)pyridine | SPE: Solid phase extraction |
| DCM: Dichloromethane | m-CPBA: 3-Chlorobenzene- |
| DMF: N,N-Dimethylformamide | carboperoxoic acid |
| dppf: 1,1'-Bis(diphenylphosphino)-ferrocene | MDAP: Mass directed auto preparation |
| DMSO: Dimethylsulfoxide | NIS: N-Iodosuccinimide |
| DIPEA: N,N-Diisopropylethylamine | HATU: O-(7-Azabenzotriazol-1-yl)- |
| DSC: differential scanning calorimetry | N,N,N',N'-tetramethyluronium |
| EtOAc: Ethyl acetate | hexafluorophosphate |
| EDC: 1-(3-Dimethylaminopropyl)-3- | HBTU: O-Benzotriazol-1-yl-N,N,N',N'- |
| ethylcarbodiimide hydrochloride | tetramethyluronium hexafluorophosphate |
| TFA: Trifluoroacetic anhydride | HOBT: 1-Hydoxybenzotriazole hydrate |
| M: molar | IPA: isopropyl alcohol |
| L: liters | THF: Tetrahydrofuran |
| mL: milliliters | mol: moles |
| g: grams | mmol: millimoles |
| mg: milligrams | satd: saturated |
| h: hours | eq: equivalents |
| NMP: 1-methyl-2-pyrrolidinone | min: minutes |
| TEA: triethylamine | mp: melting point |
| BPO: Benzoyl peroxide | rt: room temperature |
| | Aq or aq: aqueous |
| | CDI: Carbonyl diimidazole |
| | TSBCl: tert-butyldimethylsilyl chloride | under vacuum to give a crude residue. It was then purified with flash chromatography eluting with 0 to 100% ethyl acetate in hexane (product came out at 100% ethyl acetate in hexane). The product fractions were combined to give N-[(3-bromophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (632 mg, 49.9%). LC-MS m/z 620 (M+H)+, 0.89 min (ret time).

Intermediate B N-{[1,6-Diethyl-4-(tetrahydro-2H-pyran-4-ylamino)-1H-pyrazolo[3,4-b]pyridin-5-yl]methyl}-N'-[(3'-formyl-3-biphenylyl)methyl]-2,6-pyridinedicarboxamide wave reaction tube. The mixture was degassed by bubbling argon through it for 5 minutes and it was then heated in a Biotage microwave at normal absorption for 30 min at 100° C. The crude mixture was filtered through a PL-Thiol MP SPE+ and was then washed with ethyl acetate and saturated NaHCO₃. The organic layer was concentrated under vacuum to obtain the crude residue. It was purified with Gilson HPLC (with 0.1% TFA in the solvent) eluting with 15 to 80% CH₃CN in water in a flow rate of 20 mL/min. The product fractions were dried under EZ2 Genevac and then combined to give N-{[1,6-diethyl-4-(tetrahydro-2H-pyran-4-ylamino)-1H-pyrazolo[3,4-b]pyridin-5-yl]methyl}-N'-[(3'-formyl-3-

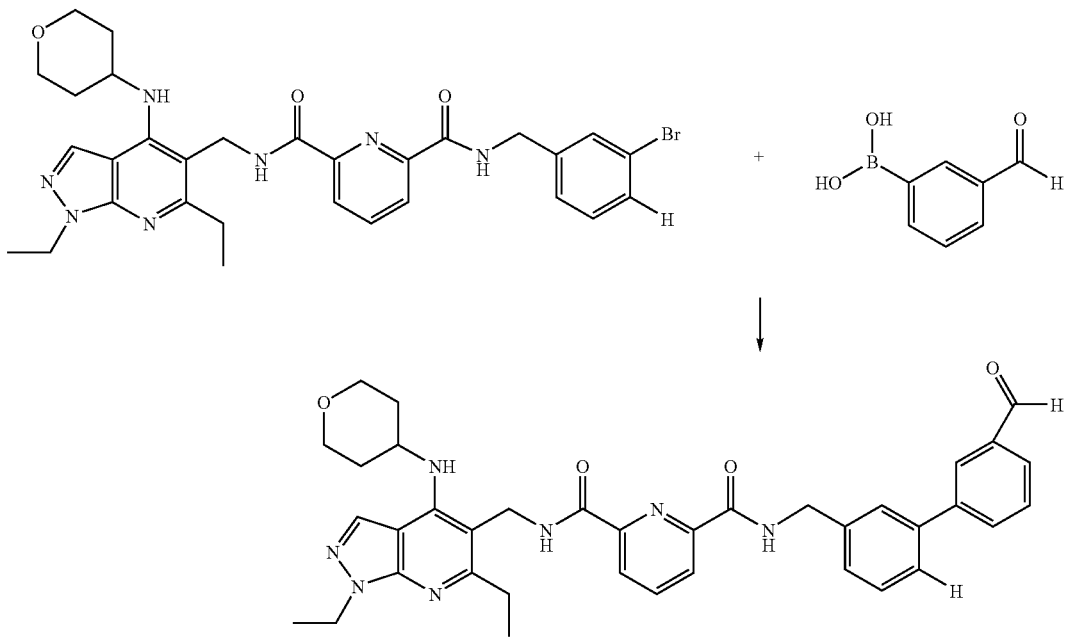

A mixture of N-[(3-bromophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (600 mg, 0.967 mmol), (3-formylphenyl)boronic acid (188 mg, 1.257 mmol), Na₂CO₃ (307 mg, 2.90 mmol) and PdCl₂(dppf) (70.7 mg, 0.097 mmol) was diluted in a mixture of 1,4-dioxane (9 mL) and water (3 mL) in a 20 mL Biotage microbiphenylyl)methyl]-2,6-pyridinedicarboxamide as a solid (278 mg, 44.5%). LC-MS m/z 646.1 (M+H)+, 0.91 min (ret time).

Intermediate C N-[(3-Bromo-4-fluorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide

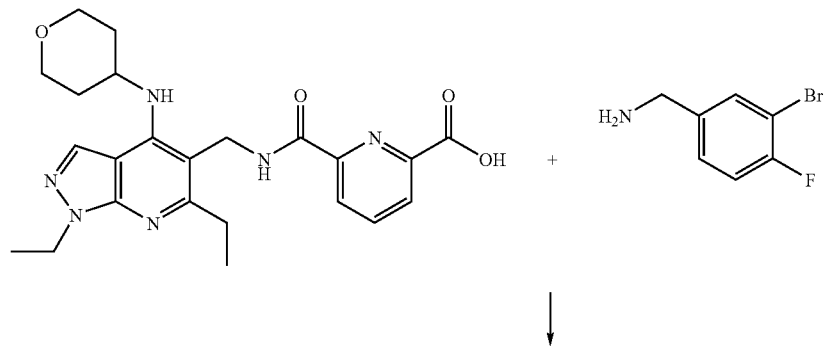

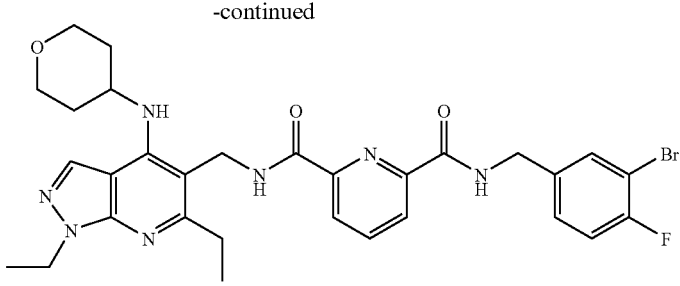

A mixture of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (900 mg, 1.989 mmol), 1-(3-bromo-4-fluorophenyl)methanamine (406 mg, 1.989 mmol), HBTU (905 mg, 2.387 mmol) and Et$_3$N (1.386 mL, 9.94 mmol) in DCM was stirred at room temperature overnight. The reaction did not go to completion overnight. An additional equivalent of each reagent was added and the reaction stirred over the weekend. The reaction mixture was quenched with saturated NaHCO$_3$ and extracted with DCM twice. The combined organic layers were washed with brine and then concentrated under vacuum to give the crude residue. It was then purified using flash chromatography eluting with 0 to 100% ethyl acetate in hexane (product came out at 100% ethyl acetate in hexane). However, this product batch was not pure. It was purified with a Gilson HPLC. Product crashed out from the HPLC solution. The solid was filtered to obtain N-[(3-bromo-4-fluorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (120 mg) as a solid. The mother liquor was purified with a Gilson HPLC to obtain another batch of N-[(3-bromo-4-fluorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (160 mg). LC-MS m/z 638.4 (M+H)$^+$, 0.89 min (ret time).

Intermediate D N-{[1,6-Diethyl-4-(tetrahydro-2H-pyran-4-ylamino)-1H-pyrazolo[3,4-b]pyridin-5-yl]methyl}-N'-[(6-fluoro-3'-formyl-3-biphenylyl)methyl]-2,6-pyridinedicarboxamide A mixture of N-[(3-bromo-4-fluorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (187 mg, 0.293 mmol), (3-formylphenyl)boronic acid (43.9 mg, 0.293 mmol), Na$_2$CO$_3$ (93 mg, 0.879 mmol) and PdCl$_2$(dppf) (21.43 mg, 0.029 mmol) was diluted in a mixture of 1,4-dioxane (9 mL) and water (3 mL) in a 20 mL Biotage microwave reaction tube. The mixture was degassed by bubbling argon through it for 5 minutes and it was then heated in a Biotage microwave at normal absorption for 10 min at 100° C. The crude mixture was filtered through a PL-Thiol MP SPE+ and then washed with ethyl acetate. The combined organic layers were washed with water and brine. The organic layer was concentrated under vacuum to give a crude residue. It was then purified with flash chromatography eluting with 0 to 100% ethyl acetate in dichloromethane (product came out at 70% ethyl acetate in DCM). The product fractions were combined and concentrated under vacuum to give N-{[1,6-diethyl-4-(tetrahydro-2H-pyran-4-ylamino)-1H-pyrazolo[3,4-b]pyridin-5-yl]methyl}-N'-[(6-fluoro-3'-formyl-3-biphenylyl)methyl]-2,6-pyridinedicarboxamide as an yellowish oil. LC-MS m/z 664.5 (M+H)$^+$, 0.89 min (ret time).

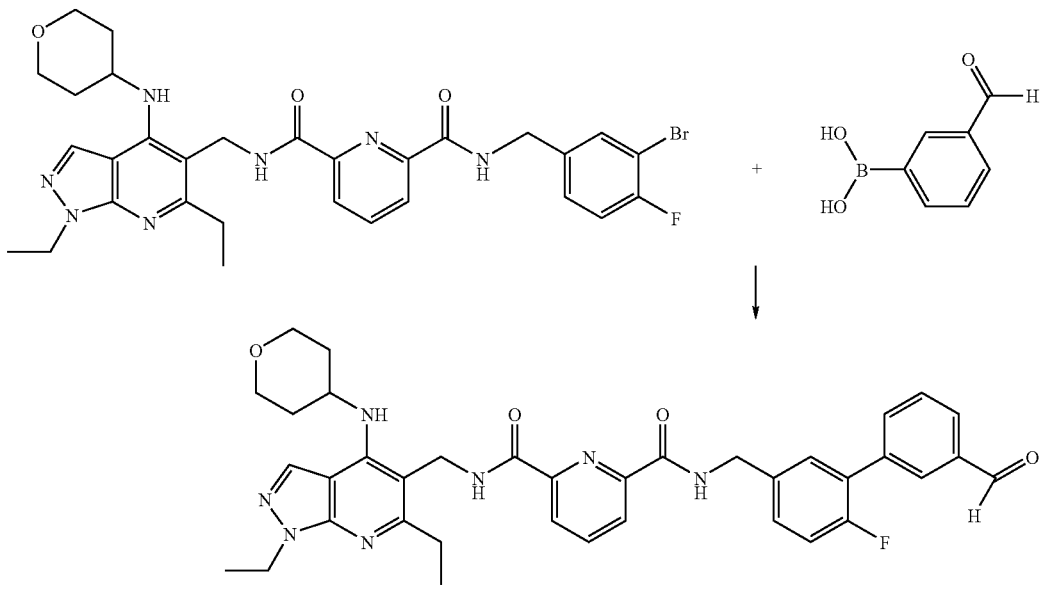

Intermediate E N-{[1,6-Diethyl-4-(tetrahydro-2H-pyran-4-ylamino)-1H-pyrazolo[3,4-b]pyridin-5-yl]methyl}-N'-{[3'-formyl-6-(methyloxy)-3-biphenylyl]methyl}-2,6-pyridinedicarboxamide

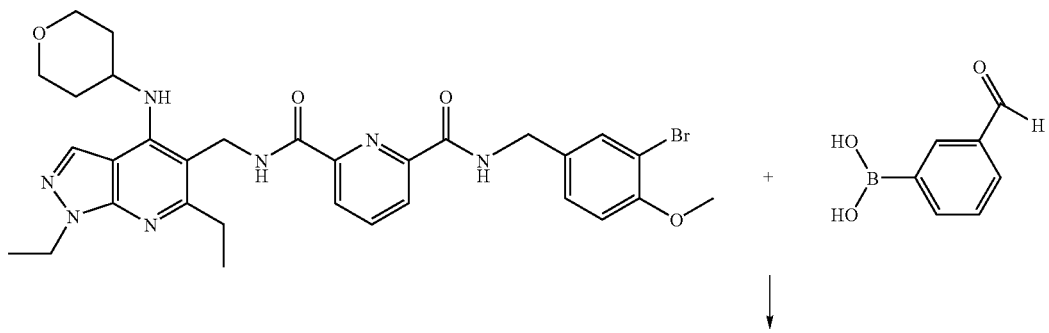

A mixture of N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide (900 mg, 1.383 mmol), (3-formylphenyl)boronic acid (207 mg, 1.383 mmol), Na$_2$CO$_3$ (440 mg, 4.15 mmol) and PdCl$_2$(dppf) (101 mg, 0.138 mmol) was diluted in a mixture of 1,4-dioxane (9 mL) and water (3 mL) in a 20 mL Biotage microwave reaction tube. The mixture was degassed by bubbling argon through it for 5 min and it was then heated in a Biotage microwave at normal absorption for 10 min at 100° C. The crude mixture was filtered through a PL-Thiol MP SPE+ and then washed with ethyl acetate. The combined organic layers were washed with brine. The organic layer was concentrated under vacuum to give a crude residue. It was then purified with flash chromatography eluting with 0 to 100% ethyl acetate in dichloromethane (product came out at 85% ethyl acetate in DCM). The product fractions were combined and concentrated under vacuum to give N-{[1,6-diethyl-4-(tetrahydro-2H-pyran-4-ylamino)-1H-pyrazolo[3,4-b]pyridin-5-yl]methyl}-N'-{[3'-formyl-6-(methyloxy)-3-biphenylyl]methyl}-2,6-pyridinedicarboxamide as an yellowish oil (458 mg, 49%). LC-MS m/z 676.5 (M+H)$^+$, 0.91 min (ret time).

Intermediate F N-[(3-Bromo-4-chlorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide

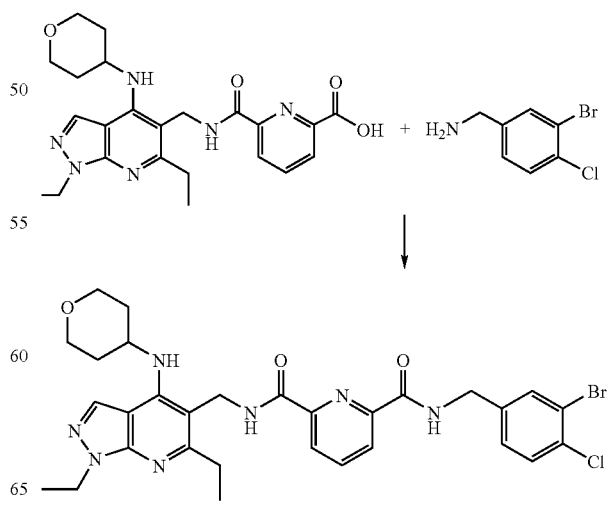

A mixture of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (1,000 mg, 2.210 mmol), 1-(3-bromo-4-chlorophenyl)methanamine (487 mg, 2.210 mmol), HBTU (1,006 mg, 2.65 mmol) and Et₃N (1.540 mL, 11.05 mmol) in DCM was stirred at room temperature over the weekend. The reaction was quenched with saturated NaHCO₃ and extracted with DCM twice. The combined organic layers were washed with brine and then concentrated under vacuum to give the crude residue. It was then purified with flash chromatography eluting with 0 to 100% ethyl acetate in hexane (product came out at 100% ethyl acetate in hexane). The product fractions were combined to give N-[(3-bromo-4-chlorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (1,100 mg, 41%). LC-MS m/z 654.4 (M+H)⁺, 0.93 min (ret time).

Intermediate G N-[(6-Chloro-3'-formyl-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide

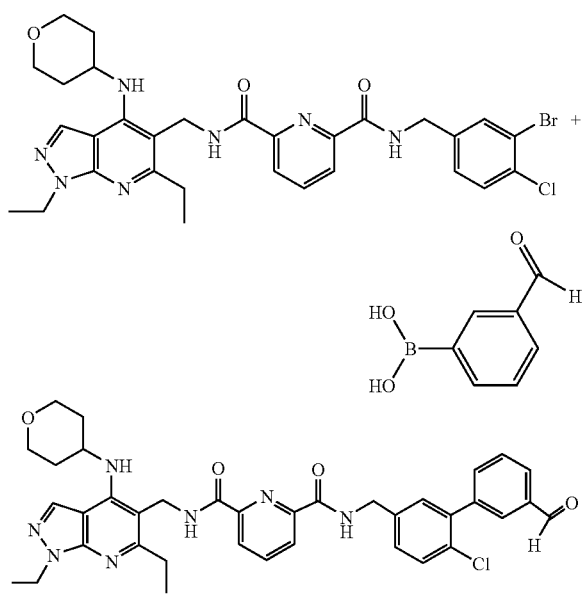

A mixture of N-[(3-bromo-4-chlorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (1,100 mg, 1.679 mmol), (3-formylphenyl)boronic acid (252 mg, 1.679 mmol), Na₂CO₃ (534 mg, 5.04 mmol) and PdCl₂(dppf) (123 mg, 0.168 mmol) was diluted in a mixture of 1,4-dioxane (9 mL) and water (3 mL) in a 20 mL Biotage microwave reaction tube. The mixture was degassed by bubbling argon through it for 5 min and it was then heated in a Biotage microwave at normal absorption for 10 min at 100° C. The crude mixture was filtered through a PL-Thiol MP SPE+ and was then washed with ethyl acetate. The combined organic layers were washed with brine. The organic layer was concentrated under vacuum to give the crude residue. It was then purified with flash chromatography eluting with 0 to 100% ethyl acetate in dichloromethane (product came out at 85% ethyl acetate in DCM). The product fractions were combined and concentrated under vacuum to give a product as yellowish oil. However, it was only 50% pure. It was then purified by HPLC and the product fractions were combined and concentrated to give N-[(6-chloro-3'-formyl-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide as a yellowish oil (447 mg, 39.1%). LC-MS m/z 680.4 (M+H)⁺, 0.93 min (ret time).

Example 1

Diethyl Propanoylpropanedioate

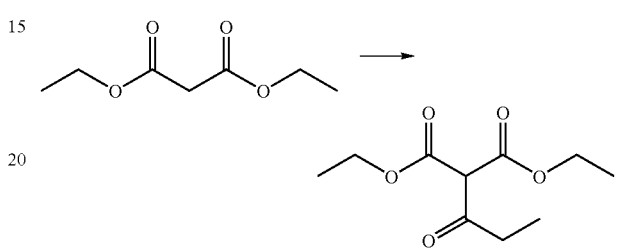

To magnesium chloride (2.96 g, 31.2 mmol) was added dry acetonitrile (5 mL) and the mixture was then cooled in ice and treated with diethyl malonate (5 g, 31.2 mmol). Once the mixture was cold, triethylamine (8.6 mL, 62.5 mmol) was added and the resulting suspension was stirred for 15 mins. Propionyl chloride (2.71 mL, 31.2 mmol) was added dropwise and the mixture was stirred at 0° C. for 1.5 h and at ambient temperature for 5 h. The mixture was cooled in an ice-bath and treated with aqueous hydrochloric acid (2M, 10 mL) and the product extracted with ether. The organic phase was washed with water then brine, dried and evaporated to afford 6.31 g of a yellow oil. This was dissolved in ether and washed with aqueous hydrochloric acid (2M) then brine, dried and evaporated to afford 5.93 g of the title compound.

Example 2

Diethyl(1-chloropropylidene)propanedioate

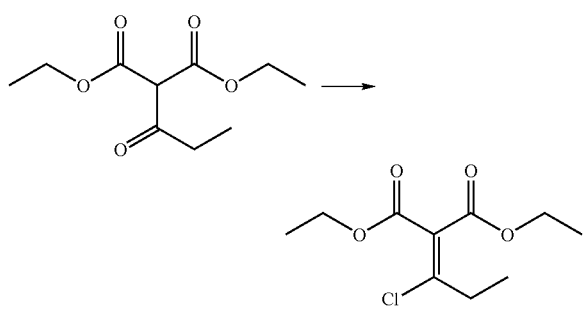

To diethyl propanoylpropanedioate (5.93 g, 27.4 mmol) was added phosphorus oxychloride (38 mL) and tributylamine (6.5 mL, 27.4 mmol) and the mixture was heated to 115° C. for 6 h then stirred at ambient temperature for 16 h. The mixture was evaporated to dryness and the residue added cautiously to aqueous hydrochloric acid (1M, 80 mL) and extracted twice with diethyl ether. The combined organic layers were washed with aqueous hydrochloric acid (1M), water, aqueous sodium hydroxide (1M) then brine, dried and evaporated to dryness to afford 6.81 g of a brown oil. The product was purified by flash chomatography on silica (250 mL), eluting with ethyl acetate/cyclohexane @1:10 to afford 3.21 g of the title compound. LC-MS m/z 235, 237 (M+H)+, 3.30 min (ret time).

Example 3

Ethyl 4-chloro-1,6-diethyl-1H-pyrazolo[3,4-b]pyridine-5-carboxylate

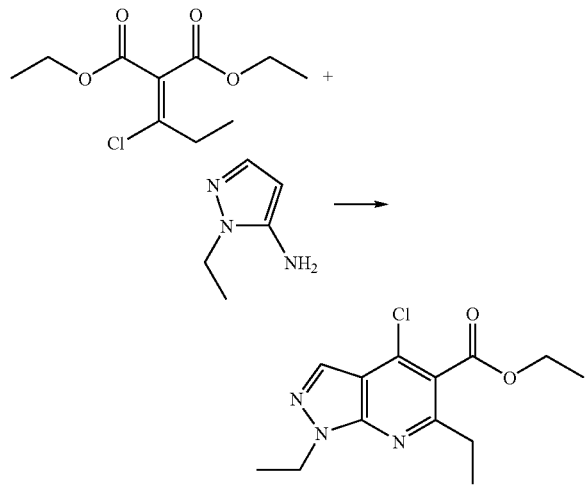

To 1-ethyl-1H-pyrazol-5-amine (Aldrich, 1.52 g, 13.7 mmol) was added a solution of diethyl (1-chloropropylidene) propanedioate (3.21 g, 13.7 mmol) in toluene (40 mL) followed by triethylamine (3.78 mL, 27.3 mmol) and then heated at reflux for 6 h. The cooled mixture was evaporated to dryness and the resulting brown residue was treated with phosphorus oxychloride (25 mL, 0.274 mol) and heated to 110° C. for 17.5 h. The cooled mixture was evaporated to dryness and the residue was to water (caution, exotherm) and extracted with ethyl acetate. The aqueous phase was treated with aqueous sodium hydroxide (2M) to achieve pH 9 and extracted with additional ethyl acetate. The combined organics were washed with aqueous sodium bicarbonate, then brine, dried and evaporated to dryness to afford 3.6 g of a dark brown oil. The product was purified by flash chomatography on silica (150 mL), eluting with ethyl acetate/cyclohexane from 1:10 to 1:8 to afford 1.8 g of the title compound. LC-MS m/z 282 (M+H)+, 3.46 min (ret time).

Example 4

Ethyl 1,6-diethyl-4-(tetrahydro-2H-pyran-4-ylamino)-1H-pyrazolo[3,4-b]pyridine-5-carboxylate

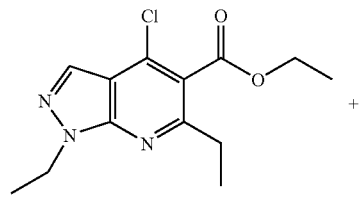

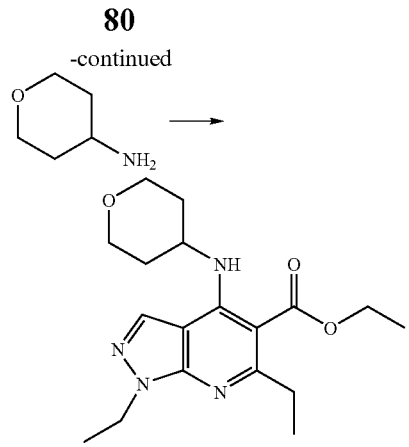

To a solution of ethyl 4-chloro-1,6-diethyl-1H-pyrazolo[3,4-b]pyridine-5-carboxylate (380 g) in 1-methylpyrrolidine (3166 mL) was added diisopropylethylamine (469.8 mL) and tetrahydro-2H-pyran-4-ylamine (163 g) and the mixture was heated at reflux for 16 h. The cooled mixture was treated with water (12 liters) and extracted with ethyl acetate (6×1250 mL). The combined organics were washed with brine, dried over magnesium sulphate, filtered and evaporated to dryness to afford 520 g of a dark brown oil. The product was purified by flash chomatography on silica using ethyl acetate/cyclohexane @1:4-1:2 as eluant to afford 336 g of the title compound. LC-MS m/z 347 (M+H)+, 3.02 min (ret time).

Example 5

[1,6-Diethyl-4-(tetrahydro-2H-pyran-4-ylamino)-1H-pyrazolo[3,4-b]pyridin-5-yl]methanol

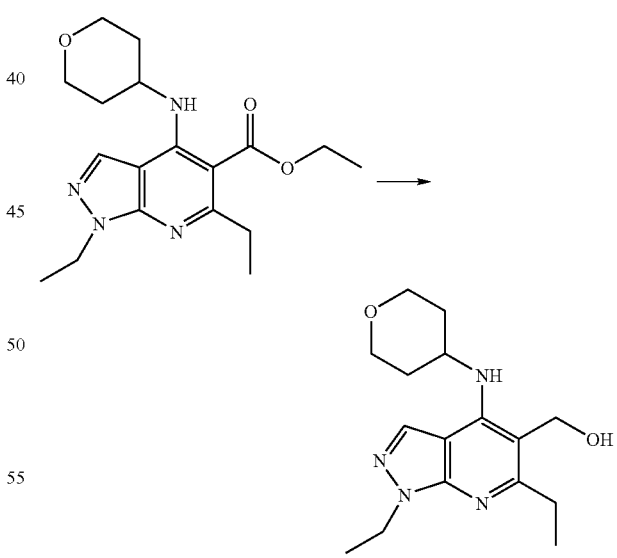

To ethyl 1,6-diethyl-4-(tetrahydro-2H-pyran-4-ylamino)-1H-pyrazolo[3,4-b]pyridine-5-carboxylate (60.43 g, 174 mmol) in dry THF (300 mL) was added dry methanol (28.3 mL) followed by the addition of lithium borohydride (2M in THF, 262 mL, 523 mmol) over 30 mins. The mixture was heated to reflux. After 1 h additional methanol (14.1 mL) was added. After a further 30 mins additional methanol (14.1 mL) was added. After a further 30 mins the mixture was cooled in an ice bath and treated with methanol (100 mL) followed (cautiously) with water (1,000 mL). The mixture was stirred for 1 h and then extracted with dichloromethane (1,500 mL total). The combined organics were washed with water, then brine, dried and evaporated to dryness to afford 49.84 g of the title compound. LC-MS m/z 305 (M+H)+, 1.79 min (ret time).

Example 6

5-(Azidomethyl)-1,6-diethyl-N-(tetrahydro-2H-pyran-4-yl)-1H-pyrazolo[3,4-b]pyridin-4-amine To [1,6-diethyl-4-(tetrahydro-2H-pyran-4-ylamino)-1H-pyrazolo[3,4-b]pyridin-5-yl]methanol (24.9 g, 82 mmol) was added thionyl chloride (90 mL, 1.23 mmol) and the mixture was heated to 80° C. under an atmosphere of nitrogen. After 2 h the mixture was cooled, evaporated and the residue azeotroped with toluene. The residue was then dissolved in a solution of sodium azide (7.98 g, 123 mmol) in DMSO (120 mL). The mixture was stirred for 16 h. The above procedure was repeated on the same scale and the 2 reactions combined for work-up. The combined DMSO mixture was partitioned between ethyl acetate and aqueous sodium bicarbonate. The aqueous phase was extracted thoroughly with ethyl acetate and the combined organics were washed with water, then brine, dried and evaporated to afford 58.9 g of a brown solid. The product was purified by flash chomatography on 1.5 kg of silica using a step gradient from 3:1 to 2:1 cyclohexane/ethyl acetate to afford 39.94 g of the title compound. LC-MS m/z 330 (M+H)+, 2.21 min (ret time).

Example 7

5-(Aminomethyl)-1,6-diethyl-N-(tetrahydro-2H-pyran-4-yl)-1H-pyrazolo[3,4-b]pyridin-4-amine

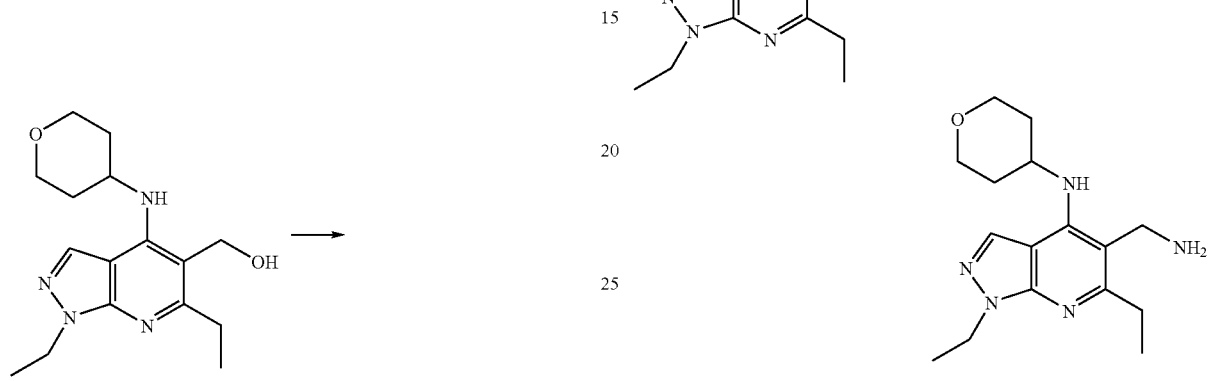

Palladium on charcoal (10%, 50% w/w water, 8 g) was treated with ethanol (200 mL) followed by a solution of 5-(azidomethyl)-1,6-diethyl-N-(tetrahydro-2H-pyran-4-yl)-1H-pyrazolo[3,4-b]pyridin-4-amine (39.94 g, 121 mmol) in ethanol (1,200 mL). The mixture was stirred under an atmosphere of hydrogen for 16 h. The catalyst was then removed by filtration and the filtrate removed of solvent in vacuo to reveal 41.24 g of a black oil. The product was purified by flash chomatography on 1 kg of silica using a step gradient from 5-20% methanol in dichloromethane to afford 32.66 g of the title compound. LC-MS m/z 304 (M+H)+, 1.71 min (ret time).

Example 8

[5'-(Aminomethyl)-2'-fluoro-3-biphenylyl]methanol

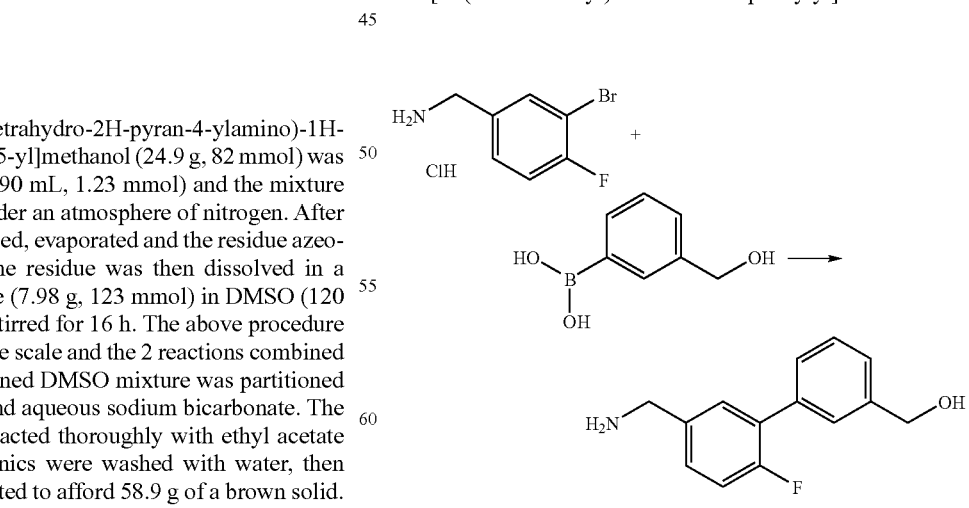

To a solution of [3-(hydroxymethyl)phenyl]boronic acid (2 g, 13.2 mmol) in 1,4-dioxan (40 mL) was added [(3-bromo-4-fluorophenyl)methyl]amine hydrochloride (3.18 g, 13.2 mmol), potassium carbonate (9.1 g, 66 mmol) and tetrakis (triphenylphosphine) palladium(0) (456 mg, 0.4 mmol). The mixture was split into 4×20 mL capacity microwave vials and each was treated with water (3 mL). The mixtures were each heated at 150° C. for 20 mins. One sixth of the total reaction mixture was treated with water (100 mL) and extracted with ethyl acetate (2×80 mL). The combined organic phase was dried (magnesium sulphate) and evaporated to dryness and the product purified by flash chomatography on silica using 0-50% ethyl acetate/cyclohexane followed by dichloromethane/ammonia solution/methanol @8:1:1 as eluants. Product-containing fractions were combined and evaporated to dryness to afford 402 mg of the title compound. LC-MS m/z 463 (M+H)+, 0.65 min (ret time). The remaining five-sixths of the reaction mixture was worked up in the same manner and purified by flash chomatography using ethyl acetate/cyclohexane @1:1 followed by dichloromethane/ammonia solution/methanol @8:1:1 as eluants. This yielded 1.97 g of the title compound. LC-MS m/z 463 (M+H)+, 0.65 min (ret time).

Example 9

2-Bromo-4-methylbenzamide

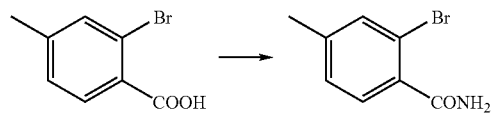

To a suspension of 2-bromo-4-methylbenzoic acid (15.0 g, 69.8 mmol) in toluene (60 mL), thionyl chloride (10.3 mL) and DMF (0.10 mL) were added and stirred at 50° C. for 3 h. After cooling to room temperature, the excess thionyl chloride was removed in vacuo. The residue was dissolved in toluene (50 mL), and the mixture was added to the solution of ammonia (25%, 60 mL). The white precipitate was filtered over Celite and dried in vacuo to afford 2-bromo-4-methylbenzamide (14.8 g, 99%).

Example 10

2-Bromo-4-methylbenzonitrile

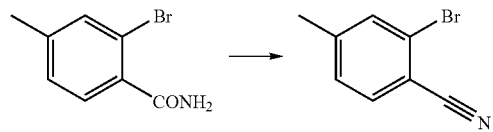

To a suspension of 2-bromo-4-methylbenzamide (14.8 g, 69.1 mmol) in CHCl3 was added phosphorous pentoxide (24.5 g, 172.8 mmol) and the mixture keep refluxing for 12 h. The reaction was allowed to cool to room temperature, and put into the ice water under the condition of stirring. The organic layer was separated and the aqueous layer was extracted with CHCl3 (150 mL×2). The combined organic phase was washed with brine, and dried over Na2SO4. Evaporation of the solvent afforded the title compound, 2-bromo-4-methylbenzonitrile (13.3 g, 98%). 1H NMR (400 MHz, CDCl3) δ 2.41 (s, 3H), 7.20 (d, J=8.0 Hz, 1H), 7.51-7.54 (m, 2H).

Example 11

2-Bromo-4-(bromomethyl)benzonitrile

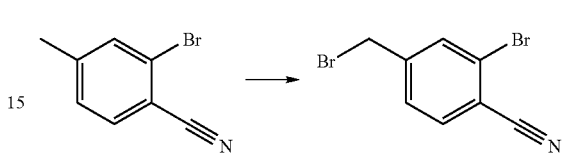

A mixture of 2-bromo-4-methylbenzonitrile (13.3 g, 81.4 mmol), NBS (14.4 g, 84.4 mmol) and BPO (0.20 g) in CCl4 (150 mL) was heated for 4 h at reflux. The reaction mixture was cooled to room temperature and filtered. Then the solid was washed with CCl4 (20 mL×2) and the combined filtrates were washed successively with saturated sodium bicarbonate (50 mL), water (2×100 mL) and sodium thiosulfate (50 mL). The organic phase was dried over NaSO4 and concentrated in vacuum afforded the titled compound, 2-bromo-4-(bromomethyl)benzonitrile (18.7 g, 100%).

Example 12

2-Bromo-4-[(1,3-dioxo-1,3-dihydro-2H-isoindol-2-yl)methyl]benzonitrile

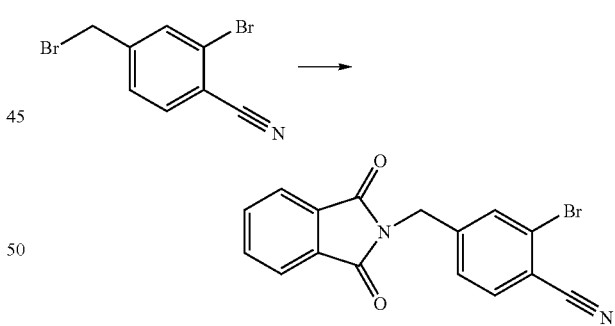

To a solution of 2-bromo-4-(bromomethyl)benzonitrile (18.0 g, 65.5 mmol) in DMF (60 mL), potassium phthalide (18.2 g, 98.2 mmol) was added, and then the mixture was stirred under reflux for 4 h. The reaction was allowed to cool to room temperature. After removing DMF under reduced pressure, the residue was dissolved in CH2Cl2 (200 mL), and washed with water (50 mL×2). The organic layer was dried over anhydrous sodium sulfate. After evaporation of the solvent, the residue was recrystallized from toluene and EtOH to give the product, 2-bromo-4-[(1,3-dioxo-1,3-dihydro-2H-isoindol-2-yl)methyl]benzonitrile (13.5 g, 61%).

Example 13

4-(Aminomethyl)-2-bromobenzonitrile

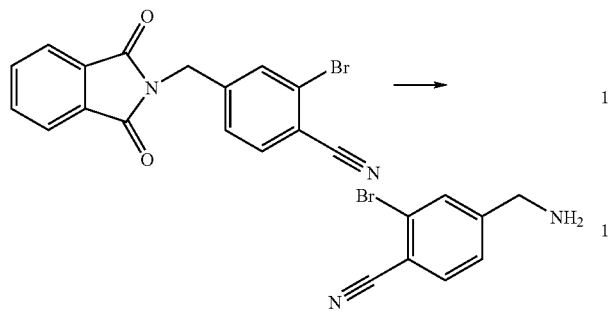

To a suspension of 2-bromo-4-[(1,3-dioxo-1,3-dihydro-2H-isoindol-2-yl)methyl]benzonitrile (8.0 g, 23.5 mmol) in EtOH (150 mL) was added hydrazine hydrate (85%, 2.76 g). The mixture was refluxed for 3 h. At room temperature 2 N HCl (60 mL) was added (pH=3), and the mixture was filtered and rinsed with water (50 mL×4). The filtrate was evaporated to about 150 mL and filtered again. After addition of $NaHCO_3$ to adjust the pH=9, the filtrate was extracted with $CH_2Cl_2$ (100 mL×3). The combined extracts were washed with brine and dried over anhydrous sodium sulfate. After removing the solvent, 1N HCl in MeOH (50 mL) was added and the solvent was evaporated to afford crude material as a white solid. Recrystallization from MeOH-$Et_2O$ yielded 4.3 g of the product, 4-(aminomethyl)-2-bromobenzonitrile (yield: 75.8%). $^1$H NMR (400 MHz, $D_2O$) δ 4.21 (S, 2H), 7.43 (dd, J=8.0 Hz, J=1.2 Hz, 1H), 7.71 (d, J=8.0 Hz, 2H); $^{13}$C NMR (100 MHz, $D_2O$): δ42.3, 115.5, 118.0, 125.6, 128.4, 133.4, 135.5, 139.9; HPLC: retention time: 4.709 min; purity: 99.7%.

Example 14

3-Bromo-5-fluorobenzonitrile

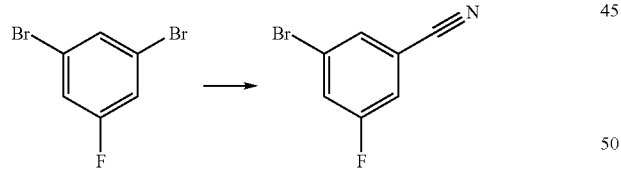

A 250-mL round-bottom flask equipped with a magnetic stir bar was charged with 1,3-dibromo-5-fluorobenzene (7.70 g, 30.3 mmol), DMF (45 mL), pyridine (4.9 mL), and copper (I) cyanide (2.72 g, 30.3 mmol) under nitrogen. A reflux condenser was attached to the flask. The green, cloudy mixture was stirred at reflux for 3 h. Once lower Rf impurities were observed, the reaction was allowed to cool to room temperature. The reaction was quenched with 30 mL of ether, and a precipitate formed in the dark solution. The precipitate was gravity-filtered though Celite. The filtrate was rinsed three times with ether (100 mL/50 g bromide). The isolated solution was added to a separatory funnel. The organic layer was washed with a 2:1 mixture of water and concentrated ammonium hydroxide (30 mL), followed by saturated ammonium chloride solution (2×30 mL) and saturated sodium bicarbonate (30 mL). The aqueous layers were extracted with ether (3×40 mL). The organic layers were combined and dried over anhydrous sodium sulfate. The product was purified by flash column chomatography to yield 3-bromo-5-fluorobenzonitrile (2.10 g, 35%). $^1$H NMR (400 MHz, $CDCl_3$) δ 7.62 (s, 1H), 7.54-7.50 (m, 1H), 7.35-7.32 (m, 1H).

Example 15

1,1-Dimethylethyl [(3-bromo-5-fluorophenyl)methyl]carbamate

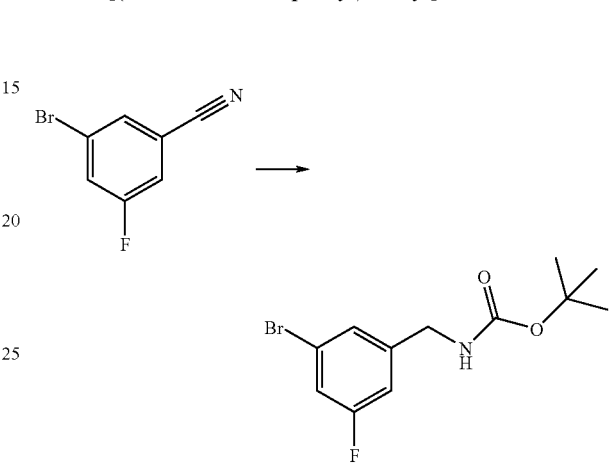

$NaBH_4$ (1.99 g, 52.5 mmol) was cautiously added to a solution of $NiCl_2$ (1.36 g, 10.5 mmol), $Boc_2O$ (4.58 g, 21.0 mmol) and 3-bromo-5-fluorobenzonitrile (2.10 g, 10.5 mmol) in absolute ethanol (30 mL) at 0° C. (vigorous reaction with the formation of a black precipitate). Once the reaction had subsided the mixture was left to stir at room temperature for 30 min. Ethanol was removed under reduced pressure and the precipitate was dissolved in EtOAc, filtered and repeatedly washed with EtOAc. The combined organic phases were washed with saturated $NaHCO_3$, and dried ($Na_2SO_4$). After removing the solvent, the product, was purified by flash column chomatography to yield 1,1-dimethylethyl [(3-bromo-5-fluorophenyl)methyl]carbamate (2.20 g, 69%). $^1$H NMR (400 MHz, $CDCl_3$) δ 1.46 (S, 9H), 4.28-4.32 (m, 2H), 4.87 (br, 1H), 6.93-7.29 (m, 3H); $^{13}$C NMR (100 MHz, $CDCl_3$) δ 20.3, 43.6, 44.1, 79.7, 80.0, 113.0, 114.0, 117.7, 122.5, 126.0, 123.0, 141.7, 155.9, 161.5, 164.0.

Example 16

3-Bromo-2-fluorobenzoic acid

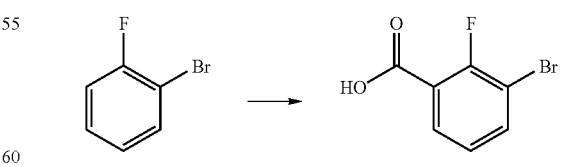

To a stirred solution of 2,2,6,6-tetramethylpiperidine (31.1 g, 0.22 mol) in THF (200 mL) was added dropwise a solution of butyl lithium (0.22 mol) in hexane (146.7 mL) at −10° C. The mixture was stirred for 1.5 h at −10° C. and the fluoroarene (1-bromo-2-fluorobenzene) in THF (100 mL) was consecutively added to the solution at −75° C. The mixture was stirred for 2 h at −75° C., before being poured on excess of CO$_2$ gas. Then the reaction mixture was warmed to room temperature and stirred over night. After evaporation of the solvent, the residue was dissolved in water (150 mL), washed with diethyl ether (2×50 mL), acidified (to pH 1) and the solid was filtered off and dried under vacuum to give 24.3 g of the title compound as a white solid (yield: 55%).

Example 17

3-Bromo-2-fluorobenzamide

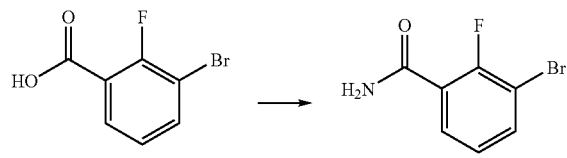

To a stirred solution of 3-bromo-2-fluorobenzoic acid (24.3 g, 111 mmol) in CH$_2$Cl$_2$ (100 mL) was added SOCl$_2$ (12.2 mL, 166 mmol). The mixture was stirred under reflux for 6 h until the solution is colorless. CH$_2$Cl$_2$ was removed under vacuum. Then the residue was dissolved in ethyl acetate (200 mL) and then added dropwise to NH$_3$H$_2$O (80 mL). The organic layer was washed with H$_2$O (50 mL×2), brine and dried over Na$_2$SO$_4$, filtered and concentrated to give 23.8 g of the title compound as a white solid (98% yield).

Example 18

[(3-Bromo-2-fluorophenyl)methyl]amine

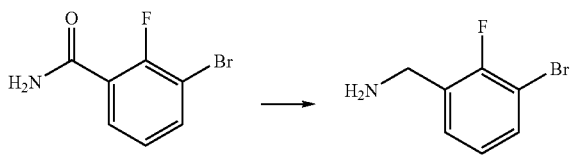

To a solution of 3-bromo-2-fluorobenzamide (3.0 g, 13.76 mmol) in THF (50 mL) was added BH$_3$.Me$_2$S (1.57 mL, 20.6 mmol) and the mixture was stirred at 50° C. for 2 h (monitored by TLC). The reaction was quenched by adding HCl (20 mL, 3 N) after which the result mixture was stirred for 2 h and then THF was removed under vacuum. The aqueous layer was extracted with AcOEt (30 mL), and then was adjusted to pH=9.0 with NaOH (1 N). Then the aqueous layer was extracted with AcOEt (50 mL×2). The combined organic layers were washed with brine, dried over Na$_2$SO$_4$, filtered and concentrated to give 1.30 g of the title compound as a colorless oil (yield: 46%). $^1$H NMR (400 MHz, D$_2$O) δ 4.30 (S, 2H), 7.19-7.22 (m, 1H), 7.47 (t, J=8.8 Hz, 1H), 7.73-7.77 (m, 1H); $^{13}$C NMR (100 MHz, D$_2$O) δ 37.4, 108.9, 121.2, 126.2, 130.7, 135.1, 156.2, 158.6.

Example 19

1-Bromo-3-(bromomethyl)-5-methylbenzene

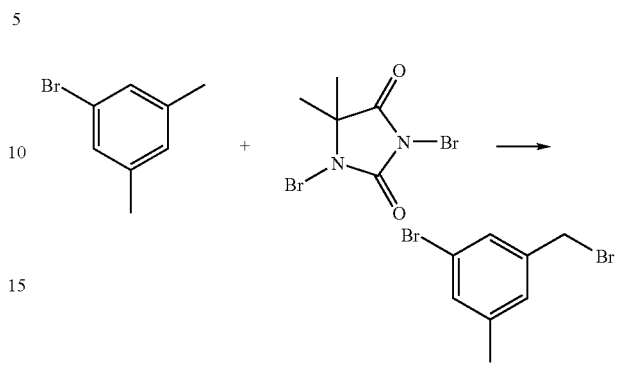

To a solution of 1-bromo-3,5-dimethylbenzene (25.0 g, 135.0 mmol) in CCl$_4$ (150 mL), was added 1,3-dibromo-5,5-dimethylimidazolidine-2,4-dione (14.5 g, 54.0 mmol) and dibenzoyl peroxide (BPO) (0.2 g) and the mixture was refluxed for 7 h. After the reaction mixture was cooled to room temperature, the precipitate was filtered out using Celite, and then the solid was rinsed two times with pentane (50 mL). The combined filtrates were washed with water (50 mL), followed by saturated sodium bicarbonate (50 mL) and sodium thiosulfate (50 mL×2). The organic layer was dried over anhydrous sodium sulfate. Evaporation of the solvent afforded the compound 1-bromo-3-(bromomethyl)-5-methylbenzene (35.6 g, 99%).

Example 20

2-[(3-Bromo-5-methylphenyl)methyl]-1H-isoindole-1,3(2H)-dione

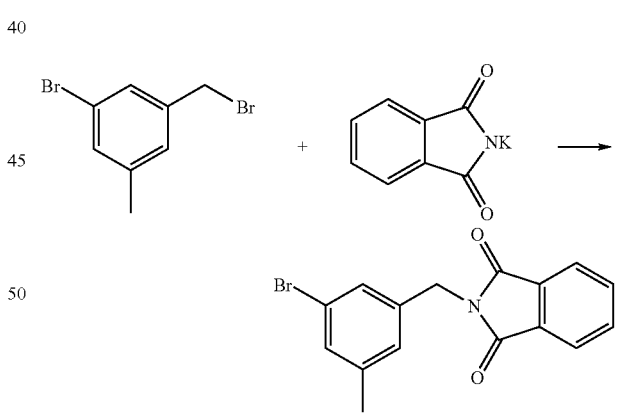

To a solution of 1-bromo-3-(bromomethyl)-5-methylbenzene (34.0 g, 128.8 mmol) in DMF (200 mL), was added potassium phthalide (28.9 g, 154.6 mmol, and the mixture was stirred under reflux for 2 h. The reaction was allowed to cool to room temperature. After the solvent was remove under reduced pressure, the residue was dissolved in CH$_2$Cl$_2$ (300 mL), and washed with water (50 mL×3). The organic layer was dried over anhydrous sodium sulfate. Evaporation of the solvent gave a white solid. The solid was recrystallized from toluene and EtOH to give the product, 2-[(3-bromo-5-methylphenyl)methyl]-1H-isoindole-1,3(2H)-dione (28.5 g, 67%). $^1$H NMR (400 MHz, CDCl$_3$) δ 7.87-7.72 (m, 4H), 7.36 (s, 1H), 7.23 (s, 1H), 7.15 (s, 1H), 4.77 (s, 2H), 2.30 (s, 3H).

Example 21

[(3-Bromo-5-methylphenyl)methyl]amine

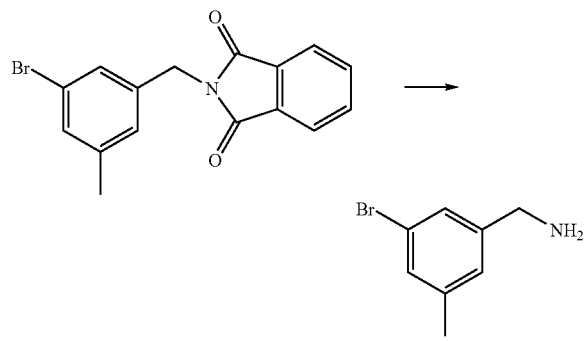

To a suspension of 2-[(3-bromo-5-methylphenyl)methyl]-1H-isoindole-1,3(2H)-dione (6.5 g, 19.7 mmol) in EtOH (120 mL) was added hydrazine hydrate (85%, 2.3 g). The mixture was refluxed for 3 h. After being cooled to room temperature, 2 N HCl (60 mL) was added to obtain a pH=3, and the mixture was filtered and rinsed with water (50 mL×4). The filtrate was evaporated to about 150 mL and filtered again. After addition of 2 N NaOH (60 mL) (pH=9), the filtrate was extracted with CH$_2$Cl$_2$ (50 mL×4). The combined extracts were washed with brine, dried over anhydrous sodium sulfate, and concentrated to give 2.9 g of the residue. MeOH (20 mL) and conc. HCl (5 mL) were added and evaporated to afford crude material as a white solid. Recrystallization from MeOH-Et$_2$O yielded the product [(3-bromo-5-methylphenyl)methyl]amine (3.1 g, 73%) as colorless fine needles. $^1$H NMR (400 MHz, D$_2$O) δ 7.36 (s, 1H), 7.29 (s, 1H), 7.10 (s, 1H), 3.98 (s, 2H), 2.20 (s, 3H); $^{13}$C NMR (400 MHz, D$_2$O) δ 141.9, 134.6, 132.7, 128.7, 128.5, 122.2, 42.6, 20.4.

Example 22

5-Bromo-2-methylbenzonitrile

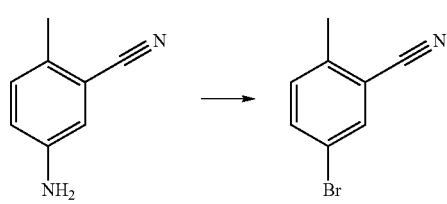

Water (13.5 mL), HBr (74%, 14.4 mL) and 5-amino-2-methylbenzonitrile (2.0 g, 15.1 mmol) dissolved in water (24 mL) was added to a flask and heated to 50° C. for 20 min. Then the mixture was cooled to 0~5° C., and a solution of NaNO$_2$ (1.2 g, 17.4 mmol) in water was added. The reaction mixture was stirred for 10 min at 0~5° C., then was warmed to 40° C. A solution of CuBr (6.5 g, 45.1 mmol) in water (36 mL) and HBr (7.2 mL) was added to the mixture, and refluxed for 2 h. The mixture was extracted with AcOEt, and the organic layer was washed by saturated NaHCO$_3$ solution and brine, and dried over Na$_2$SO$_4$. The crude product was purified by flask chromatograph (PE:EA=50:1), obtaining 2.3 g of 5-bromo-2-methylbenzonitrile as a white solid (yield: 77%). $^1$H NMR (400 MHz, CDCl$_3$) δ 7.72 (s, 1H), 7.59 (d, J=8.0 Hz, 1H), 7.19 (d, J=8.0 Hz, 1H), 2.51 (s, 3H).

Example 23

1,1-Dimethylethyl [(5-bromo-2-methylphenyl)methyl]carbamate

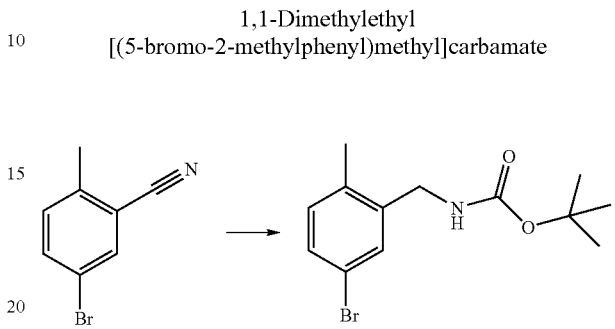

NaBH$_4$ (2.4 g, 64.3 mmol) was added cautiously to a solution of NiCl$_2$ (2.8 g, 21.6 mmol), Boc$_2$O (9.6 g, 44.0 mmol) and 5-bromo-2-methylbenzonitrile (4.2 g, 21.4 mmol) in EtOH (150 mL) at 0° C. within 0.5 h, then stirred for 40 min. After the reaction had subsided, the mixture was left to stir at room temperature for 0.5 h. Then the solvent was removed and the residue was dissolved in AcOEt and a saturated solution of NaHCO$_3$, then filtered and washed with AcOEt. The combined organic layers were washed with brine and dried over Na$_2$SO$_4$. The crude product was purified by flask chomatograph (PE:EA=30:1), obtaining 2.7 g of the product, 1,1-dimethylethyl [(5-bromo-2-methylphenyl)methyl]carbamate, as a white solid (Yield: 42%). $^1$H NMR (400 MHz, CDCl$_3$) δ7.36 (s, 1H), 7.28-7.30 (m, 1H), 7.01 (d, J=16.8 Hz, 1H), 4.72 (s, 1H), 4.26-4.30 (m, 2H), 2.25 (s, 3H), 1.46 (s, 9H); $^{13}$C NMR (100 MHz, CDCl$_3$) δ 155.9, 139.1, 132.2, 130.6, 127.7, 126.3, 119.9, 42.4, 20.6, 18.7; HPLC: retention time: 4.671 min; purity: 97.2%.

Example 24

1,3-Dibromo-2-methyl-5-nitrobenzene

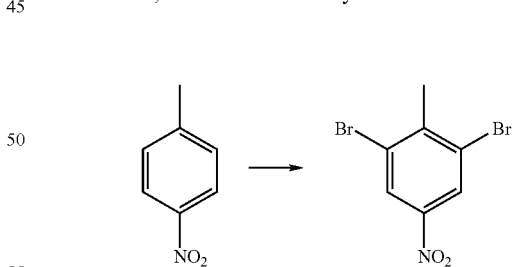

To a CHCl$_3$ solution (120 mL) of 1-methyl-4-nitrobenzene (30.0 g, 218.8 mmol), iron powder (3.6 g, 64.5 mmol) was added with mechanically stirring. Then bromine (124.8 g, 40 mL, 780.9 mmol) was added slowly while raising temperature to 40° C. After addition of the bromine, the mixture was heated to reflux for 48 h. After cooling, the solution was washed with a saturated Na$_2$SO$_3$ solution, saturated Na$_2$CO$_3$ solution, brine, and dried over anhydrous Na$_2$SO$_4$. After the solvent was removed, the residue was recrystallized from MeOH, giving 26.5 g of the title compound as yellow crystals. An additional 12.3 g of the title compound was obtained by silica column chomatography. Total yield: 60%. $^1$H NMR (400 MHz, CDCl$_3$) δ 2.67 (s, 3H), 8.38 (s, 2H).

Example 25

(3,5-Dibromo-4-methylphenyl)amine

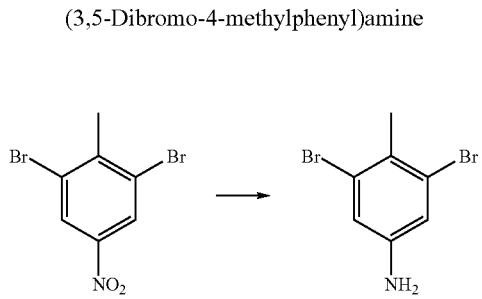

1,3-Dibromo-2-methyl-5-nitrobenzene (11.3 g, 38.3 mmol) was dissolved in THF/EtOH (100 mL/100 mL), then SnCl$_2$.2H$_2$O (43.2 g, 191.6 mmol) was added. The mixture was stirred at room temperature for 3 h. After the solvent was removed, a NaOH solution (25 g/200 mL) was added, and the mixture was stirred for 1.5 h. The solution was extracted with EtOAc (200 mL×2) and dried over anhydrous Na$_2$SO$_4$. After removing EtOAc, CH$_2$Cl$_2$ was added, and then concentrated HCl (7 mL) was added to form hydrochloric acid salt, which was collected by filteration. The solid was used in subsequent reactions without further purification. $^1$H NMR (400 MHz, D$_2$O) δ 2.43 (s, 3H), 3.61 (br, 2H), 6.86 (s, 2H).

Example 26

1,3-Dibromo-2-methylbenzene

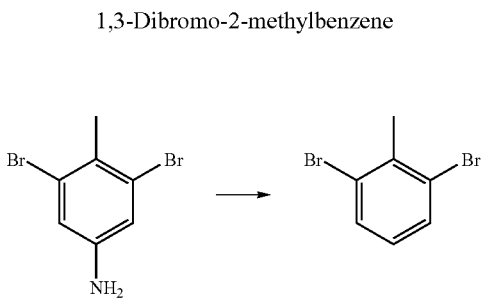

A solution of (3,5-dibromo-4-methylphenyl)amine dissolved in water (80 mL) and concentrated HCl (7.5 mL) stirring for 20 min, then the mixture was cooled to 0~5° C., and a solution of NaNO$_2$ (3.4 g/40 mL H$_2$O) was added. The reaction mixture was stirred for 2 h at 0~5° C., then the suspension was added to a solution of hypophosphorous acid (50%, 27.9 g), and the mixture was cooled to 0° C. The mixture was stirred at room temperature overnight. Then it was extracted with CH$_2$Cl$_2$ (100 mL×2). The organic layer was washed with brine (30 mL) and dried over Na$_2$SO$_4$. After silica column chomatography, (eluted with petroleum ether), 3.57 g product was obtained, as a colorless liquid. $^1$H NMR (400 MHz, CDCl$_3$) δ 2.57 (s, 3H), 6.89 (t, J=8.0 Hz, 1H), 7.50 (d, J=8.0 Hz, 2H).

Example 27

3-Bromo-2-methylbenzoic acid

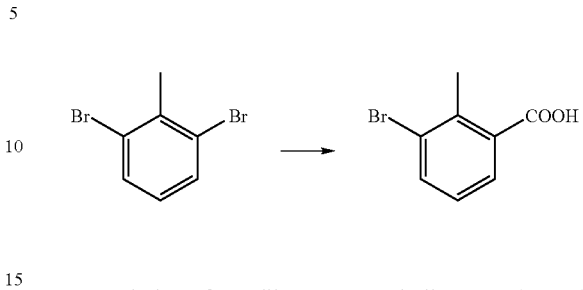

To a solution of 1,3-dibromo-2-methylbenzene (6.57 g) in dry THF (100 mL), t-BuLi solution (1.5 M in pentane, 17 mL) was added dropwise at −80° C. Then reaction mixture was stirred between −76~−78° C. for 2 h. Then the mixture was cooled to below −80° C. and dry ice was added after which the mixture was warmed to room temperature naturally. Solvent was removed, 5% NaOH solution (40 mL) added and the aqueous solution was washed with CH$_2$Cl$_2$ (10 mL×2). Then the aqueous layer was acidified with concentrated HCl to pH=1 and extracted with EtOAc (100 mL×2). The combined organic extracts were dried over anhydrous Na$_2$SO$_4$. After removing the solvent, the residue was purified by silica column chomatography, (eluted with petrol. ether: EtOAc=8:1 to 1:1), to obtain 3.58 g of the product. Yield: 63.4%. $^1$H NMR (400 MHz, CDCl$_3$) δ 2.73 (s, 3H), 7.15 (t, J=8.0 Hz, 1H), 7.77 (dd, J=8.0 Hz, J=1.2 Hz, 1H), 7.94 (dd, J=8.0 Hz, J=1.2 Hz, 1H).

Example 28

3-bromo-2-methylbenzamide

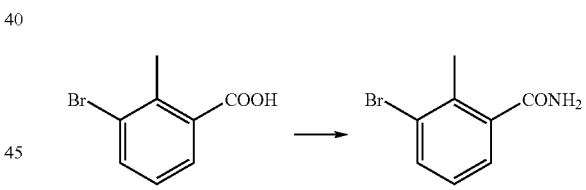

3-bromo-2-methylbenzoic acid (3.7 g) was suspended in dry toluene (50 mL), thionyl chloride (3.8 mL) was added, and then the mixture was heated to reflux for 2 h. After cooling to room temperature, the solvent was removed under reduced pressure. The residue was dissolved in dry THF (10 mL) and toluene (10 mL), added to concentrated ammonia solution (20 mL), and stirred for 1 h. The mixture was filtered and the obtained white solid was washed with petrol ether and dried under vacuum to give 1.2 g of product. The mixture was concentrated to half volume and then extracted with EtOAc, which was dried over anhydrous Na$_2$SO$_4$. After solvent was removed, the white solid was stirred with 20 mL petroleum ether: 2 mL ethyl acetate, filtered, and an additional 1.5 g product was obtained. Product which was used in next step without further purification. Yield: 84%. $^1$H NMR (400 MHz, CDCl$_3$) δ 2.52 (s, 3H), 5.75 (br, 1H), 5.94 (br, 1H), 7.08 (t, J=7.6 Hz, 1H), 7.35 (dd, J=7.4 Hz, J=110 Hz, 1H), 7.62 (dd, J=8.2 Hz, J=1.4 Hz, 1H).

Example 29

[(3-Bromo-2-methylphenyl)methyl]amine

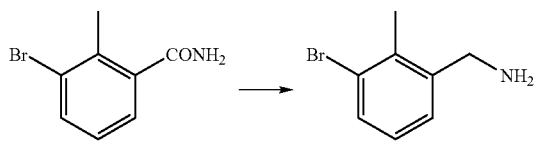

3-Bromo-2-methylbenzamide (1.4 g) was dissolved in dry THF (15 mL) under nitrogen, then Me$_2$S.BH$_3$ (94%, 1.34 mL) was added slowly. After stirred at room temperature for 1 h, the mixture was heated to 50° C. overnight. When 3-bromo-2-methylbenzamide disappeared, methanol was added dropwise until there was no more air bubble formed. Then 10 min later, 10% HCl was added dropwise, the mixture stirred for 1 h, and then solvent was removed. The white residual was recrystallized with iPrOH to obtain 1.1 g of the product. Yield: 35%. $^1$H NMR (400 MHz, DMSO-d6) δ 2.42 (s, 3H), 4.09 (s, 2H), 7.20 (t, J=7.8 Hz, 1H), 7.44 (d, J$_1$=8.0 Hz, 1H), 7.63 (d, J$_1$=7.6 Hz, 1H), 8.49 (br, 3H); $^{13}$C NMR (100 MHz, DMSO-d6) δ 18.8, 19.0, 46.1, 125.2, 127.4, 127.5, 129.0, 129.1, 132.1, 132.5, 134.7, 135.9, 136.1, 136.5; HPLC: retention time: 4.696 min; purity: 96.0%.

Example 30

2-Amino-5-bromo-3-(methyloxy)benzoic acid

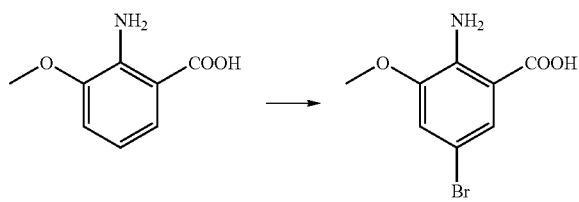

To a solution of 2-amino-3-(methyloxy)benzoic acid (15.0 g, 89.7 mmol) in MeOH (100 mL) was added NBS (16.8 g, 94.2 mmol) at −5° C. The reaction was kept stirring at 0° C. overnight, then put into the ice water under the condition of stirring. A precipitate formed and was filtered out using Celite, and dried in vacuo to afford 2-amino-5-bromo-3-(methyloxy)benzoic acid (22.0 g, 99%). $^1$H NMR (400 MHz, CDCl$_3$) δ 7.65 (s, 1H), 6.93 (s, 1H), 3.87 (s, 3H).

Example 31

3-Bromo-5-(methyloxy)benzoic acid

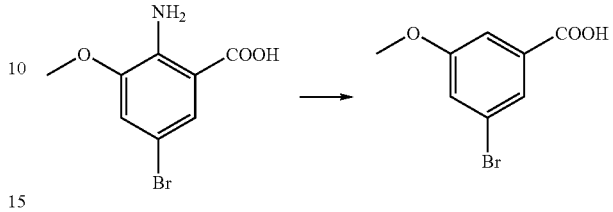

To a solution of 2-amino-5-bromo-3-(methyloxy)benzoic acid (16.40 g, 66.65 mmol) in H$_2$O (80 mL), was added conc. HCl (30 mL) and THF (5 mL) at 0° C. The reaction mixture was stirred for 30 min, and then NaNO$_2$ (14.00 g, 202.91 mmol) was cautiously added to the solution. This solution was stirred for 2 h, and then H$_3$PO$_2$ (22.00 g, 333.35 mmol) was cautiously added to the solution. The solution was kept stirring overnight at the room temperature (monitored by TLC), then filtered and rinsed with water (50 mL×2). The resulting solid was dried to afford 3-bromo-5-(methyloxy)benzoic acid (9.60 g, 62%). $^1$H NMR (400 MHz, CDCl$_3$) δ 7.46 (t, J=1.6 Hz, 1H), 7.31 (q, J=16.8 Hz, 1H), 7.21 (t, J=16.8 Hz, 1H), 3.84 (s, 1H).

Example 32

3-Bromo-5-(methyloxy)benzamide

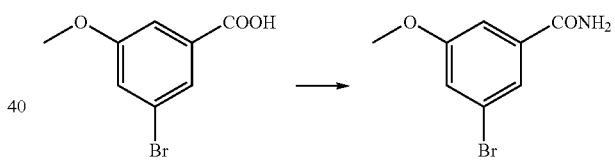

To a suspension of 3-bromo-5-(methyloxy)benzoic acid (9.6 g, 41.6 mmol) in toluene (60 mL) were added thionyl chloride (9.89 g, 83.1 mmol) and DMF (0.10 mL) and the mixture stirred at 50° C. for 4 h. The mixture was allowed to cool to room temperature, and then the excess thionyl chloride was removed in vacuo. The residue was dissolved in toluene (50 mL), and the mixture was added to a solution of ammonia (25%, 50 mL). A precipitate formed and was filtered off using Celite, and dried to afford 3-bromo-5-(methyloxy)benzamide (8.70 g, 90%).

Example 33

{[3-Bromo-5-(methyloxy)phenyl]methyl}amine

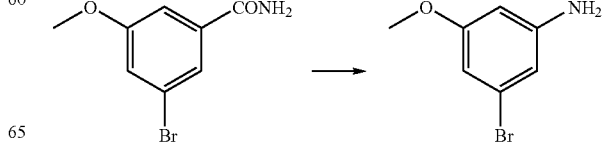

To a solution of 3-bromo-5-(methyloxy)benzamide (4.00 g, 17.4 mmol) in THF (60 mL) was added BH₃.Me₂S (2.64 g, 34.8 mol) at 0° C. After the end of the addition, the mixture was kept refluxing overnight (followed by TLC). It was then cooled to room temperature and EtOH was cautiously added to the reaction mixture. When no more air bubbles appeared, the mixture was acidified with 1N HCl to pH=2. Then the mixture was stirred at 50° C. overnight and the reactin mixture filtered and the solid rinsed with water (20 mL×2). The combined filtrate was washed with EtOAc (50 mL×3). After addition of 2N NaOH (pH=10), the aqueous layer was extracted with EtOAc (100 mL×3). The combined extracts were washed with brine, dried over anhydrous sodium sulfate, and concentrated to give 2.7 g (72%) the product. MeOH (10 mL) and conc. HCl (10 mL) were added and evaporated to afford crude material as a white solid. Recrystallization from MeOH-Et₂O gave the product (3.10 g, 71%), {[3-bromo-5-(methyloxy)phenyl]methyl}amine, as colorless fine needles. ¹H NMR (400 MHz, D₂O) δ 7.12-7.09 (m, 2H), 6.86 (s, 1H), 3.98 (s, 2H), 3.69 (s, 3H); ¹³C NMR (100 MHz, D₂O) δ160.2, 135.8, 124.2, 123.0, 117.8, 114.0, 55.8, 42.5; HPLC: retention time: 5.452 min.

Example 34

5-Bromo-2-(methyloxy)benzonitrile

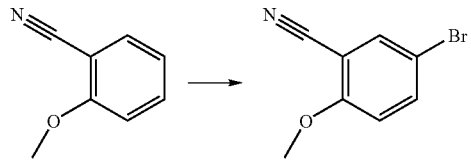

Br₂ (13.7 g, 86.0 mmol) in CHCl₃ (20 mL) was added to a solution of 2-(methyloxy)benzonitrile (10.9 g, 81.9 mmol) in CHCl₃ (50 mL). The mixture was refluxed for 29 h. The reaction was allowed to cool to room temperature, and washed with saturated sodium bisulfite (50 mL), and brine (50 mL). The organic layer was dried over anhydrous sodium sulfate. Evaporation of the solvent afforded 5-bromo-2-(methyloxy)benzonitrile (12.4 g, 71%).

Example 35

1,1-Dimethylethyl {[5-bromo-2-(methyloxy)phenyl]methyl}carbamate

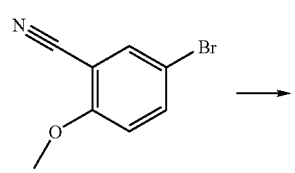

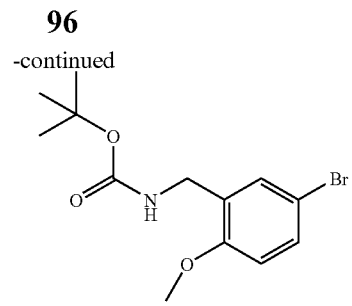

NaBH₄ (2.9 g, 75.5 mmol) was cautiously added in several portions to a solution of NiCl₂ (2.6 g, 19.8 mmol), Boc₂O (8.2 g, 37.7 mmol) and 5-bromo-2-(methyloxy)benzonitrile (4.0 g, 18.9 mmol) in dry EtOH (70 mL) at 0° C. Once the reaction had subsided, the mixture was left to stir at room temperature for 3 h. Ethanol was removed under reduced pressure and the residue was dissolved in EtOAc and saturated solution of NaHCO₃, then filtered and the aqueous layer was repeatedly washed with EtOAc. The combined organic phases were dried Na₂SO₄. The crude product was purified by flash column chromatography to give the captioned the product (1.5 g yield: 25%). ¹H NMR (400 MHz, CDCl₃) δ 7.36-7.33 (m, 2H), 6.74 (d, J=8.8 Hz, 1H), 4.97 (br, 1H), 4.27 (d, J=4.8 Hz, 1H), 3.82 (s, 3H), 1.45 (s, 9H); ¹³C NMR (400 MHz, CDCl₃) δ 156.5, 155.8, 131.7, 131.1, 129.3, 111.8, 79.5, 55.5, 39.9, 26.4. HPLC: retention time.

Example 36

2-Bromo-6-methylphenol

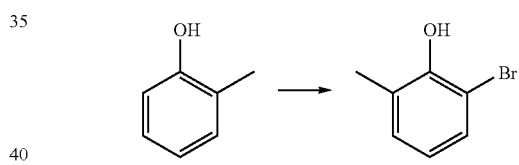

To a solution of o-cresol (20.0 g, 0.19 mol) and iPr₂NH (2.63 mL, 18.5 mmol) in CH₂Cl₂ (500 mL), a solution of NBS (32.9 g, 0.19 mol) in CH₂Cl₂ (500 mL) was added dropwise over 7 h and the mixture was stirred over night at room temperature. The reaction mixture was acidified to pH=1 with conc. sulfuric acid and water (400 mL). The organic layer was separated, dried with Na₂SO₄, and concentrated under reduced pressure. 34.6 g of the crude product was obtained (yield: 97%). ¹H NMR (400 MHz, CDCl₃) δ 2.30 (s, 3H), 5.54 (s, 2H), 6.71 (t, J=7.6 Hz, 1H), 7.05 (d, J=7.6 Hz, 1H), 7.28 (d, J=8.0 Hz, 1H).

Example 37

1-Bromo-3-methyl-2-(methyloxy)benzene

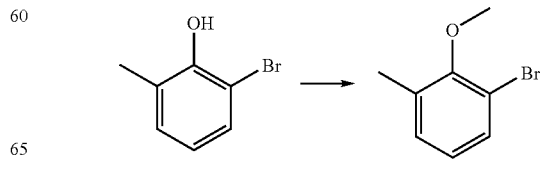

To a solution of 2-bromo-6-methylphenol (34.6 g, 0.18 mol) in THF (300 mL) was added NaH (9.6 g, 0.24 mol, 60%) in several portions. After the mixture was stirred for 1 h, Me$_2$SO$_4$ (28.0 g, 0.22 mol) was added dropwise. Then the mixture was stirred over night. Water (50 mL) was added, and the solvent was removed under reduced pressure. Then the residue was dissolved in Et$_2$O (250 mL) and the organic layer was washed with NaOH (5%, 100 mL), brine (100 mL), and dried with Na$_2$SO$_4$. After removing the solvent, 35.3 g of the crude product was obtained (yield: 95%). $^1$H NMR (400 MHz, CDCl$_3$) δ 2.33 (s, 3H), 3.81 (s, 3H), 6.88 (t, J=8.0 Hz, 1H), 7.10 (d, J=8.0 Hz, 1H), 7.30 (d, J=7.6 Hz, 1H).

Example 38

1-bromo-3-(bromomethyl)-2-(methyloxy)benzene

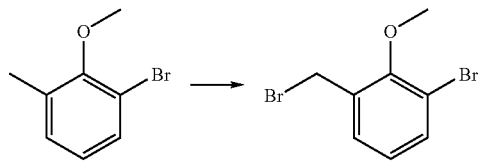

1-Bromo-3-methyl-2-(methyloxy)benzene (30.3 g, 0.15 mol), NBS (28.2 g, 0.16 mol), and BPO (1.83 g, 7.55 mmol) were suspended in 300 mL of CCl$_4$, and the mixture was heated to 80° C. over night. After cooling to room temperature, the solution was filtrated and the solid was washed with CCl$_4$ (30 mL×2). The filtrate was washed with NaHSO$_3$ (aq. 250 mL×2), Na$_2$CO$_3$ (aq. 100 mL×2), brine (100 mL) and dried over Na$_2$SO$_4$. After removing the solvent, 41.4 g of the crude product was obtained (yield: 97.9%).

Example 39

2-{[3-Bromo-2-(methyloxy)phenyl]methyl}-1H-isoindole-1,3(2H)-dione

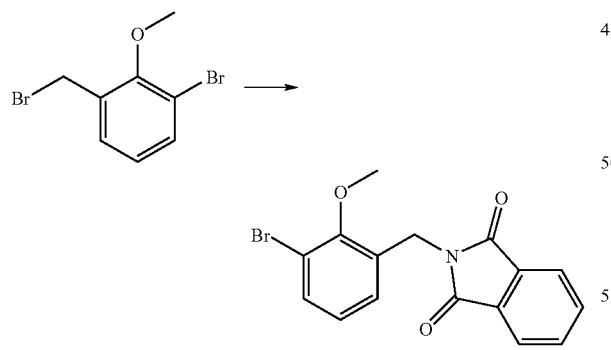

PhtK (28.8 g, 0.16 mol) was added to a solution of 1-bromo-3-(bromomethyl)-2-(methyloxy)benzene (41.4 g, 0.15 mol) in DMF (350 mL). The mixture was heated to 90° C. over night. Then the solvent was removed under reduced pressure. The residue was dissolved in CHCl$_3$ (300 mL), and filtered. The filtrate was washed with H$_2$O (100 mL×2), brine (100 mL), and dried over Na$_2$SO$_4$. After removing the solvent, the residue was recrystallized from EtOH (200 mL) giving 26.7 g of the product as white solid. (yield: 52.1%). $^1$H NMR (400 MHz, CDCl$_3$) δ 3.98 (s, 3H), 4.95 (s, 2H), 6.93 (t, J=8.0 Hz, 1H), 7.20 (d, J=0.8 Hz, 1H), 7.45 (d, J=8.0 Hz, 1H), 7.72-7.87 (m, 4H).

Example 40

{[3-Bromo-2-(methyloxy)phenyl]methyl}amine

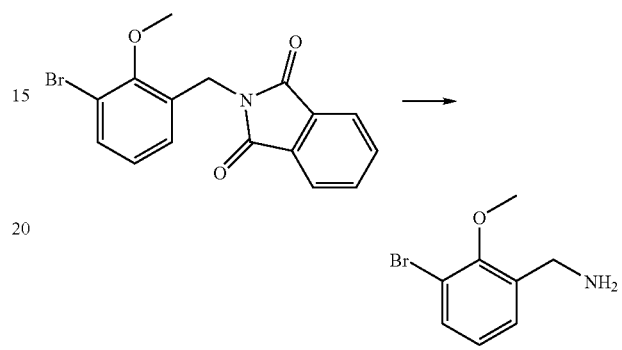

Hydrazine hydrate (7.8 g, 154 mmol) was added to a suspension of 2-{[3-bromo-2-(methyloxy)phenyl]methyl}-1H-isoindole-1,3(2H)-dione (26.7 g, 77.2 mmol) in EtOH (300 mL) and the reaction mixture was heated to 90° C. for 4 h. After cooling to room temperature, the mixture was filtered and the solid was washed with EtOAc (300 mL×2). The filtrate was evaporated to about 50 mL and filtered again. After removing the solvent, the residue was dissolved in 20 mL of MeOH, and then 1N HCl was added to obtain a white solid. Then the white solid was recrystallized from MeOH-Et$_2$O to obtain 9.0 g of the product (yield: 46.3%). $^1$H NMR (400 MHz, D$_2$O) δ 3.79 (s, 3H), 4.13 (s, 2H), 7.02 (t, J=7.6 Hz, 1H), 7.27 (d, J=8.0 Hz, 1H), 7.57 (d, J=8.0 Hz, 1H); $^{13}$C NMR (100 MHz, D$_2$O) δ 37.7, 60.2, 115.6, 125.3, 126.6, 128.8, 133.8, 153.7; MS: m/z 254.1 (M$^+$); HPLC: retention time: 7.618 min; purity: 98.8%.

Example 41

1-Bromo-3-(bromomethyl)-5-methylbenzene

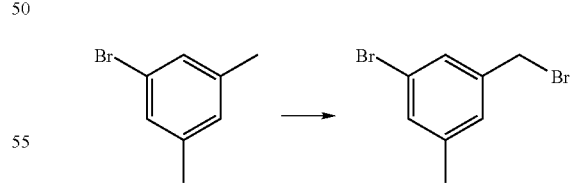

A mixture of 1-bromo-3,5-dimethylbenzene (25.0 g, 135 mmol), NBS (24.0 g, 135 mmol) and BPO (1.30 g) in CCl$_4$ (250 mL) was refluxed for 6 h. After cooling to room temperature, the mixture was filtered, and the filtrate was washed successively with saturated sodium bicarbonate (100 mL), water (2×50 mL) and brine (2×50 mL). The combined organic phases were dried (Na$_2$SO$_4$) and concentrated in vacuum to give 40.0 g of crude product 1-bromo-3-(bromomethyl)-5-methylbenzene.

Example 42

(3-Bromo-5-methylphenyl)methanol

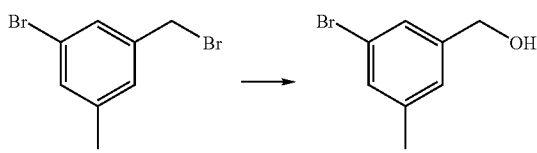

A mixture of 1-bromo-3-(bromomethyl)-5-methylbenzene (40.0 g, 151 mmol), 1,4-dioxane (150 mL), water (150 mL) and calcium carbonate (37.9 g, 379 mmol) was heated for 16 h at reflux. The mixture was filtered and the filtrate was concentrated in vacuum, then diluted with $CH_2Cl_2$ (150 mL). The organic layer was washed with HCl (2N, 50 mL) and a solution of saturated sodium bicarbonate (50 mL), dried over ($Na_2SO_4$) and concentrated in vacuum to give 25.0 g of crude product (3-bromo-5-methylphenyl)methanol.

Example 43

3-Bromo-5-methylbenzoic acid

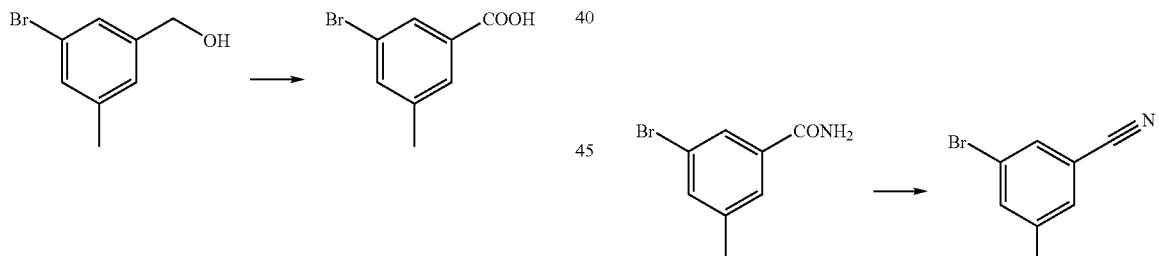

A solution of $KMnO_4$ (39.3 g, 249 mmol) in water (600 mL) was added slowly to a solution of (3-bromo-5-methylphenyl)methanol (25.0 g, 124 mmol) in acetone (500 mL). The mixture was kept at reflux for 60 mins. After cooling to room temperature, the mixture was acidified with HCl (2N, 100 mL). A brown precipitate formed and was dissolved by adding a solution of saturated sodium bicarbonate (100 mL); then acetone was evaporated in vacuum. Ammonia (150 mL) was added. The mixture was filtered over Celite and the filtrate acidified with concentrated HCl. The product was extracted with diethyl ether (3×150 mL). The combined organic phases were dried ($Na_2SO_4$) and concentrated in vacuum to obtain 16.0 g of the acid, 3-bromo-5-methylbenzoic acid, as white crystals (yield: 60%). $^1$H NMR (400 MHz, $CDCl_3$) δ 8.05 (s, 1H), 7.85-7.84 (m, 1H), 7.58 (s, 1H), 2.40 (s, 3H).

Example 44

3-Bromo-5-methylbenzamide

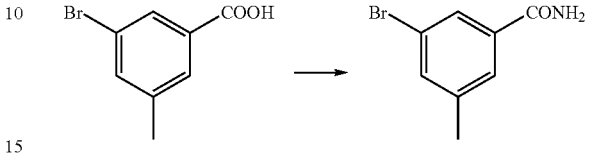

CDI (42.2 g, 260.4 mmol) was cautiously added to a solution of 3-bromo-5-methylbenzoic acid (16.0 g, 74.4 mmol) in EA (300 mL), and then the mixture was kept at reflux for 3 h. After cooling to room temperature, $NH_3$ (g) was passed though the mixture for 1 h. It was filtered and the organic layer was washed with HCl (10%, 100 mL) and water (100 mL). The organic phase was dried over $Na_2SO_4$ and concentrated in vacuum to obtain 15.0 g of 3-bromo-5-methylbenzamide as white crystals (yield: 94%). $^1$H NMR (400 MHz, $CDCl_3$) δ 7.73-7.72 (m, 1H), 7.56-7.55 (m, 1H), 7.50-7.49 (m 1H), 2.39 (s, 3H).

Example 45

3-Bromo-5-methylbenzonitrile

Phosphorous pentoxide (29.8 g, 210.2 mmol) was added to a suspension of 3-bromo-5-methylbenzamide (15.0 g, 70.1 mmol) in $CHCl_3$ and the mixture was kept refluxing for 2 days (monitored by TLC). The reaction was allowed to cool to room temperature, and put into ice water under the condition of stirring. The organic layer was separated and the aqueous layer was extracted with dichloromethane (150 mL×2). The combined extracts were washed with brine, dried over $NaSO_4$. The product, 3-bromo-5-methylbenzonitrile (7.20 g, 52%), was purified by flash column chomatography. $^1$H NMR (400 MHz, $CDCl_3$) δ 7.60-7.56 (m, 2H), 7.40-7.39 (m, 1H), 2.39 (s, 3H).

Example 46

3-Bromo-5-(bromomethyl)benzonitrile

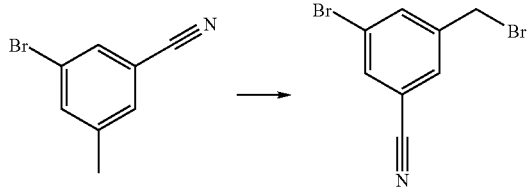

A mixture of 3-bromo-5-methylbenzonitrile (9.80 g, 45.0 mmol), NBS (8.90 g, 45.0 mmol) and BPO (0.40 g) in $CCl_4$ (250 mL) was heated for 10 h at reflux. The reaction mixture was cooled to room temperature and filtered, and the organic phase was washed successively with saturated sodium bicarbonate (100 mL), water (2×50 mL) and brine (2×50 mL). The combined organic phases were dried over $Na_2SO_4$ and concentrated in vacuum to give 12.5 g of crude 3-bromo-5-(bromomethyl)benzonitrile.

Example 47

3-Bromo-5-[(1,3-dioxo-1,3-dihydro-2H-isoindol-2-yl)methyl]benzonitrile

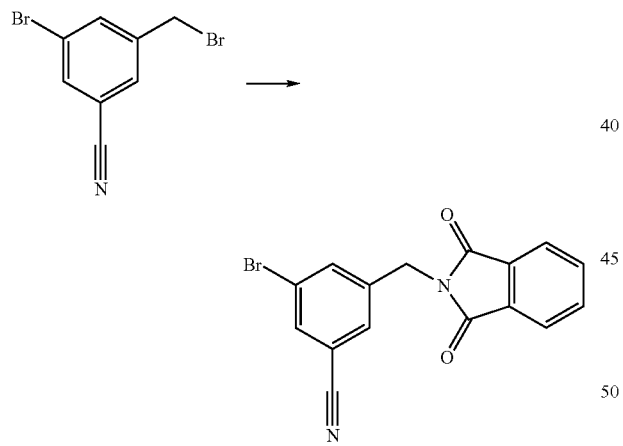

A suspension of 3-bromo-5-(bromomethyl)benzonitrile (12.5 g, 45.5 mmol), potassium phthalate (7.16 g, 38.6 mmol), and in DMF (100 mL) was stirred under reflux for 4 h. After cooling to room temperature, the solvent was remove under reduced pressure and the residue was dissolved in $CHCl_3$ (200 mL). The organic layer was washed with water (50 mL×2), dried over $Na_2SO_4$, and concentrated in vacuum to obtain 15.2 g of the crude product. The product, 3-bromo-5-[(1,3-dioxo-1,3-dihydro-2H-isoindol-2-yl)methyl]benzonitrile (3.50 g, 23%) was purified by flash column chomatography. $^1$H NMR (400 MHz, $CDCl_3$) δ 7.90-7.87 (m, 2H), 7.81-7.80 (m, 1H), 7.77-7.75 (m, 2H), 7.71-7.70 (m, 1H), 7.66-7.65 (m, 1H), 4.83 (s, 2H).

Example 48

3-(Aminomethyl)-5-bromobenzonitrile

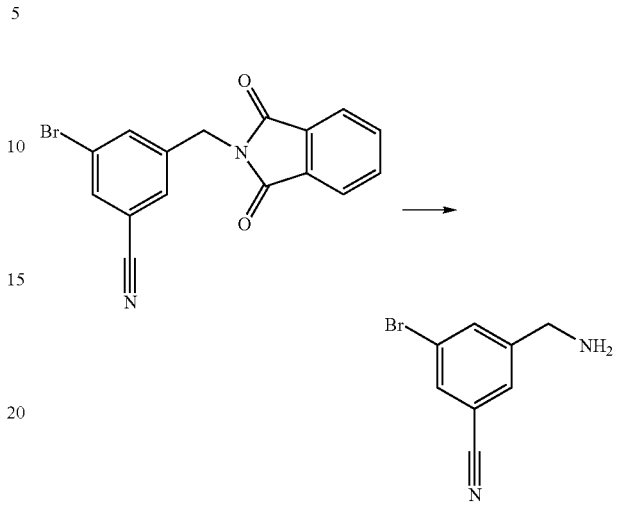

Hydrazine hydrate (85%, 1.31 g) was added to a suspension of 3-bromo-5-[(1,3-dioxo-1,3-dihydro-2H-isoindol-2-yl)methyl]benzonitrile (3.50 g, 10.3 mmol) in EtOH (60 mL). The mixture was refluxed for 3 h. Then, at room temperature, 2 N HCl (20 mL) was added (pH=3), and the mixture was filtered and the solid was rinsed with water (20 mL×2). The filtrate was evaporated to about 50 mL and filtered again. After addition of $NaHCO_3$ (pH=9), the filtrate was extracted with $CH_2Cl_2$ (50 mL×3). The combined extracts were washed with brine, dried over anhydrous sodium sulfate, and concentrated to give crude product. It was recrystallized from MeOH-$Et_2O$ yielding the product (1.40 g, 55%) as colorless fine needles. $^1$H NMR (400 MHz, $D_2O$): δ 7.92 (m, 1H), 7.84 (m, 1H), 7.69 (m, 1H), 4.11 (s, 2H); $^{13}$C NMR (400 MHz, $D_2O$): δ 137.1, 135.9, 135.8, 131.7, 123.0, 117.7, 113.8, 42.0; MS: m/z 209.0 ($M^+$-HCl); HPLC: retention time: 9.313 min; purity: 98.4%.

Example 49

(3-Bromophenyl)methanol

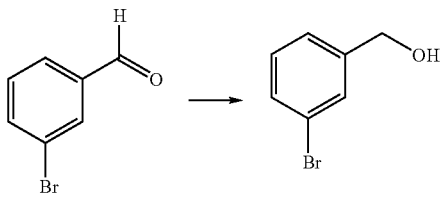

Sodium borohydride (7.1 g, 186.1 mmol) in several portions was added to a solution of 3-bromobenzaldehyde (114.8 g, 620.4 mmol) in EtOH (650 mL) at 25° C. Then the mixture was stirred for 1 h at room temperature. The reaction was quenched with water (200 mL). After removing EtOH, the residue was dissolved in AcOEt (500 mL), and filtered. The filtrate was washed with water (150 mL), brine (150 mL), and dried over Na₂SO₄. After removing the solvent, 115.8 g of the title compound was obtained (yield: 99.8%).

Example 50

{[(3-Bromophenyl)methyl]oxy}(1,1-dimethylethyl)dimethylsilane

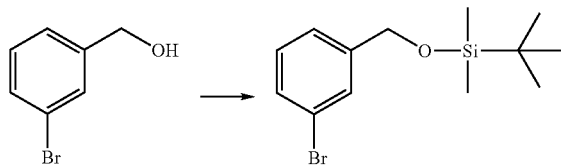

TBSCl (18.7 g, 124.3 mmol), Et₃N (14.08 g, 139.2 mmol) and DMAP (194.3 mg, 8.9 mmol) were dissolved in CH₂Cl₂ (120 mL) and the solution was cooled to 0-5° C. (3-Bromophenyl)methanol (18.5 g, 99.4 mmol) was added dropwise to the solution. After the addition of the (3-Bromophenyl)methanol, the mixture was warmed to room temperature and stirred for 2 h. 5% HCl was added to the reaction mixture to adjust the pH=4-5. Then the organic phase was separated and the aqueous layer was extracted with CH₂Cl₂ (50 mL×2). The combined organic phases were washed with water and dried over Na₂SO₄. After removing the solvent, 28.5 g of {[(3-bromophenyl)methyl]oxy}(1,1-dimethylethyl)dimethylsilane was obtained (Yield: 95.1%).

Example 51

[3-({[(1,1-Dimethylethyl)(dimethyl)silyl]oxy}methyl)phenyl]boronic

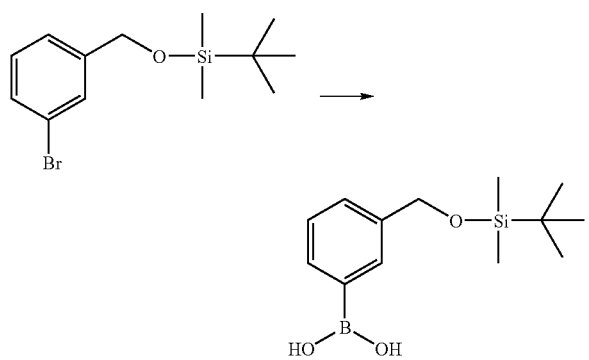

A solution of {[(3-bromophenyl)methyl]oxy}(dimethyl)silane-2,2-dimethylpropane (1:1) (100.0 g, 331.9 mmol) in THF (500 mL) was cooled to −78 C, and then n-BuLi (132.7 mL, 331.9 mmol) was added dropwise. The mixture was stirred for 1 h at −78° C. Then B(OBu)₃ (107.5 mL, 398.2 mmol) was added in one portion. The reaction mixture was warmed to room temperature, and stirred over night. After cooling to 0° C., 5% H₃PO₄ was added to pH=4-5 and the mixture stirred 0.5 h and then filtered. After removing THF, the residue was extracted with Et₂O (200 mL×2), and the organic layer was dried over Na₂SO₄. After removing the solvent, the residue was added to water, and a white solid precipitated which was dried in vacuo to give 65.7 g of [3-({[(1,1-dimethylethyl)-(dimethyl)silyl]oxy}methyl)phenyl] boronic acid (yield: 74.5%). ¹H NMR (400 MHz, CDCl₃) δ 0.14 (s, 6H), 0.98 (s 9H), 4.88 (s, 2H), 7.49-7.59 (m, 2H), 8.14 (d, J=7.6 Hz, 1H), 8.19 (s, 1H).

Example 52

1,1-Dimethylethyl [(3-bromo-4-cyanophenyl)methyl]carbamate

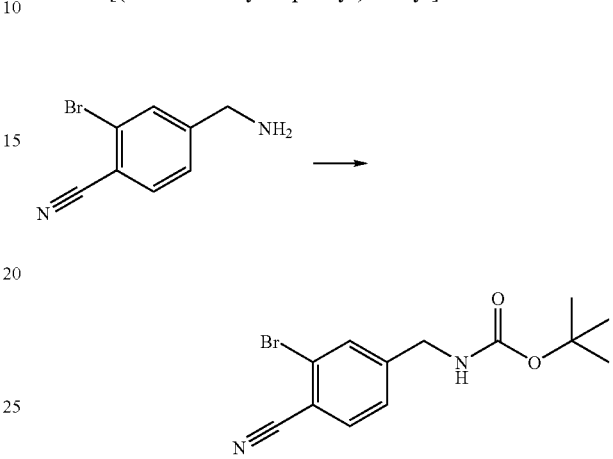

A solution of Boc₂O (2.1 g, 9.8 mmol) in CH₂Cl₂ (10 mL) was added dropwise to a suspension of 4-(aminomethyl)-2-bromobenzonitrile (2.2 g, 8.9 mmol) and Na₂CO₃ (2.4 g, 21.4 mmol) in CH₂Cl₂ (50 mL). Then the reaction mixture was stirred overnight at room temperature. After filtration, the solid was washed with CH₂Cl₂ (20 mL×2), and then the filtrate was washed with water (20 mL×2), brine (20 mL×2) and dried over Na₂SO₄. After removing the solvent, 2.6 g of 1,1-dimethylethyl [(3-bromo-4-cyanophenyl)methyl]carbamate was obtained (yield: 94%).

Example 53

1,1-Dimethylethyl {[3'-({[(1,1-dimethylethyl)-(methyl)silyl]oxy}methyl)-6-methyl-3-biphenylyl]methyl}carbamate

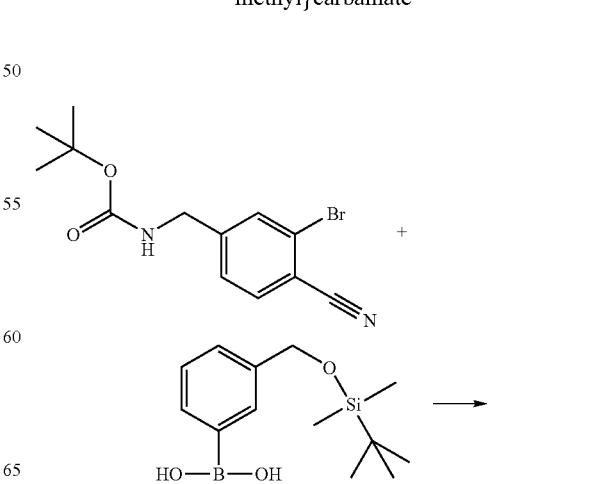

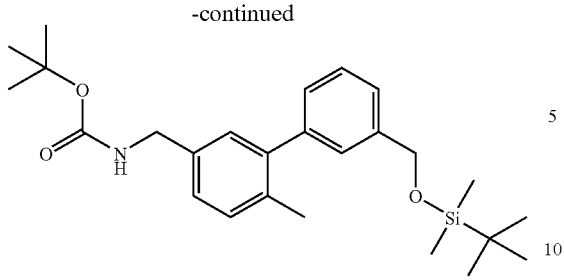

Pd(OAc)₂ (56.3 mg, 0.25 mmol), PPh₃ (263.0 mg, 1.0 mmol), K₂CO₃ (1.7 g, 12.5 mmol) and 1,1-dimethylethyl [(3-bromo-4-cyanophenyl)methyl]carbamate (2.6 g, 8.4 mmol) were suspended in 1,4-dioxane (30 mL). After the mixture was heated to 80° C. for 15 min, [3-(hydroxymethyl)phenyl]boronic acid-(1,1-dimethylethyl)(trimethyl)silane (2.7 g, 10.0 mmol) was added. Then the reaction mixture was stirred over night at 100° C. After cooling to room temperature, the solvent was removed under reduced pressure. The residue was dissolved in CH₂Cl₂ (50 mL), washed with water (20 mL), brine (20 mL), and dried over Na₂SO₄. After the solvent was removed, the crude product was purified on Al₂O₃ column chomatography, eluting with CH₂Cl₂ to yield the captioned product (2.6 g, yield: 60%). ¹H NMR (400 MHz, CDCl₃) δ 0.12 (s, 6H), 0.95 (s 9H), 1.46 (s, 9H), 4.41-4.42 (m, 2H), 4.81 (s, 2H), 7.37-7.47 (m, 6H), 7.71 (d, J=8.0 Hz, 1H); ¹³C NMR (100 MHz, CDCl₃) δ −5.3, 18.4, 25.9, 28.3, 44.2, 64.7, 80.0, 109.9, 118.6, 126.1, 126.2, 126.4, 127.3, 128.6, 134.0, 137.9, 142.0, 144.5, 145.8, 155.8; HPLC: retention time: 9.500 min; purity: 95.2% (HPLC).

Example 54

3'-({[(1,1-Dimethylethyl)(dimethyl)silyl]oxy}methyl)-5-fluoro-3-biphenylcarbonitrile

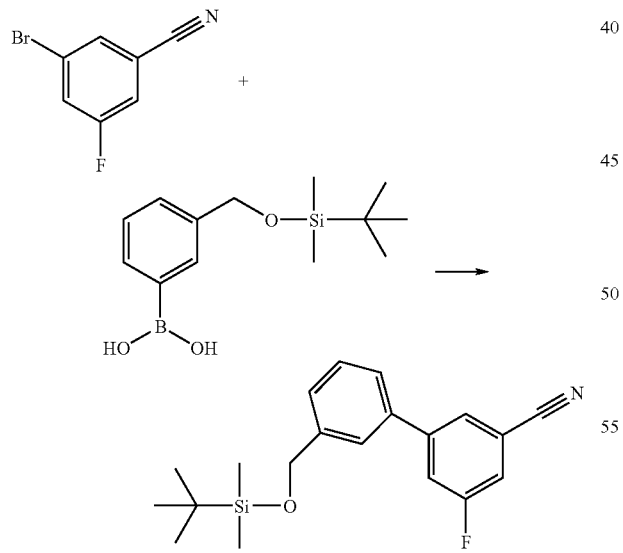

3-bromo-5-fluorobenzonitrile (5.00 g, 25.0 mmol), Pd(OAc)₂ (0.15 g), PPh₃ (0.60 g) and K₂CO₃ (5.18 g, 37.5 mmol) were dissolved in dioxane (60 mL). The mixture was heated at 70° C. for 30 min, then [3-({[(1,1-dimethylethyl)(dimethyl)silyl]oxy}methyl)phenyl]boronic acid (7.99 g, 30.0 mmol) was added. The mixture reaction was stirred at reflux overnight. The solvent was removed under reduced pressure, then diluted with CH₂Cl₂ (100 mL). The organic layer was washed with water (50 mL) and brine (50 mL). And the organic layer was dried over Na₂SO₄. The product 3'-({[(1,1-dimethylethyl)(dimethyl)silyl]oxy}methyl)-5-fluoro-3-biphenylcarbonitrile (5.10 g, 60%) was purified by flash column chomatography. ¹H NMR (400 MHz, CDCl₃) δ 7.67 (t, J=5.2 Hz, 1H), 7.54-7.32 (m, 5H), 4.81 (s, 2H), 0.94 (s, 9H), 0.13 (s, 6H).

Example 55

1,1-Dimethylethyl {[3'-({[(1,1-dimethylethyl)(dimethyl)silyl]oxy methyl)-5-fluoro-3-biphenylyl]methyl}carbamate

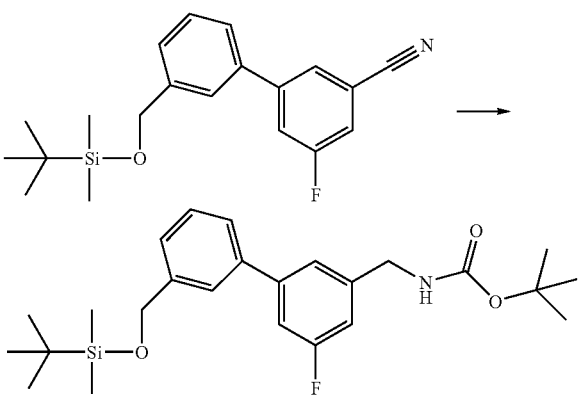

NaBH₄ (3.57 g, 94.3 mmol) was cautiously added to a solution of NiCl₂ (1.83 g, 14.1 mmol), Boc₂O (6.03 g, 27.6 mmol) and 3'-({[(1,1-dimethylethyl)-(dimethyl)silyl]oxy}methyl)-5-fluoro-3-biphenylcarbonitrile (4.60 g, 13.5 mmol) in absolute ethanol (70 mL) at 0° C. (vigorous reaction with the formation of a black precipitate). Once the reaction had subsided the mixture was left to stir at room temperature for 30 min. Ethanol was removed under reduced pressure and the precipitate dissolved in EtOAc and NaHCO₃, filtered and repeatedly washed with EtOAc. The combined organic phases were dried (Na₂SO₄). The product was purified by flash column chomatography to yield 1,1-dimethylethyl {[3'-({[(1,1-dimethylethyl)-(dimethyl)silyl]oxy}methyl)-5-fluoro-3-biphenylyl]methyl}carbamate (1.90 g, 32%). ¹H NMR (400 MHz, CDCl₃) δ 7.51-7.16 (m, 6H), 6.97 (d, J=5.2 Hz, 1H), 4.91 (s, 1H), 4.80 (s, 2H), 4.38-4.37 (m, 2H), 1.53 (s, 9H), 0.96 (s, 9H), 0.12 (s, 6H); ¹³C NMR (400 MHz, CDCl₃) δ 156.0, 143.9, 142.3, 139.8, 129.0, 125.8, 124.9, 121.8, 113.1, 79.9, 65.0, 44.4, 28.5, 26.1, 18.6, −5.1; HPLC: retention time: 4.709 min; purity: 97.9% (HPLC).

Example 56

3'-({[(1,1-Dimethylethyl)(dimethyl)silyl]oxy}methyl)-2-fluoro-3-biphenylcarboxamide

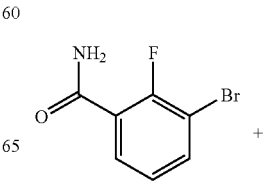

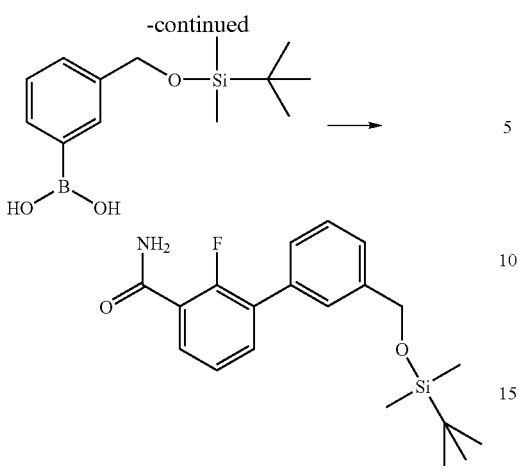

Pd(OAc)₂ (123.6 mg, 0.55 mmol), PPh₃ (557.5 mg, 2.2 mmol), K₂CO₃ (3.8 g, 27.5 mmol) and 3-bromo-2-fluorobenzamide (4.0 g, 18.4 mmol) were suspended in 1,4-dioxane (30 mL). After the mixture was heated to 80° C. for 15 min, [3-({[(1,1-dimethylethyl)(dimethyl)silyl]oxy}methyl)phenyl]boronic acid (5.9 g, 22.0 mmol) was added. Then the reaction mixture was stirred over night at 100° C. After cooling to room temperature, the solvent was removed under reduced pressure. The residue was dissolved in CH₂Cl₂ (50 mL), then was washed with water (20 mL), brine (20 mL), and dried over Na₂SO₄. After the solvent was removed, the crude product was purified on an Al₂O₃ column chomatography, eluting with CH₂Cl₂/CH₃OH (300:1). 3'-({[(1,1-Dimethylethyl)(dimethyl)silyl]oxy}methyl)-2-fluoro-3-biphenylcarboxamide, was obtained (4.1 g, yield: 63%). ¹H NMR (400 MHz, CDCl₃) δ 0.12 (s, 6H), 0.95 (s, 9H), 4.81 (s, 2H), 7.25-8.12 (m, 7H).

Example 57

[3'-(Aminomethyl)-2'-fluoro-3-biphenylyl]methanol

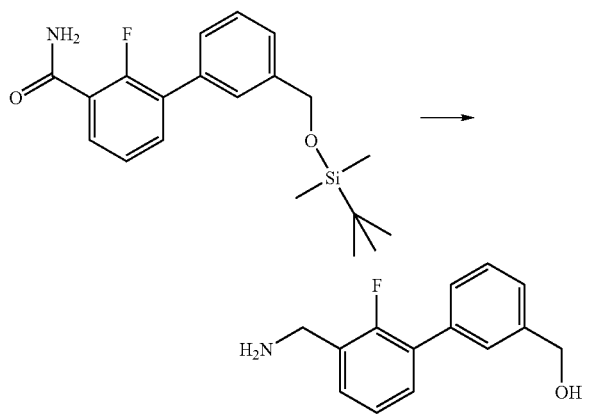

To a solution of 3'-({[(1,1-dimethylethyl)(dimethyl)silyl]oxy}methyl)-2-fluoro-3-biphenylcarboxamide (3.8 g, 10.6 mmol) in THF (40 mL) which was cooled to 0° C., BH₃Me₂S (14.0 mL, 21.2 mmol) was added dropwise. Then the reaction mixture was stirred at 50° C. overnight. The reaction mixture was quenched by adding HCl (10 mL, 3 N) and the result mixture was stirred for 2 h before THF was removed under vacuum. The aqueous layer was extracted with AcOEt (30 mL) then the pH was adjusted to around 9.0 by adding Na₂CO₃. The aqueous layer was extracted with AcOEt (50 mL×2), and dried over Na₂SO₄. After the solvent was removed, the crude product was purified on Al₂O₃ column chomatography, eluting with CH₂Cl₂/EA (10:1). [3'-(aminomethyl)-2'-fluoro-3-biphenylyl]methanol was obtained (0.83 g, yield: 33%). ¹H NMR (400 MHz, DMSO) δ 3.80 (s, 2H), 4.56 (s, 2H), 7.23-7.51 (m, 7H); ¹³C NMR (400 MHz, DMSO) δ 62.8, 124.3, 125.8, 126.9, 127.2, 128.0, 128.1, 128.3, 128.4, 128.6, 131.6, 131.8, 135.6, 142.9, 155.6, 158.1; HPLC: retention time: 4.053 min; purity: 98.6% (HPLC).

Example 58

1,1-Dimethylethyl [(3-bromo-2-fluorophenyl)methyl]carbamate

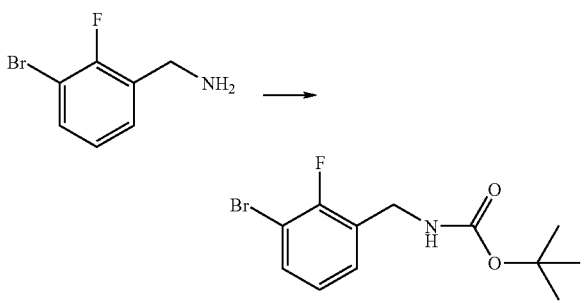

To a suspension of [(3-bromo-2-fluorophenyl)methyl]amine (5.0 g, 20.3 mmol) and Na₂CO₃ (5.5 g, 51.9 mmol) in CH₂Cl₂ (100 mL), was added dropwise a solution of Boc₂O (4.5 g, 20.6 mmol) in CH₂Cl₂ (10 ml). Then the reaction mixture was stirred overnight at room temperature. After filtration, the solid was washed with CH₂Cl₂ (50 mL×2), and then the filtrate was washed with water (70 mL×2), brine (70 mL×2) and dried over Na₂SO₄. After removing the solvent, 5.6 g of 1,1-dimethylethyl [(3-bromo-2-fluorophenyl)methyl]carbamate was obtained (yield: 94%).

Example 59

1,1-Dimethylethyl {[3'-({[(1,1-dimethylethyl)(dimethyl)silyl]oxy}methyl)-2-fluoro-3-biphenylyl]methyl}carbamate

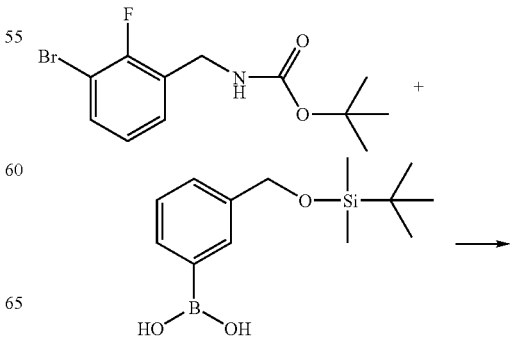

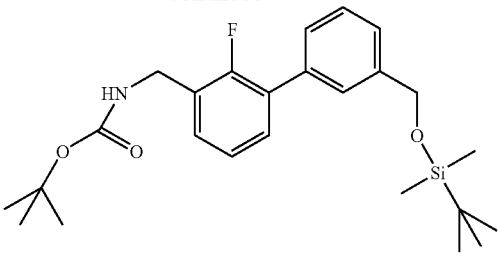

Pd(OAc)₂ (88.9 mg, 0.39 mmol), PPh₃ (415.0 mg, 1.6 mmol), K₂CO₃ (2.7 g, 19.8 mmol) and 1,1-dimethylethyl [(3-bromo-2-fluorophenyl)methyl]carbamate (4.0 g, 13.2 mmol) were suspended in 1,4-dioxane (50 mL). After the mixture was heated to 80° C. for 15 min, [3-({[(1,1-dimethylethyl)(dimethyl)silyl]oxy}methyl)phenyl]boronic acid (4.2 g, 15.8 mmol) was added. Then the reaction mixture was stirred over night at 100° C. After cooling to room temperature, the solvent was removed under reduced pressure. The residue was dissolved in CH₂Cl₂ (80 mL), then was washed with water (30 mL), brine (30 mL), and dried over Na₂SO₄. After the solvent was removed, the crude product was purified on an Al₂O₃ column chomatography, eluting with PE/EA (20:1). 1,1-Dimethylethyl {[3'-({[(1,1-dimethylethyl)(dimethyl)silyl]oxy}methyl)-2-fluoro-3-biphenylyl]methyl}carbamate, was obtained (1.98 g, yield: 34%). ¹H NMR (400 MHz, CDCl₃) δ 0.12 (s, 6H), 0.95 (s, 9H), 4.42-4.43 (m, 2H), 4.80 (s, 2H), 4.96 (s, 1H), 7.17-7.48 (m, 7H); ¹³C NMR (400 MHz, CDCl₃) δ -5.3, 18.4, 25.9, 28.3, 38.9, 64.8, 124.2, 125.4, 126.7, 127.6, 128.3, 128.7, 129.7, 129.2, 129.7, 135.4, 141.6, 155.8; HPLC: retention time: 4.630 min; purity: 99.4% (HPLC).

Example 60

2-{[3'-({[(1,1-Dimethylethyl)(dimethyl)silyl]oxy}methyl)-5-methyl-3-biphenylyl]methyl}-1H-isoindole-1,3(2H)-dione

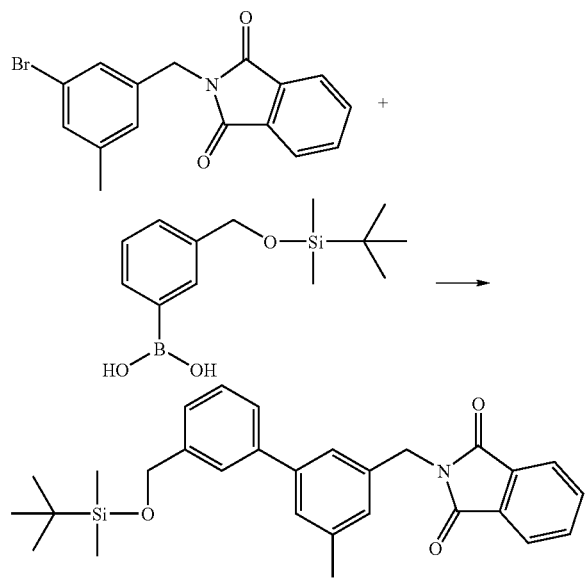

Pd(OAc)₂ (102.0 mg, 0.45 mmol, 0.03 eq.), PPh₃ (476.4 mg, 1.82 mmol, 0.12 eq.), K₂CO₃ (3.14 g, 22.7 mmol, 1.50 eq.) and 2-[(3-bromo-5-methylphenyl)methyl]-1H-isoindole-1,3(2H)-dione (5.00 g, 13.1 mmol, 1.00 eq.) were suspended in anhydrous 1,4-dioxane (30 mL) under nitrogen. After the mixture was heated to 60° C. for 10 min, [3-({[(1,1-dimethylethyl)(dimethyl)silyl]oxy}methyl)phenyl]boronic acid (4.84 g, 18.2 mmol, 1.20 eq.) was added. Then the reaction mixture was stirred over night at 100° C. After cooling it to room temperature, the solvent was removed under reduced pressure. Then water (25 mL) was added, extracted with CH₂Cl₂ twice (70 mL, 50 mL). The organic layer was washed with brine (20 mL×2), dried over anhydrous Na₂SO₄. After the solvent was removed, the crude product was purified on silica column chomatography, eluting with PE/EA (20:1 to 10:1), to give 4.2 g of product, 2-{[3'-({[(1,1-dimethylethyl)(dimethyl)silyl]oxy}methyl)-5-methyl-3-biphenylyl]methyl}-1H-isoindole-1,3(2H)-dione, as a colorless liquid (yield: 59%). ¹H NMR (400 MHz, CDCl₃) δ 0.11 (s, 6H), 0.95 (s, 9H), 2.38 (s, 3H), 4.79 (s, 2H), 4.87 (s, 2H), 7.23 (s, 1H), 7.31-7.49 (m, 6H), 7.70-7.72 (m, 2H), 7.84-7.86 (m, 2H).

Example 61

1,1-Dimethylethyl {[3'-({[(1,1-dimethylethyl)(dimethyl)silyl]oxy}methyl)-5-methyl-3-biphenylyl]methyl}carbamate

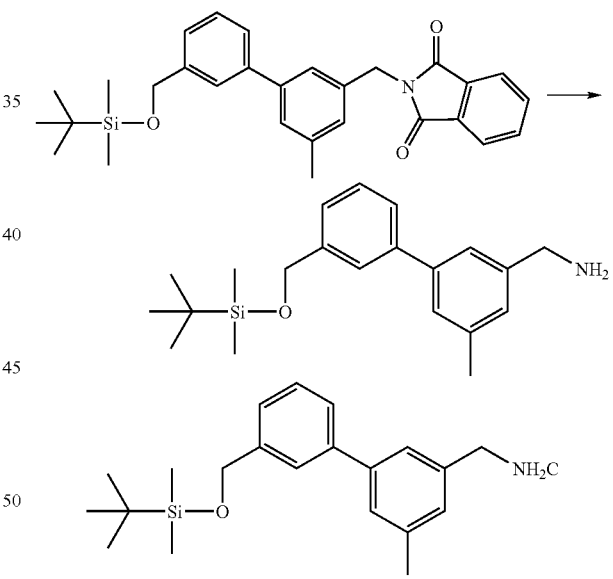

2-{[3'-({[(1,1-Dimethylethyl)(dimethyl)silyl]oxy}methyl)-5-methyl-3-biphenylyl]methyl}-1H-isoindole-1,3(2H)-dione (4.15 g, 8.8 mmol, 1.0 eq.) was dissolved in ethanol (84 mL). Then hydrazine hydrate (85%, 1.1 g, 2.0 eq.) was added. The mixture was heated to reflux for 5.5 h. It was filtered to remove 2,3-dihydrophthalazine-1,4-dione and the filtrate was concentrated. Then the residue was dissolved in THF (50 mL) and filtered. After removing the solvent, 2.5 g of colorless oil was obtained. The oil was dissolved in CH₂Cl₂ (50 mL) and THF (5 mL) followed by adding anhydrous Na₂CO₃ (1.4 g, 13.2 mmol). After stirred for 15 mins a CH₂Cl₂ solution (20 mL) of Boc₂O (2.1 g, 9.6 mmol) was added dropwise. That mixture was stirred for 30 min, filtered, and then solvent was removed. The residual was purified by chomatography (petroleum ether: ethyl acetate=30:1) on alumina basic to give 1.7 g of the above named product (yield was 43.2% overall from the two steps). $^1$H NMR (400 MHz, CDCl$_3$) δ 0.12 (s, 6H), 0.96 (s, 9H), 1.47 (s, 9H), 2.40 (s, 3H), 4.35 (d, J=6.0 Hz, 2H), 4.80 (s, 1H), 4.84 (br, 1H), 7.09 (s, 1H), 7.29-7.52 (m, 6H); $^{13}$C NMR (100 MHz, CDCl$_3$) δ −5.2, 18.4, 21.4, 25.9, 28.4, 64.9, 79.4, 123.4, 124.8, 125.0, 125.7, 127.0, 127.2, 128.6, 138.7, 139.2, 140.9, 141.6, 141.9, 155.9; HPLC: retention time: 5.296 min; purity: 99.1% (HPLC).

Example 62

1,1-dimethylethyl {[3'-({[(1,1-dimethylethyl)(dimethyl)silyl]oxy}methyl)-4-methyl-3-biphenylyl]methyl}carbamate

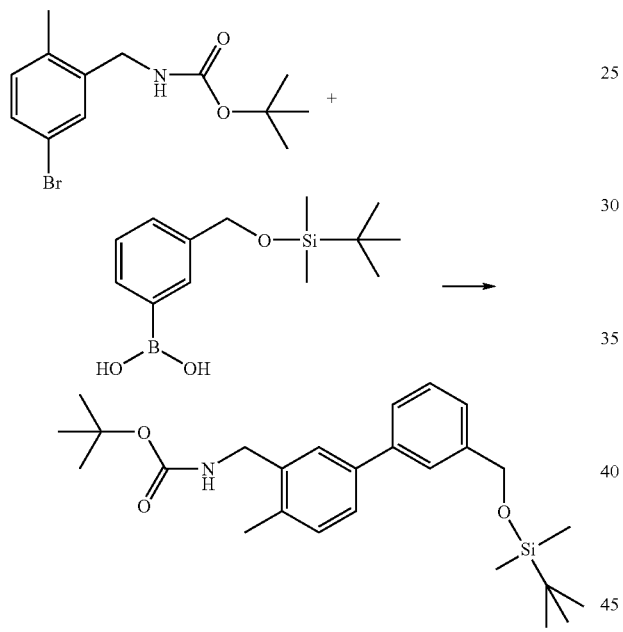

1,1-Dimethylethyl [(5-bromo-2-methylphenyl)methyl]carbamate (2.7 g, 9.0 mmol), Pd(OAc)$_2$ (81 mg, 0.36 mmol), dicyclohexyl [2'-(methyloxy)-1,1'-binaphthalen-2-yl]phosphane (216 mg, 0.45 mmol) and K$_3$PO$_4$ (2.5 g, 11.7 mmol) were dissolved in dioxane (50 mL). The mixture was heated at 80° C. for 30 min, and then [3-({[(1,1-dimethylethyl)(dimethyl)silyl]oxy}methyl)phenyl]boronic acid (3.1 g, 11.7 mmol) was added. The mixture reaction was stirred at reflux for two days. The solvent was removed under reduced pressure, then diluted with CH$_2$Cl$_2$ (100 mL). The organic layer was washed with water (30 mL), brine (30 mL), and dried over Na$_2$SO$_4$. After removing the solvent, 3.6 g of the crude product 1,1-dimethylethyl {[3'-({[(1,1-dimethylethyl)-(dimethyl)silyl]oxy}methyl)-4-methyl-3-biphenylyl]methyl}carbamate was obtained (yield: 90%).

Example 63

1,1-Dimethylethyl {[3'-(hydroxymethyl)-4-methyl-3-biphenylyl]methyl}carbamate

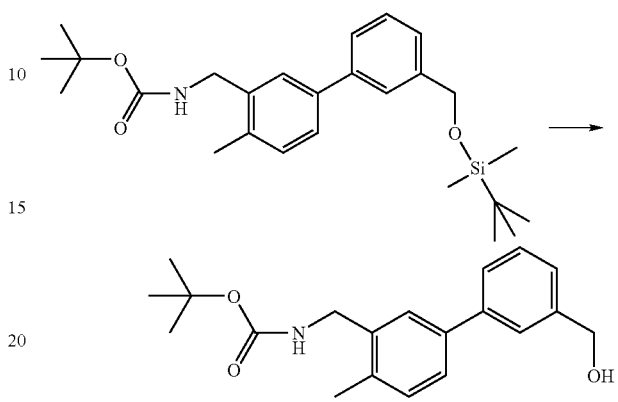

To a solution of 1,1-dimethylethyl {[3'-({[(1,1-dimethylethyl)(dimethyl)silyl]-oxy}methyl)-4-methyl-3-biphenylyl]methyl}carbamate (3.60 g, 8.2 mmol) in THF (30 mL), was added a solution of nBu$_4$NF (2.34 g, 9.0 mmol) in THF (20 mL). This mixture was stirred at room temperature over night. The solvent was removed under reduced pressure, and the residue was diluted with CH$_2$Cl$_2$ (50 mL), washed with water (15 mL×2), brine (15 mL×2), and dried over Na$_2$SO$_4$. The product 1,1-dimethylethyl {[3'-(hydroxymethyl)-4-methyl-3-biphenylyl]methyl}carbamate (1.5 g) was purified by flash column chomatography (PE:EA=4:1) (yield: 53%). $^1$H NMR (400 MHz, CDCl$_3$) δ 1.47 (s, 9H), 2.37 (s, 3H), 4.37 (d, J=5.6 Hz, 2H), 4.76 (m, 3H), 7.23-7.58 (m, 7H); $^{13}$C NMR (100 MHz, CDCl$_3$) δ 18.6, 28.4, 42.9, 65.3, 79.5, 125.6, 125.7, 126.2, 126.8, 129.0, 130.9, 135.5, 138.9, 141.2, 141.4, 155.8; HPLC: retention time: 14.965 min; purity: 95.4%; MS m/z 327 (M$^+$).

Example 64

1,1-Dimethylethyl [(3-bromo-2-methylphenyl)methyl]carbamate

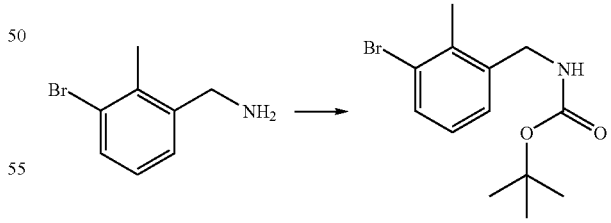

[(3-Bromo-2-methylphenyl)methyl]amine (4.0 g, 17.0 mmol) was suspended in CH$_2$Cl$_2$ (50 mL), then sodium carbonate (4.8 g, 45.3 mmol) was added. After stirred for 15 min, the solution of Boc$_2$O (4.0 g, 18.3 mmol) in CH$_2$Cl$_2$ (20 mL) was added, and then the mixture was stirred overnight. After the solvent was removed, the residue was dissolved in CH$_2$Cl$_2$ (40 mL). The solution was washed with water (15 mL), brine (15 mL) and dried over anhydrous Na$_2$SO$_4$. After silica column chomatography, (eluted with petroleum ether:

EtOAc=20:1 to 5:1), 1.3 g of the product, 1,1-dimethylethyl [(3-bromo-2-methylphenyl)methyl]carbamate, was obtained (yield: 35%). $^1$H NMR (400 MHz, CDCl$_3$): δ 1.45 (s, 9H), 2.40 (s, 3H), 4.34 (d, J=6.0 Hz, 2H), 4.71 (br, 1H), 7.02 (t, J=8.0 Hz, 1H), 7.19 (d, J=7.6 Hz, 1H), 7.48 (dd, J=7.8 Hz, J=0.6 Hz, 1H).

Example 65

1,1-Dimethylethyl {[3'-({[(1,1-dimethylethyl)(dimethyl)silyl]oxy}methyl)-2-methyl-3-biphenylyl]methyl}carbamate

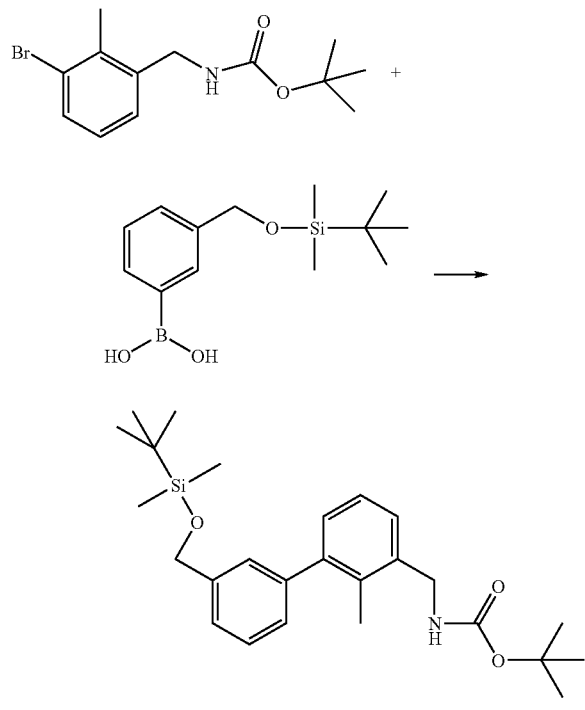

Pd(OAc)$_2$ (25.8 mg, 0.115 mmol), PPh$_3$ (120.6 mg, 0.46 mmol), K$_2$CO$_3$ (794.0 mg, 5.75 mmol) and 1,1-dimethylethyl [(3-bromo-2-methylphenyl)methyl]carbamate (1.15 g, 3.85 mmol) were suspended in anhydrous 1,4-dioxane (20 mL) under nitrogen. After the mixture was heated to 60° C. for 30 min, [3-({[(1,1-dimethylethyl)(dimethyl)silyl]oxy}methyl)phenyl]boronic acid (2.04 g, 4.62 mmol) was added. Then the mixture was stirred overnight at 100° C. After cooling to room temperature, the solvent was removed under reduced pressure. The residue was dissolved in EtOAc (20 mL), and then the solution was washed with water (7 mL), brine (7 mL), and dried over anhydrous Na$_2$SO$_4$. After silica column chomatography, eluting with PE:EA=30:1, 1.1 g of the product was obtained, as a colorless liquid (yield: 65%). $^1$H NMR (400 MHz, CDCl$_3$) δ 0.10 (s, 6H), 0.94 (s, 9H), 1.47 (s, 9H), 2.19 (s, 3H), 4.38 (d, J=5.2 Hz, 2H), 4.76 (br, 1H), 4.78 (s, 2H), 7.14-7.39 (m, 7H). $^{13}$C NMR (100 MHz, CDCl$_3$) δ −5.2, 16.1, 18.4, 25.9, 28.4, 43.4, 64.9, 79.4, 124.6, 125.6, 127.0, 127.9, 129.3, 133.7, 136.9, 141.2, 141.9, 143.0, 155.7; HPLC: retention time: 4.987 min; purity: 98.9% (HPLC).

Example 66

1,1-Dimethylethyl {[3-bromo-5-(methyloxy)phenyl]methyl}carbamate

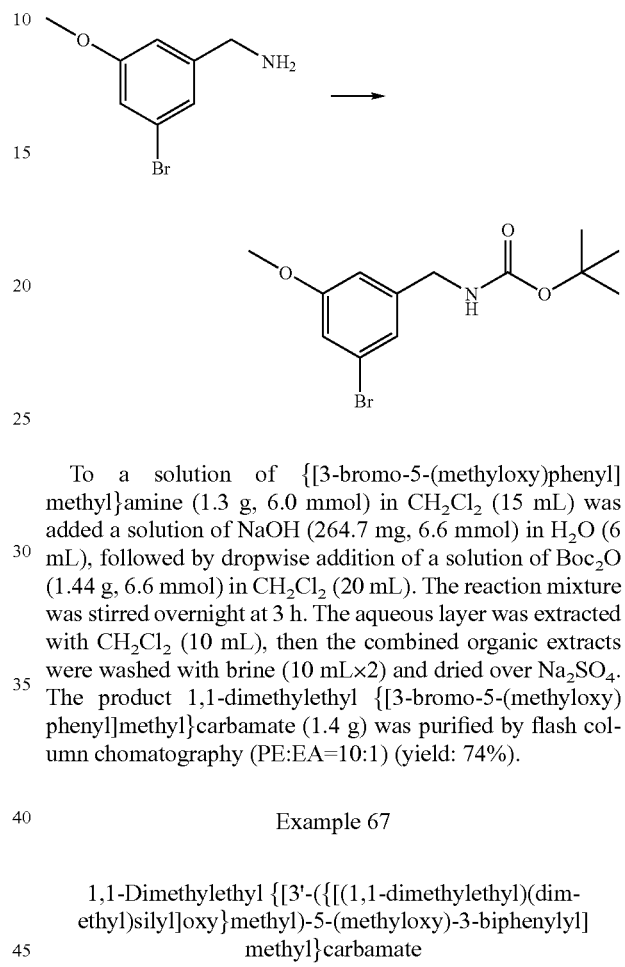

To a solution of {[3-bromo-5-(methyloxy)phenyl]methyl}amine (1.3 g, 6.0 mmol) in CH$_2$Cl$_2$ (15 mL) was added a solution of NaOH (264.7 mg, 6.6 mmol) in H$_2$O (6 mL), followed by dropwise addition of a solution of Boc$_2$O (1.44 g, 6.6 mmol) in CH$_2$Cl$_2$ (20 mL). The reaction mixture was stirred overnight at 3 h. The aqueous layer was extracted with CH$_2$Cl$_2$ (10 mL), then the combined organic extracts were washed with brine (10 mL×2) and dried over Na$_2$SO$_4$. The product 1,1-dimethylethyl {[3-bromo-5-(methyloxy)phenyl]methyl}carbamate (1.4 g) was purified by flash column chomatography (PE:EA=10:1) (yield: 74%).

Example 67

1,1-Dimethylethyl {[3'-({[(1,1-dimethylethyl)(dimethyl)silyl]oxy}methyl)-5-(methyloxy)-3-biphenylyl]methyl}carbamate

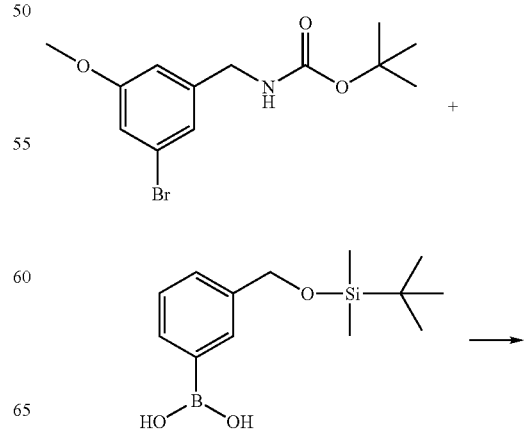

115

-continued

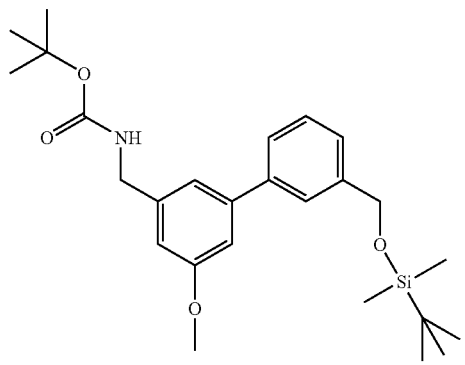

1,1-dimethylethyl {[3-bromo-5-(methyloxy)phenyl]methyl}carbamate (1.4 g, 4.43 mmol), Pd(OAc)₂ (70.0 mg, 0.14 mmol), dicyclohexyl[2'-(methyloxy)-1,1'-binaphthalen-2-yl]phosphane (84.0 mg, 0.175 mmol) and K₃PO₄ (1.2 g, 5.31 mmol) were dissolved in dioxane (30 mL). The mixture was heated at 80° C. for 30 min, and then [3-({[(1,1-dimethylethyl)(dimethyl)silyl]oxy}methyl)phenyl]boronic acid (1.5 g, 5.76 mmol) was added. The mixture reaction was stirred at reflux for two days. The solvent was removed under reduced pressure, then the residue diluted with CH₂Cl₂ (100 mL). The organic layer was washed with water (20 mL), brine (20 mL), and dried over Na₂SO₄. The product 1,1-dimethylethyl[3'-({[(1,1-dimethylethyl)(dimethyl)silyl]oxy}methyl)-5-(methyloxy)-3-biphenylyl]methyl}carbamate (1.5 g) was purified by flash column chomatography (PE:EA=15:1) (yield: 74%).

Example 68

1,1-Dimethylethyl {[3'-(hydroxymethyl)-5-(methyloxy)-3-biphenylyl]methyl}carbamate

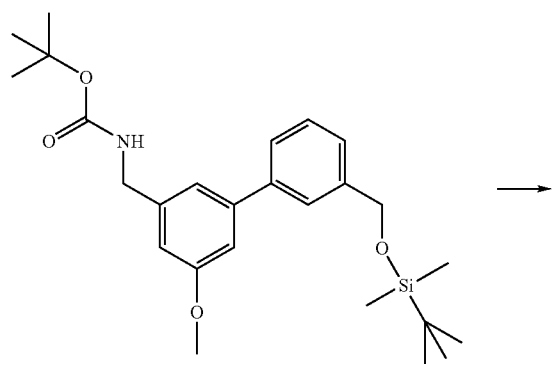

116

-continued

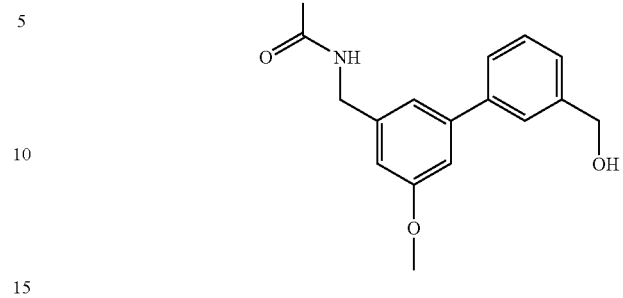

To a solution of 1,1-dimethylethyl {[3'-({[(1,1-dimethylethyl)(dimethyl)silyl]oxy}methyl)-5-(methyloxy)-3-biphenylyl]methyl}carbamate (1.5 g, 3.28 mmol) in THF (20 mL) was added a solution of nBu₄NF (0.94 g, 3.61 mmol) in THF (10 mL). This mixture was stirred at room temperature overnight. After the solvent was removed under reduced pressure, the residue was diluted with EtOAc (30 mL). The organic layer was washed with water (10 mL×2), brine (10 mL×2), and dried over Na₂SO₄. The product, 1,1-dimethylethyl {[3'-(hydroxymethyl)-5-(methyloxy)-3-biphenylyl]methyl}carbamate, (0.9 g) was purified by flash column chomatography (PE:EA=3:1). (Yield: 80%). ¹H NMR (400 MHz, CDCl₃) δ 1.47 (s, 9H), 3.86 (s, 3H), 4.35 (d, J=7.6 Hz, 2H), 4.76 (s, 2H), 4.89 (s, 1H), 6.83 (s, 1H), 7.02 (s, 1H), 7.09 (s, 1H), 7.34-7.58 (m, 4H); ¹³C NMR (100 MHz, CDCl₃) δ 28.4, 44.7, 55.4, 65.2, 79.6, 111.9, 118.7, 125.8, 126.1, 126.4, 129.0, 140.9, 141.2, 141.5, 142.8, 156.0, 160.3. HPLC: retention time: 11.558 min; purity: 98.7%; MS: m/z 343 (M⁺).

Example 69

1,1-Dimethylethyl {[3-bromo-2-(methyloxy)phenyl]methyl}carbamate

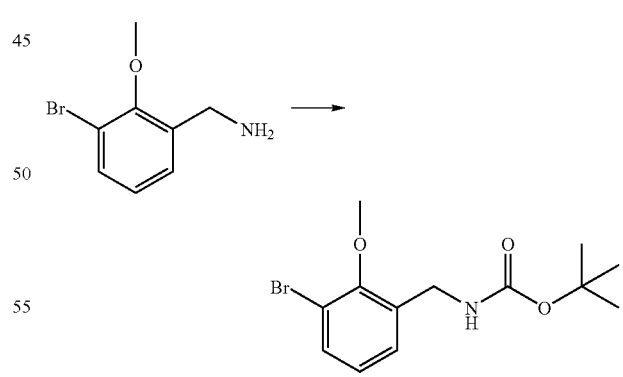

To a suspension of {[3-bromo-2-(methyloxy)phenyl]methyl}amine (5.0 g, 19.8 mmol) and Na₂CO₃ (5.3 g, 49.5 mmol) in CH₂Cl₂ (100 mL) was added dropwise a solution of Boc₂O (4.8 g, 21.8 mmol) in CH₂Cl₂ (10 mL). Then the reaction mixture was stirred overnight at room temperature. After filtration, the solid was washed with CH₂Cl₂ (50 mL×2), and then the filtrate was washed with water (70 mL×2), brine (70 mL×2) and dried over Na₂SO₄. After removing the solvent, 5.5 g of 1,1-dimethylethyl {[3-bromo-2-(methyloxy)phenyl]methyl}carbamate was obtained (yield: 87.8%).

Example 70

1,1-Dimethylethyl {[3'-({[(1,1-dimethylethyl)(dimethyl)silyl]oxy}methyl)-2-(methyloxy)-3-biphenylyl]methyl}carbamate

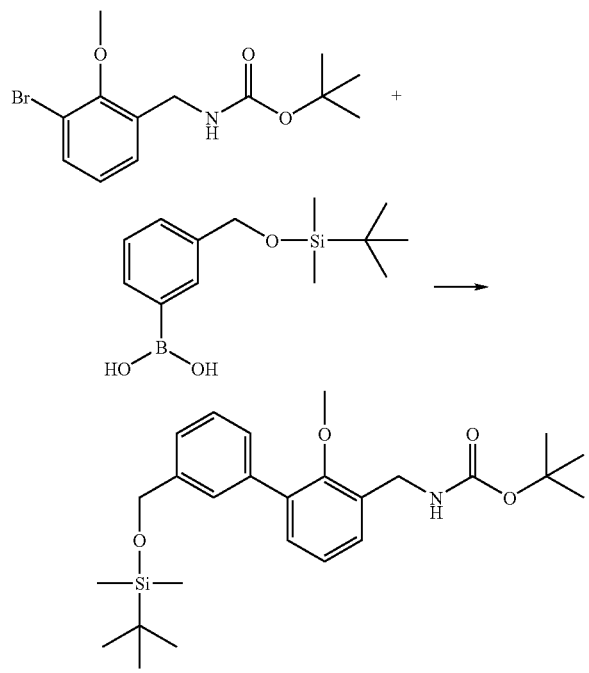

1,1-Dimethylethyl {[3-bromo-2-(methyloxy)phenyl]methyl}carbamate (5.2 g, 16.4 mmol), Pd(OAc)$_2$ (110.4 mg, 0.49 mmol), dicyclohexyl[2'-(methyloxy)-1,1'-binaphthalen-2-yl]phosphane (317.2 mg, 0.66 mmol) and K$_3$PO$_4$ (4.2 g, 19.7 mmol) were dissolved in dioxane (60 mL). The mixture was heated at 80° C. for 30 min, and then [3-({[(1,1-dimethylethyl)(dimethyl)silyl]oxy}methyl)phenyl]boronic acid (5.2 g, 19.7 mmol) was added. The mixture reaction was stirred at reflux overnight. The solvent was removed under reduced pressure, then the residue was diluted with CH$_2$Cl$_2$ (100 mL). The organic layer was washed with water (30 mL), brine (30 mL), and dried over Na$_2$SO$_4$. The product 1,1-dimethylethyl {[3'-({[(1,1-dimethylethyl)(dimethyl)silyl]oxy}methyl)-2-(methyloxy)-3-biphenylyl]-methyl}carbamate (5.0 g) was purified by flash column chomatography (PE:EA=15:1) (yield: 72%). $^1$H NMR (400 MHz, CDCl$_3$) δ 0.11 (s, 6H), 0.94 (s, 9H), 1.46 (s, 9H), 3.37 (s, 3H), 4.40 (d, J=6 Hz, 2H), 4.80 (s, 2H), 5.04 (s, 1H), 7.12-7.51 (m, 7H); $^{13}$C NMR (100 MHz, CDCl$_3$) δ −5.2, 18.4, 25.9, 28.4, 40.3, 60.4, 65.0, 124.2, 125.0, 126.6, 127.5, 128.3, 128.4, 130.6, 132.3, 134.8, 138.2, 141.5, 155.8; HPLC: retention time: 4.348 min; purity: 99.9%; MS m/z 453 (M$^+$), 344 (M$^+$-TBS).

Example 71

1,1-Dimethylethyl [(3-bromo-5-cyanophenyl)methyl]carbamate

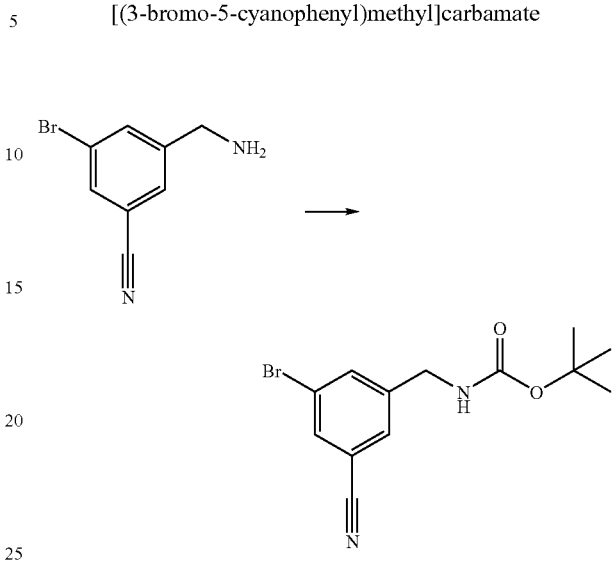

To a suspension of 3-(aminomethyl)-5-bromobenzonitrile (1.6 g, 6.5 mmol) and Na$_2$CO$_3$ (1.7 g, 16.2 mmol) in CH$_2$Cl$_2$ (25 mL) was added dropwise a solution of Boc$_2$O (1.6 g, 7.1 mmol) in CH$_2$Cl$_2$ (10 mL). Then the reaction mixture was stirred overnight at room temperature. After filtration, the solid was washed with CH$_2$Cl$_2$ (10 mL×2), and then the filtrate was washed with water (20 mL×2), brine (20 mL×2) and dried over Na$_2$SO$_4$. After removing the solvent, 1.9 g of 1,1-dimethylethyl [(3-bromo-5-cyanophenyl)methyl]carbamate was obtained (yield: 94.5%).

Example 72

1,1-Dimethylethyl {[5-cyano-3'-({[dimethyl(1-methylethyl)-silyl]oxy}methyl)-3-biphenylyl]methyl}carbamate-ethane (1:1)

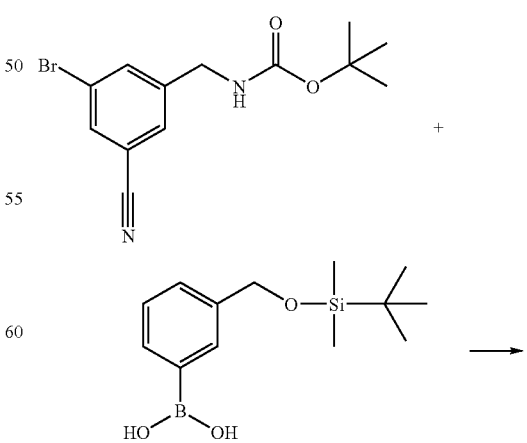

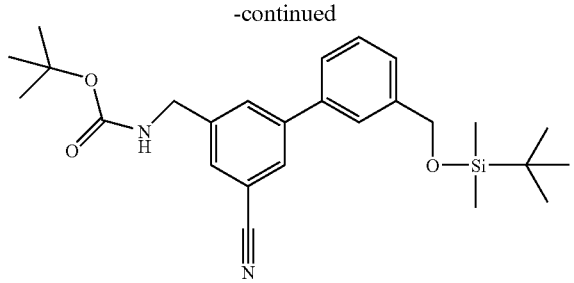

1,1-Dimethylethyl [(3-bromo-5-cyanophenyl)methyl]carbamate (1.90 g, 6.11 mmol), Pd(OAc)$_2$ (76 mg), PPh$_3$ (228 mg) and K$_2$CO$_3$ (1.27 g, 9.16 mmol) were dissolved in dioxane (50 mL). The mixture was heated at 70° C. for 30 min, and then [3-({[(1,1-dimethylethyl)(dimethyl)silyl]oxy}methyl)phenyl]boronic acid (2.11 g, 7.94 mmol) was added. The mixture reaction was stirred at reflux overnight. The solvent was removed under reduced pressure, then the residue diluted with CH$_2$Cl$_2$ (100 mL). The organic layer was washed with water (30 mL) and brine (30 mL), and dried over Na$_2$SO$_4$. The product, 1,1-dimethylethyl {[5-cyano-3'-({[dimethyl(1-methylethyl)silyl]oxy}methyl)-3-biphenylyl]methyl}carbamate-ethane was purified by flash column chomatography (2.0 g, yield: 72%). $^1$H NMR (400 MHz, CDCl$_3$) δ 0.12 (s, 6H), 0.96 (s, 9H), 1.47 (s, 9H), 4.41 (d, J=6 Hz, 2H), 4.81 (s, 2H), 7.38-7.44 (m, 3H), 7.50 (s, 1H), 7.55 (s, 1H), 7.70 (s, 1H), 7.75 (s, 1H); $^{13}$C NMR (100 MHz, CDCl$_3$) δ −5.2, 18.4, 25.9, 28.3, 43.4, 64.7, 80.1, 113.1, 118.7, 124.7, 125.6, 126.1, 129.0, 129.2, 129.6, 130.4, 133.4, 134.8, 138.6, 141.2, 142.5, 142.9, 155.9; HPLC: retention time: 4.670 min; purity: 94.4%; MS m/z 453 (M$^+$, 32), 339 (M$^+$-TBS, 100).

Example 73

[5'-(Aminomethyl)-2'-fluoro-3-biphenylyl]methanol

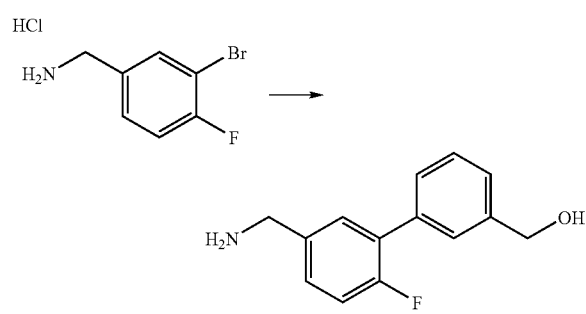

[(3-Bromo-4-fluorophenyl)methyl]amine hydrochloride (0.795 g, 3.29 mmol), [3-(hydroxymethyl)phenyl]boronic acid (0.5 g, 3.29 mmol), potassium carbonate (2.275 g, 16.5 mmol), and tetrakis(triphenylphosphine)palladium(0) (0.114 g, 0.1 mmol) were combined in dioxane (10 mL) and water (3 mL). The mixture was microwaved at 150° C. for 30 min. The solvents were evaporated and the residue taken up in EtOAc and H$_2$O. The aqueous phase was extracted 2× with EtOAc. The combined organic phases were dried over anhydrous Na$_2$SO$_4$, filtered and evaporated. The residue was purified by CombiFlash on a silica gel column eluting with 0-100% CH$_2$Cl$_2$/CH$_2$Cl$_2$: 20% MeOH:1% NH$_4$OH to afford the title compound as a viscous oil. LC-MS m/z 231.8 (M+H)$^+$, 1.03 min (ret time).

Example 74

3-Bromo-4-methylbenzamide

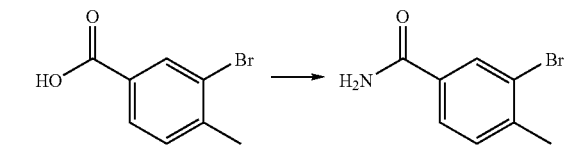

3-Bromo-4-methylbenzoic acid (5 g, 23.25 mmol) was suspended in CH$_2$Cl$_2$ (100 mL) and stirred under argon at room temperature. Oxalyl chloride (5.9 g, 46.5 mmol) was added followed by DMF (20 µL). Gas evolution began, and the mixture was stirred for 2 days during which time complete solution occurred. The solvents were pumped off and toluene was added and stripped off to remove excess oxalyl chloride. The residue was taken up in EtOAc and added to concentrated ammonium hydroxide (20 mL). This was stirred for thirty mins. The phases were separated and the organic phase washed 1× with brine, dried over anhydrous Na$_2$SO$_4$, filtered, and evaporated. The residue was crystallized from EtOAc/hexane and dried under vacuum to afford the title compound as a white crystalline solid. LC-MS m/z 213.8 (M+H)$^+$, 1.41 min (ret time).

Example 75

[(3-Bromo-4-methylphenyl)methyl]amine

To 3-bromo-4-methylbenzamide (2.14 g, 10 mmol) in THF (10 mL) was added borane dimethyl sulfide complex (2 mL, 20 mmol) at 0° C. The mixture was then heated to 50° C. for 16 h. Additional borane dimethyl sulfide complex (1 mL, 10 mmol) was added and heating continued at 60° C. for an additional 5 days. The reaction mixture was cooled to room temperature and ethanol was cautiously added. When bubbling ceased, 1N HCl was added until the pH was ~2. This mixture was stirred at 50° C. for 4 h. The mixture was partitioned between EtOAc and water. The aqueous was washed 3× with EtOAc. The aqueous was then adjusted to pH 10 with 2N NaOH and extracted 3× with EtOAc. The combined organics phases were dried over anhydrous Na$_2$SO$_4$, filtered, and evaporated to afford the title compound. LC-MS m/z 199.8 (M+H)$^+$, 1.01 min (ret time).

Example 76

{[3-Bromo-4-(methyloxy)phenyl]methyl}amine

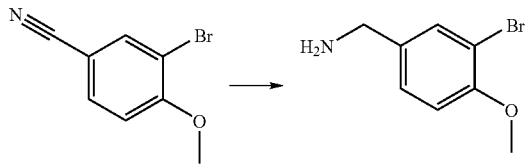

3-Bromo-4-(methyloxy)benzonitrile (2.12 g, 10 mmol), THF (30 mL), and 1.5 M borane in THF (30 mL, 45 mmols) were combined and stirred under argon at reflux, Then additional 1.5 M borane in THF (30 mL, 45 mmols) was added and refluxing was continued. THF (30 mL), and 1.5 M borane in THF (30 mL, 45 mmols) was again added and the mixture refluxed for a total of ten days to drive the reaction to completion. Reaction worked up by the cautious addition of ethanol followed by 1N HCl until the pH was 2. The mixture was then heated to 50° C. for 4 h. The solvents were pumped off and the residue partitioned between EtOAc and water. The aqueous phase was washed 3× with EtOAc, and adjusted to pH 10 by the addition of 2.5 N NaOH. The aqueous phase was extracted 3× with EtOAc. The combined organic phases were dried over anhydrous $Na_2SO_4$, filtered and evaporated to give the title compound.

Example 77

3-Bromo-4-chlorobenzamide

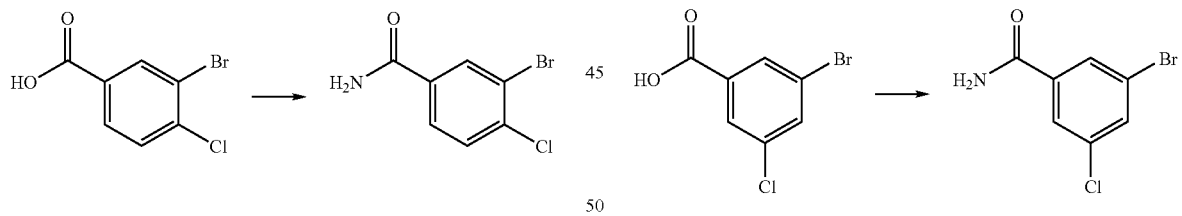

3-Bromo-4-chlorobenzoic acid (2.35 g, 10 mmol) was suspended in $CH_2Cl_2$ (50 mL) and stirred under argon at room temperature. Oxalyl chloride (2.53 g, 20 mmol) was added followed by DMF (10 μL). Gas evolution began, and the mixture was stirred until gas evolution ceased. The solvents were pumped off and toluene was added and stripped off to remove excess oxalyl chloride. The residue was taken up in EtOAc and added to concentrated ammonium hydroxide (10 mL). This was stirred for 30 min. The phases were separated and the organic washed 1× with brine dried over anhydrous $Na_2SO_4$, filtered, and evaporated. The residue was crystallized from EtOAc/hexane to give the title compound as a white crystalline solid. LC-MS m/z 233.7 $(M+H)^+$, 1.54 min (ret time); mp 146-147° C.; analytical HPLC shows 100% purity, (ret time: 11.835 min).

Example 78

[(3-Bromo-4-chlorophenyl)methyl]amine

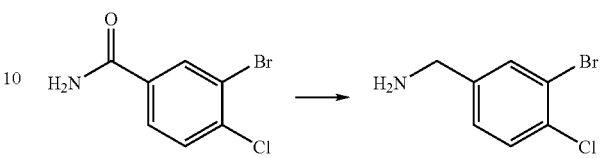

To 3-bromo-4-chlorobenzamide (1.6 g, 6.8 mmol) in THF (10 mL) was added borane dimethyl sulfide complex (1.36 mL, 13.6 mmol) at room temperature. The mixture was then heated to 60° C. for 8 days. The solvent was pumped off and the reaction cautiously quenched with ethanol. When bubbling ceased, 1N HCl was added until the pH was ~2. The mixture was stirred at 50° C. for 4 h. The mixture was partitioned between EtOAc and water. The aqueous phase was washed 3× with EtOAc. The aqueous phase was then adjusted to pH 10 with 2N NaOH and extracted 3× with EtOAc. The combined organics phases were washed with brine, dried over anhydrous $Na_2SO_4$, filtered, and evaporated to afford the title compound as a clear oil. LC-MS m/z 219.6 $(M+H)^+$, 1.41 min (ret time).

Example 79

3-Bromo-5-chlorobenzamide

3-Bromo-5-chlorobenzoic acid (2.35 g, 10 mmol) was suspended in $CH_2Cl_2$ (50 mL) and stirred under argon at room temperature. Oxalyl chloride (2.53 g, 20 mmol) was added followed by DMF (10 μL), and the mixture stirred overnight. The solvents were pumped off. The residue was taken up in EtOAc and added to concentrated ammonium hydroxide (10 mL). This was stirred for thirty mins. The phases were separated and the organic phase washed 1× with brine, dried over anhydrous $Na_2SO_4$, filtered, and evaporated. The residue was crystallized from EtOAc/hexane to give the title compound as a white crystalline solid. LC-MS m/z 233.7 $(M+H)^+$, 1.57 min (ret time); analytical HPLC shows 96.5% purity, (ret time: 12.131 min).

Example 80

[(3-Bromo-5-chlorophenyl)methyl]amine

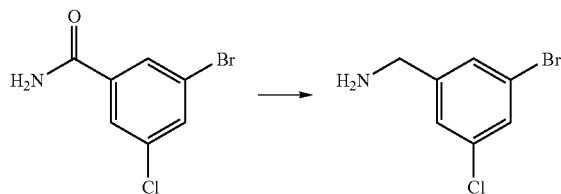

To 3-bromo-5-chlorobenzamide (1.6 g, 6.8 mmol) in THF (10 mL) was added borane dimethyl sulfide complex (1.36 mL, 13.6 mmol) at room temperature. The mixture was then heated to 60° C. for 7 days. The solvent was pumped off and the reaction cautiously quenched with ethanol. When the bubbling ceased, 1N HCl was added until the pH was ~2. The mixture was stirred at 50° C. for 4 h. The mixture was partitioned between EtOAc and water. The aqueous layer was washed 3× with EtOAC. The aqueous phase was then adjusted to pH 10 with 2N NaOH and extracted 3× with EtOAc. The combined organics phases were dried over anhydrous $Na_2SO_4$, filtered, and evaporated to give the title compound as a clear oil. LC-MS m/z 219.7 (M+H)$^+$, 1.42 min (ret time).

Example 81

1,6-Diethyl-5-[(methylamino)methyl]-N-(tetrahydro-2H-pyran-4-yl)-1H-pyrazolo[3,4-b]pyridin-4-amine

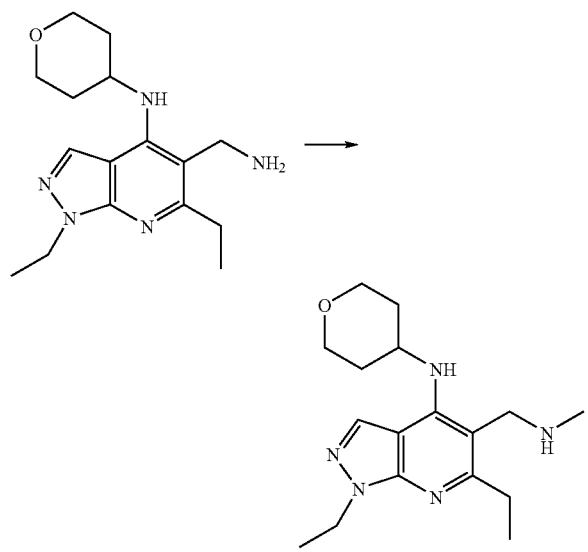

To the solution of 5-(aminomethyl)-1,6-diethyl-N-(tetrahydro-2H-pyran-4-yl)-1H-pyrazolo[3,4-b]pyridine-4-amine (0.303 g, 1.0 mmol) in THF (1 mL) was added $Boc_2O$ (0.229 g, 1.05 mmol). This mixture was stirred at room temperature for 30 mins and then LAH (5.0 mL, 1.0 M in THF) was added, and that mixture heated with a microwave machine at 100° C. for 30 mins. The reaction was then quenched with $Na_2SO_4$ (sat. aq.) slowly, filtered, dried over $Na_2SO_4$, filtered, and concentrated to afford 0.252 g (79%) of the title compound. LC-MS m/z 318 (M+H)$^+$.

Example 82

{3-[(4-{[(1,1-dimethylethyl)oxy]carbonyl}-1-piperazinyl)methyl]phenyl}boronic acid

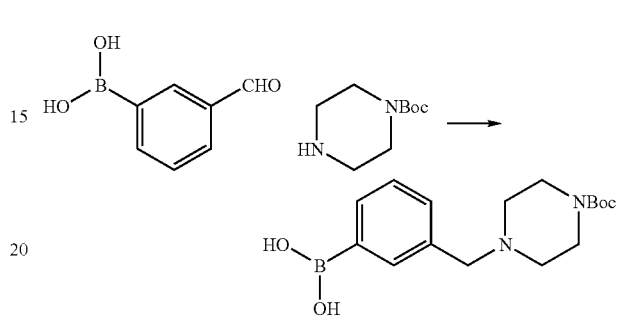

To the solution of (3-formylphenyl)boronic acid (3.0 g, 20.0 mmol) in DCM (100 mL) was added 1,1-dimethylethyl 1-piperazinecarboxylate (3.91 g, 21.0 mmol), and NaBH(OAc)$_3$ (6.36 g, 30.0 mmol), and the mixture stirred at room temperature for 17 h. The organic layer was diluted with EtOAc (100 mL), washed with $H_2O$ (30 mL), dried over $Na_2SO_4$, filtered and concentrated to afford 7.72 g (quantitative) of the title compound. LC-MS m/z 321 (M+H)$^+$.

Example 83

1,1-Dimethylethyl 4-{[5'-(aminomethyl)-2'-fluoro-3-biphenylyl]methyl}-1-piperazinecarboxylate

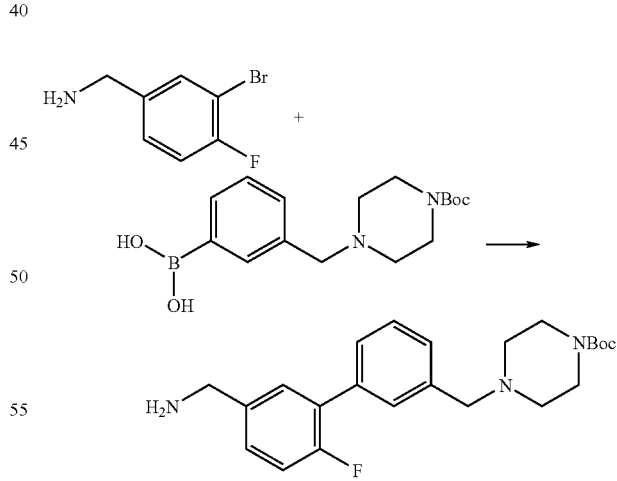

To two vials which each contained a solution of [(3-bromo-4-fluorophenyl)methyl]amine hydrochloric salt (0.601 g, 2.5 mmol) in p-dioxane/$H_2O$ (15/5 mL) was each added {3-[(4-{[(1,1-dimethylethyl)oxy]carbonyl}-1-piperazinyl)methyl]phenyl}boronic acid (1.2 g, 3.75 mmol), Pd(PPh$_3$)$_4$ (145 mg, 0.125 mmol), and $K_2CO_3$ (1.38 g, 10 mmol). The resulting mixture was heated in a microwave machine at about 15° C. for about 15 mins. The organic layer of both vials was separated, combined, concentrated and purified by CombiFlash chomatograph to afford 1.98 g (99%) of the title compound. LC-MS m/z 400 (M+H)+.

Example 84

1,1-Dimethylethyl [(3-bromo-4-fluorophenyl)methyl]carbamate

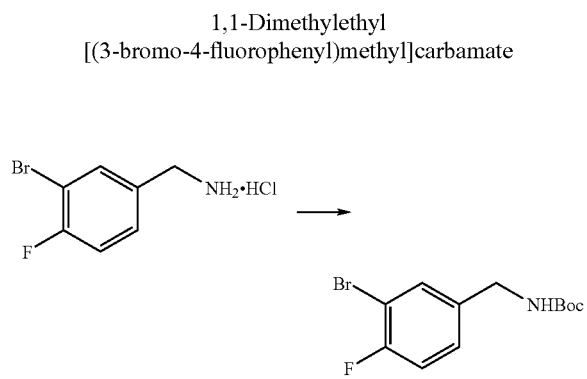

To the solution of [(3-bromo-4-fluorophenyl)methyl] amine hydrochloric salt (0.64 g, 2.0 mmol) in THF (10 mL) was added NaOH (2 mL, 1.0 M, 2.0 mmol). This mixture was stirred for 10 mins after which was added Boc$_2$O (0.523 g, 2.4 mmol). Then the mixture was stirred for another 2 h. The organic layer was then separated, dried, filtered, concentrated and purified by CombiFlash chomatograph to afford 0.66 g (quantitative) of the title compound. LC-MS m/z 609 (2M+H)+.

Example 85

[(3-bromo-4-fluorophenyl)methyl]methylamine

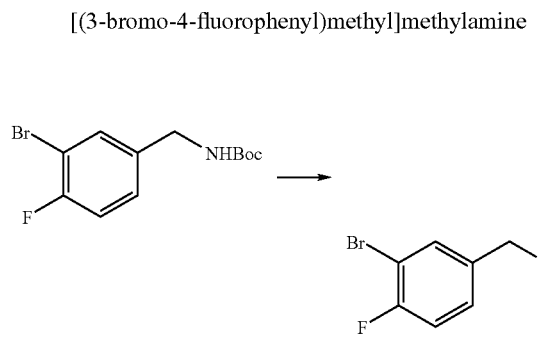

To the solution of 1,1-dimethylethyl [(3-bromo-4-fluorophenyl)methyl]carbamate (0.755 g, 2.48 mmol) in THF (1 mL) was added BH$_3$.THF (12.5 mL, 1.0 M in THF). The mixture was heated in a microwave machine at about 8° C. for about 30 mins twice. The reaction was then quenched with HCl (10 mL, 1 N) slowly, stirred for 2 h at room temperature, basified with NaHCO$_3$ to pH ~9, and extracted with EtOAc (50+20 mL). The organic layer was washed with brine, dried over Na$_2$SO$_4$, filtered, concentrated to afford 0.52 g (96%) of the title compound. LC-MS m/z 218 (M+H)+.

Example 86

1,1-Dimethylethyl 4-({2'-fluoro-5'-[(methylamino)methyl]-3-biphenylyl}methyl)-1-piperazine carboxylate

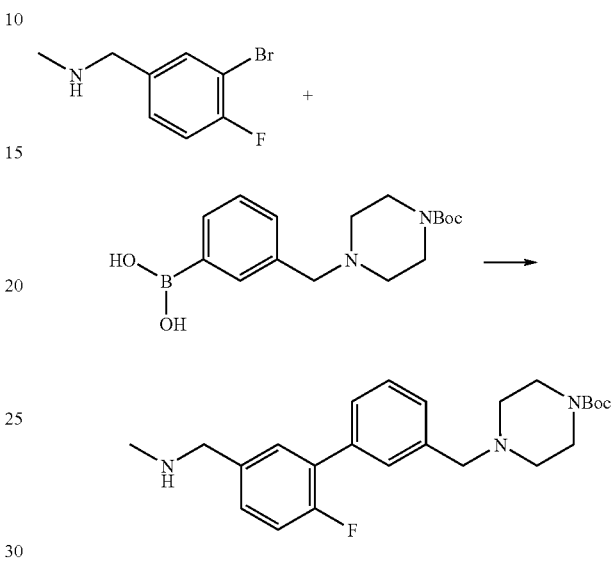

To the solution of [(3-bromo-4-fluorophenyl)methyl]methylamine (0.52 g, 2.39 mmol) in p-dioxane/H$_2$O (15/5 mL) was added {3-[(4-{[(1,1-dimethylethyl)oxy]carbonyl}-1-piperazinyl)methyl]phenyl}boronic acid (1.15 g, 3.60 mmol), Pd(PPh$_3$)$_4$ (139 mg, 0.12 mmol), and K$_2$CO$_3$ (1.33 g, 9.6 mmol). The result mixture was heated in a microwave machine at 150° C. for 15 mins. The organic layer was separated and concentrated. The residue was redissolved in EtOAc (~70 mL), washed with H$_2$O (20 mL), brine (20 mL), dried over Na$_2$SO$_4$, filtered, concentrated and purified by CombiFlash chomatograph to afford 0.65 g (66%) of the title compound. LC-MS m/z 414 (M+H)+.

Example 87

5-(Chloromethyl)-1,6-diethyl-N-(tetrahydro-2H-pyran-4-yl)-1H-pyrazolo[3,4-b]pyridin-4-amine

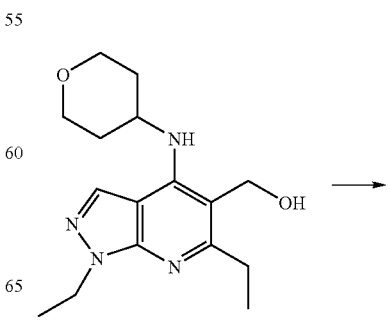

-continued

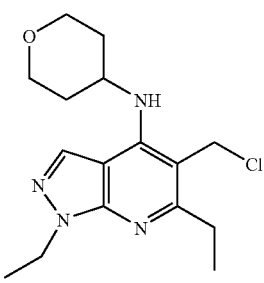

To the solution of thionyl chloride (1.46 mL, 20.0 mmol) was added [1,6-diethyl-4-(tetrahydro-2H-pyran-4-ylamino)-1H-pyrazolo[3,4-b]pyridin-5-yl]methanol (0.609 g, 2.0 mmol) slowly. The mixture was stirred at room temperature for about 30 mins before it was concentrated on rotavap under vacuum. DCM (5 ml) was added to the residue and concentrated on rotavap twice to afford 0.386 g (60%) of the title compound.

Example 88

1,1-Dimethylethyl [(5-fluoro-3'-formyl-3-biphenylyl)methyl]carbamate

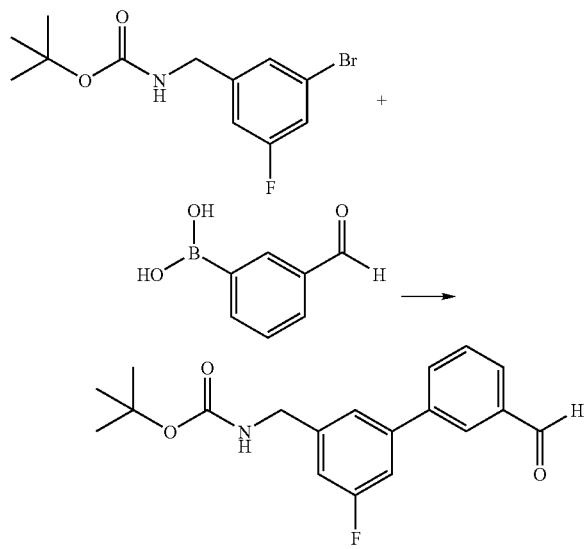

A mixture of 1,1-dimethylethyl [(3-bromo-5-fluorophenyl)methyl]carbamate (300 mg, 0.99 mmol), 3-formylphenyl Boronic acid (194 mg, 1.30 mmol), Na$_2$CO$_3$ (316 mg, 2.98 mmol), Pd(PPh$_3$)$_4$ (58 mg, 0.05 mmol), and water (2 mL) in dioxane (6 mL) was degassed for 5 min. and then heated in a microwave oven for about 30 min at about 150° C. It was quenched with water and then extracted with ethyl acetate twice. The combined organic layers were washed with water and brine. The organic layer was filtered though a syringe filter to get rid of the Pd and then concentrated to give a crude residue. It was then purified with Combi Flash companion eluting with 40% ethyl acetate in hexane. The product fractions were combined and concentrated under vacuum to give 1,1-dimethylethyl [(5-fluoro-3'-formyl-3-biphenylyl)methyl]carbamate as an oil. LC-MS m/z 330 (M+H)$^+$.

Example 89

1,6-Diethyl-4-(tetrahydro-2H-pyran-4-ylamino)-1H-pyrazolo[3,4-b]pyridine-5-carboxylic acid A mixture of ethyl 1,6-diethyl-4-(tetrahydro-2H-pyran-4-ylamino)-1H-pyrazolo[3,4-b]pyridine-5-carboxylate (2 g, 4.30 mmol), LiOH (901 mg, 21.48 mmol), water (4 mL) and methanol (8 mL) was heated in a microwave oven for about 20 min at about 80° C. The reaction mixture was diluted with water and then washed with ethyl acetate to get rid of starting material. The aqueous layer was then acidified with 2N HCl, saturated with brine and then extracted with a mixture of DCM and IPA (3:1 ratio) twice. The combined organic layer was dried under vacuum to give the crude product. It was then triturated with ether to give pure product 1,6-diethyl-4-(tetrahydro-2H-pyran-4-ylamino)-1H-pyrazolo[3,4-b]pyridine-5-carboxylic acid as a yellow solid (2.78 g, 95%). LC-MS m/z 319 (M+H)$^+$.

Example 90

1,1-Dimethylethyl 4-{[3'-(aminomethyl)-3-biphenylyl]methyl}-1-piperazinecarboxylate

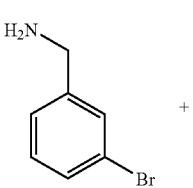

129

-continued

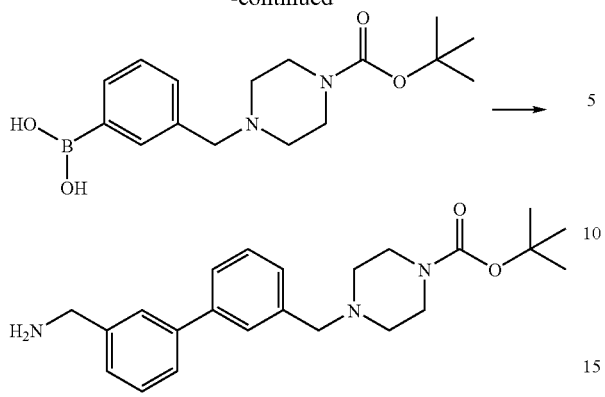

To a solution of [(3-bromophenyl)methyl]amine hydrochloric salt (0.556 g, 2.5 mmol) in 1,4-dioxane (15 mL) and H$_2$O (5 mL) was added {3-[(4-{[(1,1-dimethylethyl)-oxy]carbonyl}-1-piperazinyl)methyl]phenyl}boronic acid (1.041 g, 3.25 mmol), Pd(PPH$_3$)$_4$ (0.144 g, 0.125 mmol), and K$_2$CO$_3$ (1.382 g, 10 mmol). This mixture was heated in a microwave oven at about 150° C. for about 15 mins. The organic layer was separated, dried using a Glas-Col evaporator (Sigma-Aldrich), and was then purified by CombiFlash chromatograph to afford the title compound 0.798 g (84%). LC-MS m/z 382 (M+H)$^+$.

Example 91

1,1-Dimethylethyl 4-{[3-(4,4,5,5-tetramethyl-1,3,2-dioxaborolan-2-yl)phenyl]methyl}-1-piperidinecarboxylate

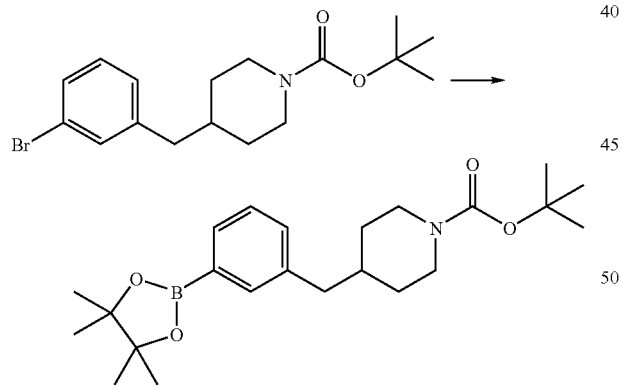

To the solution of 1,1-dimethylethyl 4-[(3-bromophenyl)methyl]-1-piperidinecarboxylate (191 mg, 0.539 mmol) in DMF (1 mL) was added PdCl$_2$(dppf) (15.78 mg, 0.022 mmol), Bis(pinacolato)diboron (144 mg, 0.566 mmol), and potassium acetate (106 mg, 1.078 mmol). This mixture was placed in a microwave and heated at about 100° C. for about 1 h. The reaction mixture was diluted with EtOAc (10 mL), washed with H$_2$O (3×3 mL), brine (3 mL) and dried over Na$_2$SO$_4$. The mixture was filtered, concentrated and purified by CombiFlash chromatograph to afford the title compound 0.162 g (74%). LC-MS m/z 402 (M+H)$^+$.

130

Example 92

1,1-Dimethylethyl 4-[(3-bromophenyl)methyl]-1-piperidinecarboxylate

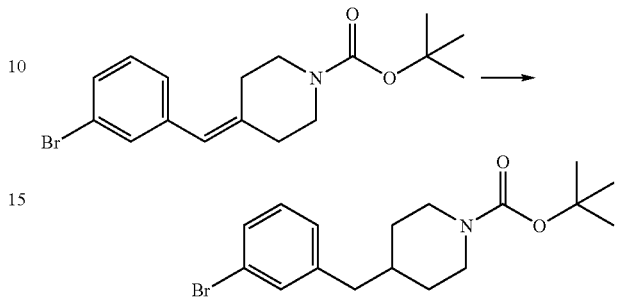

To a solution of 1,1-dimethylethyl 4-[(3-bromophenyl)methylidene]-1-piperidine-carboxylate (201 mg, 0.571 mmol) in THF (1 mL) was applied onto an H-Cube hydrogenation device (H-Cube, LLC, Dallas, Tex., USA; http://www.h-cubeinc.com/) 10% PD/C at a flow rate of 1 mL/min and 1 atm H$_2$. The mixture was concentrated to afford the title compound 0.1909 g (94%). LC-MS m/z 354 (M+H)$^+$.

Example 93

1,1-Dimethylethyl 4-[(3-bromophenyl)methylidene]-1-piperidinecarboxylate

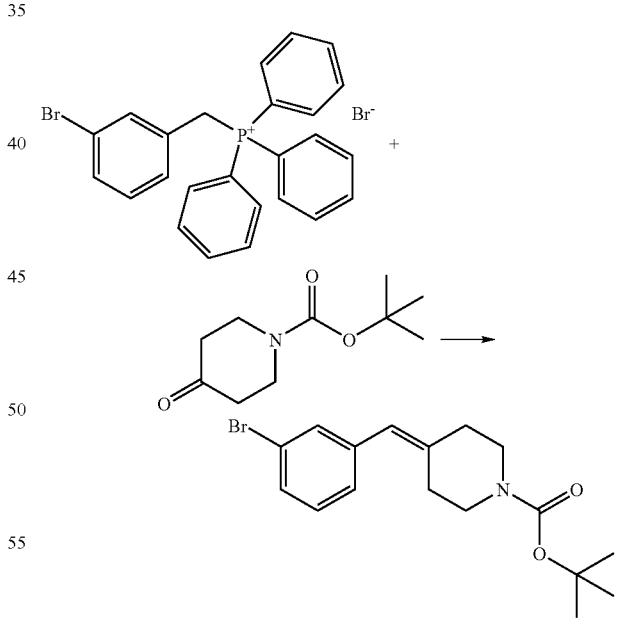

To [(3-Bromophenyl)methyl](triphenyl)phosphonium bromide (1.13 mg, 2.2 mmol) in DMF (4 mL) was added NaH (52.8 mg, 2.2 mmol). This mixture was stirred at RT for 5 min, then 1,1-dimethylethyl 4-oxo-1-piperidinecarboxylate (400 mg, 2.0 mmol) was added and the pot stirred at RT for 1 h. The resultant mixture was diluted with Et$_2$O (25 mL), washed with H$_2$O (12+2×8 mL), brine (8 mL), dried over NaSO$_4$, and filtered. The mixture was concentrated and purified with CombiFlash chromatograph to afford the title compound (0.2014 g, 28%). LC-MS m/z 352 (M+H)+.

Example 94

[(3-Bromophenyl)methyl](triphenyl)phosphonium bromide

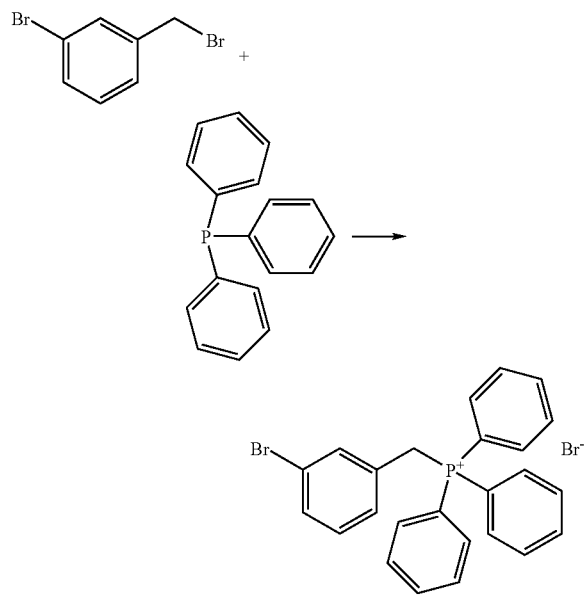

Triphenylphosphane (2.62 g, 10.0 mmol) was added to 1-bromo-3-(bromomethyl)benzene (2.5 g, 10.0 mmol) in toluene (15 mL) and the mixture heated in a microwave at 100° C. for about 1 h. The mixture was filtered to afford the title compound (4.55 g, 89%). LC-MS m/z 431 (cationic part)+.

Example 95

1-(3-Bromophenyl)-N-methylmethanamine

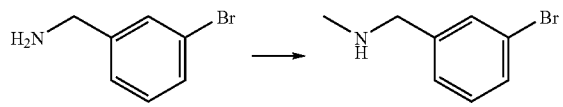

To bromobenzylamine (0.890 g, 4 mmol) in THF (9 mL) was added NaOH (4.20 mL, 1 N, 4.20 mmol) and the solution was stirred at room temperature for 5 mins, when BOC$_2$O (0.975 mL, 4.20 mmol) was added. This mixture was stirred for an additional 30 mins. The reaction mixture was diluted with EtOAc (20 mL). The organic layer was separated, washed with brine (5 mL), dried over Na$_2$SO$_4$, filtered and concentrated. Lithium aluminum hydride (12.00 mL, 12.00 mmol) was added to the above crude product and heated in a microwave at about 100° C. for about 1 h. The reaction mixture was diluted with Et$_2$O (~50 mL) and quenched slowly with Na$_2$SO$_4$ (sat.). The organic layer was separated, dried over, filtered, and concentrated to afford the title compound (0.472 g, 59%). LC-MS m/z 200 (M+H)+.

Example 96

Methyl 3-[(4-hydroxy-1-piperidinyl)carbonyl]benzoate

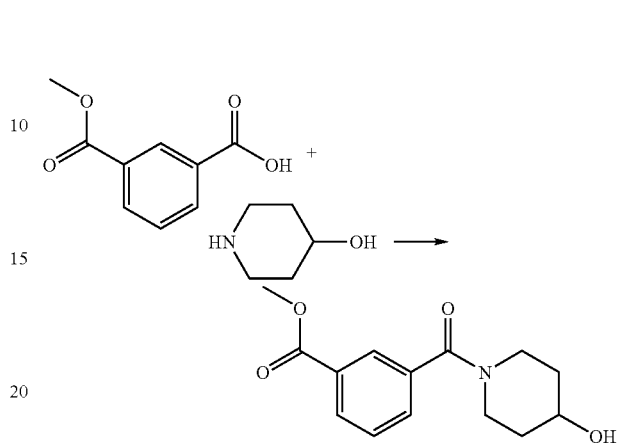

To 3-[(methyloxy)carbonyl]benzoic acid (0.901 g, 5 mmol) in DCM (25 mL) was added TEA (0.697 mL, 5.00 mmol), EtOCOCl (0.480 mL, 5.0 mmol). This mixture was stirred at 0° C. for 10 mins and then 4-piperidinol (0.506 g, 5.00 mmol) was added. Stirring was continued at room temperature for 16 h. The reaction mixture was diluted with DCM (35 mL), washed with HOAc (20 mL, 10%), NaHCO$_3$ (20 mL, 10%), water (20 mL), dried over Na$_2$SO$_4$, filtered and concentrated and purified by CombiFlash chomatograph to afford the title compound (0.696 g, 53%). LC-MS m/z 264 (M+H)+.

Example 97 tert-Butyl 4-{[3'-(aminomethyl)biphenyl-3-yl]methyl}piperidine-1-carboxylate

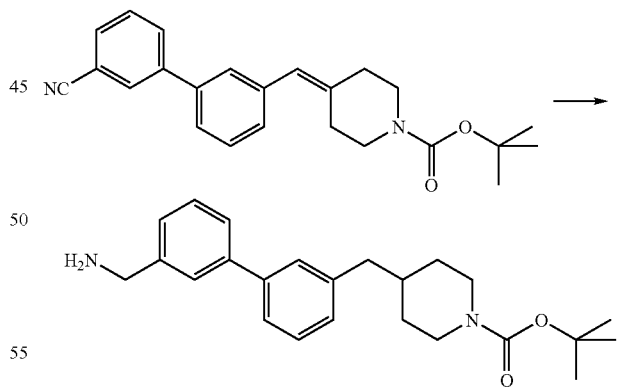

1,1-Dimethylethyl 4-[(3'-cyano-3-biphenylyl)methylidene]-1-piperidinecarboxylate (0.517 g, 1.381 mmol) in methanol (138 mL) was applied to H-Cube hydrogenation apparatus. This resultant mixture was run with a Pd(OH)$_2$ cartridge at 1 mL/min, with 1 atmosphere at 20° C. HCl (1.38 mL, 1 N) was then added. One portion was run one time with Pd(OH)$_2$ cartridge at 1 mL/min, 1 atmosphere at 20° C. Another portion was run with 1 run, Pd(OH)$_2$ cartridge at 1 mL/min with 50 atmosphere and 20° C. Both portions were combined for 1 run, Pd(OH)$_2$ cartridge, 1 mL/min with 1 atmosphere at 20° C. The reaction mixture was concentrated to afford the title compound (0.501 g, 87%). LC-MS m/z 381 (M+H)+.

Example 98

1,1-Dimethylethyl 4-[(3'-cyano-3-biphenylyl)methylidene]-1-piperidinecarboxylate

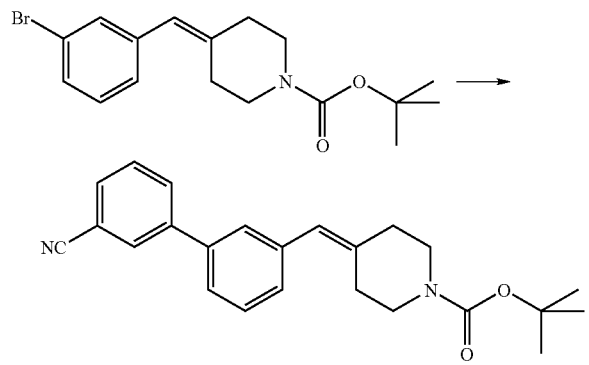

To 1,1-dimethylethyl 4-[(3-bromophenyl)methylidene]-1-piperidinecarboxylate (2.11 g, 5.99 mmol) in 1,4-dioxane (30 mL) and water (10.00 mL) was added m-NC(C$_6$H$_4$)B(OH)$_2$ (1.056 g, 7.19 mmol), Pd(Ph$_3$P)$_4$ 0.277 g, 0.240 mmol), K$_2$CO$_3$ (2.483 g, 17.97 mmol). The resulting mixture was split into two equal portions and each portion was heated in a microwave at about 130° C. for about 15 min. The reaction mixture was evaporated using a Glas-Col evaporator and purified with CombiFlash chomatograph to afford the title compound (1.93 g, 86%). LC-MS m/z 749 (2M+H)+.

Example 99

[1,6-Diethyl-4-(tetrahydro-2H-pyran-4-ylamino)-1H-pyrazolo[3,4-b]pyridin-5-yl]acetic acid

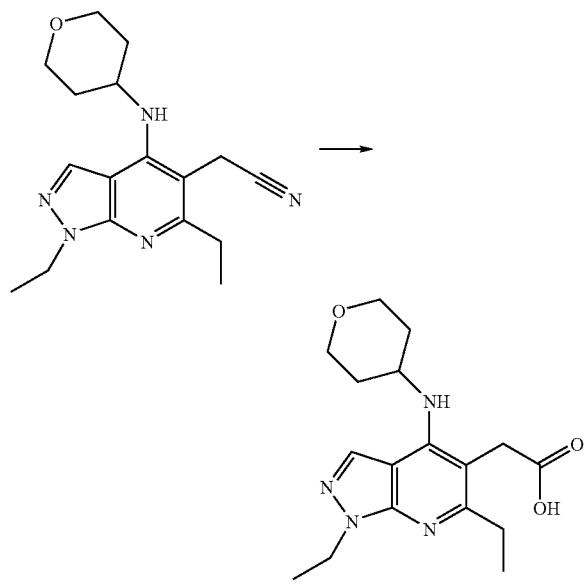

To [1,6-diethyl-4-(tetrahydro-2H-pyran-4-ylamino)-1H-pyrazolo[3,4-b]pyridin-5-yl]acetonitrile (0.667 g, 2.128 mmol) in ethanol (10 mL) was added KOH 40% (10 mL, 2.128 mmol). This mixture was heated in a microwave at 100° C. for 1 h, then again heated in a microwave at 100° C. for 10 h. The mixture was heated a third time in a microwave at 120° C. for 1 h and a fourth time in the microwave at about 120° C. for about 5 h. Then EtOH was removed under vacuum and acidified to pH~5, extracted with DCM/1-PrOH (3/1, 2×30 mL), concentrated, and purified using a Gilson HPLC (with TFA) to afford the title compound (0.317 g, 45%). LC-MS m/z 333 (M+H)+.

Example 100

6-[({[1,6-Diethyl-4-(tetrahydro-2H-pyran-4-ylamino)-1H-pyrazolo[3,4-b]pyridin-5-yl]methyl}amino)carbonyl]-2-pyridinecarboxylic acid

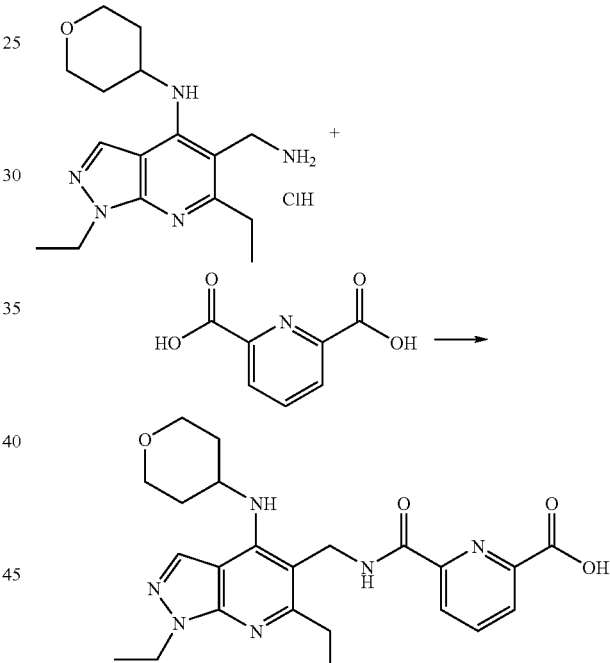

A mixture of 1,1-dimethylethyl 4-{[3'-(aminomethyl)-3-biphenylyl]methyl}-1-piperidinecarboxylate hydrochloride (300 mg, 0.88 mmol), 2,6-pyridinedicarboxylic acid (177 mg, 1.06 mmol), HBTU (402 mg, 1.06 mmol) and Et$_3$N (0.62 mL, 4.41 mmol) in DCM (8 mL) was stirred at room temperature for 30 min. The reaction solution was quenched with saturated NaHCO$_3$ and extracted with DCM twice. The combined organic layers were washed with water followed by a brine wash. The organic layer was dried over sodium sulfate, filtered, concentrated and purified using a Gilson HPLC (with 0.1% TFA condition), eluting with 10 to 70% CH$_3$CN in water in a flowrate of 20 mL/min. The appropriate fractions were dried with EZ GeneVac to give 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid as a solid (167 mg, 42%). LC-MS m/z 453 (M+H)+.

Example 101

4-[({[1,6-Diethyl-4-(tetrahydro-2H-pyran-4-ylamino)-1H-pyrazolo[3,4-b]pyridin-5-yl]methyl}amino)carbonyl]-2-pyridinecarboxylic acid and 2-[({[1,6-Diethyl-4-(tetrahydro-2H-pyran-4-ylamino)-1H-pyrazolo[3,4-b]pyridin-5-yl]methyl}amino)carbonyl]-4-pyridinecarboxylic acid

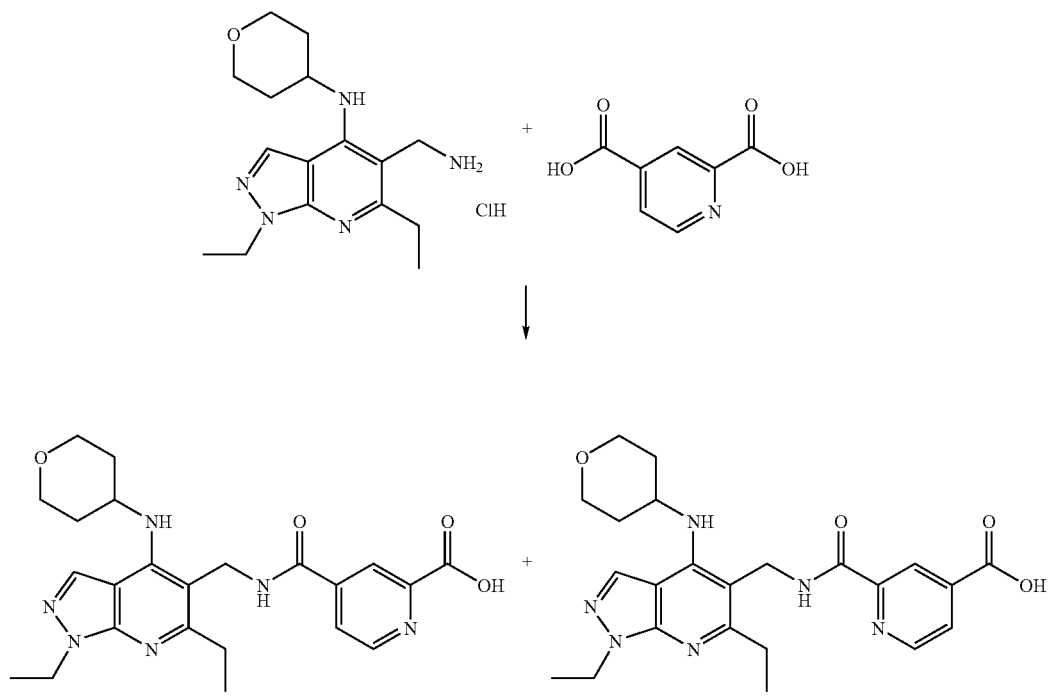

To a solution of 5-(aminomethyl)-1,6-diethyl-N-(tetrahydro-2H-pyran-4-yl)-1H-pyrazolo[3,4-b]pyridin-4-amine hydrochloride (197 mg, 1.177 mmol) in DCM (5 mL) was added Et$_3$N (0.820 mL, 5.88 mmol), 5-(aminomethyl)-1,6-diethyl-N-(tetrahydro-2H-pyran-4-yl)-1H-pyrazolo[3,4-b]pyridin-4-amine hydrochloride (400 mg, 1.177 mmol) followed by HBTU (o-benzotriazol-1-yl-N,N,N',N'-tetramethyluronium hexafluorophosphate) (536 mg, 1.412 mmol). The reaction mixture was stirred at room temperature for 30 min. It was then quenched with 1 N HCl to pH<1. It was then extracted with 1:3 ratio of IPA:DCM three times. The combined organic layers were dried over sodium sulfate, filtered and then concentrated under vacuum to give the crude product. It was then purified using a Gilson HPLC (with 0.1% TFA in the solvents), eluting with 10 to 70% CH$_3$CN in water at a flow rate of 20 mL/min. The product fractions were dried under GeneVac (Ipswich, England, http://www.genevac.org/) to obtain 4-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid [109 mg, 20.5%, LC-MS m/z 453 (M+H)$^+$, 0.59 min (ret time)] and 2-[({[1,6-diethyl-4-(tetrahydro-2H-pyran-4-ylamino)-1H-pyrazolo[3,4-b]pyridin-5-yl]methyl}amino)carbonyl]-4-pyridinecarboxylic acid [207 mg, 38.9%, LC-MS m/z 453 (M+H)$^+$, 0.64 min (ret time)].

Example 102

5-[({[1,6-Diethyl-4-(tetrahydro-2H-pyran-4-ylamino)-1H-pyrazolo[3,4-b]pyridin-5-yl]methyl}amino)carbonyl]-3-pyridinecarboxylic acid

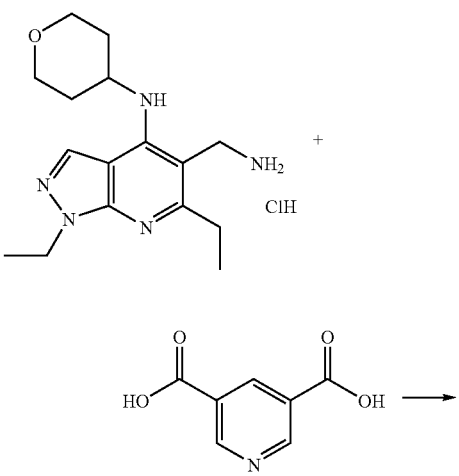

137

-continued

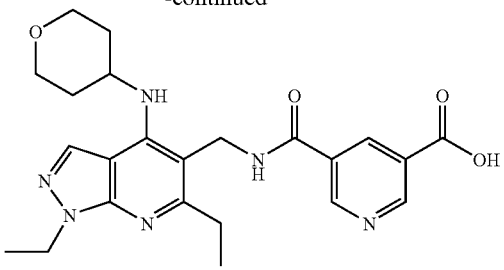

To a solution of 5-(aminomethyl)-1,6-diethyl-N-(tetrahydro-2H-pyran-4-yl)-1H-pyrazolo[3,4-b]pyridin-4-amine hydrochloride (148 mg, 0.883 mmol) in DCM (5 mL) was added Et$_3$N (0.615 mL, 4.41 mmol), 5-(aminomethyl)-1,6-diethyl-N-(tetrahydro-2H-pyran-4-yl)-1H-pyrazolo[3,4-b]pyridin-4-amine hydrochloride (300 mg, 0.883 mmol) followed by HBTU (o-Benzotriazol-1-yl-N,N,N',N'-tetramethyluronium hexafluorophosphate) (402 mg, 1.059 mmol). The mixture was stirred at room temperature for 30 min. It was quenched with 1N HCl to pH<1 and then extracted with 1:3 ratio of IPA:DCM three times. The combined organic layers were concentrated under vacuum to give the crude product. It was then purified with a Gilson HPLC (with 0.1% TFA in the solvents), eluting with 10 to 70% CH$_3$CN in water at a flow rate of 20 mL/min. The product fractions were dried using a EZ2 GeneVac evaporator and then combined to give 5-[({[1,6-diethyl-4-(tetrahydro-2H-pyran-4-ylamino)-1H-pyrazolo[3,4-b]pyridin-5-yl]methyl}amino)carbonyl]-3-pyridinecarboxylic acid as a solid (206, 51.6%). LC-MS m/z 453 (M+H)$^+$, 0.57 min (ret time).

Example 103

6-[(Methyloxy)carbonyl]-2-pyridinecarboxylic acid

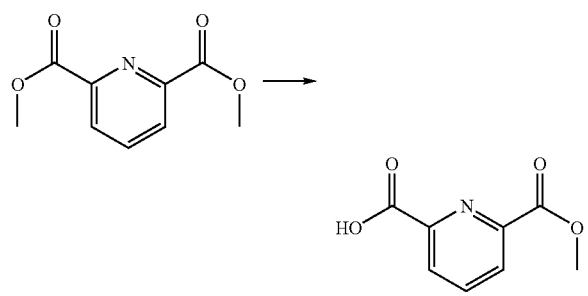

Dimethyl 2,6-pyridinedicarboxylate (11.7 g, 59.9 mmol) was dissolved in methanol (300 mL). The solution was cooled in an ice bath while stirring under argon some starting material came back out of solution. Potassium hydroxide (3.52 g, 62.7 mmol) pellets were added and the mixture and it was stirred in an ice bath for 2 h. The mixture was then allowed to gradually warm to room temperature and stirred for 20 h. The solvent was removed under reduced pressure, and the pinkish residue was suspended in ethyl acetate (250 mL). The mixture stirred for 15 minutes and then the potassium salt was collected by filtration and washed with 2×25 mL of ethyl acetate. The solid was dissolved in water (200 mL). The solution was acidified to pH-3 with concentrated hydrochloric acid and extracted with chloroform (4×80 mL). The combined organic layers were dried over anhydrous Na$_2$SO$_4$, filtered, evaporated, and dried under vacuum to give the 6-[(methyloxy)carbonyl]-2-pyridinecarboxylic acid (6.71 g, 36.2 mmol, 60.4% yield) as a white solid. LC-MS m/z 182 (M+H)$^+$, 0.75 min (ret time).

Example 104

Methyl 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylate

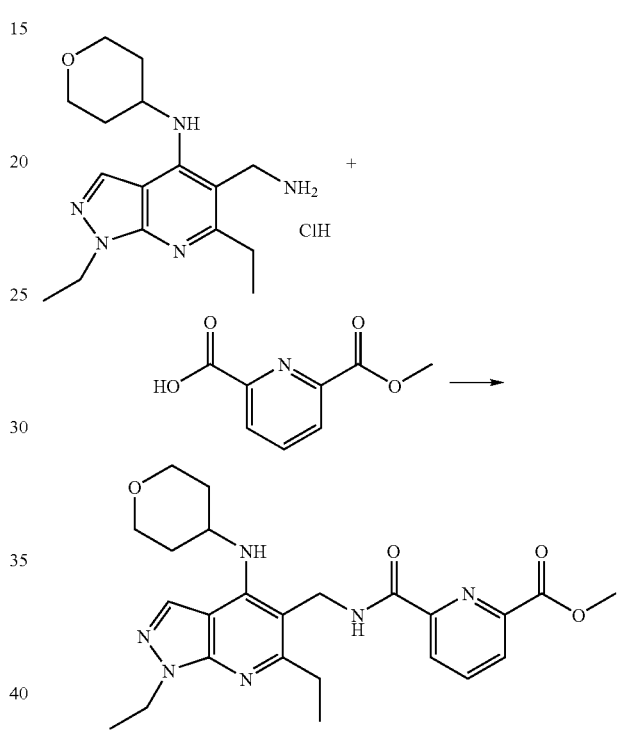

6-[(Methyloxy)carbonyl]-2-pyridinecarboxylic acid (272 mg, 1.500 mmol) was dissolved in dichloromethane (50 mL) and stirred under argon at room temperature. Then HBTU (569 mg, 1.500 mmol) was added followed by 5-(aminomethyl)-1,6-diethyl-N-(tetrahydro-2H-pyran-4-yl)-1H-pyrazolo[3,4-b]pyridin-4-amine hydrochloride (510 mg, 1.5 mmol) and then the TEA (0.418 mL, 3.00 mmol). The mixture was stirred under argon overnight. The solvent was evaporated, and the residue partitioned between EtOAc (75 mL) and water (25 ml). The organic phase was washed with water (3×25 mL), brine, dried over anhydrous sodium sulfate, filtered and evaporated to give the crude residue. It was purified by CombiFlash on a 12 gram silica column eluted with 60-100% EtOAc in hexane. Product fractions were combined and concentrated to give methyl 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylate (609 mg, 1.305 mmol, 87% yield) as a white solid. LC-MS m/z 467 (M+H)$^+$, 0.74 min (ret time).

Example 105

6-[({[1,6-Diethyl-4-(tetrahydro-2H-pyran-4-ylamino)-1H-pyrazolo[3,4-b]pyridin-5-yl]methyl}amino)carbonyl]-2-pyridinecarboxylic acid

Example 106

N-[(3-Bromo-4-methylphenyl)methyl]-N'-{1,6-diethyl-4-(tetrahydro-2H-pyran-4-ylamino)-1H-pyrazolo[3,4-b]pyridin-5-yl]methyl}-2,6-pyridinedicarboxamide

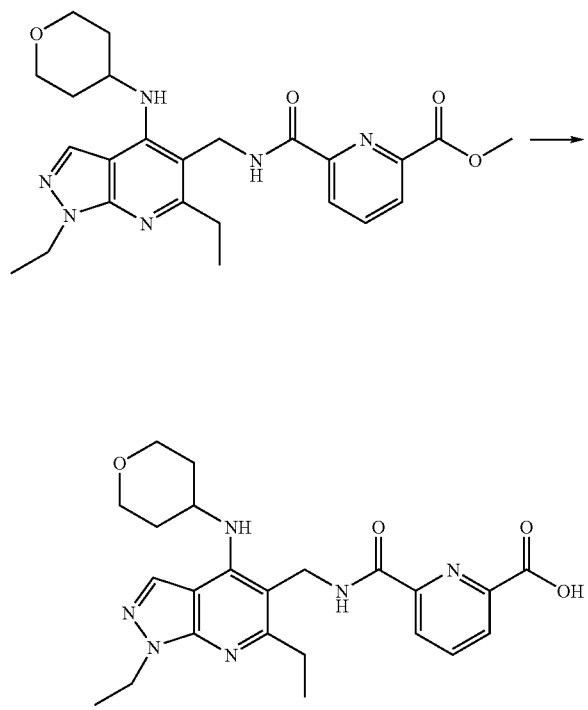

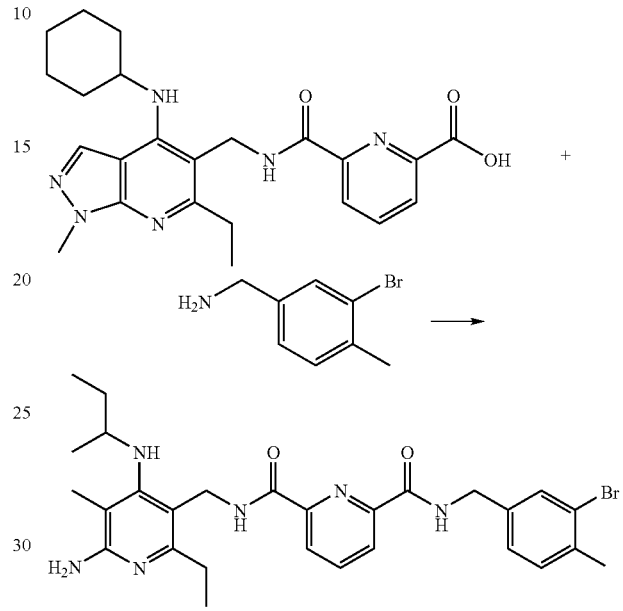

Methyl 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylate (580 mg, 1.243 mmol) was dissolved in tetrahydrofuran (15 mL) and water (5.00 ml) was added. Lithium hydroxide (78 mg, 1.865 mmol) was added and the mixture stirred under argon at room temperature overnight. The THF was evaporated off and the aqueous residue was adjusted to ~pH of 6 with 1N HCL. A white solid slowly formed. The white solid was filtered and washed 2× with water (5 mL). The pH of the filtrate was checked and was found to be 8. The pH was gradually lowered to 4 with 1N HCl. At this point no additional solid appeared to be forming. The solid was filtered and washed 2× with water (5 mL). The combined solid was dried at 50° C. in a vacuum oven for 6 hours to give 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (533 mg, 1.178 mmol, 95% yield) as a white solid. LC-MS m/z 453 (M+H)$^+$, 0.71 min (ret time).

6-[({[1,6-Diethyl-4-(tetrahydro-2H-pyran-4-ylamino)-1H-pyrazolo[3,4-b]pyridin-5-yl]methyl}amino)carbonyl]-2-pyridinecarboxylic acid (2 g, 4.42 mmol) was partially dissolved in dichloromethane (100 mL), and HBTU (1.676 g, 4.42 mmol) was added followed sequentially by [(3-bromo-4-methylphenyl)methyl]amine (0.884 g, 4.42 mmol), and TEA (1.232 mL, 8.84 mmol). The mixture was allowed to stir under argon over night at room temperature. The reaction was not complete so additional HBTU (0.167 g, 0.44 mmol) and [(3-bromo-4-methylphenyl)methyl]amine (0.088 g, 0.44 mmol) was added and the mixture was again stirred overnight. The reaction was still not complete so additional HBTU (0.167 g, 0.44 mmol) and [(3-bromo-4-methylphenyl)methyl]amine (0.088 g, 0.44 mmol) was again added and the mixture was stirred overnight. The reaction mixture was taken up in EtOAc (100 mL) and washed 3× with water (50 mL). Solid was recovered and washed with water and ethyl acetate. Drying the solid under vacuum gave N-[(3-bromo-4-methylphenyl)methyl]-N'-{1,6-diethyl-4-(tetrahydro-2H-pyran-4-ylamino)-1H-pyrazolo[3,4-b]pyridin-5-yl]methyl}-2,6-pyridinedicarboxamide (1.97 g, 2.95 mmol, 66.7% yield). The ethyl acetate layer was washed with brine, dried over anhydrous Na$_2$SO$_4$, filtered and evaporated to give another batch. This batch was taken up in methylene chloride and absorbed on Isolute® Sorbent (Biotage, Uppsala, Sweden; http://www.biotage.com/) and purified with a Combiflash on an 80 g silica column eluted with 0-10% DCM/MeOH. Product fractions were combined and evaporated to give N-[(3-bromo-4-methylphenyl)methyl]-N'-{1,6-diethyl-4-(tetrahydro-2H-pyran-4-ylamino)-1H-pyrazolo[3,4-b]pyridin-5-yl]methyl}-2,6-pyridinedicarboxamide (704 mg, 0.987 mmol, 22.34% yield) as a white solid. LC-MS m/z 435 (M+H)$^+$, 0.94 min (ret time).

Example 107

N-{[1,6-Diethyl-4-(tetrahydro-2H-pyran-4-ylamino)-1H-pyrazolo[3,4-b]pyridin-5-yl]methyl}-N'-[(3'-formyl-6-methyl-3-biphenylyl)methyl]-2,6-pyridinedicarboxamide

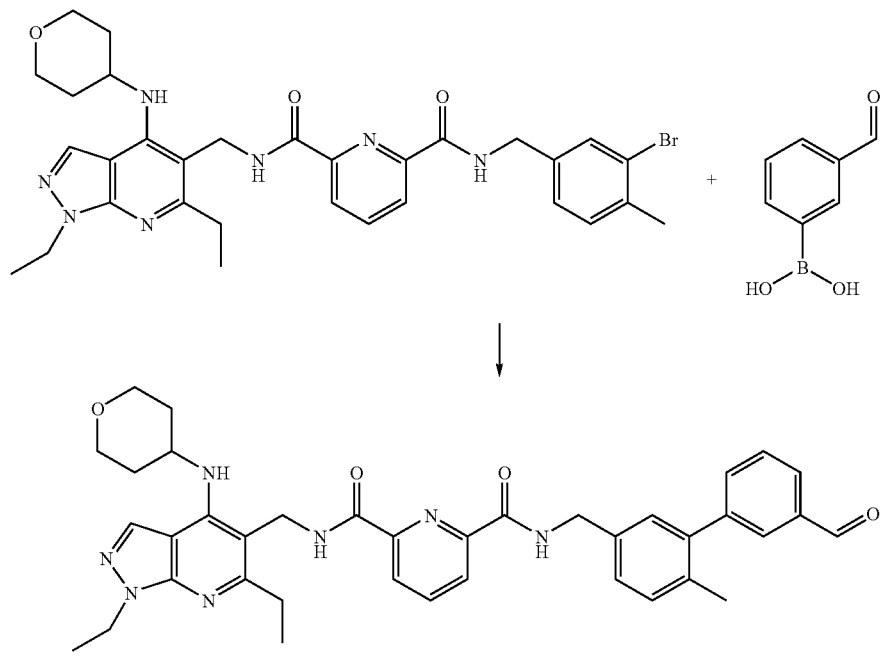

N-[(3-Bromo-4-methylphenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (1.86 g, 2.93 mmol), (3-formylphenyl)boronic acid (0.439 g, 2.93 mmol), potassium carbonate (1.215 g, 8.79 mmol), and Pd(Ph$_3$P)$_4$ (0.169 g, 0.147 mmol) were combined in three 10-20 mL Biotage microwave vials in 1,4-dioxane (27 mL) and water (9 mL). The vials were capped and the mixture was heated in the microwave at normal power at 100° C. for 15 min. The crude product was partitioned between EtOAc (200 mL) and water (70 mL). The phases were separated, and the organic phase was washed with water (2×50 mL), brine (50 mL), dried over anhydrous Na$_2$SO$_4$, filtered and evaporated to give the crude residues. It was taken up in DCM and absorbed on Isolute® Sorbent and purified by a CombiFlash on a 120 g silica column eluted with 0-10% MeOH/DCM. Product fractions were combined and concentrated under vacuum to give (N-{[1,6-diethyl-4-(tetrahydro-2H-pyran-4-ylamino)-1H-pyrazolo[3,4-b]pyridin-5-yl]methyl}-N'-[(3'-formyl-6-methyl-3-biphenylyl)methyl]-2,6-pyridinedicarboxamide (1.85 g, 2.72 mmol, 93% yield)) as a white solid. LC-MS m/z 660 (M+H)$^+$, 0.94 min (ret time).

Example 108

1,1-Dimethylethyl 4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-1-piperazinecarboxylate

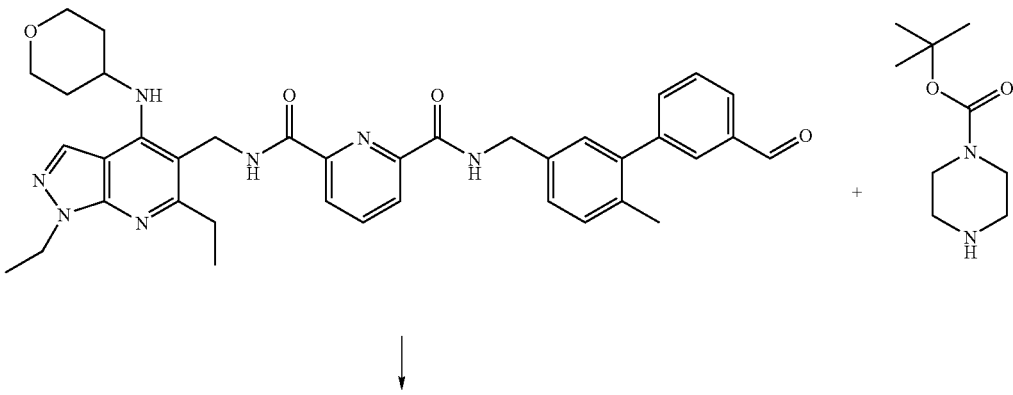

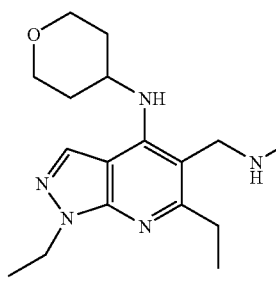 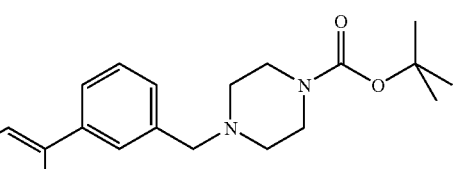

N-{[1,6-Diethyl-4-(tetrahydro-2H-pyran-4-ylamino)-1H-pyrazolo[3,4-b]pyridin-5-yl]methyl}-N'-[(3'-formyl-6-methyl-3-biphenylyl)methyl]-2,6-pyridinedicarboxamide (1.85 g, 2.80 mmol) and 1,1-dimethylethyl 1-piperazinecarboxylate (1.055 g, 5.61 mmol) were dissolved in 1,2-dichloroethane (30 mL) and acetic acid (0.177 ml, 3.08 mmol) was added. The mixture was stirred for 30 minutes and then MP-Triacetoxyborohydride (3.61 g, 8.41 mmol) was added. The mixture was stirred overnight. It was then filtered through a glass fiber filter paper and washed 2× with 20 mL of DCE. The solvent was evaporated and the residue was taken up in methylene chloride and absorbed on Isolute® Sorbent and purified on a Combiflash on an 80 g silica column eluted with 0-10% MeOH/CH$_2$Cl$_2$. Product fractions were combined and concentrated under vacuum to give 1,1-dimethylethyl 4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl]-2'-methyl-3-biphenylyl)methyl]-1-piperazinecarboxylate (1.8 g, 2.140 mmol, 76% yield) as a white solid. LC-MS m/z 830 (M+H)$^+$, 0.86 min (ret time).

Example 109

1,1-Dimethylethyl (2S)-4-{[3-(4-cyano-2-pyridinyl)phenyl]methyl}-2-methyl-1-piperazinecarboxylate

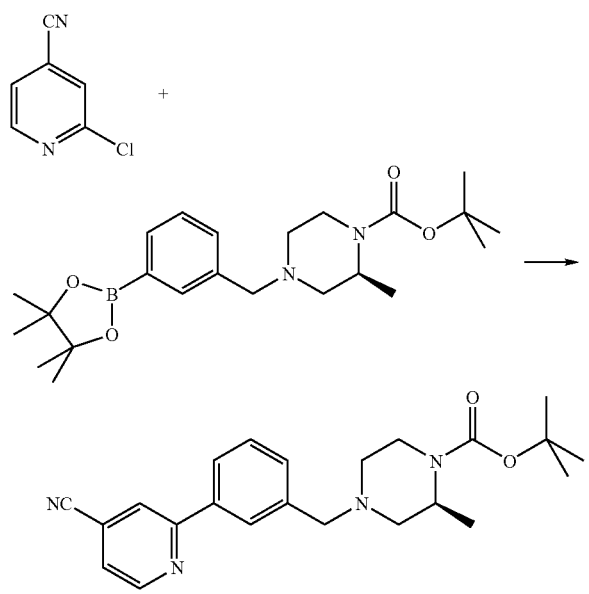

To 2-chloro-4-pyridinecarbonitrile (0.416 g, 3 mmol) was added 1,1-dimethylethyl (2S)-2-methyl-4-{[3-(4,4,5,5-tetramethyl-1,3,2-dioxaborolan-2-yl)phenyl]methyl}-1-piperazinecarboxylate (1.499 g, 3.60 mmol) followed by K$_2$CO$_3$ (1.244 g, 9.00 mmol) and Pd(Ph$_3$P)$_4$ (0.139 g, 0.120 mmol) in 1,4-dioxane (15.00 mL) and water (5.00 mL). The mixture was heated in a microwave for 30 min at 140° C. The organic layer was collected and the aqueous layer was extracted once with EtOAc (3 mL). The organic layer was filtered, evaporated on Glas-Coll, redissolved in hexane/DCM 4 mL (3/1), loaded onto Redisep gel column (12 g) (Teledyne Isco Co. Lincoln, Nebr., USA; http://www.isco.com/combiflash/) and purified with Combiflash chromatography. Fractions were collected and the solvent was removed under reduced pressure to afford 1.10 g (94%) of the title compound. LC-MS m/z 393 (M+H)$^+$.

Example 110

1,1-Dimethylethyl (2S)-4-({3-[4-(aminomethyl)-2-pyridinyl]phenyl}methyl)-2-methyl-1-piperazinecarboxylate

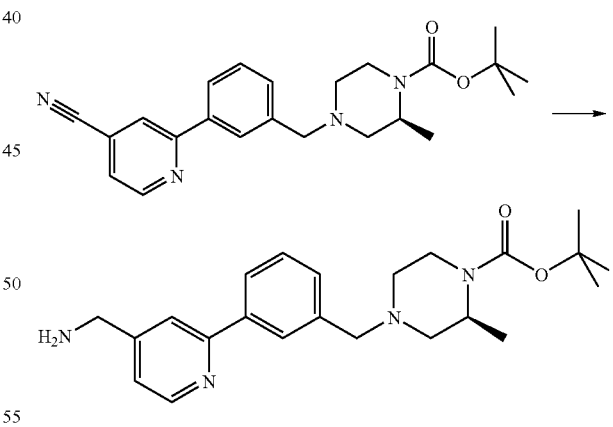

To 1,1-dimethylethyl (2S)-4-{[3-(4-cyano-2-pyridinyl)phenyl]methyl}-2-methyl-1-piperazinecarboxylate (1.20 g, 3.06 mmol) was added methanol (306 mL) to give a 0.01 molar yellow solution. Then the solution was applied to an H-Cube hydrogenation apparatus: 1st run: 10% Pd/C cartridge, H$_2$ (1 atm), 1 mL/min, 20° C. (reaction not completed); 2nd run: 10% Pd/C cartridge, H$_2$ (1 atm), 1 mL/min, 20° C. (reaction not completed); 3rd run: 10% Pd/C cartridge, H$_2$ (1 atm), 1 mL/min, 20° C. (reaction completed). The mixture was concentrated, redissolved in hexane/DCM (3:1, 5 mL), loaded onto Redisep silica gel column (40 g) and purified with

Example 111

1,1-Dimethylethyl 4-{[3-(4-cyano-2-pyridinyl)phenyl]methyl}-1-piperidinecarboxylate

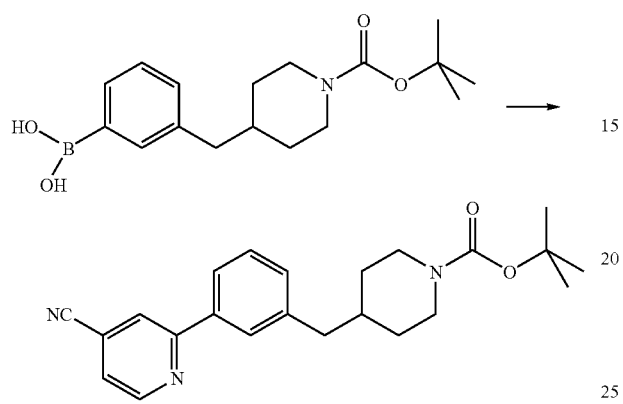

To 2-chloro-4-pyridinecarbonitrile (416 mg, 3 mmol) was added {3-[(1-{[(1,1-dimethylethyl)oxy]carbonyl}-4-piperidinyl)methyl]phenyl}boronic acid (958 mg, 3.00 mmol) followed by $K_2CO_3$ (1,244 mg, 9.00 mmol) and $Pd(Ph_3P)_4$ (139 mg, 0.120 mmol) in 1,4-dioxane (15 mL) and water (5 mL). The mixture was heated in a microwave for 30 min at 140° C. The organic layer was collected and the aqueous layer was extracted with EtOAc (3 mL). The combined organic layers were filtered, evaporated on Glas-Col, redissolved in hexane/DCM 4 mL (3/1), loaded onto Redisep gel column (40 g) and purified with the Combiflash chromatograph to afford 640 mg (57%) of the title compound. LC-MS m/z 378 (M+H)$^+$.

Example 112

1,1-Dimethylethyl 4-({3-[4-(aminomethyl)-2-pyridinyl]phenyl}methyl)-1-piperidinecarboxylate

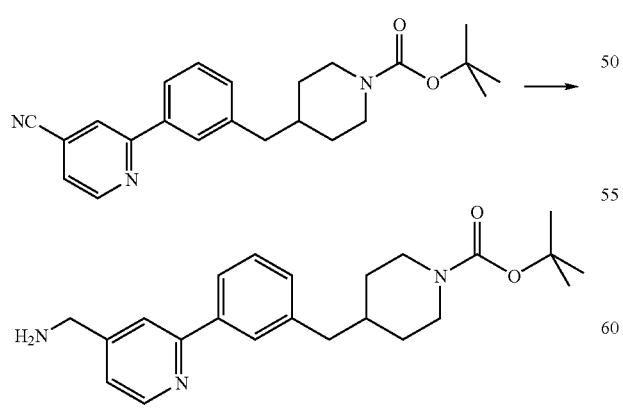

To 1,1-dimethylethyl 4-{[3-(4-cyano-2-pyridinyl)phenyl]methyl}-1-piperidinecarboxylate (640 mg, 1.695 mmol) was added methanol (1,695 μL) to give a 0.01 molar solution. Then the solution was applied to an H-Cube hydrogenation apparatus: 1st run: 20% Pd(OH) cartridge, $H_2$ (1 atm), 1 mL/min, 20° C. (reaction not completed); 2nd run: 20% Pd(OH) cartridge, $H_2$ (1 atm), 1 mL/min, 20° C. (reaction not completed); 3rd run, 20% Pd(OH) cartridge, $H_2$ (1 atm), 1 mL/min, 20° C. (reaction not completed); 4th run: 20% Pd(OH) cartridge, $H_2$ (1 atm), 1 mL/min, 20° C. (reaction not completed); 5th run: 20% Pd(OH) cartridge, $H_2$ (1 atm), 1 mL/min, 20° C. (reaction not completed); 6th run: 20% Pd(OH) cartridge, $H_2$ (1 atm), 1 mL/min, 20° C. (reaction not completed); 7th run: 20% Pd(OH) cartridge, $H_2$ (1 atm), 1 mL/min, 20° C. (reaction completed). The mixture was concentrated, redissolved in hexane/DCM 5 mL (3/1), loaded onto Redisep gel column (40 g) and purified with Combiflash chromatography to afford 413 mg (64%) of the title compound. LC-MS m/z 382 (M+H)$^+$.

Example 113

Diethyl[(3-bromophenyl)methyl]phosphonate

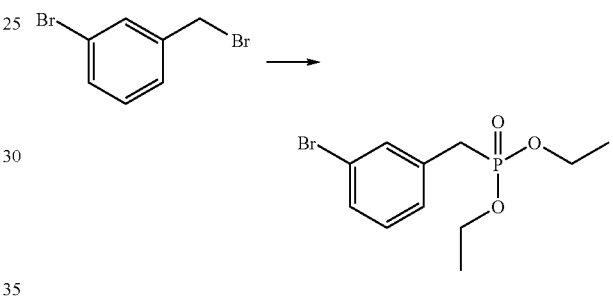

To 1-bromo-3-(bromomethyl)benzene (100 g, 400 mmol) in a 500 mL round-bottom flask under nitrogen was added triethyl phosphite (69.6 mL, 400 mmol) and the solution was heated to 130° C. The apparatus was set up ready for distillation. As the heating block reached 130° C. the mixture began to reflux and a large volume of colourless liquid was allowed to distill off. Lab HPLC of the reaction after 40 min showed some starting material so another 0.5 eq of the phosphite was added, and heating with distillation continued. The reaction was then heated under vacuum and the excess phosphite was distilled off under vacuum (130° C. heater and 15 mbar, gradually going down to 0.5 mbar). This gave 120.8 g (98%) of a colourless oil that the lab HPLC showed to be 97% pure with a 2.20 min retention time. LC-MS m/z 307, 309 (M+H)$^+$, 1.01 min (ret time).

Example 114

1,1-Dimethylethyl 4-[(3-bromophenyl)methylidene]-1-piperidinecarboxylate

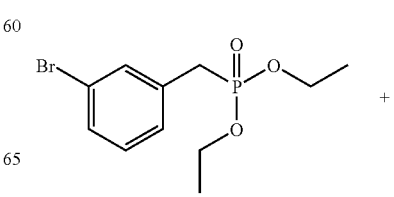 + the Combiflash chromatograph to afford 937 mg (77%) of the title compound. LC-MS m/z 397 (M+H)$^+$.

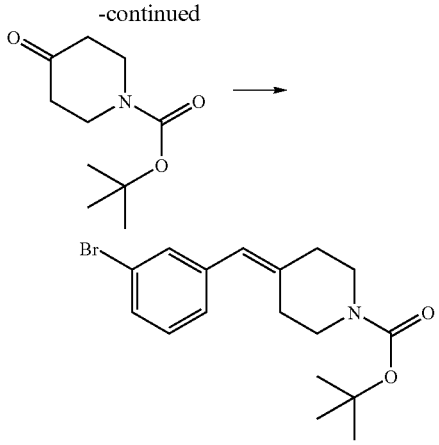

To diethyl[(3-bromophenyl)methyl]phosphonate (100 g, 326 mmol) in a 2 L 3-neck flask with mechanical stirrer was added tetrahydrofuran (THF) (700 mL) followed by 1,1-dimethylethyl 4-oxo-1-piperidinecarboxylate (71.4 g, 358 mmol) and potassium tert-butoxide (38.4 g, 342 mmol), portion-wise with ice-bath cooling to keep the temperature between 20° C. and 25° C. The mixture became more orange and was then stirred at room temperature under nitrogen. Some material was present as a suspension and it was slightly more viscous. Another 3.8 gm (0.1 eq) of potassium tert-butoxide was added. After 1.25 h the mixture had practically gelled and an extra 150 mL of THF were added.

The mixture was partitioned between water and ethyl acetate and the aqueous layer extracted well with ethyl acetate. The combined organic extracts were washed with water, brine, dried (MgSO$_4$), filtered and evaporated to give 120.73 g of a pale yellow oil. The crude product was purified on a 750 g Companion XL silica cartridge, eluting with 0-25% ethyl acetate in cyclohexane over 8 column volumes. This gave a colorless oil which became a white solid, 94.68 g (83%) that the lab HPLC showed to be 99.5% pure with a 2.97 min retention time. LC-MS m/z 352, 354 (M+H)$^+$, 3.96 min (ret time).

Example 115

1,1-Dimethylethyl 4-{[3-(4,4,5,5-tetramethyl-1,3,2-dioxaborolan-2-yl)phenyl]methylidene}-1-piperidinecarboxylate

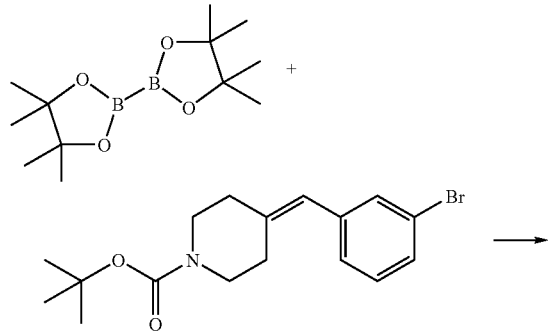

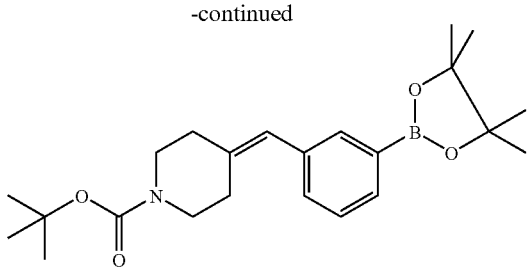

To a solution of 1,1-dimethylethyl 4-[(3-bromophenyl)methylidene]-1-piperidinecarboxylate (94.68 g, 269 mmol) in nitrogen purged DMF (700 mL) was added potassium acetate (52.8 g, 538 mmol) and bis(pinacolato)diboron (82 g, 323 mmol). The resulting reaction mixture was flushed with nitrogen and then put under vacuum alternatively five times. PdCl$_2$ (dppf)-CH$_2$Cl$_2$-adduct (10.97 g, 13.44 mmol) was then added and the reaction mixture heated to 100° C. for 2 h. The reaction mixture was then cooled to room temperature and was filtered through celite washing the pad well with DMF. The filtrate was then concentrated in vacuo and the resulting residue dissolved in water and ethyl acetate. The organic layer was separated, filtered through celite, then washed with brine, re-filtered through celite, dried over magnesium sulfate, filtered, then concentrated in vacuo. The resulting residue was dissolved in 100 mL of DCM, loaded onto a 1,500 g ISCO™ silica column and purified on a 0-25% EtOAc in cyclohexane gradient but the compound eluted at the beginning of the run due to use of DCM. The appropriate fractions were combined and concentrated to yield a viscous oil which was then dissolved in cyclohexane (100 mL) and loaded onto a 1,500 g ISCO™ silica column and purified on a 0-25% EtOAc in cyclohexane gradient. This gave 92.48 g (86%) of a pale green solid. HPLC showed 14.74% of boronic acid (boronate hydrolyses partially on HPLC column) with a retention time of 2.33 min and 82.71% of the boronate with a retention time of 3.12 min. LC-MS m/z 343.95 (M+H)$^+$, 1.59 min (ret time) [above named product minus tBu group].

Example 116

1,1-Dimethylethyl 4-{[3-(4,4,5,5-tetramethyl-1,3,2-dioxaborolan-2-yl)phenyl]methyl}-1-piperidinecarboxylate

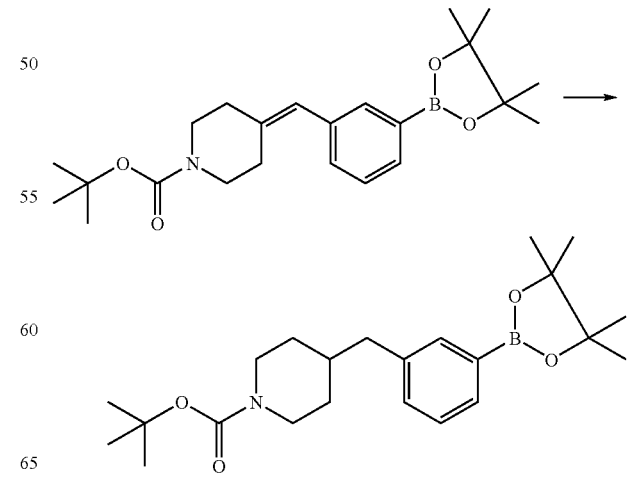

1,1-Dimethylethyl 4-{[3-(4,4,5,5-tetramethyl-1,3,2-dioxaborolan-2-yl)phenyl]methylidene}-1-piperidinecarboxylate (92.48 g, 232 mmol) was dissolved in ethanol (1,500 mL) and added to $N_2$ purged 10% palladium on carbon (9 g, 4.25 mmol) in a 5 L hydrogenation flask. The resulting mixture was then deoxygenated by alternating $N_2$ and vacuum supplies to the vessel. The flask was then placed under a hydrogen atmosphere with stirring. After 1 h the reaction had absorbed the theoretical volume of hydrogen and the hydrogen in the vessel was replaced by nitrogen by alternating the vacuum and nitrogen supplies. The mixture was then filtered through celite and the pad was washed well with ethanol. The filtrate was then concentrated to yield 87.6 g (94%) of a straw colored gum. HPLC showed 14.74% of boronic acid (boronate hydrolyses partially on HPLC column) with a retention time of 2.33 min and 82.71% of the boronate with a retention time of 3.12 min. HPLC showed 6.66% of boronic acid (boronate partially hydrolyses under HPLC conditions) with a retention time of 2.33 min and 87.76% of the boronate with a retention time of 3.11 min. LC-MS m/z 346 (M+H)$^+$, 1.58 min (ret time) [above named product minus tBu group].

Example 117

6-[(Methyloxy)carbonyl]-2-pyridinecarboxylate potassium salt

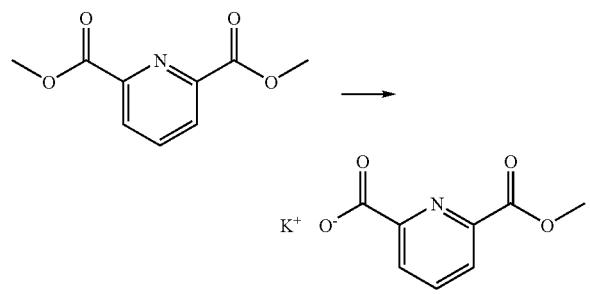

To a suspension of dimethyl 2,6-pyridinedicarboxylate (95.22 g, 488 mmol) in a 2 L round-bottom flask under nitrogen in methanol (1,200 mL; ~12.5 volumes) was added powdered potassium hydroxide (27.4 g, 488 mmol). The mixture was stirred and after 3 min was almost all in solution. After 20 min lab HPLC showed a 33:62 ratio of starting material to product. Solvent was evaporated and the resulting solid was stirred well with 1000 mL ethyl acetate, then filtered under vacuum, then dried at 40° C. under high vacuum to give 84.5 g (79%) of a white solid that lab HPLC showed to be 98.2% pure (ret time 1.41 min). LC-MS m/z 182 (M+H)$^+$, 0.57 min (ret time).

Example 118

Methyl 6-[({[1,6-Diethyl-4-(tetrahydro-2H-pyran-4-ylamino)-1H-pyrazolo[3,4-b]pyridin-5-yl]methyl}amino)carbonyl]-2-pyridinecarboxylate

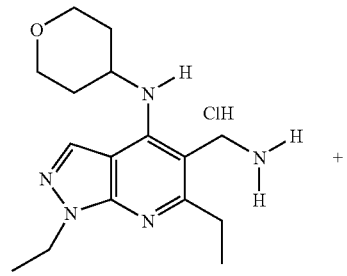

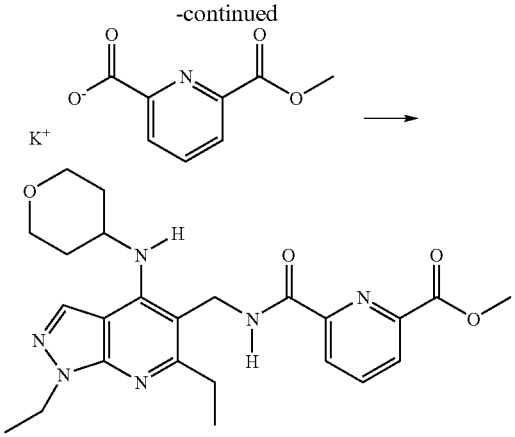

To a suspension of 6-[(methyloxy)carbonyl]-2-pyridinecarboxylate potassium salt (39.5 g, 180 mmol) in a 500 mL 3-neck flask was added N,N-dimethylformamide (DMF) (1,700 mL) followed by TBTU (60.4 g, 188 mmol) [still a suspension]. After 2 min the 5-(aminomethyl)-1,6-diethyl-N-(tetrahydro-2H-pyran-4-yl)-1H-pyrazolo[3,4-b]pyridin-4-amine (55.6 g, 164 mmol) was added as a solid and after 15 min nearly all the material had gone into solution. After 2.5 h the slightly cloudy mixture was evaporated off to remove as much DMF as possible using high vacuum and this gave a beige oily solid which was partitioned between saturated sodium bicarbonate and ethyl acetate. Solid started to come out of solution from the organics so they it was filtered off dried under high vacuum. This gave 29.56 g (39%) of the above named compound as a white solid. Lab HPLC of this material showed 95.8% of desired product (ret time 1.87 min) contaminated with 3.4% of HOBt. (ret time 1.16 min). LC-MS m/z 467 (M+H)$^+$, 0.78 min (ret time).

The filtrate organics from above were washed with water, aqueous lithium chloride, brine, dried (MgSO$_4$), filtered and evaporated. This gave 48.3 g (64%) of a cream solid, which was triturated with ether then filtered to give 39.73 g (52%) of a cream solid. Lab HPLC showed two peaks with a retention time of 1.87 min (84%) and 1.91 min (15%). LC-MS m/z 467 (M+H)$^+$, 1.88 min (ret time) [90% above named compound] and m/z 467, 738 (M+H)$^+$, 2.06 min (ret time) [10% possible dimer amide].

Example 119

6-[({[1,6-Diethyl-4-(tetrahydro-2H-pyran-4-ylamino)-1H-pyrazolo[3,4-b]pyridin-5-yl]methyl}amino)carbonyl]-2-pyridinecarboxylic acid

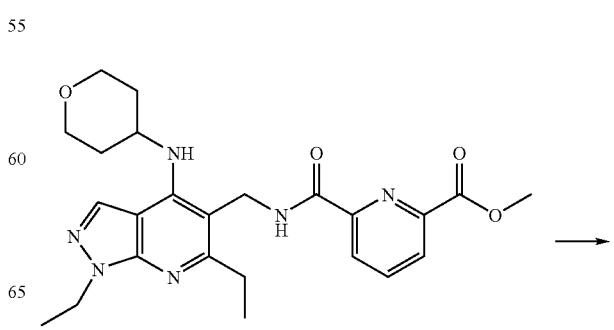

-continued

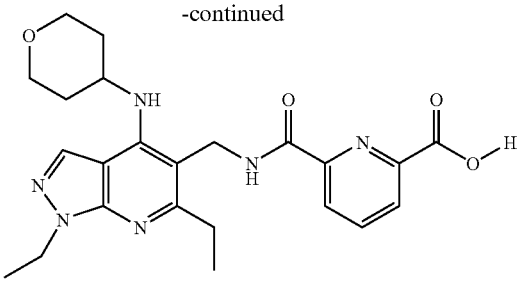

To methyl 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylate (32 g, 68.6 mmol) in a 1 L round-bottom flask under nitrogen in tetrahydrofuran (THF) (600 mL) was added water (150 mL), then lithium hydroxide (2.464 g, 103 mmol). After 22 min the slightly cloudy mixture was filtered and the THF was evaporated off to give a slight suspension. The aqueous mixture was cooled in an ice-bath and taken to pH 6 using 2M hydrochloric acid. This mixture was stirred for 10 min in an ice-bath, the pH re-checked but not much material seemed to have come out of solution. So the pH was further reduced to pH 5 and this seemed to bring more material out of solution. The solid was collected by vacuum filtration, washed with water then dried under high vacuum at 40° C. to give 19.2 g (62%) of a white solid that the Lab HPLC showed to be 98.7% pure with a retention time of 1.76 min. LC-MS m/z 453 (M+H)$^+$, 0.72 min (ret time) [split peak].

Example 120

N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide To a suspension of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (30 g, 66.3 mmol) in a 1 L round-bottom flask in dichloromethane (DCM) (300 mL) was added triethylamine (46.2 mL, 331 mmol) giving a solution to which was added TBTU (31.9 g, 99 mmol). The mixture became cloudy and was then stirred at room temperature under nitrogen for 5 min when 1-[3-bromo-4-(methyloxy)phenyl]methanamine hydrochloride (18.42 g, 72.9 mmol) was added. After 1.5 h the reaction was worked up. The mixture was partitioned between dichloromethane and water and the aqueous layer extracted well with dichloromethane. The combined organics were washed with saturated sodium bicarbonate, brine, dried (MgSO$_4$), filtered and evaporated to give 52.41 g (121%) of a golden foam. The crude product was purified on a 750 g Companion XL silica cartridge, eluting with 20-100% of {1% MeOH in EtOAc) in dichloromethane over 12 column volumes. The fractions were checked by HPLC and product fractions were combined and solvent evaporated to give 30.15 g (~65%) of a cream foam that lab HPLC showed to be 97.2% pure (ret time 2.11 min) LC-MS m/z 650, 652 (M+H)$^+$, 1.03 min (ret time).

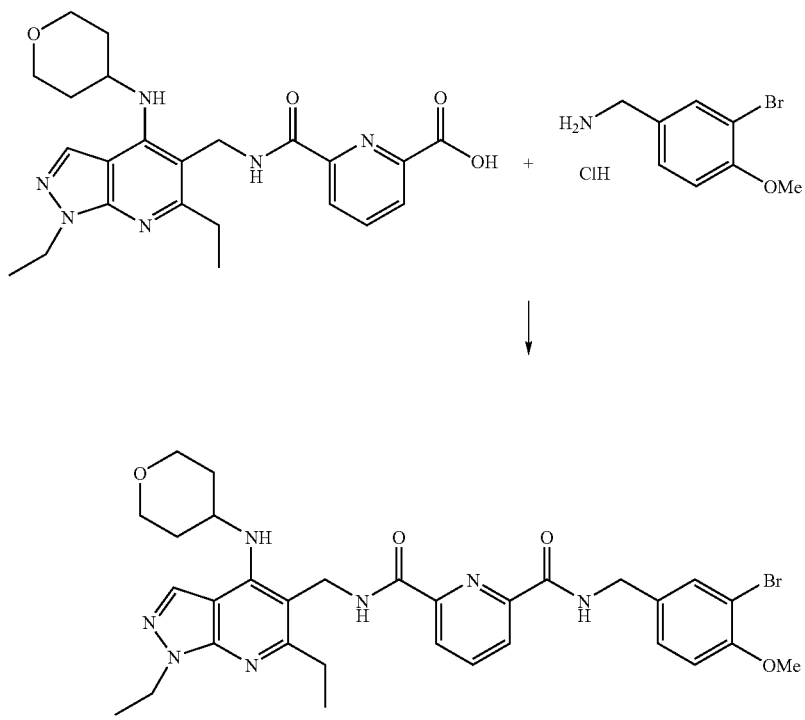

Example 121

1,1-Dimethylethyl 4-{[5'-{[[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-(methyloxy)-3-biphenylyl]methyl}-1-piperidinecarboxylate

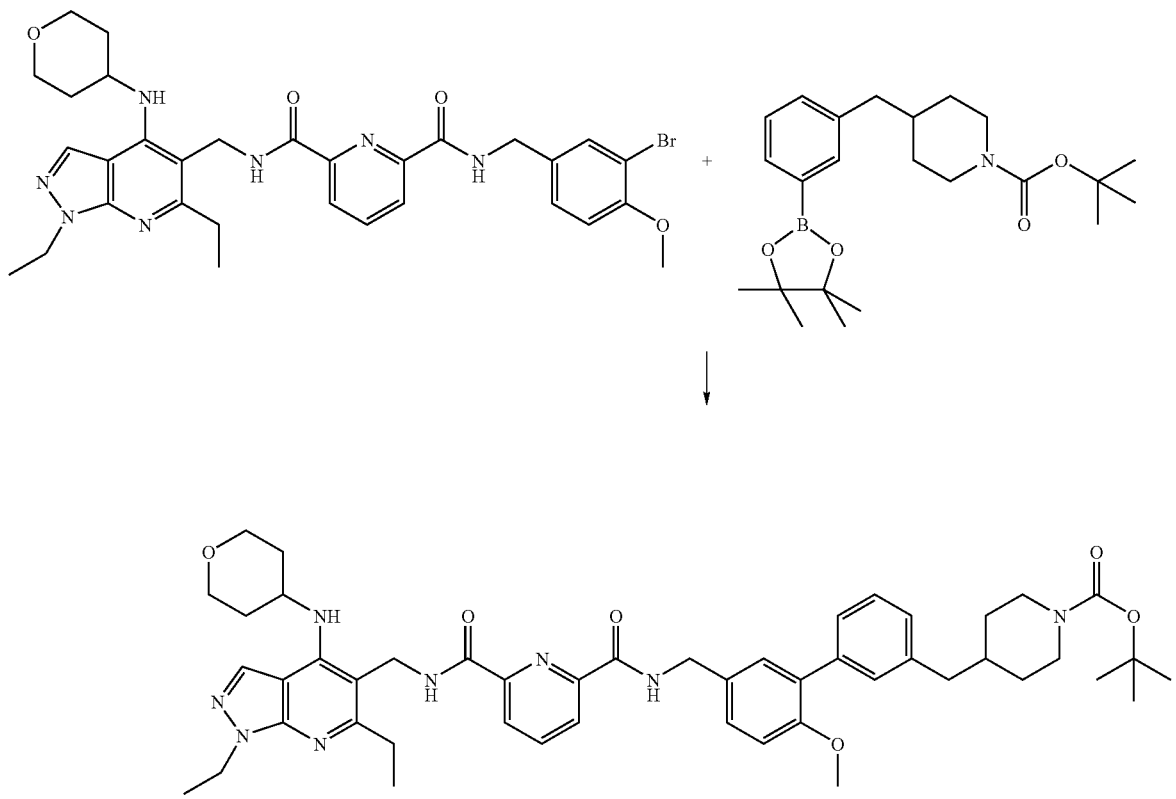

To N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide (40.46 g, 62.2 mmol) in a 2 L 3-neck flask was added 1,1-dimethylethyl 4-{[3-(4,4,5,5-tetramethyl-1,3,2-dioxaborolan-2-yl)phenyl]methyl}-1-piperidinecarboxylate (24.96 g, 62.2 mmol) and 1,4-dioxane (700 mL). Then potassium carbonate (25.8 g, 187 mmol) and water (233 mL) were added followed by tetrakis(triphenylphosphine)palladium(0) (3.59 g, 3.11 mmol) and the mixture was then stirred at 100° C. under nitrogen with conventional heating. After 2 h the reaction was cooled and the mixture was partitioned between ethyl acetate and water and the aqueous layer extracted well with ethyl acetate. The combined organics were washed with water, brine, dried (MgSO$_4$), filtered and evaporated to give 59.49 g (113%) of a brown foam. The crude product was purified on a 750 g Companion XL silica cartridge, eluting with 0-100% of {1% MeOH in ethyl acetate} in dichloromethane over 14 column volumes. This gave 25.38 g (48%) of a pale beige foam that the lab HPLC showed to be 97.23% pure with a retention time of 2.60 min. LC-MS m/z 845 (M+H)$^+$, 3.02 min (ret time).

Example 122

1-(3-Bromo-4-methylphenyl)methanamine hydrochloride

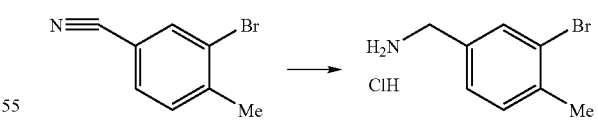

To LiAlH$_4$ (1M in ether) (400 mL, 400 mmol) in a 2 L 3-neck flask with mechanical stirring under nitrogen at −5° C. was added concentrated H$_2$SO$_4$ (10.94 mL, 219 mmol) dropwise. Gas evolution was observed and the solution became cloudy and the foamy mixture was not as easy to stir. Temperature got as high as 3° C. The addition took 28 min. This mixture was stirred for 60 min and then the 3-bromo-4-methylbenzonitrile (37.3 g, 190 mmol) in THF (850 mL) was added over 18 min (max temp=10° C.). The slightly peach-colored mixture was stirred in the ice bath. After 30 min water (90 mL) was added carefully to give a white mixture, followed by 2M sodium hydroxide. After adding 100 mL, a solid that appeared to be amenable to filtration had formed. This was stirred for 30 min. The slightly waxy solid was filtered off and the single-phase filtrate washed with brine, dried and evaporated. This gave a slightly cloudy yellowish oil, 39.64 g (>100%) that was re-dissolved in ether (350 mL), filtered to remove some solid, and to the oil was added 1M hydrogen chloride in ether (1 eq based on starting nitrile, 190 mmol, 190 mL) slowly with stirring under nitrogen, This gave a solid that was collected by vacuum filtration and sucked dry, then dried under high vacuum to give 41.34 g (92%) of a white solid that the lab HPLC showed to be 98.8% pure with a retention time of 1.56 min. LC-MS m/z 200, 202 (M+H)$^+$, 1.05 min (ret time).

Example 123

1,1-Dimethylethyl 4-{[3-(4,4,5,5-tetramethyl-1,3,2-dioxaborolan-2-yl)phenyl]methyl}-1-piperazinecarboxylate

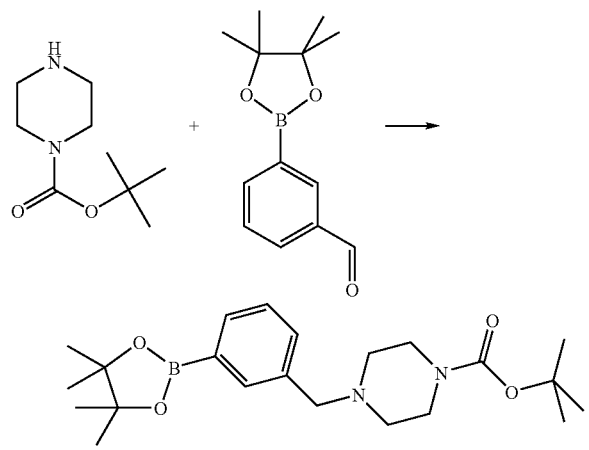

Benzaldehye-3-pinacolboronate (Fluorochem) (32 g, 138 mmol) was stirred in 300 mL of dry DCM in a 2000 mL 3-necked flask under nitrogen. A solution of Boc-piperidine (38.5 g, 207 mmol) in 350 mL of dry DCM was added dropwise over 6 min (negligible exotherm). Acetic acid (8.82 mL, 154 mmol) was then added dropwise over 6 min and washed in with a little more dry DCM. The mixture was stirred at ambient temperature for about 2.5 h. Then sodium triacetoxyborohydride (58.7 g, 277 mmol) was added portionwise over 10 min with cooling in an ice water bath to keep reaction temp at 10-15° C. After all had been added, the mixture was stirred at ambient temperature under nitrogen overnight. After a total of 21 h the reaction mixture was poured slowly onto 800 mL water with stirring. Gas evolution was observed. The mixture was stirred at room temperature until gas evolution had subsided. The mixture was partitioned between dichloromethane and water and the aqueous layer extracted well with dichloromethane. The combined organics were washed with water, brine, dried (MgSO$_4$), filtered and evaporated then put under high vacuum to give 57.8 g (104%) of a sticky white foam. Lab HPLC showed two major peaks: retention time 1.63 min (55%) and retention time 2.15 min (39%). LC-MS m/z 403 (M+H)$^+$, 0.94-1.04 min (ret time-broad peak) [84% above named product] and m/z 320 (M+H)$^+$, 0.65 min (ret time) [12% boronic acid product].

Example 124

N-[(3-Bromo-4-methylphenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide

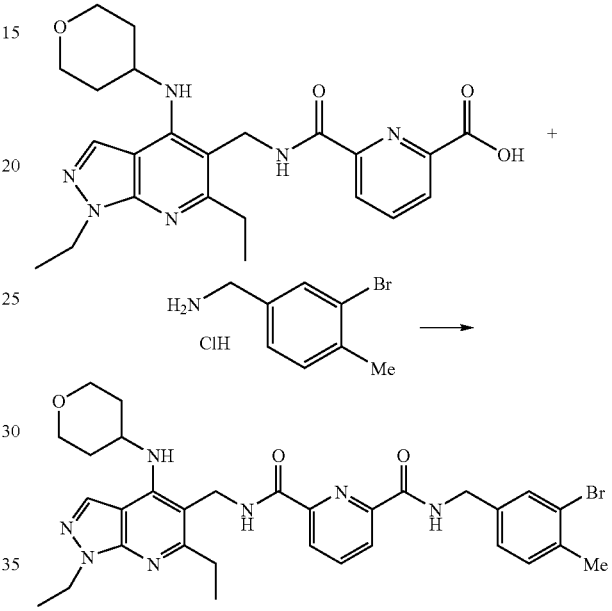

To a suspension of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (50.8 g, 112 mmol) in a 2 L 3-neck flask was added dichloromethane (DCM) (600 mL) followed by DIPEA (98 ml, 561 mmol), giving a solution. To it was added TBTU (39.7 g, 123 mmol) and the mixture was then stirred at room temperature for 2 min whereupon 1-(3-bromo-4-methylphenyl)methanamine hydrochloride (29.2 g, 123 mmol) was added. The mixture was stirred under nitrogen at room temperature. After 2.5 h the mixture was partitioned between dichloromethane and water and the aqueous layer extracted well with dichloromethane. The combined organics were washed with water, saturated sodium bicarbonate, brine, dried (MgSO$_4$), filtered and evaporated to give 95.5 g of a pale golden foam that was purified on a 750 g Companion XL silica cartridge, eluting with 0-100% ethyl acetate in dichloromethane over 8 column volumes. However, halfway through loading, the material started to crystallise on the column, blocking the loading so this material already on the column was eluted as above to give 30.01 gm, (26%) of a white solid (combined theoretical yield of the two preparations was 116.6 g). The lab HPLC showed 99.4% purity (retention time 2.22 min). LC-MS m/z 634, 636 (M+H)$^+$, 1.06 min (ret time).

The material not yet loaded on the column was recovered and added to that still in the flask which had also started to crystallise. The solution was re-evaporated to ~150 mL, cooled and ~50 mL of ether was added. The material started to crystallise out. The solid was collected by vacuum filtration and washed with 1:1 ether:DCM and sucked dry to give 35.65 g (31%) of a white solid. The lab HPLC showed 98.9% purity (retention time 2.21 min). LC-MS m/z 634, 636 (M+H)+, 1.07 min (ret time).

The filtrate from this solid was evaporated to give ~36 g of a golden oil that was re-chromatographed on a 330 g Companion XL silica cartridge, eluting with 0-100% ethyl acetate in dichloromethane over 8 column volumes. This gave 13.34 g (19%) of a white solid. The lab HPLC showed 98% purity (retention time 2.22 min).

Example 125

1,1-Dimethylethyl 4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-1-piperazinecarboxylate dium(0) (4.37 g, 3.78 mmol) and the mixture was then stirred at 100° C. under nitrogen with conventional heating. The mixture became a yellow solution and after 2.5 h the reaction was cooled and the mixture was partitioned between ethyl acetate and water and the aqueous layer extracted well with ethyl acetate. The combined organics were washed with water, dried (MgSO4), and the yellow solution evaporated to give 80 g (127%) of a yellow foam. Some crude material from a similar reaction was combined with this yellow foam and gave some solid: even with ~5% EtOAc in the DCM and warming there was still some solid so it was filtered off and discarded. The crude filtrate containing products was purified on a 750 gm Companion XL silica cartridge, eluting with 10-100% of {3% MeOH in EtOAc} in dichloromethane over 10 column volumes. Two major peaks eluted to give 35.91 g (35% based on the two reactions) of a pale cream foam. Lab HPLC showed 99.77% purity (retention time 2.06 min). LC-

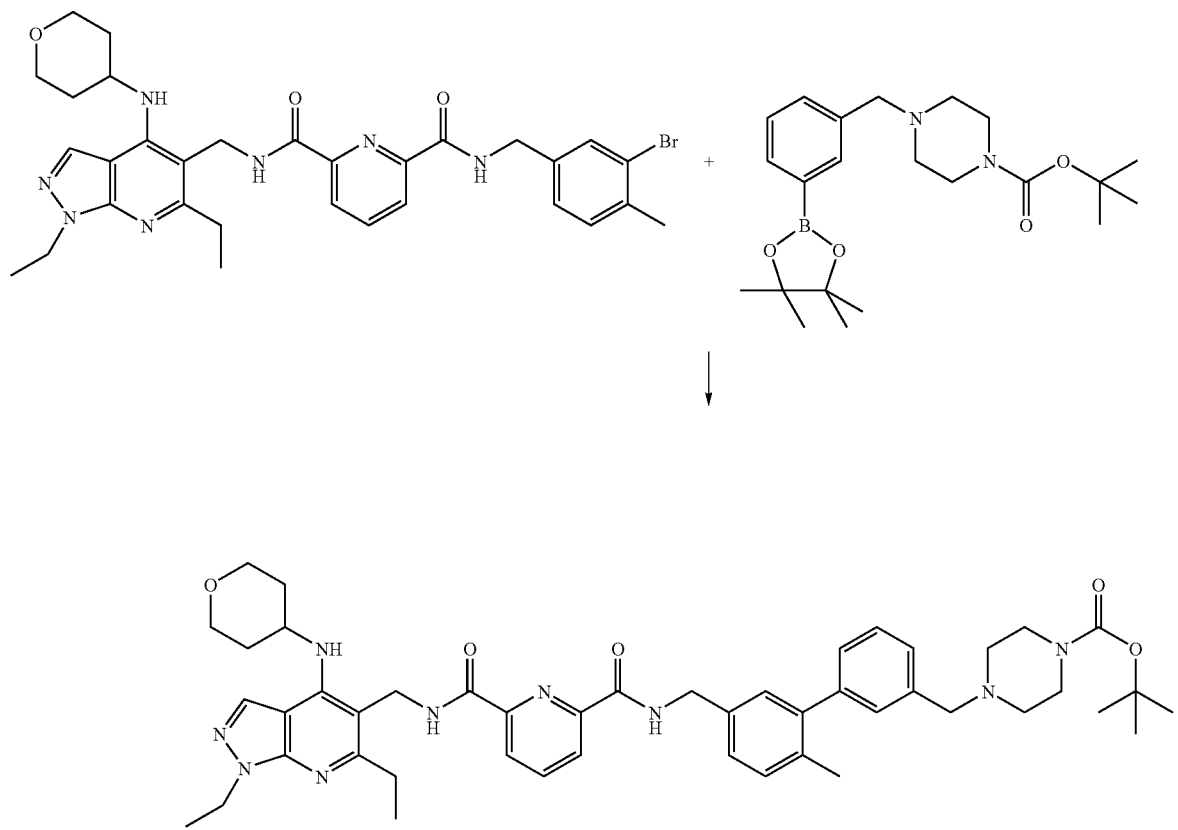

To N-[(3-bromo-4-methylphenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (48.03 g, 76 mmol) in a 2 L 3-neck flask was added 1,1-dimethylethyl 4-{[3-(4,4,5,5-tetramethyl-1,3,2-dioxaborolan-2-yl)phenyl]methyl}-1-piperazinecarboxylate (30.5 g, 76 mmol) and 1,4-dioxane (900 mL). To this white suspension was then added potassium carbonate (31.4 g, 227 mmol) and water (300 mL) followed by tetrakis(triphenylphosphine) palla- MS m/z 830 (M+H)+, 2.09 min (ret time) 92.6%; m/z 830 (M+H)+, 2.16 min (ret time) 7.4%.

Less pure fractions were re-chromatographed on a 750 g Companion XL silica cartridge, eluting with 0-100% of {1% MeOH in EtOAc} in dichloromethane over 12 column volumes to give 42.34 g (41% based on 2 reactions) of a pale cream foam. The lab HPLC showed 99.18% purity (retention time 2.07 min). LC-MS m/z 830 (M+H)+, 2.25 min (ret time).

Examples

Compounds of Formula (I)

Example 126

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,6-pyridinedicarboxamide

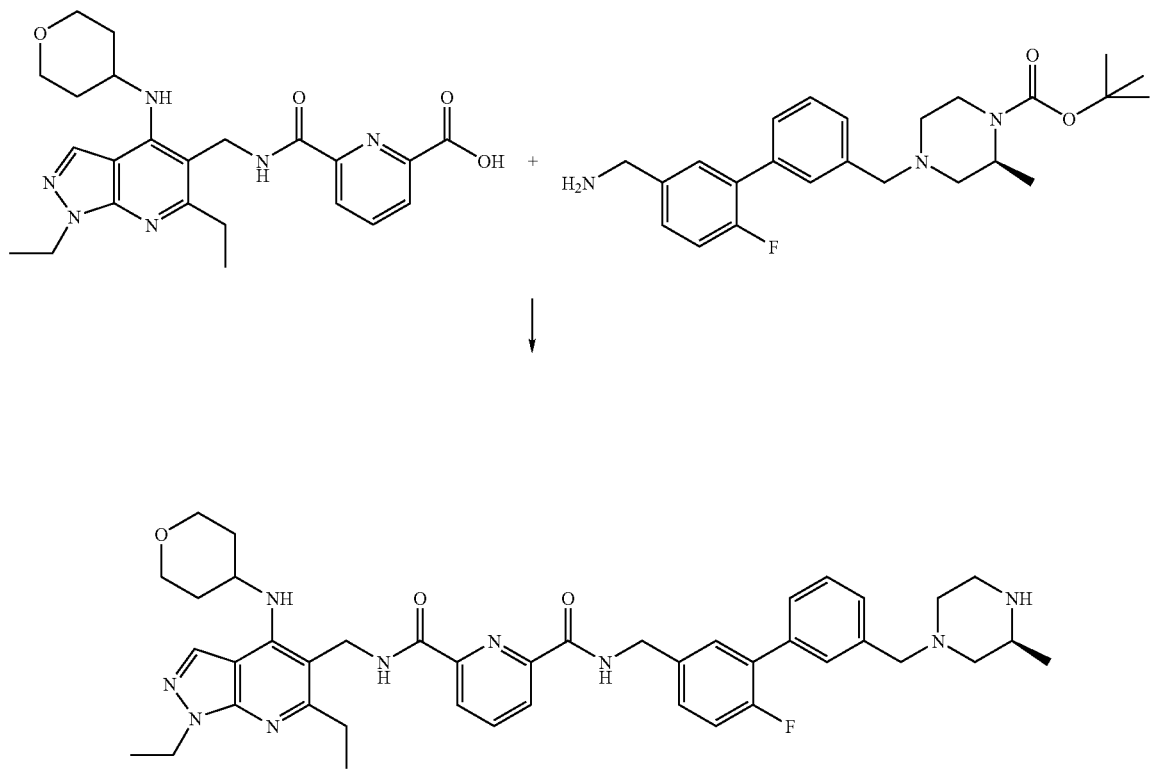

Process (A) A mixture of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (80 mg, 0.18 mmol), 1,1-dimethylethyl (2S)-4-{[5'-(aminomethyl)-2'-fluoro-3-biphenylyl]methyl}-2-methyl-1-piperazinecarboxylate (76 mg, 0.18 mmol), HBTU (80 mg, 0.21 mmol) and Et$_3$N (0.12 mL, 0.88 mmol) in DCM (3 mL) was stirred at room temperature overnight. The reaction was quenched with saturated NaHCO$_3$, and extracted with DCM twice. The combined organic layers were then washed with water followed by a brine wash. The organic layer was then concentrated under vacuum to give a crude residue: LC-MS m/z 848 (M+H)$^+$. The crude residue was dissolved in 25% TFA in DCM (2 mL) and stirred at RT for 2 h. It was purified with a Gilson HPLC (with 0.1% TFA condition), eluting with 10 to 70% CH$_3$CN in water in a flowrate of 20 mL/min. The fractions were combined and then converted to the free base with saturated NaHCO$_3$. The organic layer was recovered and dried over sodium sulfate, filtered and then concentrated to give N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,6-pyridinedicarboxamide as a solid (51 mg, 39%). LC-MS m/z 748 (M+H)$^+$.

Process (B) In an alternate process for preparing the above titled compound, N-{[1,6-diethyl-4-(tetrahydro-2H-pyran-4-ylamino)-1H-pyrazolo[3,4-b]pyridin-5-yl]methyl}-N'-[(6-fluoro-3'-formyl-3-biphenylyl)methyl]-2,6-pyridinedicarboxamide (50.0 mg. 0.075 mmol) was diluted in DMSO (1.5 mL) and dispensed into a 1 dram vial, fitted with a magnetic stir bar, containing 1,1-dimethylethyl (2S)-2-methyl-1-piperazinecarboxylate (0.226 mmol) and acetic acid (4.52 mg, 0.075 mmol). The resulting solution was stirred at room temperature for 4 h. Then MP-B(OAc)$_3$H (0.753 mmol, 176 mg) was added and the solution was stirred for another 12 h. The polymer reagent was filtered off and MeOH was added to the filtrate along with 1 drop of concentrated HCl. The solution was heated at 60° C. for 12 h. Purification was completed via a Gilson HPLC (basic conditions) to afford 12.1 mg (27.1%) of the titled compound. LC-MS m/z 749 (M+H)$^+$, 1.309 min (ret time).

Example 127

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,6-pyridinedicarboxamide

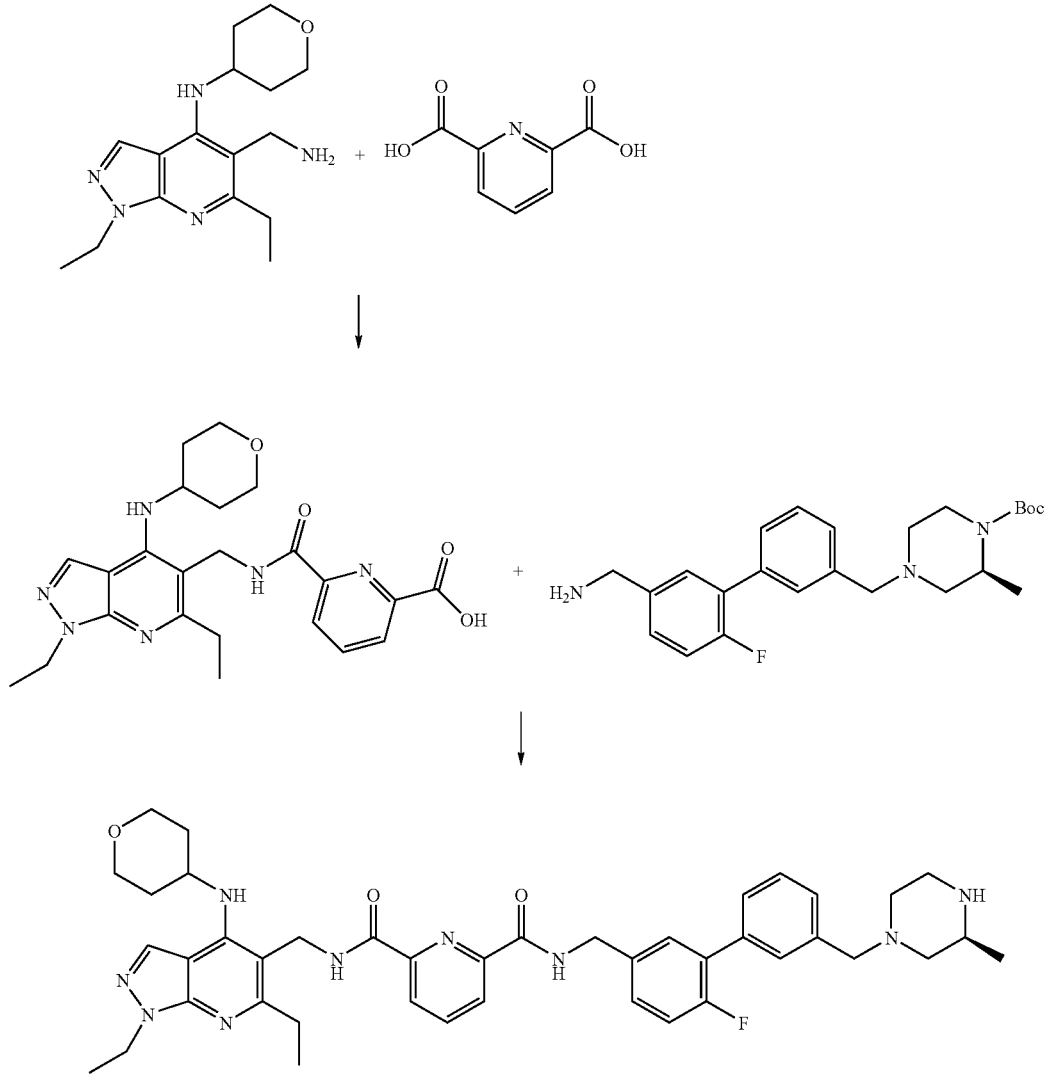

In a third alternate process for preparing the above named compound, 5-(aminomethyl)-1,6-diethyl-N-(tetrahydro-2H-pyran-4-yl)-1H-pyrazolo[3,4-b]pyridin-4-amine (0.1 mmol) and 2,6-pyridinedicarboxylic acid (0.1 mmol) was dissolved in DCM (3 mL), and HOBt was added (1.0 eq, 14.0 mg) along with EDC (1.0 eq, 19.0 mg). The resultant solution was stirred overnight. The solution was purified by preparative HPLC (Gilson) to yield 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid. This compound was dissolved in 3 mL of DCM along with 1,1-dimethylethyl (2S)-4-{[5'-(aminomethyl)-2'-fluoro-3-biphenylyl]methyl}-2-methyl-1-piperazinecarboxylate (41.3 mg, 0.1 mmol), followed by the addition of HOBt (1.0 eq, 14.0 mg) and EDC (1.0 eq, 19.0 mg). The resultant solution was stirred overnight and product was purified by preparative HPLC (Gilson) to give 1,1-dimethylethyl (2S)-4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-fluoro-3-biphenylyl)methyl]-2-methyl-1-piperazinecarboxylate. This compound was then dissolved in 2 mL of dioxane:MeOH (3:1). Three drops of HCl (concentrated) were added to the resultant solution and it was heated at 60° C. for 1 h. The solution was applied to the amine column, rinsed with 10 mL of dioxane:MeOH (3:1) to afford 2.2 mg (2.9%) of the above named product. LC-MS m/z 749 (M+H)$^+$, 1.32 min (ret time).

Example 128

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-3,4-bis(methyloxy)-2,5-furandicarboxamide

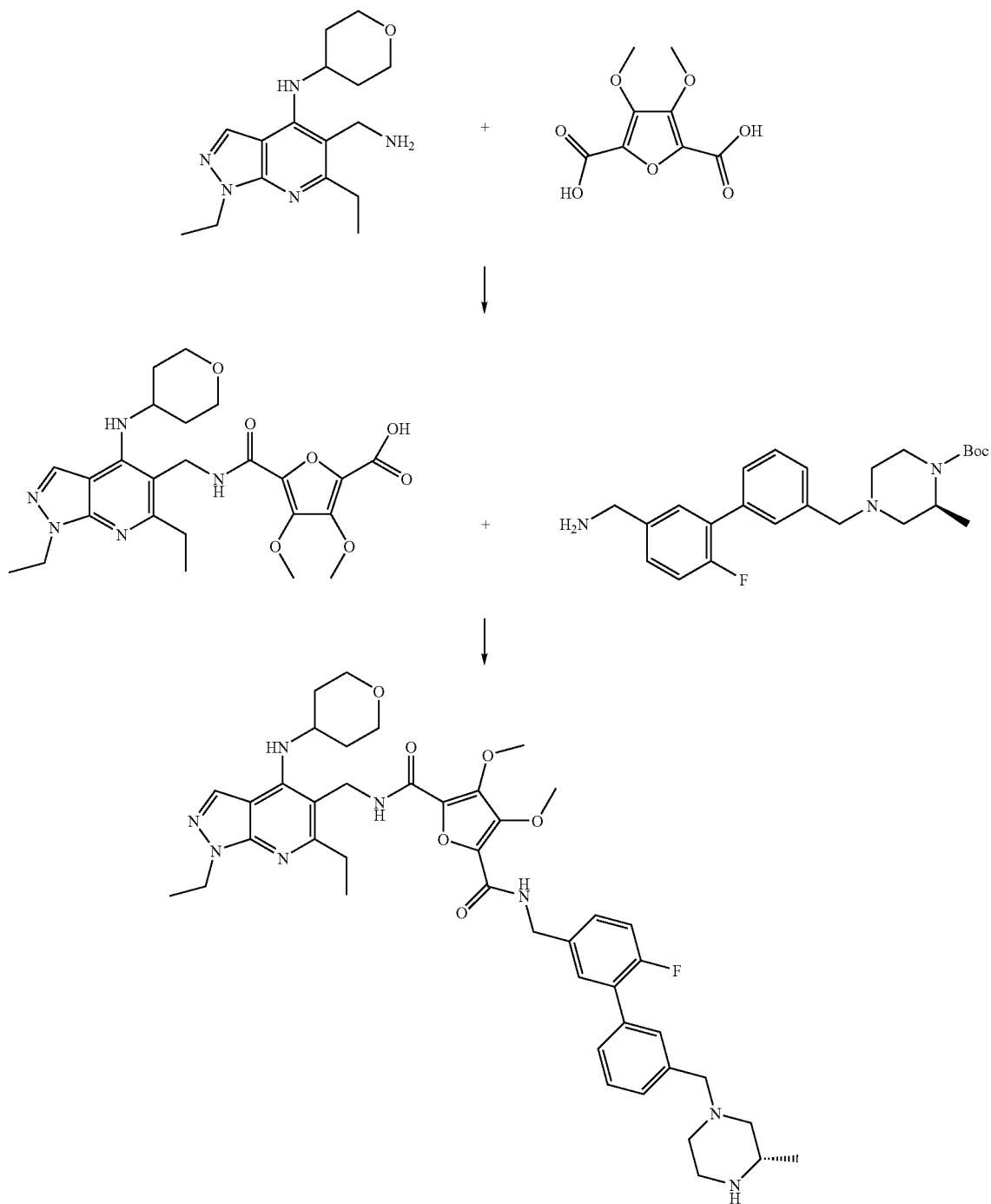

The title compound was prepared according to the general procedure of Example 127, substituting 3,4-bis(methyloxy)-2,5-furandicarboxylic acid (0.1 mmol) for 2,6-pyridinedicarboxylic acid, to afford 13.0 mg of the title compound (16.3%). LC-MS m/z 798 (M+H)+, 1.4 min (ret time).

Example 129

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,3-dihydro-6H-[1,4]dioxino[2,3-c]pyrrole-5,7-dicarboxamide

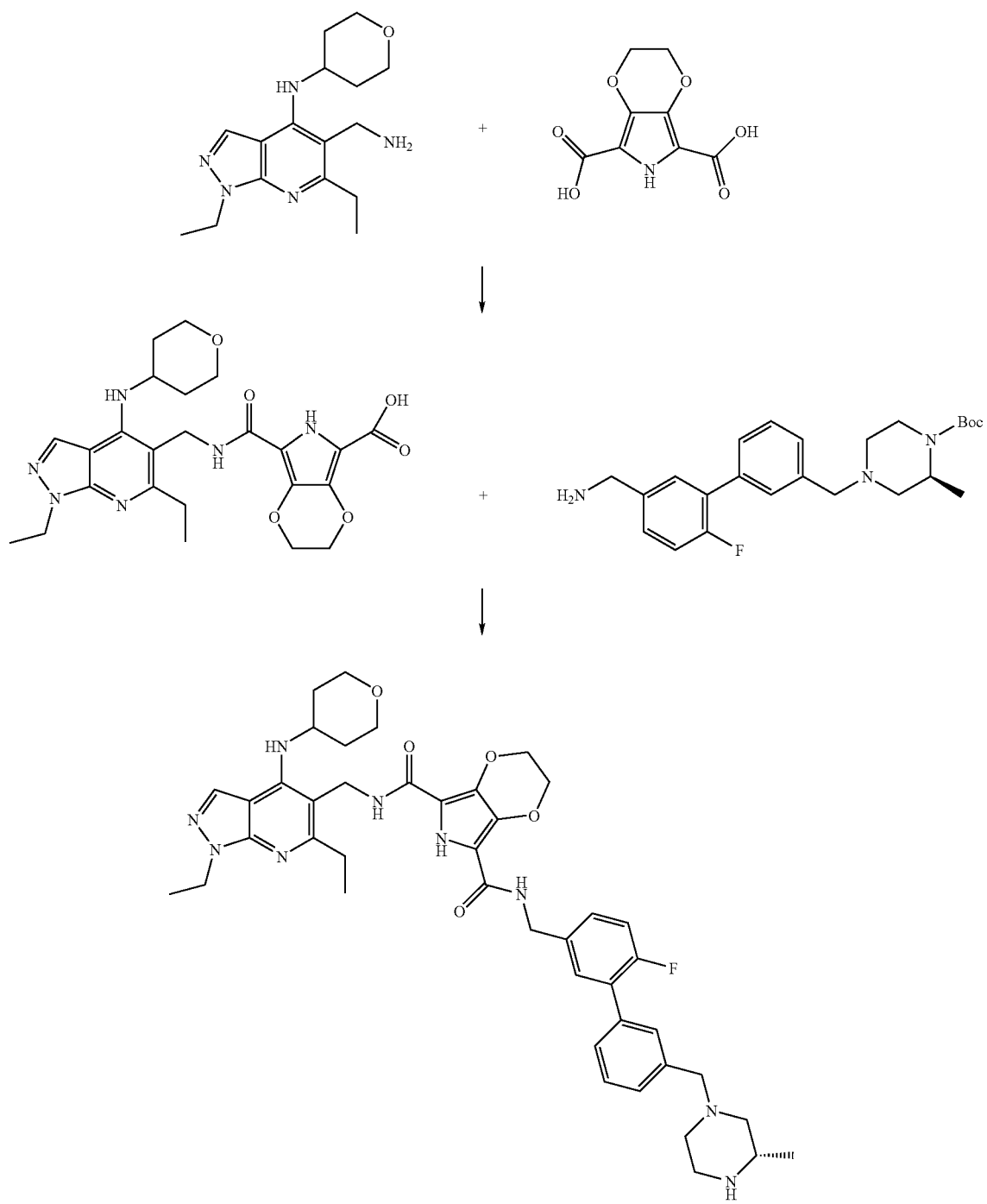

The title compound was prepared according to the general procedure of Example 127 by substituting 2,3-dihydro-6H-[1,4]dioxino[2,3-c]pyrrole-5,7-dicarboxylic acid (0.1 mmol), for 2,6-pyridinedicarboxylic acid to afford 23.2 mg of the title compound (29.2%). LC-MS m/z 795 (M+H)$^+$, 1.31 min (ret time).

Example 130

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,5-thiophenedicarboxamide

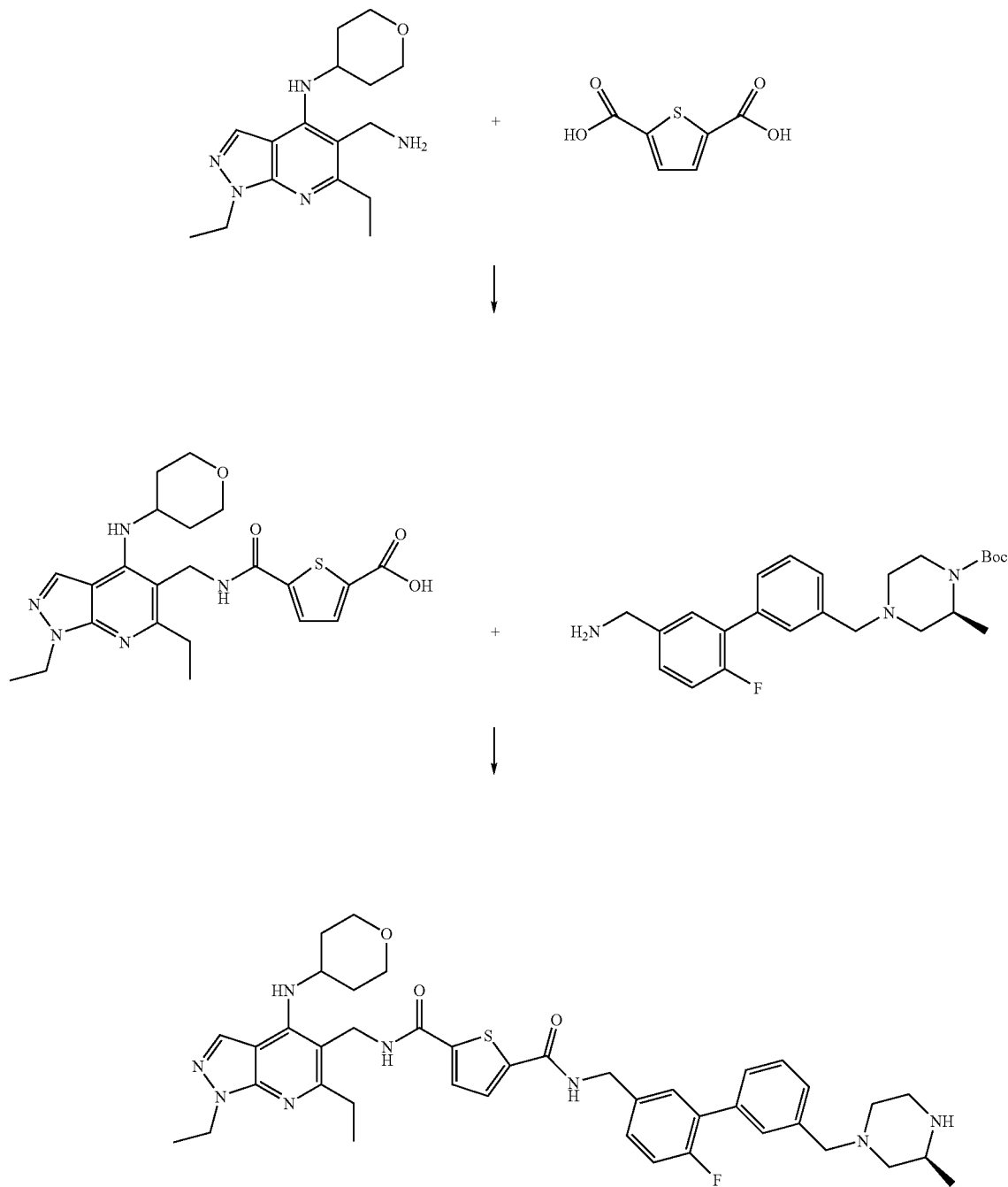

The title compound was prepared according to the general procedure of Example 127 by substituting 2,5-thiophenedicarboxylic acid (0.1 mmol) for 2,6-pyridinedicarboxylic acid to afford 29.0 mg of the title compound (38.5%). LC-MS m/z 754 (M+H)$^+$, 1.33 min (ret time).

Example 131

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-3,5-pyridinedicarboxamide

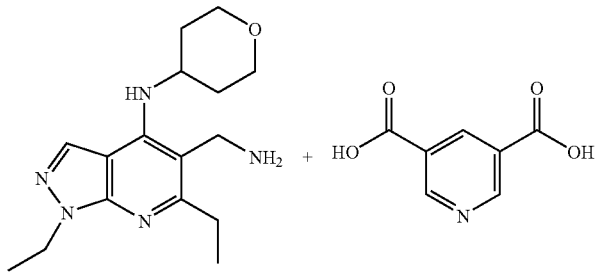

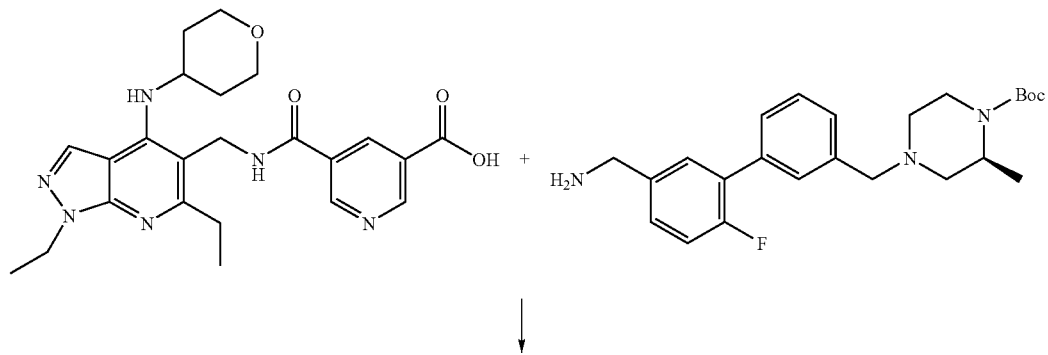

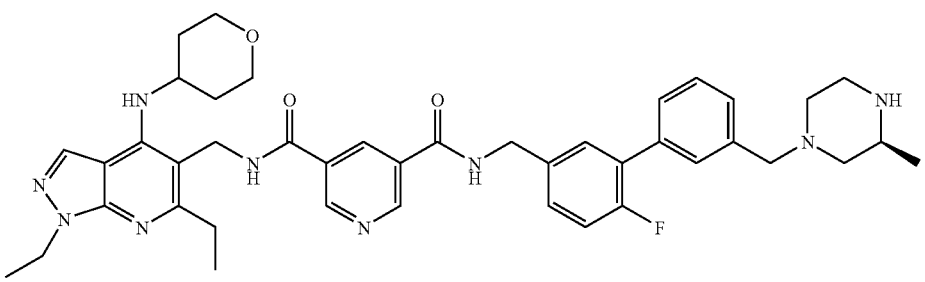

The title compound was prepared according to the general procedure of Example 127 by substituting 3,5-pyridinedicarboxylic acid (0.1 mmol) for 2,6-pyridinedicarboxylic acid to afford 24.2 mg of the title compound (32.4%). LC-MS m/z 749 (M+H)$^+$, 1.24 min (ret time).

Example 132

N-{[1,6-Diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-3,5-pyridinedicarboxamide

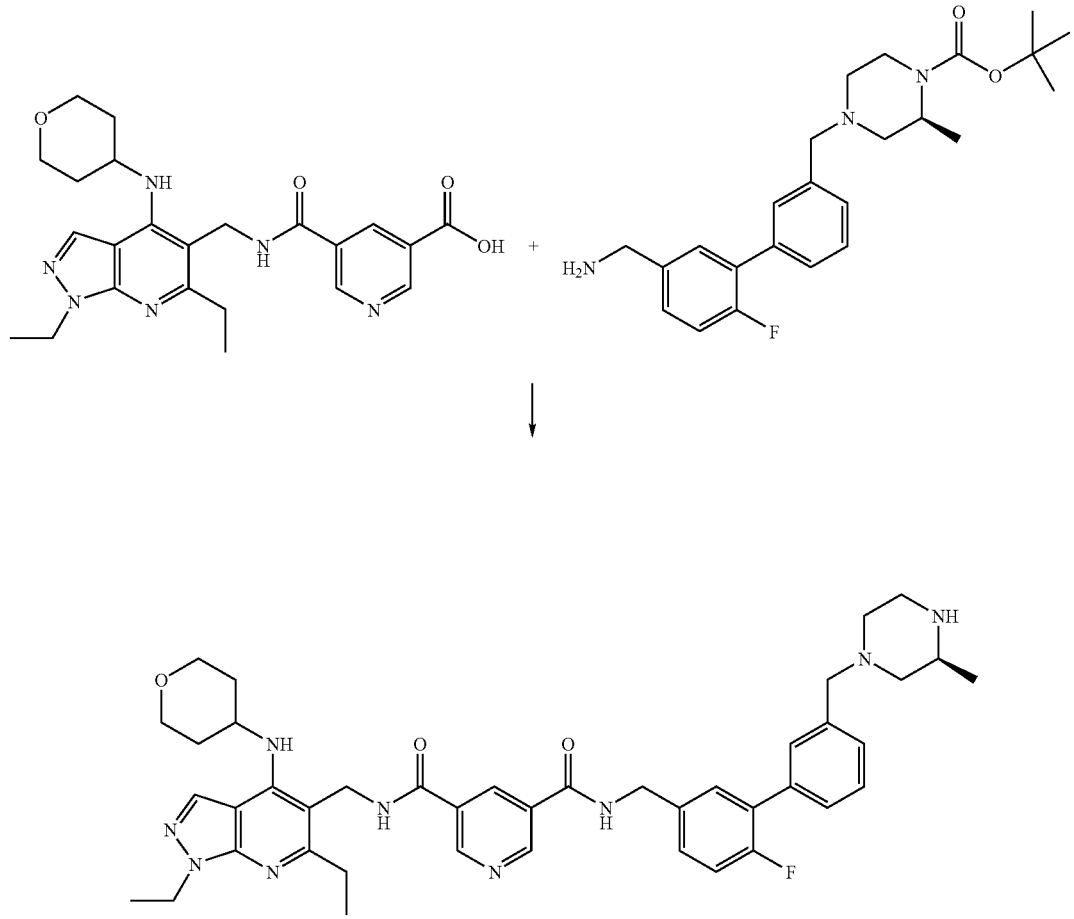

As an alternate process for preparing the compound of Example 131, a mixture of 5-[({[1,6-diethyl-4-(tetrahydro-2H-pyran-4-ylamino)-1H-pyrazolo[3,4-b]pyridin-5-yl]methyl}amino)carbonyl]-3-pyridinecarboxylic acid (50 mg, 0.110 mmol), 1,1-dimethylethyl (2S)-4-{[5'-(aminomethyl)-2'-fluoro-3-biphenylyl]methyl}-2-methyl-1-piperazinecarboxylate (45.7 mg, 0.110 mmol), HBTU (o-benzotriazol-1-yl-N,N,N',N'-tetramethyluronium hexafluorophosphate) (50.3 mg, 0.133 mmol) and Et₃N (0.046 ml, 0.331 mmol) in DCM was stirred at room temperature over the weekend. The reaction was quenched with saturated NaHCO₃, and extracted with DCM twice. The combined organic layers were washed with brine and then concentrated under vacuum to give the crude residue. It was then purified with a Gilson HPLC (with 0.1% TFA in the solvents), eluting with 10 to 70% CH₃CN in water at a flow rate of 20 mL/min. The product fractions were dried under GeneVac and then combined to give the intermediate 1,1-dimethylethyl (2S)-4-[(5'-{[({5-[({[1,6-diethyl-4-(tetrahydro-2H-pyran-4-ylamino)-1H-pyrazolo[3,4-b]pyridin-5-yl]methyl}amino)carbonyl]-3-pyridinyl}carbonyl)amino]methyl}-2'-fluoro-3-biphenylyl)methyl]-2-methyl-1-piperazinecarboxylate. This intermediate was then dissolved in 2 mL of 25% TFA in DCM and stirred at room temperature for 3 h. The crude products were purified with a Gilson HPLC (with 0.1% TFA in the solvents), eluting with 10 to 70% CH₃CN in water at a flow rate of 20 mL/min. The product fractions were combined and the free base was obtained by adding 1 N NaOH, and the aqueous layer was extracted with ethyl acetate twice. The combined organic layers were washed with brine, dried over sodium sulfate, filtered and concentrated under vacuum to N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-3,5-pyridinedicarboxamide as a solid (10 mg, 12.1%). LC-MS m/z 748 (M+H)⁺, 0.70 min (ret time).

Example 133

N-{[1,6-Diethyl-4-(tetrahydro-2H-pyran-4-ylamino)-1H-pyrazolo[3,4-b]pyridin-5-yl]methyl}-N'-{[3'-(4-piperidinylmethyl)-3-biphenylyl]methyl}-2,6-pyridinedicarboxamide

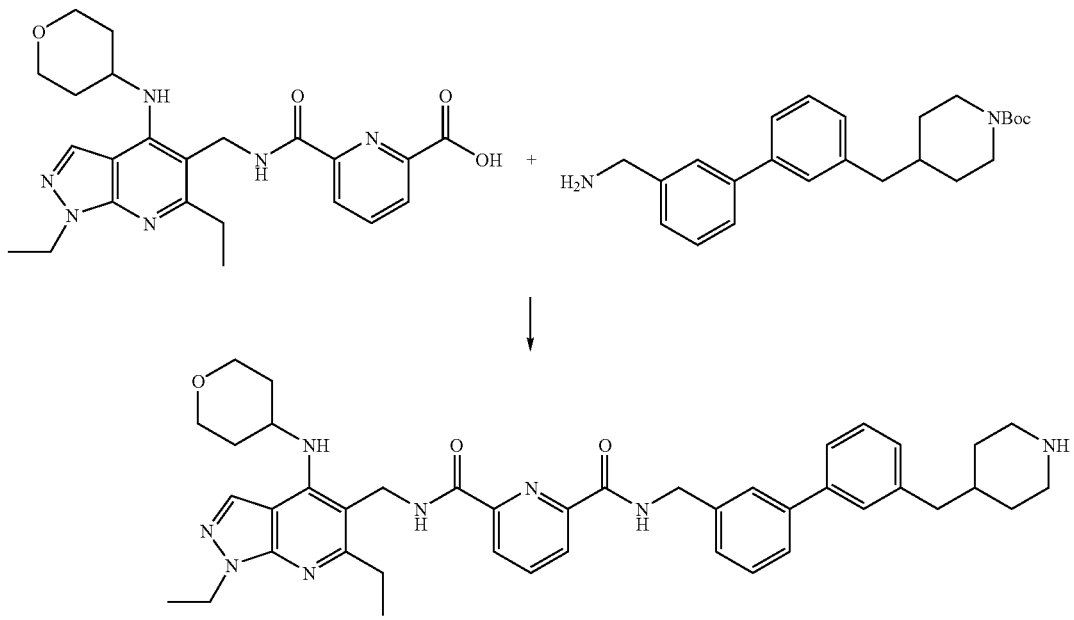

A mixture of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (80 mg, 0.177 mmol), 1,1-dimethylethyl 4-{[3'-(aminomethyl)-3-biphenylyl]methyl}-1-piperidinecarboxylate (74 mg, 0.177 mmol), HBTU (o-benzotriazol-1-yl-N,N,N',N'-tetramethyluronium hexafluorophosphate) (80 mg, 0.212 mmol) and Et₃N (0.12 mL, 0.884 mmol) in DCM was stirred at room temperature overnight. The reaction mixture was quenched with saturated NaHCO₃ and extracted with DCM twice. The combined organic layers were washed with brine and then concentrated under vacuum to give a crude residue. It was re-dissolved in 25% TFA in DCM (2 mL) and stirred for 2 h. Solvent was evaporated under a stream of nitrogen and then the residue was purified with a Gilson HPLC (with 1% TFA in the solvent), eluting with 10 to 70% CH₃CN in water at a flow rate of 20 mL/min. The product fractions were combined, product converted to the free base with saturated NaHCO₃ and extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-{[3'-(4-piperidinylmethyl)-3-biphenylyl]methyl}-2,6-pyridinedicarboxamide as a solid (14 mg, 11.1%). LC-MS m/z 716 (M+H)⁺, 1.58 min (ret time).

Example 134

N-{[1,6-Diethyl-4-(tetrahydro-2H-pyran-4-ylamino)-1H-pyrazolo[3,4-b]pyridin-5-yl]methyl}-N'-{[6-fluoro-3'-(4-piperidinylmethyl)-3-biphenylyl]methyl}-2,6-pyridinedicarboxamide

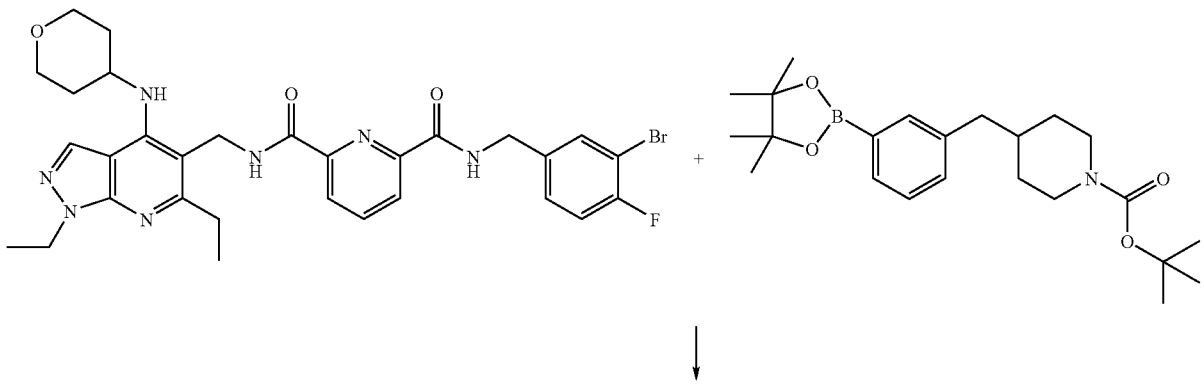

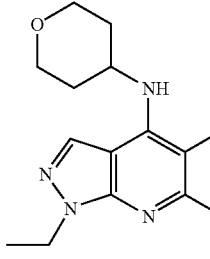
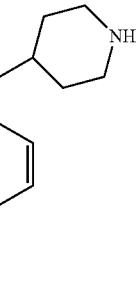

A mixture of N-[(3-bromo-4-fluorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (370 mg, 0.579 mmol), 1,1-dimethylethyl 4-{[3-(4,4,5,5-tetramethyl-1,3,2-dioxaborolan-2-yl)phenyl]methyl}-1-piperidinecarboxylate (233 mg, 0.579 mmol), $Na_2CO_3$ (184 mg, 1.738 mmol) and $PdCl_2(dppf)$ (42.4 mg, 0.058 mmol) was diluted in a mixture of 1,4-dioxane (3 mL) and water (1 mL) in a 2-5 mL biotage microwave reaction tube. The mixture was degassed by bubbling argon through it for 5 minutes and it was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 15 to 80% $CH_3CN$ in water at a flow rate of 20 mL/min. The product fractions were dried using a EZ2 GeneVac evaporator and then combined to give 1,1-dimethylethyl 4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-fluoro-3-biphenylyl)methyl]-1-piperidinecarboxylate as a solid. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% $CH_3CN$ in water at a flow rate of 20 mL/min. The product fractions were combined and converted to the free base with 1 N NaOH and extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-{[6-fluoro-3'-(4-piperidinylmethyl)-3-biphenylyl]methyl}-2,6-pyridinedicarboxamide as a solid (92 mg, 21.7%). LC-MS m/z 733 (M+H)$^+$, 0.87 min (ret time); $^1$H NMR (400 MHz, DMSO-d$_6$) δ 0.99-1.05 (m, 2H) 1.20 (t, J=7.40 Hz, 3H) 1.32 (t, J=7.15 Hz, 3H) 1.42-1.61 (m, 5H) 1.83-1.96 (m, 2H) 2.32-2.36 (m, 2H) 2.45-2.50 (m, 2H) 2.82-2.89 (m, 2H) 2.97 (q, J=7.28 Hz, 2H) 3.50-3.58 (m, 2H) 3.81-3.88 (m, 2H) 4.06-4.17 (m, 1H) 4.31 (q, J=7.19 Hz, 2H) 4.59-4.65 (m, 4H) 6.92 (d, J=7.53 Hz, 1H) 7.17 (d, J=7.28 Hz, 1H) 7.20-7.39 (m, 5H) 7.42-7.46 (m, 1H) 8.01 (s, 1H) 8.15-8.33 (m, 3H) 9.50 (t, J=6.27 Hz, 1H) 9.74 (t, J=6.27 Hz, 1H).

Example 135

N-{[6-Chloro-3'-(4-piperidinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide

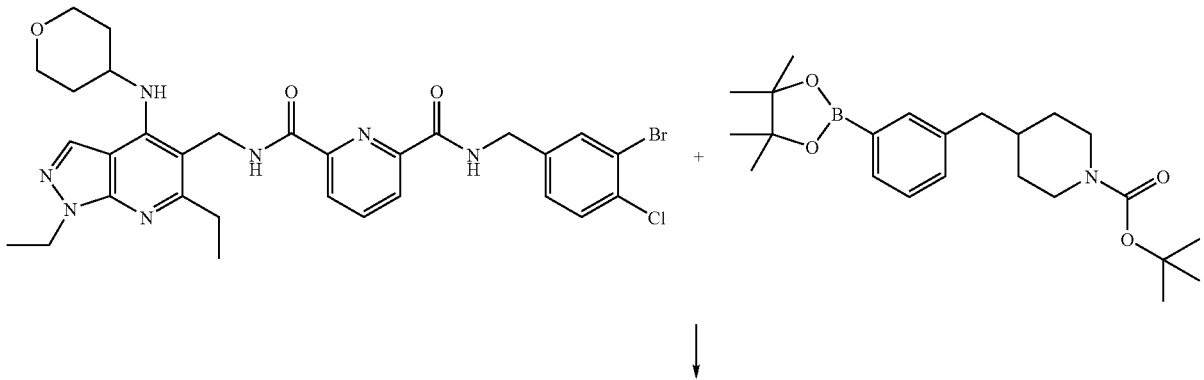

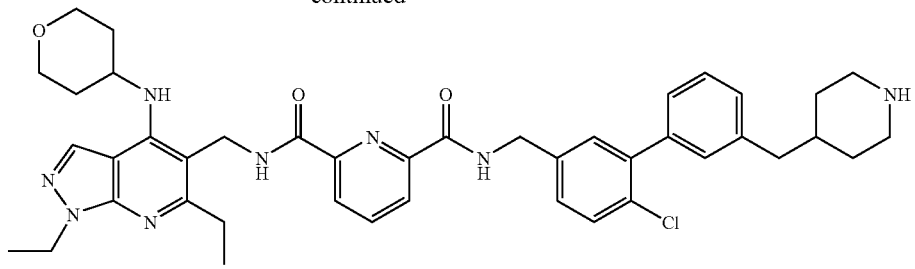

A mixture of N-[(3-bromo-4-chlorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.076 mmol), 1,1-dimethylethyl 4-{[3-(4,4,5,5-tetramethyl-1,3,2-dioxaborolan-2-yl)phenyl]methyl}-1-piperidinecarboxylate (24.07 mg, 0.076 mmol), $Na_2CO_3$ (24.27 mg, 0.229 mmol) and $PdCl_2(dppf)$ (5.59 mg, 7.63 μmol) was diluted in a mixture of 1,4-dioxane (3 mL) and water (1 mL) in a 2-5 mL Biotage microwave reaction tube. The mixture was degassed by bubbling argon through it for 5 minutes and was then heated in the Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% $CH_3CN$ in water at a flow rate of 20 mL/min. The product fractions were dried using a EZ2 GeneVac evaporator and then combined to give 1,1-dimethylethyl 4-[(2'-chloro-5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-3-biphenylyl)methyl]-1-piperidinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% $CH_3CN$ in water at a flow rate of 20 mL/min. The product fractions were combined and converted to the free base with saturated 1 N NaOH and the basified solution was extracted with ethyl acetate twice. The combined organic layers were washed with brine, dried over sodium sulfate, filtered and then concentrated under vacuum to give N-{[6-chloro-3'-(4-piperidinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide as a solid (13 mg, 22.7%). LC-MS m/z 749 $M^+$, 0.80 min (ret time).

Example 136

N-{[1,6-Diethyl-4-(tetrahydro-2H-pyran-4-ylamino)-1H-pyrazolo[3,4-b]pyridin-5-yl]methyl}-N'-{[6-methyl-3'-(4-piperidinylmethyl)-3-biphenylyl]methyl}-2,6-pyridinedicarboxamide

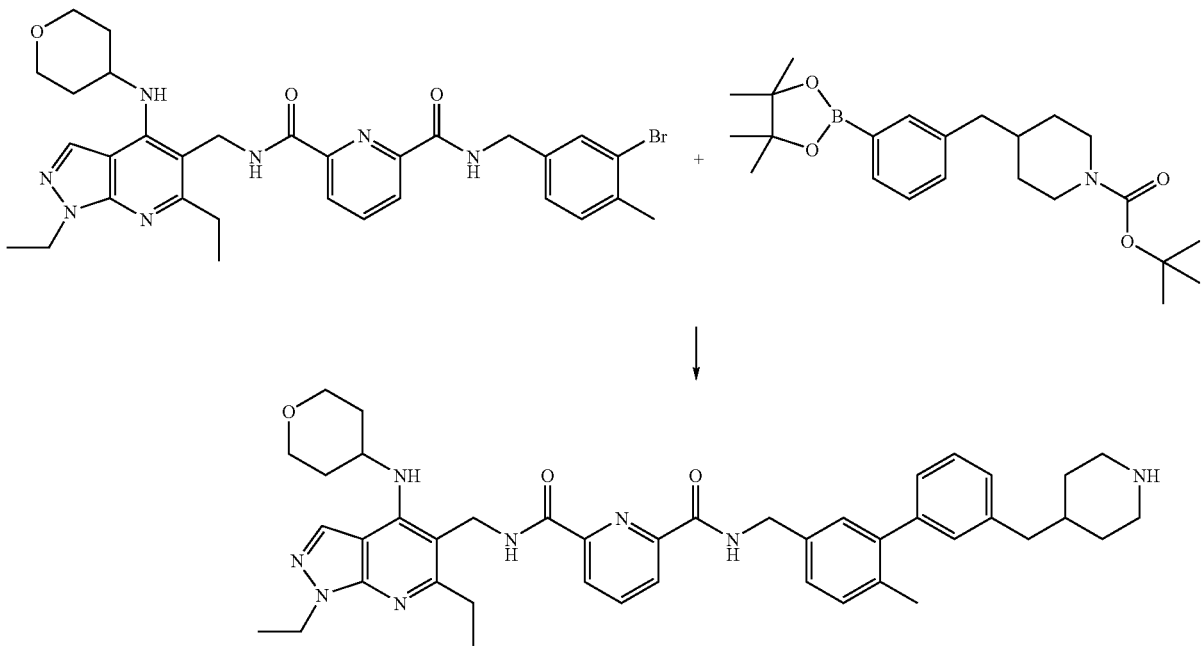

A mixture of N-[(3-bromo-4-methylphenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.079 mmol), 1,1-dimethylethyl 4-{[3-(4,4,5,5-tetramethyl-1,3,2-dioxaborolan-2-yl)phenyl]methyl}-1-piperidinecarboxylate (24.8 mg, 0.079 mmol), $Na_2CO_3$ (25.05 mg, 0.236 mmol) and $PdCl_2(dppf)$ (5.77 mg, 7.88 μmol) was diluted in a mixture of 1,4-dioxane (3 mL) and water (1 mL) in a 2-5 mL in a Biotage microwave reaction tube. The mixture was degassed by bubbling argon through it for 5 minutes and was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% $CH_3CN$ in water at a flow rate of 20 mL/min. The product fractions were dried using a EZ2 GeneVac evaporator and then combined to give 1,1-dimethylethyl 4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-1-piperidinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% $CH_3CN$ in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-{[6-methyl-3'-(4-piperidinylmethyl)-3-biphenylyl]methyl}-2,6-pyridinedicarboxamide as a solid (10 mg, 17.4%). LC-MS m/z 729 (M+H)$^+$, 0.79 min (ret time).

Example 137

N-{[1,6-diethyl-4-(tetrahydro-2H-pyran-4-ylamino)-1H-pyrazolo[3,4-b]pyridin-5-yl]methyl}-N'-{[6-(methyloxy)-3'-(4-piperidinylmethyl)-3-biphenylyl]methyl}-2,6-pyridinedicarboxamide Process (A). A mixture of N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.077 mmol), 1,1-dimethylethyl 4-{[3-(4,4,5,5-tetramethyl-1,3,2-dioxaborolan-2-yl)phenyl]methyl}-1-piperidinecarboxylate (24.23 mg, 0.077 mmol), $Na_2CO_3$ (24.44 mg, 0.236 mmol) and $PdCl_2$(dppf) (5.62 mg, 7.69 μmol) was diluted in a mixture of 1,4-dioxane (3 mL) and water (1 mL) in a 2-5 mL Biotage microwave reaction tube. The mixture was degassed by bubbling argon through it for 5 minutes and was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% $CH_3CN$ in water at a flow rate of 20 mL/min. The product fractions were dried using a EZ2 GeneVac evaporator and then combined to give 1,1-dimethylethyl 4-{[5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-(methyloxy)-3-biphenylyl]methyl}-1-piperidinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% $CH_3CN$ in water at a flow rate of 20 mL/min. The product fractions were combined and converted to the free base with 1 N NaOH, and the basified solution extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-{[6-(methyloxy)-3'-(4-piperidinylmethyl)-3-biphenylyl]methyl}-2,6-pyridinedicarboxamide as a solid (13 mg, 22.7%). LC-MS m/z 745 (M+H)$^+$, 0.76 min (ret time); $^1$H NMR (400 MHz, DMSO-$d_6$) δ 1.06-1.26 (m, 7H) 1.32 (t, J=7.28 Hz, 3H) 1.54-1.60 (m, 5H) 1.87-1.94 (m, 2H) 2.52-2.57 (m, 2H) 2.94-3.02 (m, 4H) 3.50-3.58 (m, 2H)

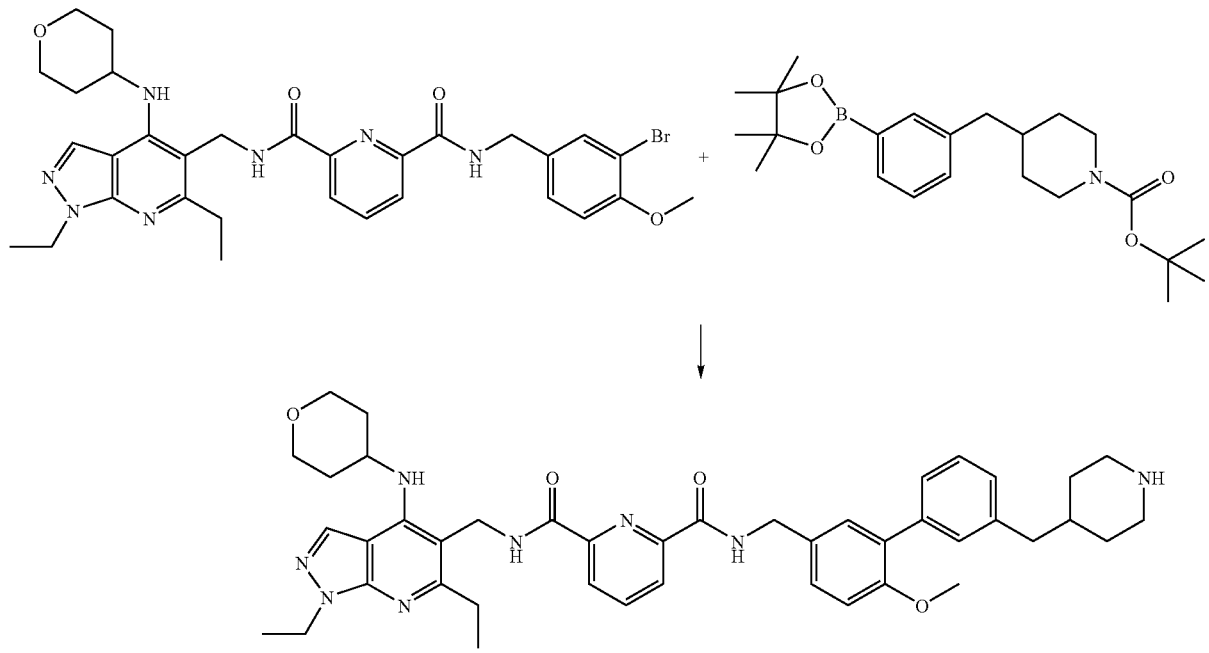

3.72 (s, 3H) 3.82-3.88 (m, 2H) 4.07-4.15 (m, 1H) 4.32 (q, J=7.28 Hz, 2H) 4.55 (d, J=6.02 Hz, 2H) 4.62 (d, J=6.27 Hz, 2H) 6.91 (d, J=7.78 Hz, 1H) 7.01-7.13 (m, 2H) 7.17-7.34 (m, 5H) 8.01 (s, 1H) 8.15-8.31 (m, 3H) 9.50 (t, J=6.27 Hz, 1H) 9.68 (t, J=6.27 Hz, 1H).

Process (B) In an alternate process for the preparation of the title compound, to 1,1-dimethylethyl 4-{[5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-(methyloxy)-3-biphenylyl]methyl}-1-piperidinecarboxylate (13.92 g, 16.47 mmol) in a 1 L round-bottom flask under nitrogen in dichloromethane (DCM) (140 mL) was added TFA (25.4 mL, 329 mmol), and the solution stirred at room temperature. After 90 min, the volatile solvent was evaporated and the remaining mixture was partitioned between dichloromethane and 1M sodium hydroxide. The pH was checked before proceeding to separate the layers (pH=10) and the aqueous layer extracted well with dichloromethane. The combined organics were washed with 1M sodium hydroxide several times then brine, dried (MgSO$_4$), filtered and evaporated to give 12.67 g (104%) of a beige foam. The crude product was purified on a 330 g Companion XL silica cartridge, eluting with 0-100% of (3% Et$_3$N in methanol) in dichloromethane over 12 column volumes. The isolated product contained triethylamine that needed to be removed. The product was dissolved in DCM and washed with 0.5M sodium hydroxide, water, brine, dried (MgSO$_4$) and evaporated to give 7.64 g (62%) of a white foam. Rather than trying to remove all the DCM, the foam was broken up and stirred in ether (50 mL) and then filtered, washed with more ether, sucked dry then put under high vacuum at 40° C. This gave 6.91 g (56%) of a white powdery solid that the lab HPLC showed to be 99.06% pure (retention time 1.94 min). LC-MS m/z 745 (M+H)$^+$, 2.07 min (ret time).

Example 138

N-{[1,6-Diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide

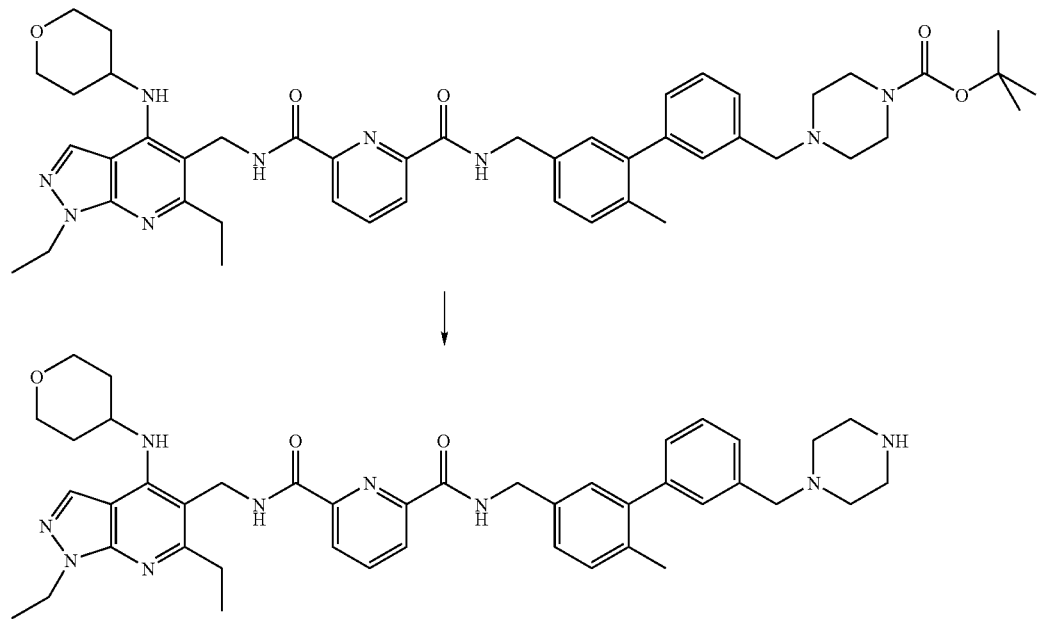

Process (A) 1,1-Dimethylethyl-4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-1-piperazinecarboxylate (1.8 g, 2.169 mmol) was treated with trifluoroacetic acid (3 ml, 38.9 mmol) in dichloromethane (27 mL) and the mixture stirred at room temperature overnight. Solvent was evaporated to give a crude product as a TFA salt. It was re-dissolved in DCM and then washed with saturated NaHCO$_3$. The organic layer was washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide as a white solid (1.6 g, 66.1%). LC-MS m/z 730 (M+H)$^+$, 0.78 min (ret time); $^1$H NMR (400 MHz, DMSO-d$_6$) δ 1.21 (t, J=7.15 Hz, 3H) 1.32 (t, J=7.15 Hz, 3H) 1.46-1.62 (m, 2H) 1.83-1.94 (m, 2H) 2.18 (s, 3H) 2.21-2.33 (m, 4H) 2.62 (t, J=4.64 Hz, 4H) 2.97 (q, J=7.36 Hz, 2H) 3.43 (s, 2H) 3.53 (td, J=11.36, 1.88 Hz, 2H) 3.81-3.88 (m, 2H) 4.06-4.17 (m, 1H) 4.32 (q, J=7.11 Hz, 2H) 4.60 (dd, J=17.57, 6.27 Hz, 4H) 6.91 (d, J=8.03 Hz, 1H) 7.11-7.29 (m, 6H) 7.35 (t, J=7.53 Hz, 1H) 8.01 (s, 1H) 8.14-8.33 (m, 3H) 9.50 (t, J=6.27 Hz, 1H) 9.70 (t, J=6.27 Hz, 1H).

Process (B) In an alternate process for the preparation of the title compound, to 1,1-dimethylethyl 4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-1-piperazinecarboxylate (8.13 g, 9.79 mmol) in a 2 L round-bottom flask under nitrogen in dichloromethane (DCM) (100 mL) was added TFA (15.09 mL, 196 mmol) and the solution was stirred at room temperature. After 1.75 h the volatile solvent was evaporated and the resulting mixture was partitioned between dichloromethane and 2M sodium hydroxide. The pH was checked before proceeding to separate the layers (pH=10) and the aqueous layer extracted well with dichloromethane. The combined organics were washed with 0.5M NaOH then water, brine, dried (MgSO$_4$), filtered and evaporated. This gave ~9 g of a white foam. This crude product was purified on a 330 g Companion XL silica cartridge, eluting with 0-50% of (3% Et$_3$N in methanol) in dichloromethane over 8 column volumes. Fractions were analysed by HPLC and appropriate ones evaporated to 10.85 g of a white foam. This material was re-dissolved in DCM and washed with 0.5M sodium hydroxide, water, brine, dried (MgSO₄) and evaporated to give 10.35 g of a white foam. This 10.35 g of product was dissolved in DCM (600 mL) and washed with water (2×300 mL), brine (2×), dried (MgSO₄) and the solvent evaporated. This gave a white foam that was put under high vacuum. The next morning the foam was broken up and crushed and put on a rotary evaporator at 42° C. and tumbled under high vacuum for ~8 h, then put under high vacuum overnight. This gave a white powdery solid. NMR (DMSO-D6) was run to check Et₃N and DCM levels: showed no Et₃N but still some DCM, calculated as 1.51% w/w. The material was crushed again and put on a rotary evaporator at 42° C. and tumbled under high vacuum for ~5 h once more. Another NMR (DMSO) was run to see any progress: showed virtually no change. This material was stirred in diethyl ether (400 mL) for 3.5 h then filtered, washed with ether and sucked dry and put under high vacuum at 40° C. on an evaporator for 3 h, then on a vacuum manifold overnight at room temperature. This gave 62.27 g (82%) of a white powdery solid. The lab HPLC showed a purity of 100% with a retention time of 1.82 min. LC-MS m/z 730 (M+H)⁺, 1.91 min (ret time).

Example 139

N-{[1,6-Diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide hydrochloride To a solution of N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide (565 mg, 0.774 mmol) in ethanol (1 mL) was added 1N HCl (0.735 mL, 0.735 mmol). The mixture was stirred at RT for 2 h. It was concentrated under vacuum. The residue was re-dissolved in ethanol and stripped down (this was repeated for three times). Then a 1:1 mixture of DCM:hexane (5 mL) was added and concentrated (this was repeated twice). Finally, the white solid that formed was dried under high vacuum for two days to give N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide hydrochloride as a solid (530 mg, 89%). LC-MS m/z 730 (M+H)⁺, 0.79 min (ret time).

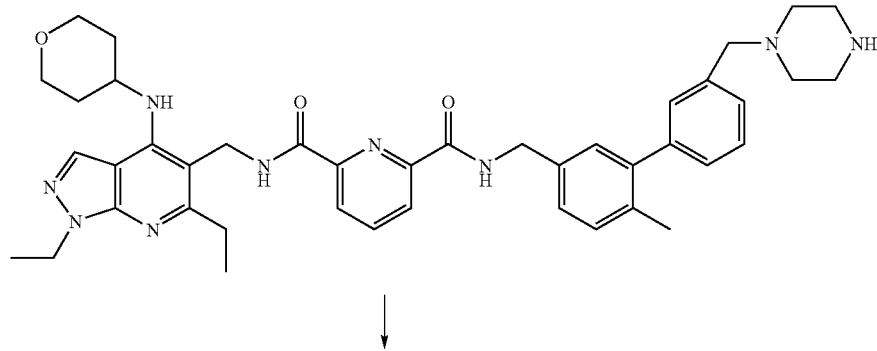

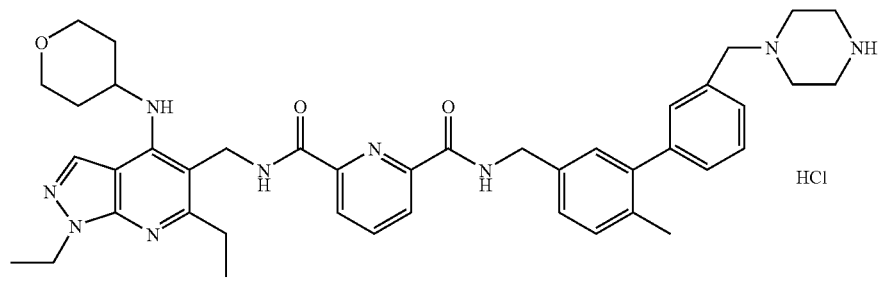

Example 140

N-({3'-[(1S,4S)-2,5-Diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide

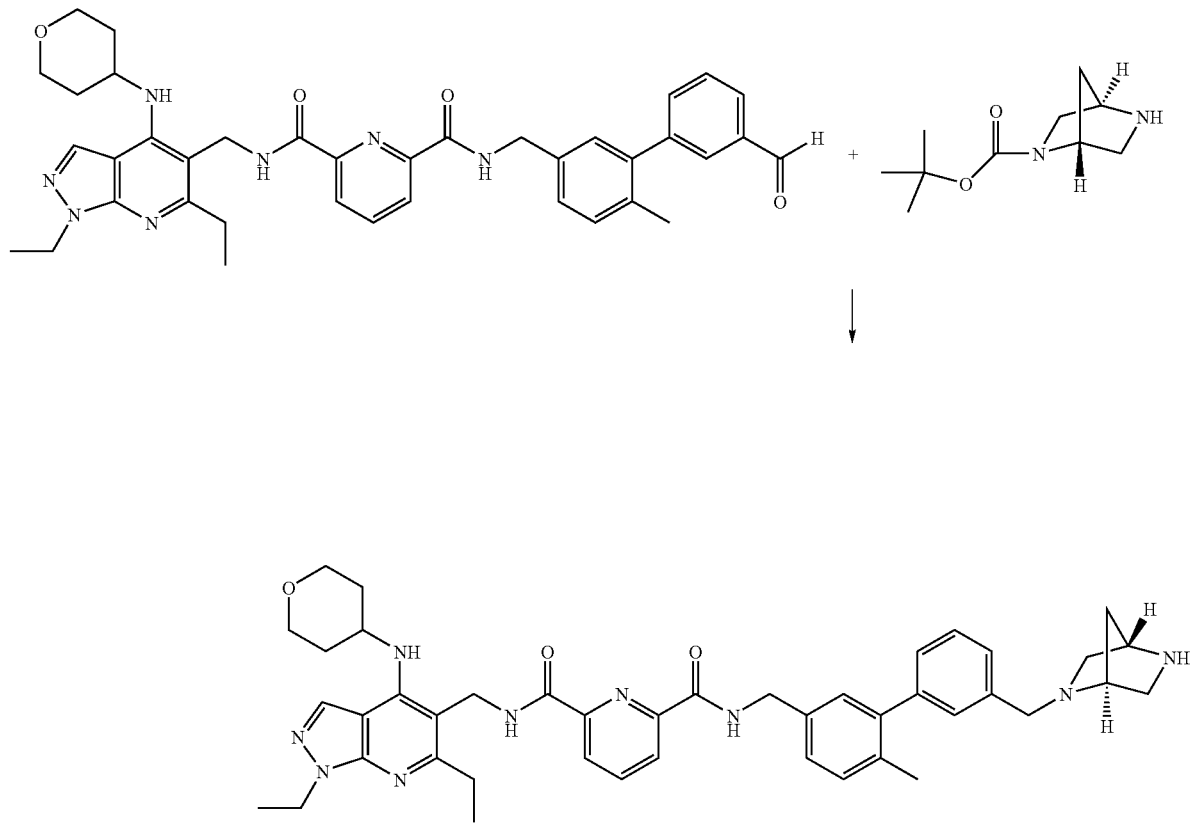

A mixture of N-{[1,6-diethyl-4-(tetrahydro-2H-pyran-4-ylamino)-1H-pyrazolo[3,4-b]pyridin-5-yl]methyl}-N'-[(3'-formyl-6-methyl-3-biphenylyl)methyl]-2,6-pyridinedicarboxamide (610 mg, 0.925 mmol), 1,1-dimethylethyl (1R,4R)-2,5-diazabicyclo[2.2.1]heptane-2-carboxylate (183 mg, 0.925 mmol), sodium triacetoxyborohydride (392 mg, 1.849 mmol) and acetic acid (0.064 mL, 1.109 mmol) in DCM (10 mL) was stirred at room temperature overnight. The reaction mixture was quenched with saturated NaHCO$_3$ and extracted with DCM twice. The combined organic layers were concentrated under vacuum to give a crude residue. It was purified with Companion, eluting with 0 to 100% ethyl acetate in hexane to get rid of impurities and then 10% methanol in DCM to elute the product. The product fractions were combined and concentrated under vacuum to give 1,1-dimethylethyl (1S,4S)-5-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-2,5-diazabicyclo[2.2.1]heptane-2-carboxylate as a solid. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 70% CH$_3$CN in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N-({3'-[(1S,4S)-2,5-diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide as a solid (431 mg, 62.8%). LC-MS m/z 743 (M+H)$^+$, 1.18 min (ret time).

Example 141

N-{[1,6-Diethyl-4-(tetrahydro-2H-pyran-4-ylamino)-1H-pyrazolo[3,4-b]pyridin-5-yl]methyl}-N'-[(6-methyl-3'-{[(3S)-3-methyl-1-piperazinyl]methyl}-3-biphenylyl)methyl]-2,6-pyridinedicarboxamide

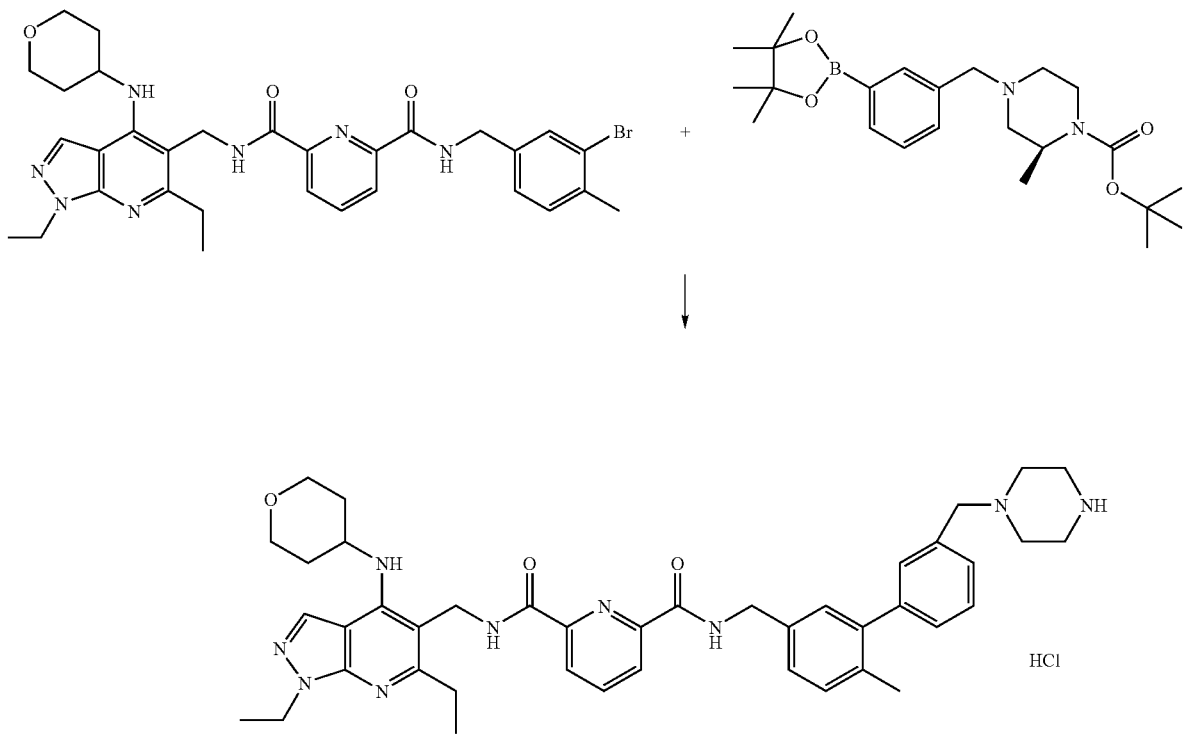

A mixture of N-[(3-bromo-4-methylphenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (100 mg, 0.158 mmol), 1,1-dimethylethyl (2S)-2-methyl-4-{[3-(4,4,5,5-tetramethyl-1,3,2-dioxaborolan-2-yl)phenyl]methyl}-1-piperazinecarboxylate (65.6 mg, 0.158 mmol), Na$_2$CO$_3$ (50.1 mg, 0.473 mmol) and PdCl$_2$(dppf) (11.53 mg, 0.016 mmol) was diluted in a mixture of 1,4-dioxane (3 mL) and water (1 mL) in a 2-5 mL Biotage microwave reaction tube. The mixture was degassed by bubbling argon through it for 5 minutes and it was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% CH$_3$CN in water at a flow rate of 20 mL/min. The product fractions were dried using a EZ2 GeneVac evaporator and then combined to give 1,1-dimethylethyl (2S)-4-[(5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-methyl-3-biphenylyl)methyl]-2-methyl-1-piperazinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% CH$_3$CN in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-[(6-methyl-3'-{[(3S)-3-methyl-1-piperazinyl]methyl}-3-biphenylyl)methyl]-2,6-pyridinedicarboxamide as a solid (10 mg, 8.53%). LC-MS m/z 744 (M+H)$^+$, 1.33 min (ret time); $^1$H NMR (400 MHz, DMSO-d$_6$) δ 0.91 (d, J=6.27 Hz, 3H) 1.21 (t, J=7.53 Hz, 3H) 1.33 (t, J=7.15 Hz, 3H) 1.47-1.64 (m, 3H) 1.87-1.94 (m, 2H) 2.18 (s, 3H) 2.64-2.68 (m, 6H) 2.94-3.00 (m, 2H) 3.46 (s, 2H) 3.49-3.62 (m, 2H) 3.82-3.87 (m, 2H) 4.08-4.14 (m, 1H) 4.29-4.35 (m, 2H) 4.56-4.59 (m, 4H) 6.90 (d, J=8.53 Hz, 1H) 7.09-7.29 (m, 6H) 7.35 (t, J=7.53 Hz, 1H) 8.01 (s, 1H) 8.13-8.33 (m, 3H) 9.50 (t, J=6.27 Hz, 1H) 9.70 (t, J=6.27 Hz, 1H).

Example 142

N-{[1,6-Diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide

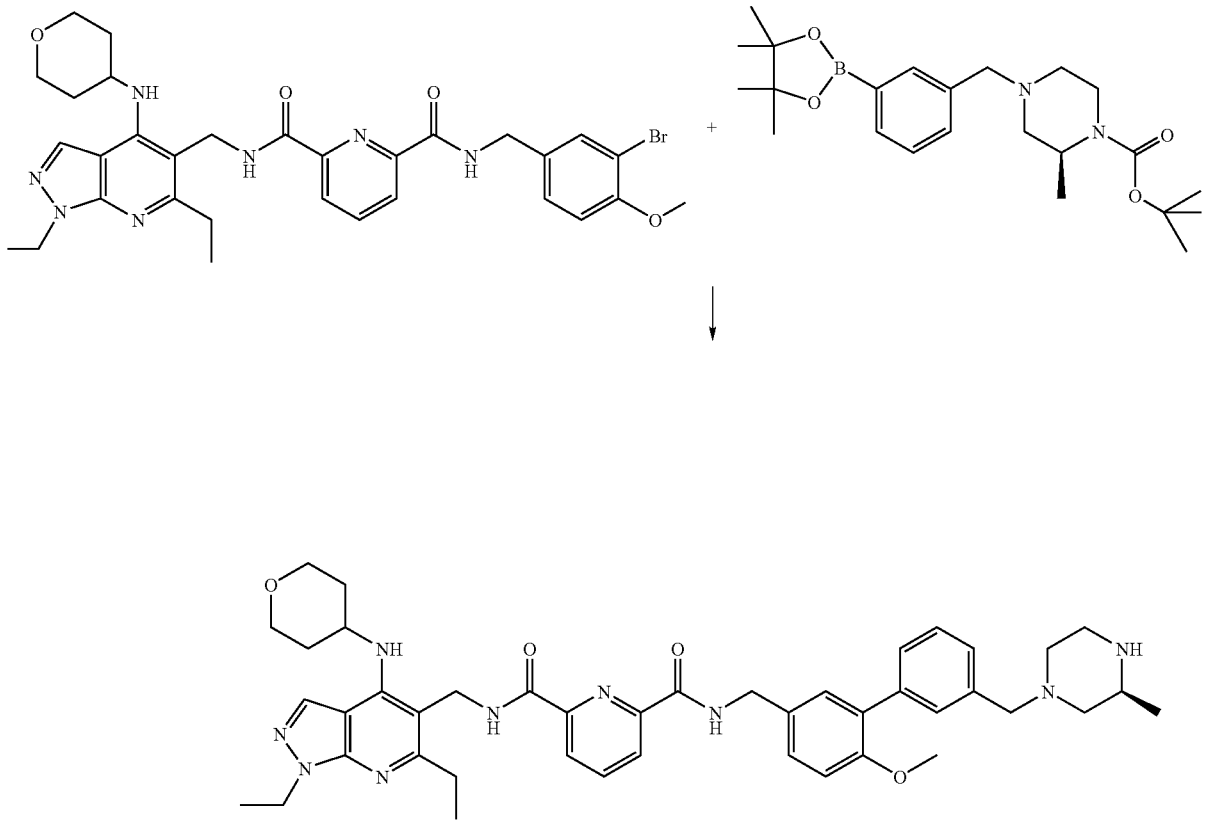

A mixture of N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide (260 mg, 0.400 mmol), 1,1-dimethylethyl (2S)-2-methyl-4-{[3-(4,4,5,5-tetramethyl-1,3,2-dioxaborolan-2-yl)phenyl]methyl}-1-piperazinecarboxylate (166 mg, 0.400 mmol), $Na_2CO_3$ (127 mg, 1.199 mmol) and $PdCl_2$(dppf) (29.2 mg, 0.040 mmol)) was diluted in a mixture of 1,4-dioxane (3 mL) and water (1 mL) in a 2-5 mL Biotage microwave reaction tube. The mixture was degassed by bubbling argon through it for 5 minutes and it was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain the crude residue. It was purified with a Gilson HPLC (with 0.1% TFA in the solvents), eluting with 10 to 70% $CH_3CN$ in water at a flow rate of 20 mL/min. The product fractions were dried using a EZ2 GeneVac evaporator and then combined to give 1,1-dimethylethyl (2S)-4-{[5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-(methyloxy)-3-biphenylyl]methyl}-2-methyl-1-piperazinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% $CH_3CN$ in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide as a solid (48 mg, 15.8%). LC-MS m/z 760 $(M+H)^+$, 0.80 min (ret time).

Example 143

N-{[1,6-Diethyl-4-(tetrahydro-2H-pyran-4-ylamino)-1H-pyrazolo[3,4-b]pyridin-5-yl]methyl}-N'-{[3'-(1-piperazinylmethyl)-3-biphenylyl]methyl}-2,6-pyridinedicarboxamide

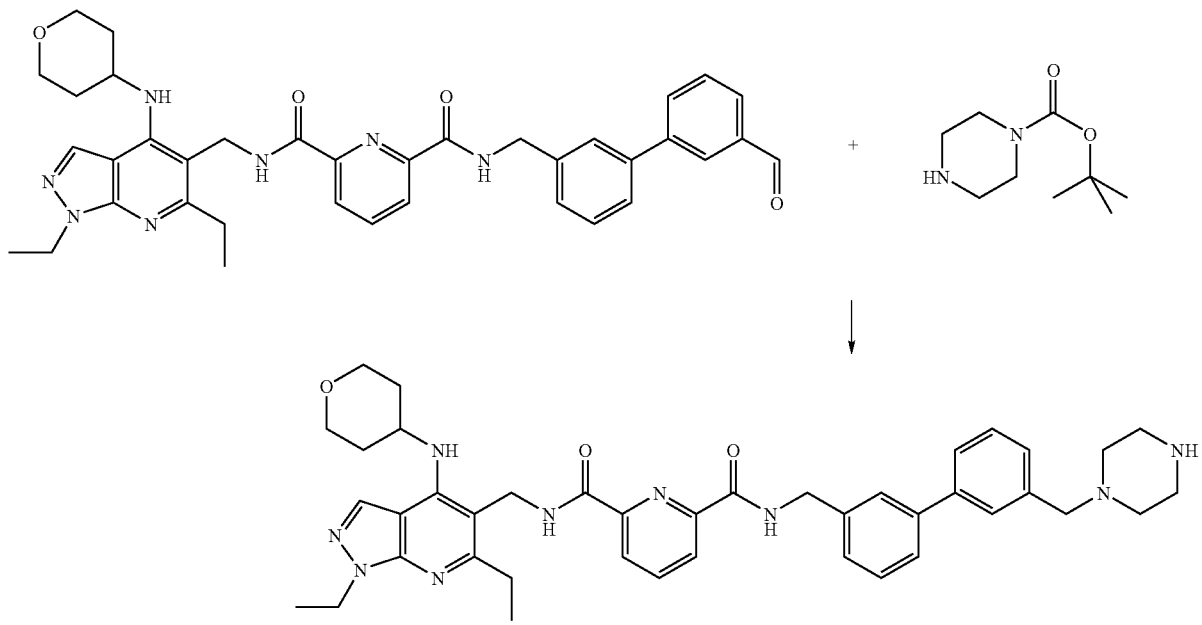

N-{[1,6-Diethyl-4-(tetrahydro-2H-pyran-4-ylamino)-1H-pyrazolo[3,4-b]pyridin-5-yl]methyl}-N'-[(3'-formyl-3-biphenylyl)methyl]-2,6-pyridinedicarboxamide (40 mg, 0.062 mmol), 1,1-dimethylethyl 1-piperazinecarboxylate (115.37 mg, 0.619 mmol, 10 eq) and acetic acid (3.55 μL, 0.062 mmol, 1 eq) were dissolved in DMSO (1.5 mL). The mixture was stirred in a VX-2500 Multi-Tube Vortexer overnight at room temperature. MP-triacetoxyborohydride (195 mg, 0.482 mmol, 7.78 eq) was then added and the mixture was stirred again in the VX-2500 Multi-Tube Vortexer overnight at room temperature. The reaction mixture was filtered through a polypropylene cartridge (10 mL tube) on a Bohdan Miniblock (Artisian Scientific, Champaign, Ill., USA, http://www.artisan-scientific.com/51413.htm) in a reaction tube and concentrated in a Glas-Col evaporator. Methanol (2 mL) and hydrochloric acid (5 μL) were then added and the vial containing the reaction mixture was closed and stirred in a Glas-Col evaporator over the weekend at 60° C. The reaction mixture was then concentrated and purified by Gilson HPLC with a water-acetonitrile with 0.1% TFA buffer. The desired product fractions were combined, filtered through amine cartouche (500 mg) on a Bohdan Miniblock and concentrated in a Glas-Col evaporator, giving 16.4 mg (41.1%) of the title compound. LC-MS m/z 716 (M+H)$^+$, 1.25 min (ret time).

Example 144

N-{[1,6-Diethyl-4-(tetrahydro-2H-pyran-4-ylamino)-1H-pyrazolo[3,4-b]pyridin-5-yl]methyl}-N'-[(3'-{[(3R)-3-methyl-1-piperazinyl]methyl}-3-biphenylyl)methyl]-2,6-pyridinedicarboxamide

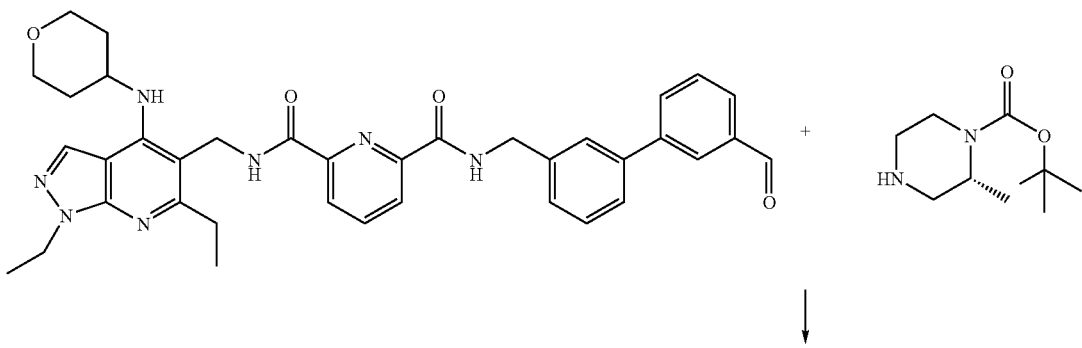

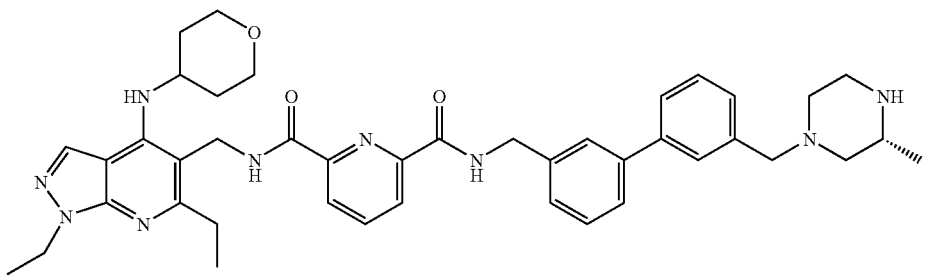

Using the procedure described in Example 143, replacing 1,1-dimethylethyl 1-piperazinecarboxylate with 1,1-dimethylethyl (2R)-2-methyl-1-piperazinecarboxylate, gave the above titled compound. LC-MS m/z 730 (M+H)$^+$, 1.29 min (ret time).

Example 145

N-({3'-[(1S,4S)-2,5-Diazabicyclo[2.2.1]hept-2-ylmethyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide

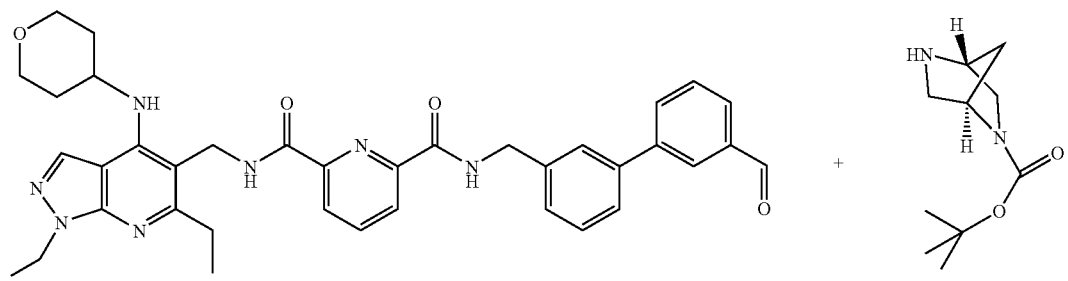

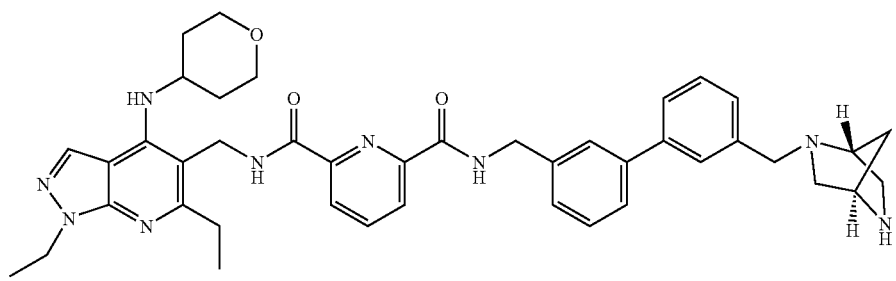

Using the procedure described in Example 143, but replacing 1,1-dimethylethyl 1-piperazinecarboxylate with 1,1-dimethylethyl (1R,4R)-2,5-diazabicyclo[2.2.1]heptane-2-carboxylate, gave the above titled compound. LC-MS m/z 728 (M+H)$^+$, 1.32 min (ret time).

Example 146

N-{[1,6-Diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-3-biphenylyl)methyl]-2,6-pyridinedicarboxamide

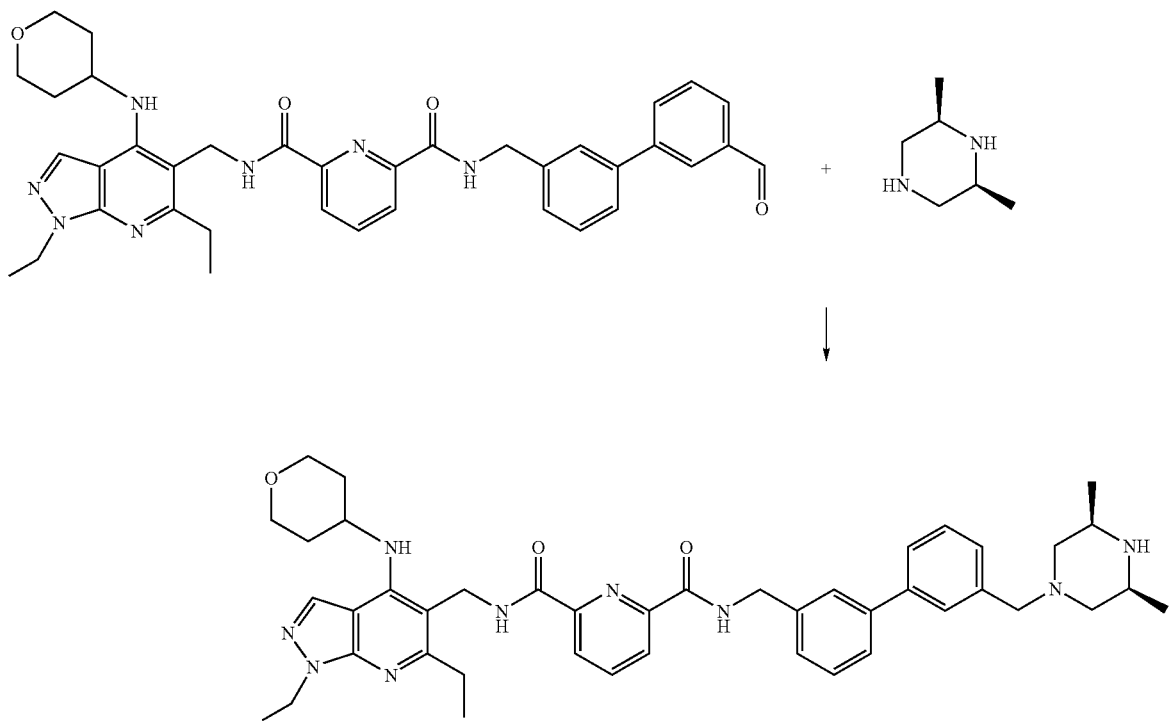

N-{[1,6-Diethyl-4-(tetrahydro-2H-pyran-4-ylamino)-1H-pyrazolo[3,4-b]pyridin-5-yl]methyl}-N'-[(3'-formyl-3-biphenylyl)methyl]-2,6-pyridinedicarboxamide (40 mg, 0.062 mmol), (2R,6S)-2,6-dimethylpiperazine (70.73 mg, 0.619 mmol, 10 eq) and acetic acid (3.55 µL, 0.062 mmol, 1 eq) were dissolved in DMSO (1.5 mL). The mixture was stirred in a VX-2500 Multi-Tube Vortexer overnight at room temperature. MP-triacetoxyborohydride (195 mg, 0.482 mmol, 7.78 eq) was then added and the mixture was stirred again in the VX-2500 Multi-Tube Vortexer overnight at room temperature. The reaction mixture was filtered through a polypropylene cartridge (10 mL tube) on a Bohdan Miniblock in a reaction tube and concentrated in a Glas-Col evaporator. The reaction mixture was then purified by Gilson HPLC with a water-acetonitrile with 0.1% TFA buffer. The desired product fractions were combined, filtered through amine cartouche (500 mg) on a Bohdan Miniblock and concentrated in a Glas-Col evaporator, giving 11.3 mg (27.2%) of the title compound. LC-MS m/z 744 (M+H)$^+$, 1.41 min (ret time).

Example 147

N-{[1,6-Diethyl-4-(tetrahydro-2H-pyran-4-ylamino)-1H-pyrazolo[3,4-b]pyridin-5-yl]methyl}-N'-[(3'-{[(3S)-3-methyl-1-piperazinyl]methyl}-3-biphenylyl)methyl]-2,6-pyridinedicarboxamide

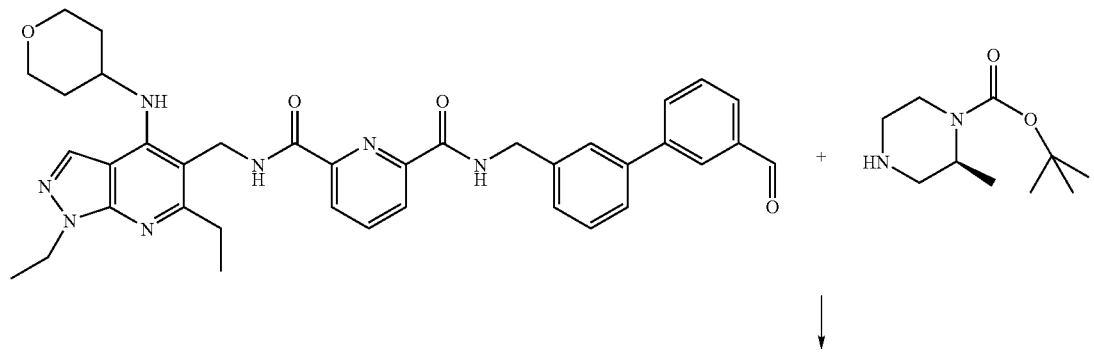

-continued

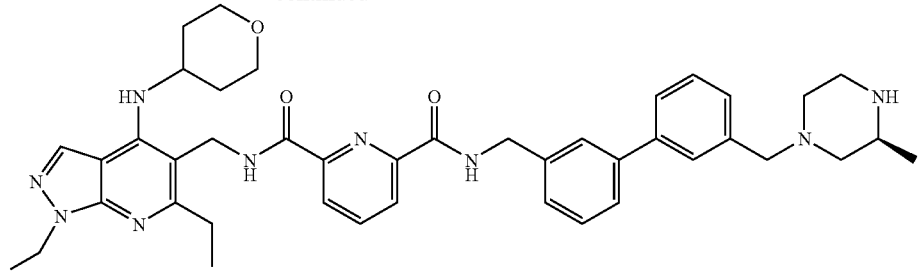

Using the procedure described in Example 143, but replacing 1,1-dimethylethyl 1-piperazinecarboxylate with 1,1-dimethylethyl (2S)-2-methyl-1-piperazinecarboxylate, gave the above titled compound. LC-MS m/z 730 (M+H)+, 1.30 min (ret time).

Example 148

N²-{[1,6-Diethyl-4-(tetrahydro-2H-pyran-4-ylamino)-1H-pyrazolo[3,4-b]pyridin-5-yl]methyl}-N⁴-[(6-fluoro-3'-{[(3S)-3-methyl-1-piperazinyl]methyl}-3-biphenylyl)methyl]-2,4-pyridinedicarboxamide

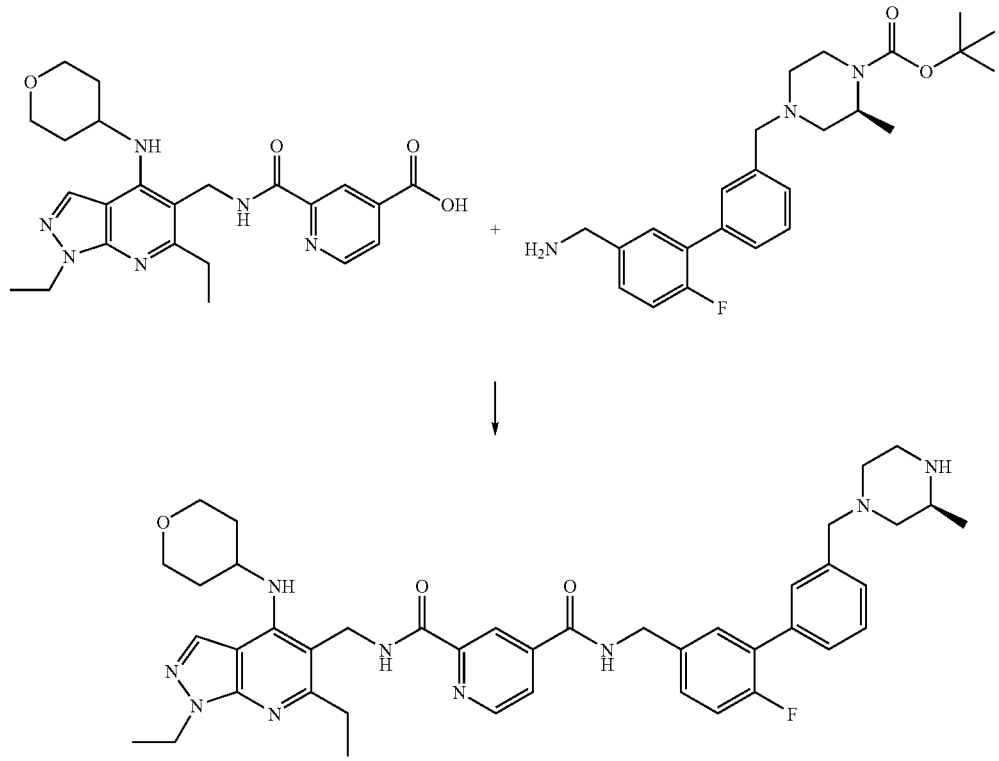

A mixture of 4-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (50.0 mg, 0.110 mmol), 1,1-dimethylethyl(2S)-4-{[5'-(aminomethyl)-2'-fluoro-3-biphenylyl]methyl}-2-methyl-1-piperazinecarboxylate (45.7 mg, 0.110 mmol), HBTU (o-benzotriazol-1-yl-N,N,N',N'-tetramethyluronium hexafluorophosphate) (50.3 mg, 0.133 mmol) and Et₃N (0.046 ml, 0.331 mmol) in DCM (3 mL) was stirred at room temperature for overnight. The reaction was quenched with saturated NaHCO₃ and extracted with DCM twice. The combined organic layers were washed with brine and then concentrated under vacuum to give the crude residue. It was then purified with a Gilson HPLC (with 0.1% TFA in the solvents), eluting with 10 to 70% CH₃CN in water at a flow rate of 20 mL/min. The product fractions were dried using a GeneVac to give 1,1-dimethylethyl (2S)-4-[(5'-{[({2-[({[1,6-diethyl-4-(tetrahydro-2H-pyran-4-ylamino)-1H-pyrazolo[3,4-b]pyridin-5-yl]methyl}amino)carbonyl]-4-pyridinyl}carbonyl)amino]methyl}-2'-fluoro-3-biphenylyl)methyl]-2-methyl-1-piperazinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 70% CH₃CN in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give $N^2$-{[1,6-diethyl-4-(tetrahydro-2H-pyran-4-ylamino)-1H-pyrazolo[3,4-b]pyridin-5-yl]methyl}-$N^4$-[(6-fluoro-3'-{[(3S)-3-methyl-1-piperazinyl]methyl}-3-biphenylyl)methyl]-2,4-pyridinedicarboxamide as a solid (30 mg, 36.3%). LC-MS m/z 748 (M+H)$^+$, 0.76 min (ret time).

Example 149

N-({6-chloro-3'-[(4-methyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide was purified with a Gilson HPLC (with 0.1% TFA in the solvents), eluting with 10 to 70% $CH_3CN$ in water at a flow rate of 20 mL/min. The product fractions were combined, converted to the free base with saturated $NaHCO_3$ and the basified solution was extracted with ethyl acetate twice. The combined organic layers were washed with brine, dried over sodium sulfate, filtered and then concentrated under vacuum to give N-({6-chloro-3'-[(4-methyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,

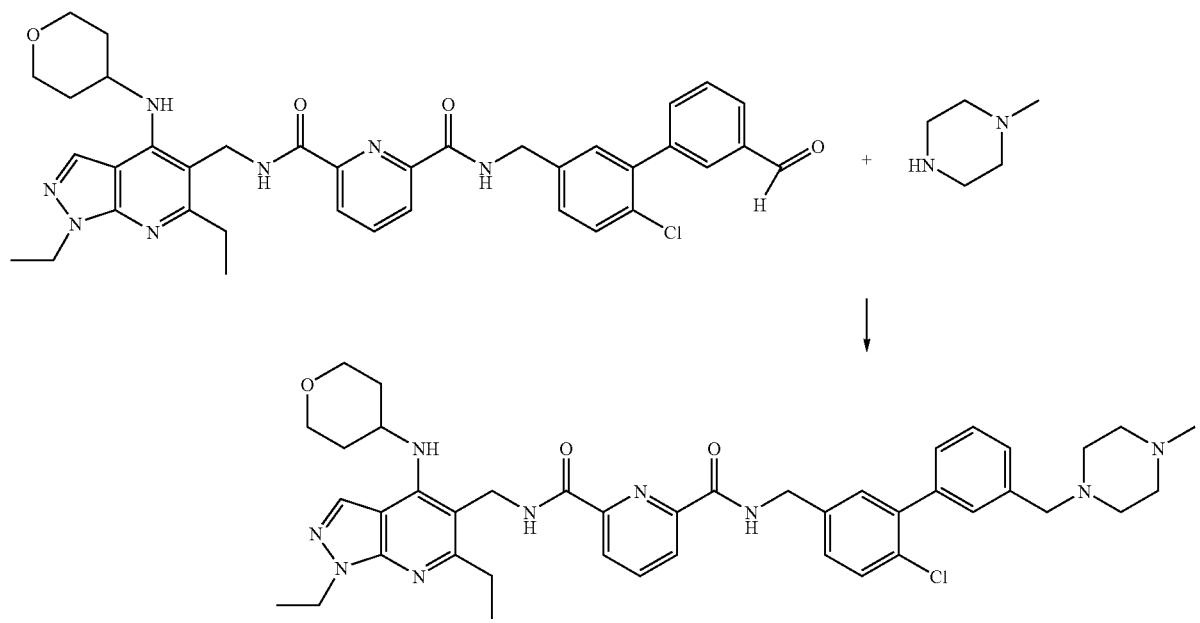

A mixture of N-[(6-chloro-3'-formyl-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.074 mmol), 1-methylpiperazine (7.36 mg, 0.074 mmol), sodium triacetoxyborohydride (31.2 mg, 0.147 mmol) and acetic acid (5.05 µL, 0.088 mmol) in DCM (1 mL) was stirred at room temperature over the weekend. The reaction mixture was quenched with saturated $NaHCO_3$, and extracted with DCM twice. The combined organic layers were concentrated under vacuum to give a crude residue. It 6-pyridinedicarboxamide as a solid (19 mg, 33.8%). LC-MS m/z 765 (M+H)$^+$, 1.44 min (ret time).

Example 150

N-{[1,6-Diethyl-4-(tetrahydro-2H-pyran-4-ylamino)-1H-pyrazolo[3,4-b]pyridin-5-yl]methyl}-N'-({3'-[(4-methyl-1-piperazinyl)methyl]-3-biphenylyl}methyl)-2,6-pyridinedicarboxamide

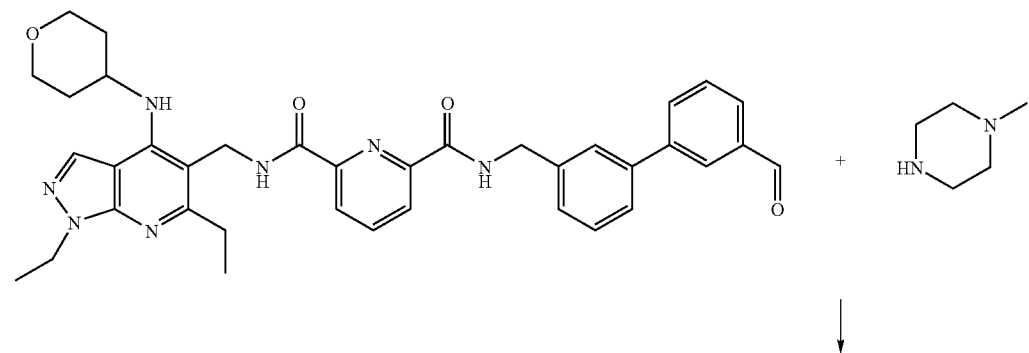

-continued

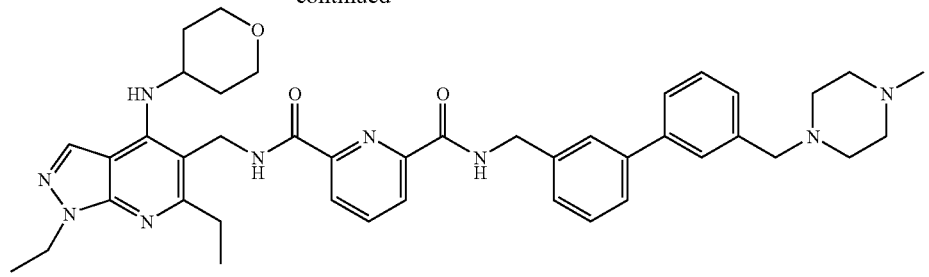

Using the procedure described in Example 146 but using (2R,6S)-2,6-dimethylpiperazine instead of 1-methylpiperazine gave the above titled compound. LC-MS m/z 730 (M+H)+, 1.38 min (ret time).

Example 151

N4-{[1,6-Diethyl-4-(tetrahydro-2H-pyran-4-ylamino)-1H-pyrazolo[3,4-b]pyridin-5-yl]methyl}-N2-[(6-fluoro-3'-{[(3S)-3-methyl-1-piperazinyl]methyl}-3-biphenylyl)methyl]-2,4-pyridinedicarboxamide

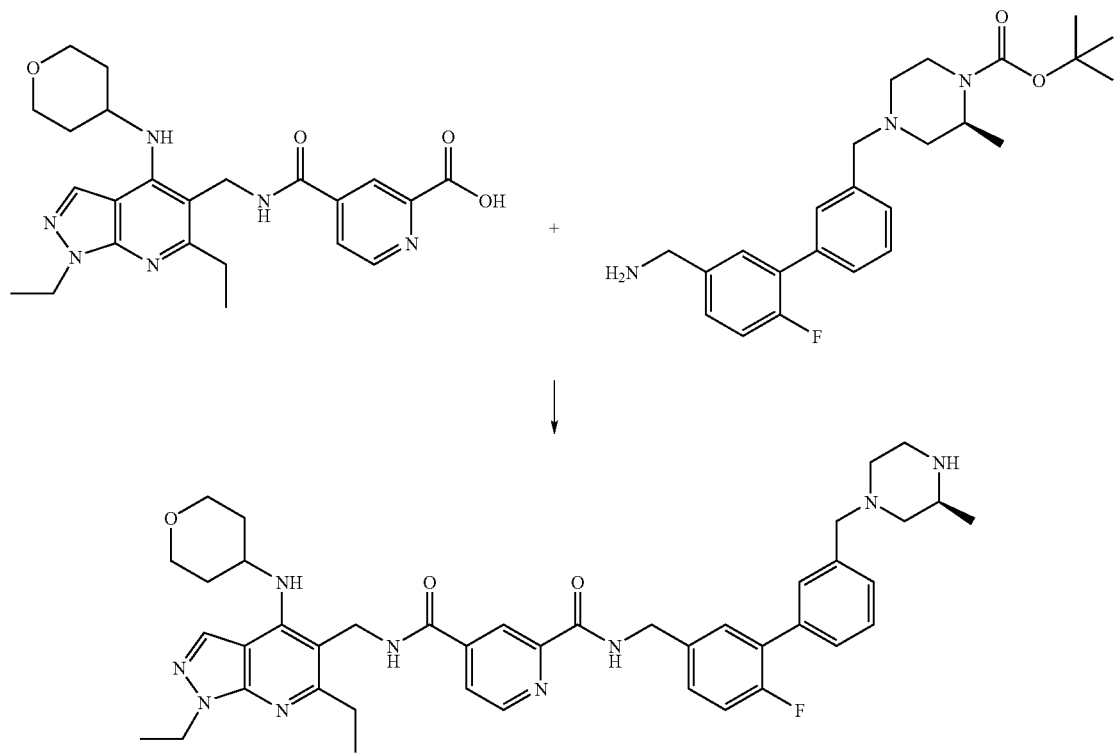

A mixture of 2-[({[1,6-diethyl-4-(tetrahydro-2H-pyran-4-ylamino)-1H-pyrazolo[3,4-b]pyridin-5-yl]methyl}amino)carbonyl]-4-pyridinecarboxylic acid (50 mg, 0.110 mmol), 1,1-dimethylethyl(2S)-4-{[5'-(aminomethyl)-2'-fluoro-3-biphenylyl]methyl}-2-methyl-1-piperazinecarboxylate (45.7 mg, 0.110 mmol), HBTU (o-benzotriazol-1-yl-N,N,N',N'-tetramethyluronium hexafluorophosphate) (50.3 mg, 0.133 mmol) and Et3N (0.046 ml, 0.331 mmol) in DCM (3 mL) was stirred at room temperature overnight. The reaction mixture was quenched with saturated NaHCO3, and extracted with DCM twice. The combined organic layers were washed with brine and then concentrated under vacuum to give a crude residue. It was then purified with a Gilson HPLC (with 0.1% TFA in the solvents), eluting with 10 to 70% CH3CN in water at a flow rate of 20 mL/min. The product fractions were dried under GeneVac to give 1,1-dimethylethyl (2S)-4-[(5'-{[({4-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-fluoro-3-biphenylyl)methyl]-2-methyl-1-piperazinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 70% CH3CN in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N4-{[1,6-diethyl-4-

(tetrahydro-2H-pyran-4-ylamino)-1H-pyrazolo[3,4-b]pyridin-5-yl]methyl}-N²-[(6-fluoro-3'-{[(3S)-3-methyl-1-piperazinyl]methyl}-3-biphenylyl)methyl]-2,4-pyridinedicarboxamide as a solid (17 mg, 20.1%). LC-MS m/z 748 (M+H)⁺, 0.77 min (ret time).

Example 152

N-{[1,6-Diethyl-4-(tetrahydro-2H-pyran-4-ylamino)-1H-pyrazolo[3,4-b]pyridin-5-yl]methyl}-N'-({6-fluoro-3'-[(1-methyl-4-piperidinyl)methyl]-3-biphenylyl}methyl)-2,6-pyridinedicarboxamide 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% CH₃CN in water at a flow rate of 20 mL/min. The product fractions were combined and converted to the free base with saturated 1 N NaOH, and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]me-

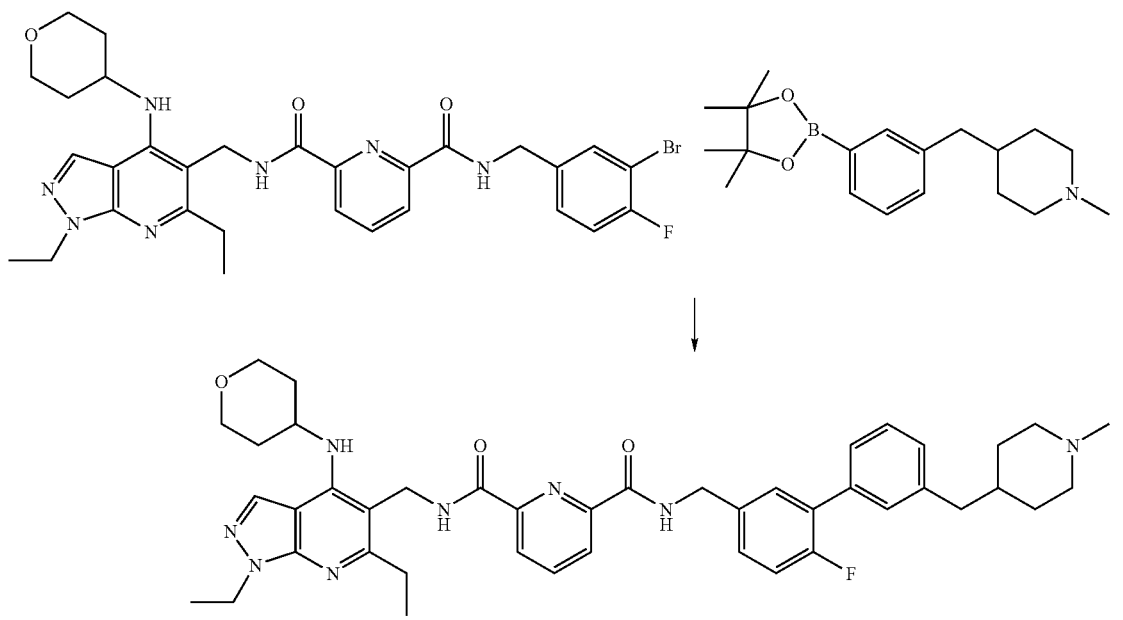

A mixture of N-[(3-bromo-4-fluorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.078 mmol), 1-methyl-4-{[3-(4,4,5,5-tetramethyl-1,3,2-dioxaborolan-2-yl)phenyl]methyl}piperidine (31.4 mg, 0.078 mmol), Na₂CO₃ (24.90 mg, 0.235 mmol) and PdCl₂(dppf) (5.73 mg, 7.83 μmol) was diluted in a mixture of 1,4-dioxane (3 mL) and water (1 mL) in a 2-5 mL Biotage microwave reaction tube. The mixture was degassed by bubbling argon through it for 5 minutes and was then heated in a Biotage microwave at normal absorption for 10 minutes at thyl}-N'-({6-fluoro-3'-[(1-methyl-4-piperidinyl)methyl]-3-biphenylyl}methyl)-2,6-pyridinedicarboxamide as a solid (9 mg, 15.4%). LC-MS m/z 747 (M+H)⁺, 0.79 min (ret time).

Example 153

N-({6-Chloro-3'-[(1-methyl-4-piperidinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide

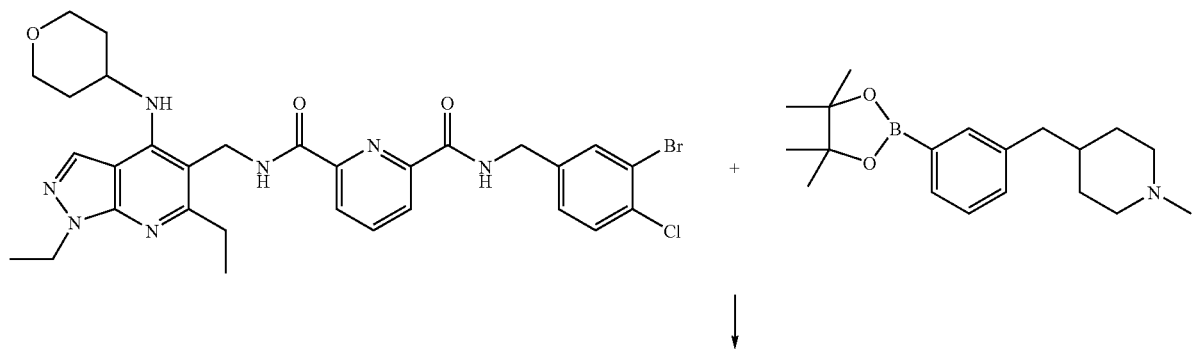

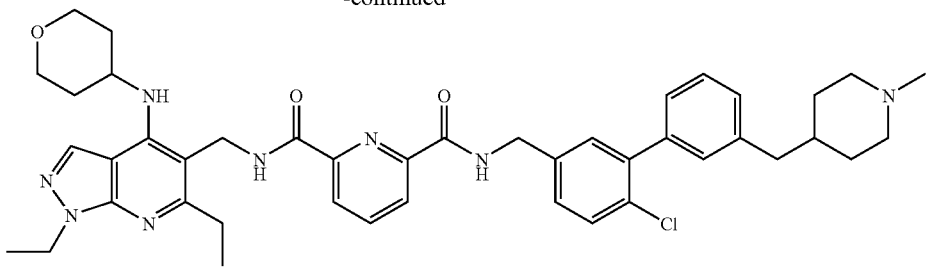

A mixture of N-[(3-bromo-4-chlorophenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.076 mmol), 1-methyl-4-{[3-(4,4,5,5-tetramethyl-1,3,2-dioxaborolan-2-yl)phenyl]methyl}piperidine (30.6 mg, 0.076 mmol), Na₂CO₃ (24.27 mg, 0.229 mmol) and PdCl₂(dppf) (5.59 mg, 7.63 μmol) was diluted in a mixture of 1,4-dioxane (3 mL) and water (1 mL) in a 2-5 mL Biotage microwave reaction tube. The mixture was degassed by bubbling argon through it for 5 minutes and was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain the crude residue. It was purified with a Gilson HPLC (with 0.1% TFA in the solvents), eluting with 10 to 70% CH₃CN in water at a flow rate of 20 mL/min. The product fractions were combined and converted to the free base with saturated 1 N NaOH, and the basified solution was extracted with ethyl acetate twice. The combined organic layers were washed with brine, dried over sodium sulfate, filtered and then concentrated under vacuum to give N-({6-chloro-3'-[(1-methyl-4-piperidinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide as a solid (10 mg, 17.2%). LC-MS m/z 763 M⁺, 0.81 min (ret time).

Example 154

N-{[1,6-Diethyl-4-(tetrahydro-2H-pyran-4-ylamino)-1H-pyrazolo[3,4-b]pyridin-5-yl]methyl}-N'-({6-methyl-3'-[(1-methyl-4-piperidinyl)methyl]-3-biphenylyl}methyl)-2,6-pyridinedicarboxamide

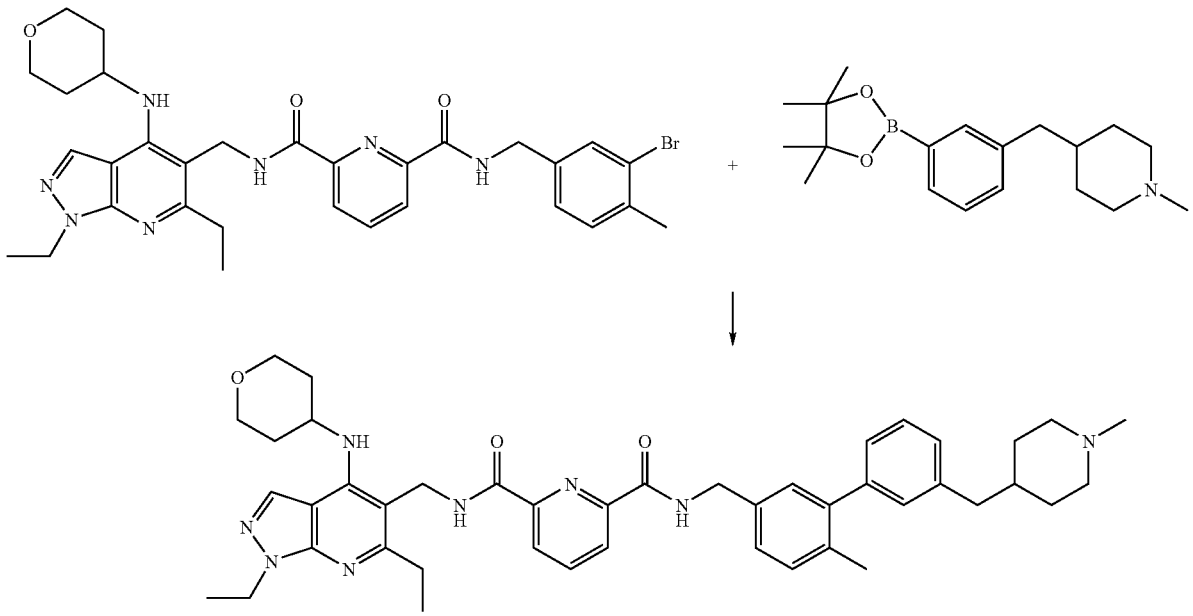

A mixture of N-[(3-bromo-4-methylphenyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.079 mmol), 1-methyl-4-{[3-(4,4,5,5-tetramethyl-1,3,2-dioxaborolan-2-yl)phenyl]methyl}piperidine (31.6 mg, 0.079 mmol), Na₂CO₃ (25.05 mg, 0.236 mmol) and PdCl₂(dppf) (5.77 mg, 7.88 μmol) was diluted in a mixture of 1,4-dioxane (3 mL) and water (1 mL) in a 2-5 mL Biotage microwave reaction tube. The mixture was degassed by bubbling argon through it for 5 minutes and it was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% CH₃CN in water at a flow rate of 20 mL/min. The product fractions were combined and converted to the free base with 1 N NaOH, and the basified solution was extracted with ethyl acetate twice.

The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-({6-methyl-3'-[(1-methyl-4-piperidinyl)methyl]-3-biphenylyl}methyl)-2,6-pyridinedicarboxamide as a solid (5 mg, 8.54%). LC-MS m/z 743 (M+H)$^+$, 0.87 min (ret time); $^1$H NMR (400 MHz, CD$_3$OD) δ 1.24-1.30 (m, 5H) 1.37-1.43 (m, 3H) 1.54-1.78 (m, 5H) 1.86-1.93 (m, 2H) 1.98-2.08 (m, 2H) 2.15-2.24 (m, 6H) 2.53 (d, J=7.03 Hz, 2H) 2.76-2.82 (m, 2H) 2.97-3.04 (m, 2H) 3.58-3.65 (m, 2H) 3.98 (d, J=11.54 Hz, 2H) 4.09-4.14 (m, 1H) 4.41 (q, J=7.03 Hz, 2H) 4.60 (s, 2H) 4.75 (s, 2H) 6.96-7.34 (m, 7H) 7.99 (s, 1H) 8.15 (t, J=7.91 Hz, 1H) 8.25-8.31 (m, 1H) 8.36 (dd, J=7.78, 1.00 Hz, 1H).

Example 155

N-{[1,6-Diethyl-4-(tetrahydro-2H-pyran-4-ylamino)-1H-pyrazolo[3,4-b]pyridin-5-yl]methyl}-N'-({6-(methyloxy)-3'-[(1-methyl-4-piperidinyl)methyl]-3-biphenylyl}methyl)-2,6-pyridinedicarboxamide in a 2-5 mL Biotage microwave reaction tube. The mixture was degassed by bubbling argon through it for 5 minutes and it was then heated in a Biotage microwave at normal absorption for 10 minutes at 100° C. The crude mixture was filtered through a PL-Thiol MP SPE+ and was then washed with ethyl acetate and water. The organic layer was concentrated under vacuum to obtain a crude residue. It was purified with a Gilson HPLC (with 0.1% TFA in the solvents), eluting with 10 to 70% CH$_3$CN in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-({6-(methyloxy)-3'-[(1-methyl-4-piperidinyl)methyl]-3-biphenylyl}methyl)-2,6-pyridinedicarboxamide as a solid (7.5 mg, 12.9%). LC-MS m/z 759 (M+H)$^+$, 0.77 min (ret time); $^1$H NMR (400 MHz,

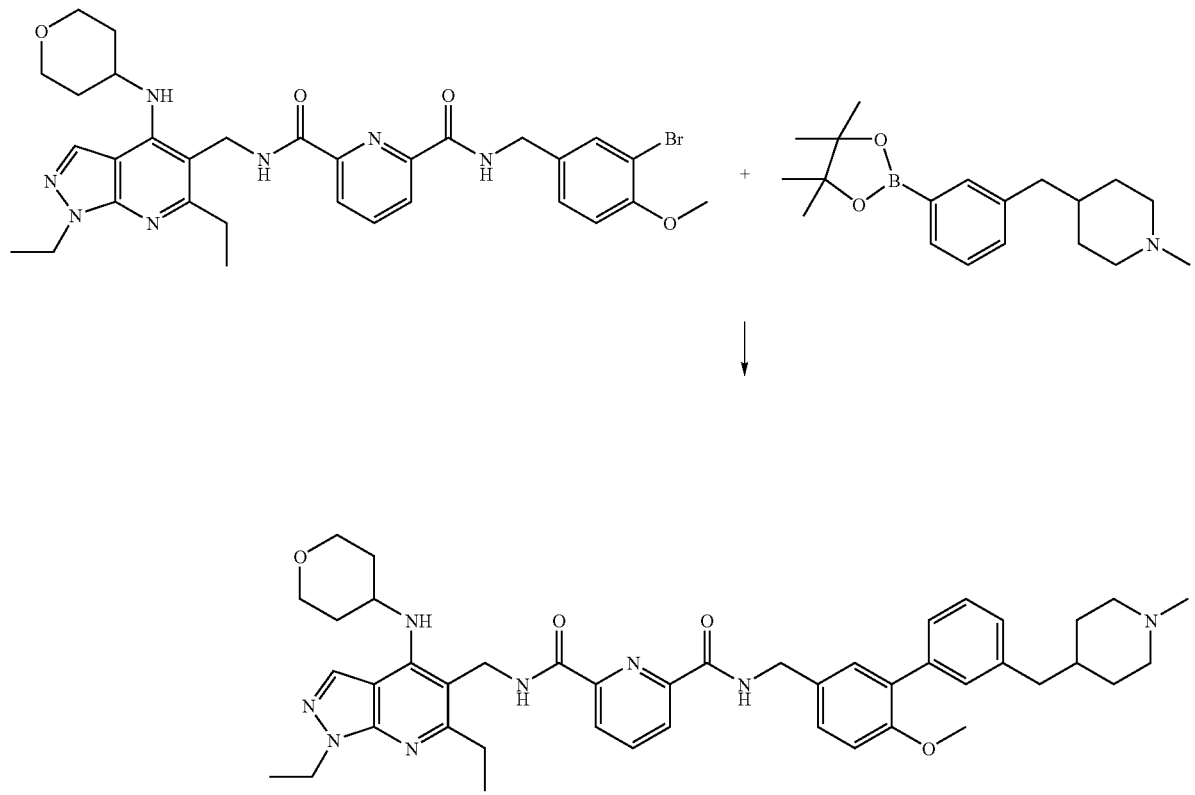

A mixture of N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide (50 mg, 0.077 mmol), 1-methyl-4-{[3-(4,4,5,5-tetramethyl-1,3,2-dioxaborolan-2-yl)phenyl]methyl}piperidine (30.8 mg, 0.077 mmol), Na$_2$CO$_3$ (24.44 mg, 0.231 mmol) and PdCl$_2$(dppf) (5.62 mg, 7.69 μmol) was diluted in a mixture of 1,4-dioxane (3 mL) and water (1 mL)

CD$_3$OD) δ 1.22-1.29 (m, 5H) 1.39 (t, J=7.15 Hz, 3H) 1.49-1.76 (m, 5H) 1.90-1.97 (m, 2H) 1.99-2.05 (m, 2H) 2.23 (s, 3H) 2.51 (d, J=7.03 Hz, 2H) 2.78-2.84 (m, 2H) 2.99 (q, J=7.53 Hz, 2H) 3.61 (td, J=11.42, 2.51 Hz, 2H) 3.74 (s, 3H) 3.90-4.02 (m, 2H) 4.12-4.19 (m, 1H) 4.40 (q, J=7.19 Hz, 2H) 4.58 (s, 2H) 4.74 (s, 2H) 6.97 (d, J=8.53 Hz, 1H) 7.01-7.08 (m, 1H) 7.16-7.32 (m, 5H) 7.98 (s, 1H) 8.15 (t, J=7.78 Hz, 1H) 8.28 (dd, J=7.91, 1.13 Hz, 1H) 8.36 (dd, J=7.78, 1.25 Hz, 1H).

Example 156

N-({3'-[(1S,4S)-2,5-Diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide hydrochloride

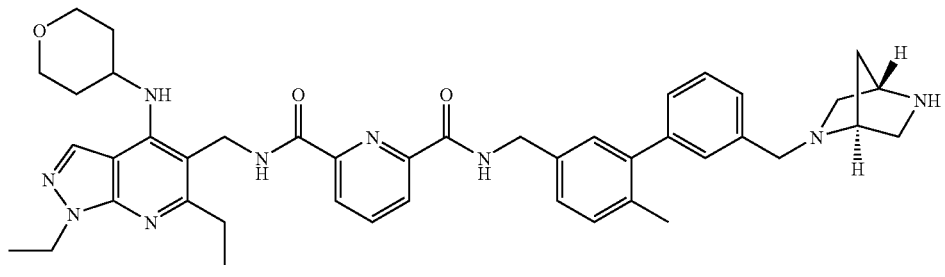

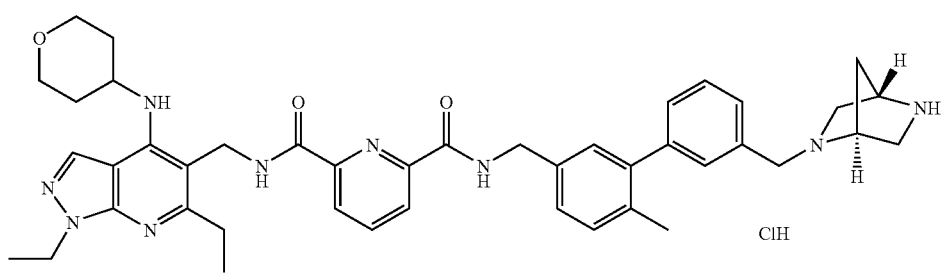

To a solution of N-({3'-[(1S,4S)-2,5-diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide (390 mg, 0.526 mmol) in ethanol 95 mL) was added 1N HCl (0.526 mL, 0.526 mmol). The mixture was stirred at RT for 2 h. It was concentrated under vacuum. The residue was re-dissolved in ethanol and it was evaporated (this was repeated three times). Then a 1:1 mixture of DCM:hexane (5 mL) was added and concentrated (this was repeated twice). Finally, the solid, a white material, was dried under high vacuum for two days to give N-({3'-[(1S,4S)-2,5-diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide hydrochloride as a solid (404 mg, 99%). LC-MS m/z 742 (M+H)$^+$, 0.79 min (ret time).

Example 157

N-{[1,6-Diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide

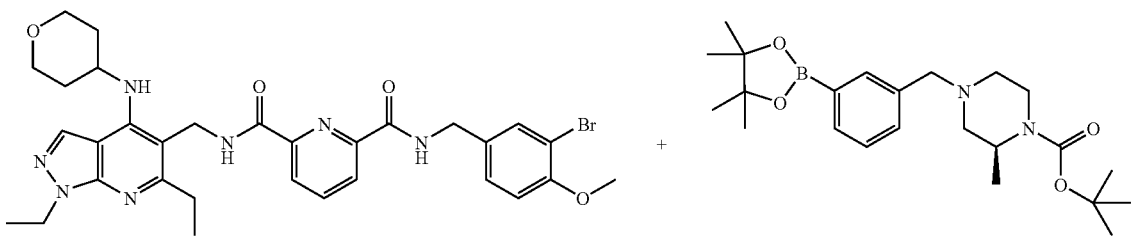

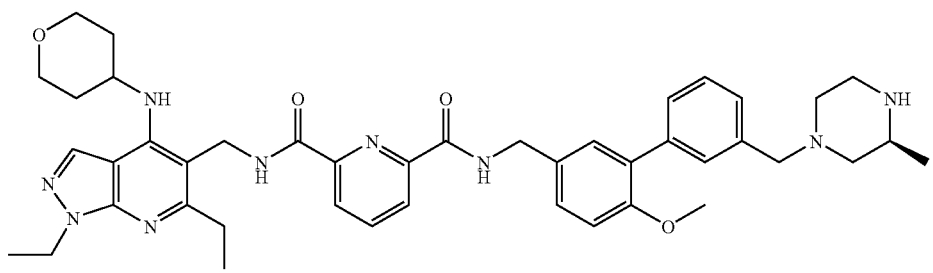

A mixture of N-{[3-bromo-4-(methyloxy)phenyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide (200 mg, 0.307 mmol), 1,1-dimethylethyl (2S)-2-methyl-4-{[3-(4,4,5,5-tetramethyl-1,3,2-dioxaborolan-2-yl)phenyl]methyl}-1-piperazinecarboxylate (128 mg, 0.307 mmol), Na$_2$CO$_3$ (98 mg, 0.922 mmol) and PdCl$_2$(dppf) (22.49 mg, 0.031 mmol) was diluted in a mixture of 1,4-dioxane (3 mL) and water (1 mL) in a 2-5 mL Biotage microwave reaction tube. The mixture was degassed by bubbling argon through it for 5 minutes and was then heated in a Biotage microwave at normal absorption for 30 minutes at 100° C. The crude mixture was filtered through a PL-Thiol MP SPE+ and was then washed with ethyl acetate and water. The organic layer was concentrated under vacuum to obtain the crude residue. It was purified with a Gilson HPLC (with 0.1% TFA in the solvents), eluting with 10 to 70% CH$_3$CN in water at a flow rate of 20 mL/min. The product fractions were dried using a EZ2 GeneVac evaporator and then combined to give 1,1-dimethylethyl (2S)-4-{[5'-{[({6-[({[1,6-diethyl-4-(tetrahydro-2H-pyran-4-ylamino)-1H-pyrazolo[3,4-b]pyridin-5-yl]methyl}amino)carbonyl]-2-pyridinyl}carbonyl)amino]methyl}-2'-(methyloxy)-3-biphenylyl]methyl}-2-methyl-1-piperazinecarboxylate. It was re-dissolved in 25% TFA in DCM (2 mL) and stirred at room temperature for 2 h. Solvent was evaporated under a stream of nitrogen and then the residue was purified with a Gilson HPLC (with 0.1% TFA in the solvents), eluting with 10 to 60% CH$_3$CN in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide as a solid (75 mg, 32.1%). LC-MS m/z 760 (M+H)$^+$, 0.80 min (ret time).

Example 158

N-{[1,6-Diethyl-4-(tetrahydro-2H-pyran-4-ylamino)-1H-pyrazolo[3,4-b]pyridin-5-yl]methyl}-N'-{[3'-(4-piperidinylmethyl)-3-biphenylyl]methyl}-3,5-pyridinedicarboxamide

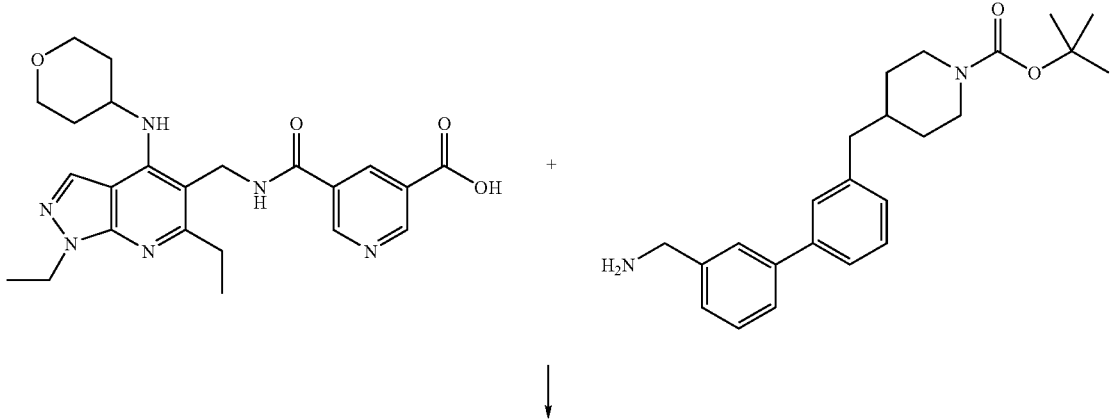

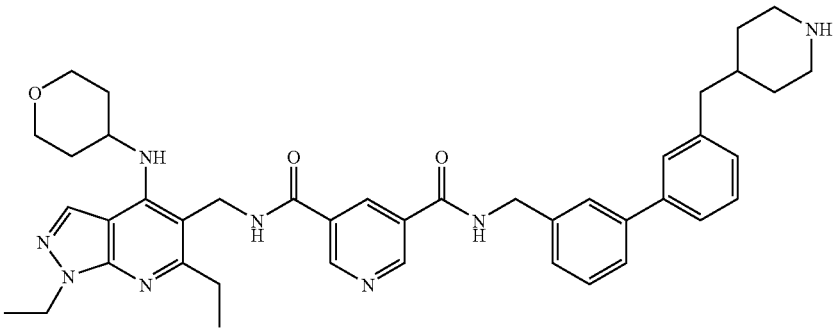

A mixture of 5-[({[1,6-diethyl-4-(tetrahydro-2H-pyran-4-ylamino)-1H-pyrazolo[3,4-b]pyridin-5-yl]methyl}amino)carbonyl]-3-pyridinecarboxylic acid (50 mg, 0.110 mmol), 1,1-dimethylethyl 4-{[3'-(aminomethyl)-3-biphenylyl]methyl}-1-piperidinecarboxylate (42.0 mg, 0.110 mmol), HBTU (o-benzotriazol-1-yl-N,N,N',N'-tetramethyluronium hexafluorophosphate) (50.3 mg, 0.133 mmol) and $Et_3N$ (0.046 ml, 0.331 mmol) in DCM was stirred at room temperature over the weekend. The reaction was quenched with saturated $NaHCO_3$, and extracted with DCM twice. The combined organic layers were washed with brine and then concentrated under vacuum to give a crude residue. It was then purified with a Gilson HPLC (with 0.1% TFA in the solvents), eluting with 10 to 70% $CH_3CN$ in water at a flow rate of 20 mL/min. The product fractions were dried using a GeneVac and then combined to give 1,1-dimethylethyl 4-[(3'-{[({5-[({[1,6-diethyl-4-(tetrahydro-2H-pyran-4-ylamino)-1H-pyrazolo[3,4-b]pyridin-5-yl]methyl}amino)carbonyl]-3-pyridinyl}carbonyl)amino]methyl}-3-biphenylyl)methyl]-1-piperidinecarboxylate. It was then dissolved in 2 mL of 25% TFA in DCM and stirred at room temperature for 3 h. The crude product was purified with a Gilson HPLC (with 0.1% TFA in the solvents), eluting with 10 to 70% $CH_3CN$ in water at a flow rate of 20 mL/min. The product fractions were combined and converted to the free base with 1 N NaOH, and the basified solution was extracted with ethyl acetate twice. The combined organic layers were washed with brine, dried over sodium sulfate, filtered and concentrated under vacuum to N-{[1,6-diethyl-4-(tetrahydro-2H-pyran-4-ylamino)-1H-pyrazolo[3,4-b]pyridin-5-yl]methyl}-N'-{[3'-(4-piperidinylmethyl)-3-biphenylyl]methyl}-3,5-pyridinedicarboxamide as a solid (3.5 mg, 4.4%). LC-MS m/z 715 $(M+H)^+$, 0.77 min (ret time).

Example 159

N-{[1,6-Diethyl-4-(tetrahydro-2H-pyran-4-ylamino)-1H-pyrazolo[3,4-b]pyridin-5-yl]methyl}-N'-({3'-[(1-methyl-4-piperidinyl)methyl]-3-biphenylyl}methyl)-2,6-pyridinedicarboxamide

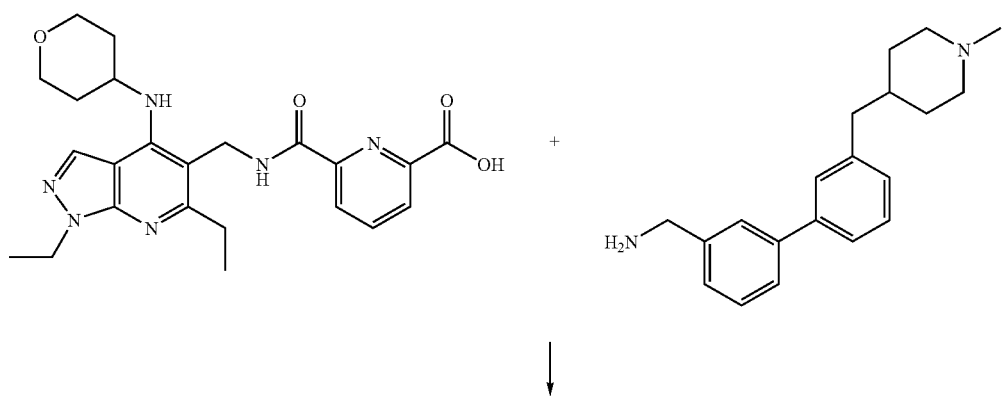

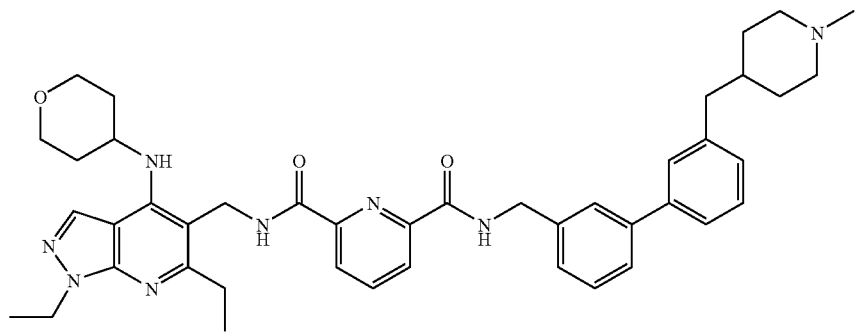

Process (A) A mixture of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (84 mg, 0.186 mmol), 1,1-dimethylethyl 4-{[3'-(aminomethyl)-3-biphenylyl]methyl}-1-piperidinecarboxylate (54.7 mg, 0.186 mmol), HBTU (o-benzotriazol-1-yl-N,N,N',N'-tetramethyluronium hexafluorophosphate) (84 mg, 0.223 mmol) and Et₃N (0.129 mL, 0.928 mmol) in DCM (3 mL) was stirred at room temperature overnight. The crude mixture was quenched with saturated NaHCO₃, and extracted with DCM twice. The combined organic layers were washed with brine and then concentrated under vacuum to give crude residue. The crude product was purified with a Gilson HPLC (with 0.1% TFA in the solvents), eluting with 10 to 70% CH₃CN in water at a flow rate of 20 mL/min. The product fractions were combined, converted to the free base with saturated NaHCO₃ and the basified solution was extracted with ethyl acetate twice. The combined organic layers were washed with brine, dried over sodium sulfate, filtered and then concentrated under vacuum to give N-{[1,6-diethyl-4-(tetrahydro-2H-pyran-4-ylamino)-1H-pyrazolo[3,4-b]pyridin-5-yl]methyl}-N'-({3'-[(1-methyl-4-piperidinyl)methyl]-3-biphenylyl}methyl)-2,6-pyridinedicarboxamide as a white solid (30 mg, 22.2%). LC-MS m/z 729 (M+H)⁺, 0.80 min (ret time).

Process (B) In an alternate preparation of the titled compound, to a solution of 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (45 mg, 0.1 mmol) in DMSO (1 mL) was added 1-{3'-[(1-methyl-4-piperidinyl)methyl]-3-biphenylyl}methanamine (28 mg, 0.095 mmol), HBTU (42 mg, 0.11 mmol) and Et₃N (0.021 mL, 0.15 mmol) in DCM (3 mL). The resulting mixture was stirred at room temperature for 18 h. The reaction was quenched with H₂O (2 drops), purified with a Gilson HPLC (with 0.1% TFA), concentrated, re-dissolved in EtOAc, washed with NaOH (1N), dried over Na₂SO₄, filtered, concentrated and dried with a high vacuum oil pump to afford the title compound as a white solid 38.5 mg (53%). LC-MS m/z 729 (M+H)⁺.

Example 160

N-{[1,6-Diethyl-4-(tetrahydro-2H-pyran-4-ylamino)-1H-pyrazolo[3,4-b]pyridin-5-yl]methyl}-N'-{[2-(3-{[(3S)-3-methyl-1-piperazinyl]methyl}phenyl)-4-pyridinyl]methyl}-2,6-pyridinedicarboxamide

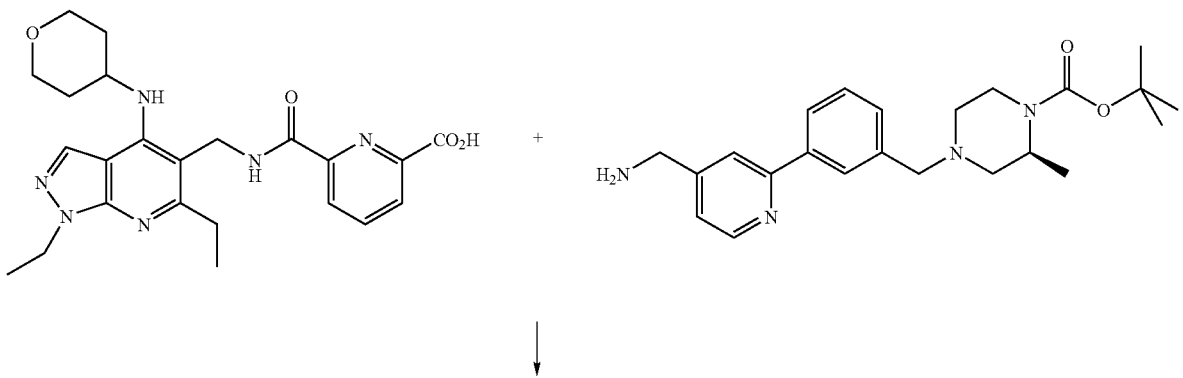

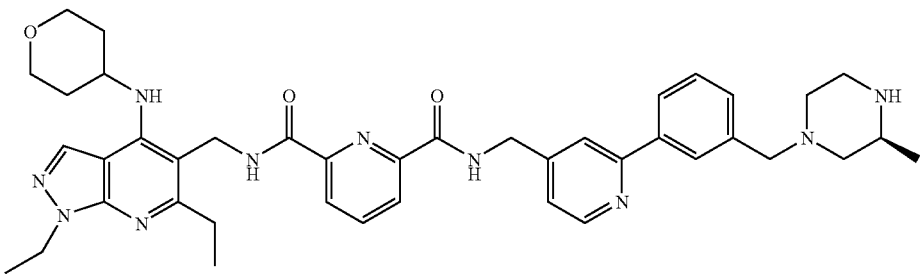

To 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (30 mg, 0.066 mmol) was added 1,1-dimethylethyl (2S)-4-({3-[4-(aminomethyl)-2-pyridinyl]phenyl}methyl)-2-methyl-1-piperazinecarboxylate (26.3 mg, 0.066 mmol), followed by HBTU (30.2 mg, 0.080 mmol) and TEA (18.48 μl, 0.133 mmol) in dichloromethane (DCM) (663 μL) to give a reaction mixture which was stirred at room temperature overnight. Then the reaction was quenched with H₂O (1 drop) and the solvent was removed using a Glas-Col. The crude product was redissolved in MeOH/DMSO (1/1) and purified by Gilson HPLC (acidic condition). Product fractions were evaporated by GeneVac EZ-2 evaporator. To this material was added TFA (0.102 mL, 1.33 mmol) in dichloromethane (0.2 mL) and it was placed in the Glas-Col evaporator overnight. It was redissolved in MeOH/DMSO and purified using a Gilson HPLC (acidic condition). Product fractions were evaporated by GeneVac EZ-2 evaporator, basified by cartridge to afford 19.1 mg (37%) of the title compound. LC-MS m/z 731 (M+H)⁺.

Example 161

N-{[1,6-Diethyl-4-(tetrahydro-2H-pyran-4-ylamino)-1H-pyrazolo[3,4-b]pyridin-5-yl]methyl}-N'-({3'-[(4-methylhexahydro-1H-1,4-diazepin-1-yl)methyl]-3-biphenylyl}methyl)-2,6-pyridinedicarboxamide

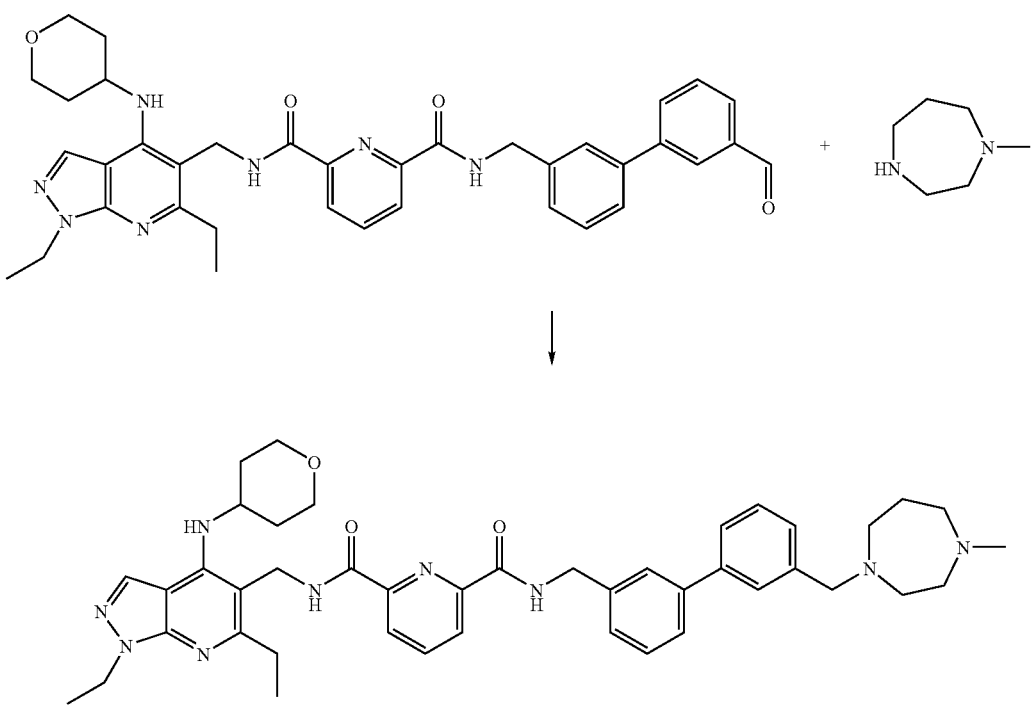

Using the procedure described in Example 146, but replacing (2R,6S)-2,6-dimethylpiperazine with 1-methylhexahydro-1H-1,4-diazepine, gave the above titled compound. LC-MS m/z 744 (M+H)⁺, 1.28 min (ret time).

Example 162

N-{[1,6-Diethyl-4-(tetrahydro-2H-pyran-4-ylamino)-1H-pyrazolo[3,4-b]pyridin-5-yl]methyl}-N'-({2-[3-(4-piperidinylmethyl)phenyl]-4-pyridinyl}methyl)-2,6-pyridinedicarboxamide

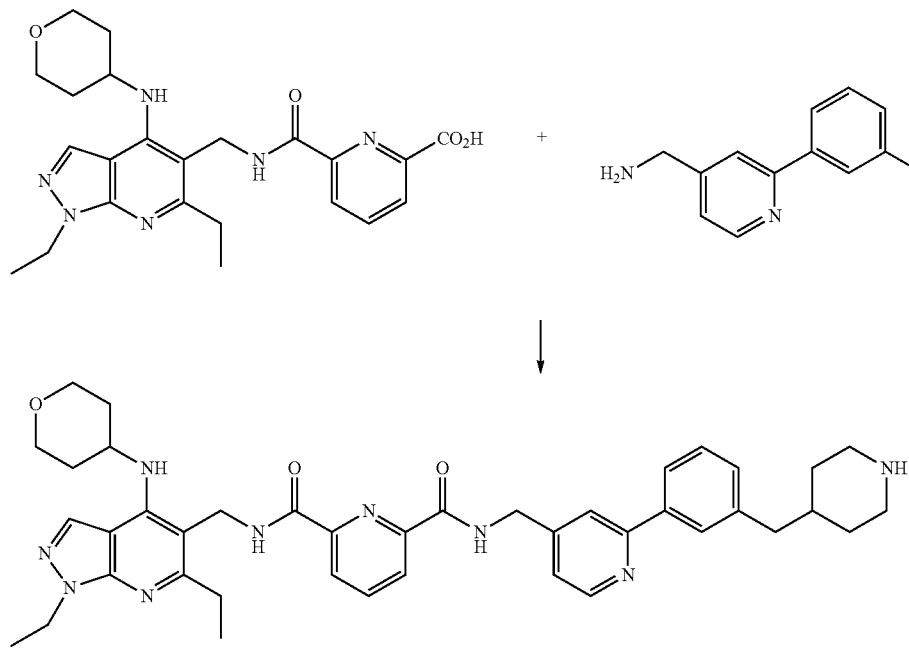

To 6-[({[1,6-diethyl-4-(tetrahydro-2H-pyran-4-ylamino)-1H-pyrazolo[3,4-b]pyridin-5-yl]methyl}amino)carbonyl]-2-pyridinecarboxylic acid (50 mg, 0.110 mmol) was added 1,1-dimethylethyl 4-({3-[4-(aminomethyl)-2-pyridinyl]phenyl}methyl)-1-piperidinecarboxylate (42.2 mg, 0.110 mmol) followed by HBTU (50.3 mg, 0.133 mmol) and TEA (30.8 μl, 0.221 mmol) in dichloromethane (DCM) (1105 μL) to give a reaction mixture. This was stirred at room temperature overnight. Then the reaction was quenched with H₂O (1 drop) and the solvent was removed by Glas-Col. The crude product was redissolved in MeOH/DMSO (1/1) and purified using a Gilson HPLC (acidic condition). Product-containing fractions were combined and evaporated by GeneVac EZ-2 evaporator. To this residue was added TFA (0.170 mL, 2.21 mmol) in dichloromethane (0.2 mL) and the mixture was placed in the Glas-Col evaporator overnight. Then it was redissolved in MeOH/DMSO and purified using a Gilson HPLC (acidic condition). Product-containing fractions were combined and evaporated by GeneVac EZ-2 evaporator, basified by cartridge to afford 25.4 mg (31%) of the title compound. LC-MS m/z 716 (M+H)⁺.

Example 163

N-({3'-[(1S,4S)-2,5-diazabicyclo[2.2.1]hept-2-ylmethyl]-6-fluoro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide

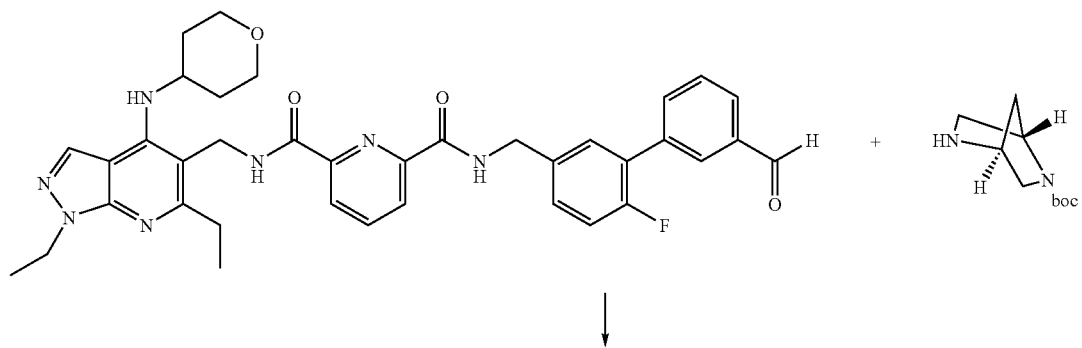

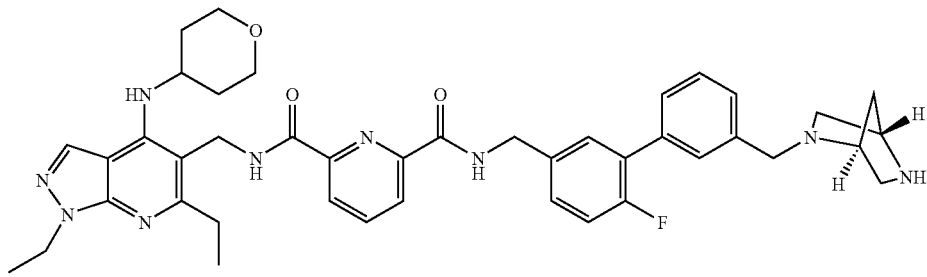

N-{[1,6-Diethyl-4-(tetrahydro-2H-pyran-4-ylamino)-1H-pyrazolo[3,4-b]pyridin-5-yl]methyl}-N'-[(6-fluoro-3'-formyl-3-biphenylyl)methyl]-2,6-pyridinedicarboxamide (50.0 mg. 0.075 mmol) was diluted in DMSO (1.5 mL) and dispensed into a 1 dram vial containing 1,1-dimethylethyl (1S,4S)-2,5-diazabicyclo[2.2.1]heptane-2-carboxylate (0.226 mmol) and acetic acid (4.52 mg, 0.075 mmol) and fitted magnetic stir bar. The resulting solution was stirred at room temperature for 4 h. MP-B(OAc)$_3$H (0.753 mmol, 176 mg) was added and the solution was stirred for another 12 h. The polymer reagent was filtered off and to the filtrate was added MeOH (2.0 mL) and 1 drop of concentrated HCl. This solution was heated at 60° C.° for 12 h. Purification was completed via a Gilson HPLC (basic conditions) to afford 10.26 mg (18.4%) of the title compound. LC-MS m/z 746 (M+H)$^+$, 0.69 min (ret time).

Using array chemistry, following the procedure as described above for the preparation of N-({3'-[(1S,4S)-2,5-diazabicyclo[2.2.1]hept-2-ylmethyl]-6-fluoro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide (Example 163), an appropriate aldehyde was reacted with an appropriate amine to give the Examples 164-171 listed in Table 1

Examples 164-171

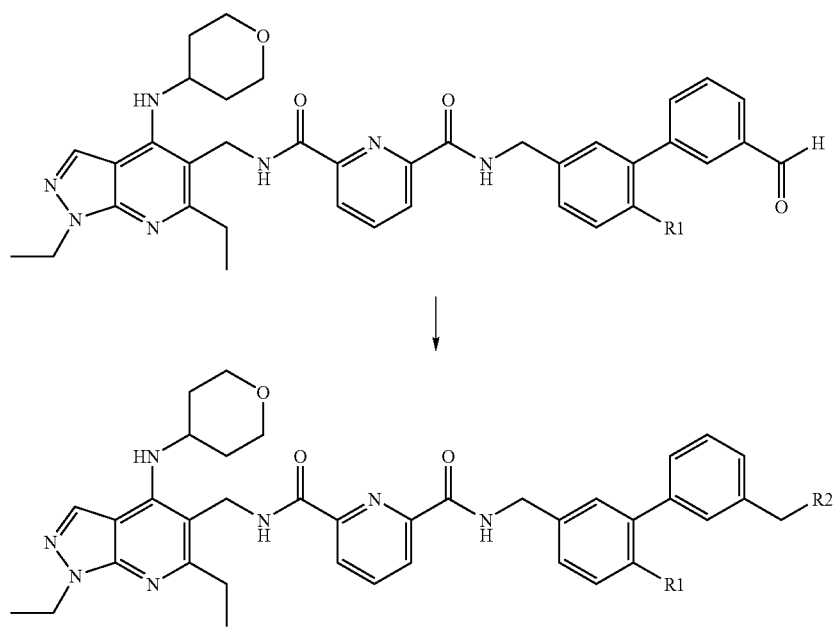

TABLE 1

Examples 164-171.

| Example | R1 | R2 | Name | LC-MS m/z (M + H)+ | RT (min) |
|---|---|---|---|---|---|
| 164 | OMe | | N-{[3'-[(1R,4R)-2,5-diazabicyclo[2.2.1]hept-2-ylmethyl]-6-(methyloxy)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide | 758 | 1.34 |
| 165 | OMe | | N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(2S)-2-methyl-1-piperazinyl]methyl}-3-biphenylyl)methyl]-2,6-pyridinedicarboxamide | 760 | 1.36 |
| 166 | Me | | N-({3'-[(1R,4R)-2,5-diazabicyclo[2.2.1]hept-2-ylmethyl]-6-methyl-3-biphenylyl}methyl)-N'-{[1,6-diethyl-4-(tetrahydro-2H-pyan-4-ylamino)-1H-pyrazolo[3,4-b]pyridin-5-yl]methyl}-2,6-pyridinedicarboxamide | 742 | 1.37 |
| 167 | F | | N-{[1,6-diethyl-4-(tetrahydro-2H-pyran-4-ylamino)-1H-pyrazolo[3,4-b]pyridin-5-yl]methyl}-N'-{[6-fluoro-3'-(hexahydro-1H-1,4-diazepin-1-ylmethyl)-3-biphenylyl]methyl}-2,6-pyridinedicarboxamide | 748 | 0.7 |
| 168 | OMe | | N-{[1,6-diethyl-4-(tetrahydro-2H-pyran-4-ylamino)-1H-pyrazolo[3,4-b]pyridin-5-yl]methyl}-N'-{[3'-(hexahydro-1H-1,4-diazepin-1-ylmethyl)-6-(methyloxy)-3-biphenylyl]methyl}-2,6-pyridinedicarboxamide | 760 | 1.32 |
| 169 | Me | | N-{[1,6-diethyl-4-(tetrahydro-2H-pyran-4-ylamino)-1H-pyrazolo[3,4-b]pyridin-5-yl]methyl}-N'-{[3'-(hexahydro-1H-1,4-diazepin-1-ylmethyl)-6-methyl-3-biphenylyl]methyl}-2,6-pyridinedicarboxamide | 744 | 1.36 |

TABLE 1-continued

Examples 164-171.

| Example | R1 | R2 | Name | LC-MS m/z (M + H)+ | RT (min) |
|---|---|---|---|---|---|
| 170 | OMe | ![pyrrolidine with NH2] | N-{[3'-{[(3S)-3-amino-1-pyrrolidinyl]methyl}-6-(methyloxy)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide | 746 | 1.3 |
| 171 | Me | ![pyrrolidine with NH2] | N-[(3'-{[(3S)-3-amino-1-pyrrolidinyl]methyl}-6-methyl-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 730 | 1.35 |

Example 172

N-{[1,6-diethyl-4-(tetrahydro-2H-pyran-4-ylamino)-1H-pyrazolo[3,4-b]pyridin-5-yl]methyl}-N'-{[6-(methyloxy)-3'-(1-piperazinylmethyl)-3-biphenylyl]methyl}-2,6-pyridinedicarboxamide

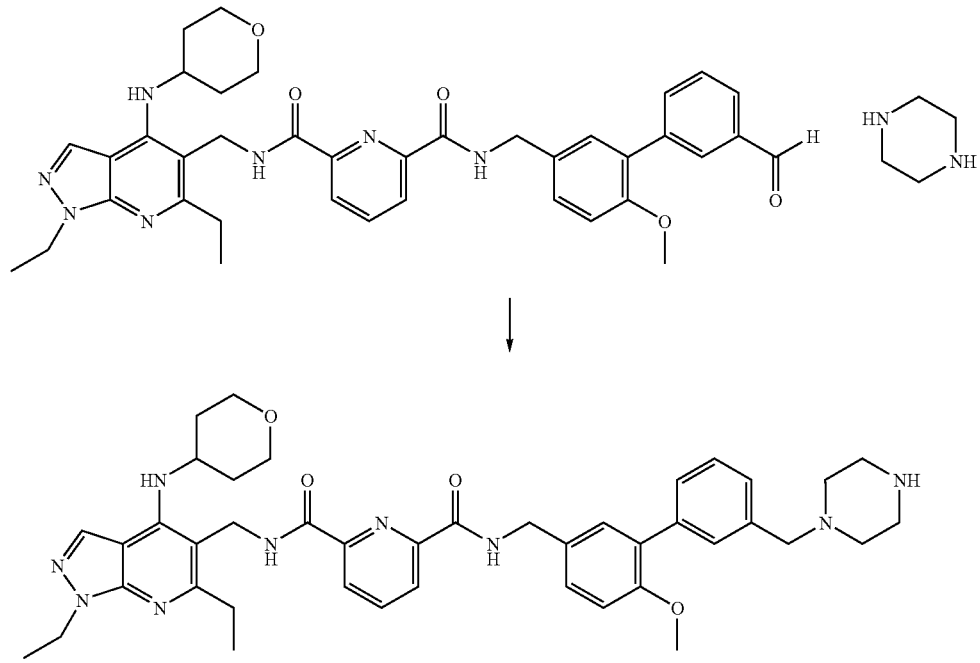

N-{[1,6-Diethyl-4-(tetrahydro-2H-pyran-4-ylamino)-1H-pyrazolo[3,4-b]pyridin-5-yl]methyl}-N'-{[3'-formyl-6-(methyloxy)-3-biphenylyl]methyl}-2,6-pyridinedicarboxamide (40.0 mg. 0.059 mmol) was diluted in DMSO (1.5 mL) and dispensed into a 1 dram vial containing piperazine (0.178 mmol) and acetic acid (0.059 mmol, 3.55 mg) and with fitted magnetic stir bar. The resulting solution was stirred at room temperature for 4 h. MP-B(OAc)$_3$H (0.592 mmol, 138 mg) was added and the solution was stirred for another 12 h. The polymer reagent was filtered off and purification was completed via a Gilson HPLC (basic conditions) to afford 8.32 mg of the title compound (18.9%). LC-MS m/z 746 (M+H)+, 1.27 min (ret time).

Examples 173-188

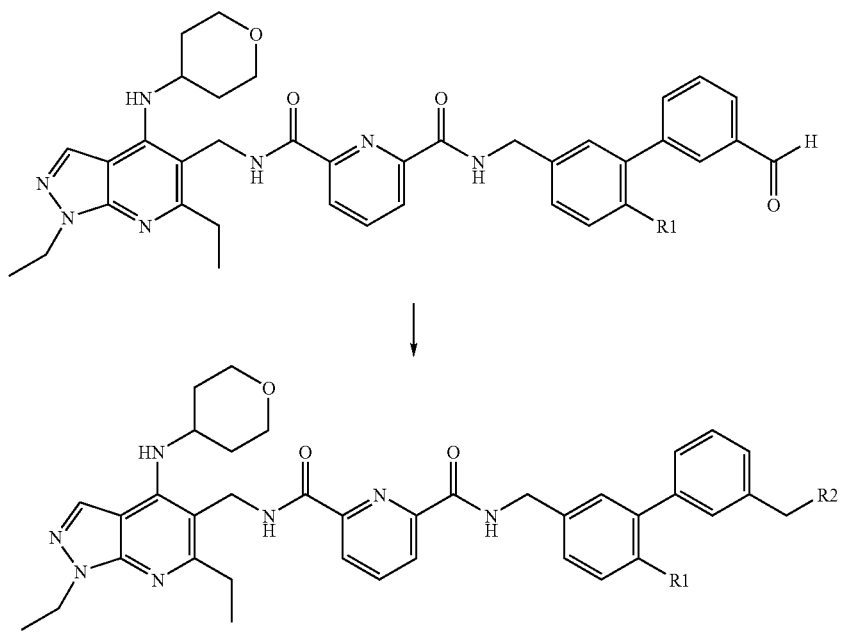

Using array chemistry, following the procedure as described for the preparation of N-{[1,6-diethyl-4-(tetrahydro-2H-pyran-4-ylamino)-1H-pyrazolo[3,4-b]pyridin-5-yl]methyl}-N'-{[6-(methyloxy)-3'-(1-piperazinylmethyl)-3-biphenylyl]methyl}-2,6-pyridinedicarboxamide (Example 172), an appropriate aldehyde was reacted with an appropriate amine to give the Examples 173-188 listed in Table 2.

TABLE 2

Examples 173-188.

| Example | R1 | R2 | Name | LC-MS m/z (M + H)+ | RT (min) |
|---|---|---|---|---|---|
| 173 | Me | ![piperazine] | N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide | 730 | 1.29 |
| 174 | OMe | ![3,5-dimethylpiperazine] | N-{[1,6-diethyl-4-(tetrahydro-2H-pyran-4-ylamino)-1H-pyrazolo[3,4-b]pyridin-5-yl]methyl}-N'-{[3'-{[(3R,S)-3,5-dimethyl-1-piperazinyl]methyl}-6-(methyloxy)-3-biphenylyl]methyl}-2,6-pyridinedicarboxamide | 774 | 1.34 |
| 175 | Me | ![3,5-dimethylpiperazine] | N-{[1,6-diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-6-methyl-3-biphenylyl)methyl]-2,6-pyridinedicarboxamide | 758 | 1.36 |

TABLE 2-continued

Examples 173-188.

| Example | R1 | R2 | Name | LC-MS m/z (M + H)+ | RT (min) |
|---|---|---|---|---|---|
| 176 | F | piperazine, N-methyl | N-{[1,6-diethyl-4-(tetrahydro-2H-pyran-4-ylamino)-1H-pyrazolo[3,4-b]pyridin-5-yl]methyl}-N'-({6-fluoro-3'-[(4-methyl-1-piperazinyl)methyl]-3-biphenylyl}methyl)-2,6-pyridinedicarboxamide | 748 | 0.74 |
| 177 | OMe | piperazine, N-methyl | N-{[1,6-diethyl-4-(tetrahydro-2H-pyran-4-ylamino)-1H-pyrazolo[3,4-b]pyridin-5-yl]methyl}-N'-({6-(methyloxy)-3'-[(4-methyl-1-piperazinyl)methyl]-3-biphenylyl}methyl)-2,6-pyridinedicarboxamide | 760 | 1.30 |
| 178 | Me | piperazine, N-methyl | N-{[1,6-diethyl-4-(tetrahydro-2H-pyran-4-ylamino)-1H-pyrazolo[3,4-b]pyridin-5-yl]methyl}-N'-({6-methyl-3'-[(4-methyl-1-piperazinyl)methyl]-3-biphenylyl}methyl)-2,6-pyridinedicarboxamide | 744 | 1.41 |
| 179 | F | piperazine, N-acetyl | N-({3'-[(4-acetyl-1-piperazinyl)methyl]-6-fluoro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 776 | 0.73 |
| 180 | F | piperazine, N-ethyl | N-{[1,6-diethyl-4-(tetrahydro-2H-pyran-4-ylamino)-1H-pyrazolo[3,4-b]pyridin-5-yl]methyl}-N'-({3'-[(4-ethyl-1-piperazinyl)methyl]-6-fluoro-3-biphenylyl}methyl)-2,6-pyridinedicarboxamide | 762 | 0.73 |
| 181 | F | N,N,N'-trimethylethylenediamine | N-{[1,6-diethyl-4-(tetrahydro-2H-pyran-4-ylamino)-1H-pyrazolo[3,4-b]pyridin-5-yl]methyl}-N'-[(3'-{[[2-(dimethylamino)ethyl](methyl)amino]methyl}-6-fluoro-3-biphenylyl)methyl]-2,6-pyridinedicarboxamide | 750 | 0.7 |
| 182 | F | piperidine | N-{[1,6-diethyl-4-(tetrahydro-2H-pyran-4-ylamino)-1H-pyrazolo[3,4-b]pyridin-5-yl]methyl}-N'-{[6-fluoro-3'-(1-piperidinylmethyl)-3-biphenylyl]methyl}-2,6-pyridinedicarboxamide | 733 | 0.76 |

TABLE 2-continued

Examples 173-188.

| Example | R1 | R2 | Name | LC-MS m/z (M + H)+ | RT (min) |
|---|---|---|---|---|---|
| 183 | OMe | | N-{[1,6-diethyl-4-(tetrahydro-2H-pyran-4-ylamino)-1H-pyrazolo[3,4-b]pyridin-5-yl]methyl}-N'-{[3'-[(4-methylhexahydro-1H-1,4-diazepin-1-yl)methyl]-6-(methyloxy)-3-biphenylyl]methyl}-2,6-pyridinedicarboxamide | 774 | 1.27 |
| 184 | OMe | | N-{[3'-[(4-acetyl-1-piperazinyl)methyl]-6-(methyloxy)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide | 788 | 1.32 |
| 185 | OMe | | N-{[1,6-diethyl-4-(tetrahydro-2H-pyran-4-ylamino)-1H-pyrazolo[3,4-b]pyridin-5-yl]methyl}-N'-{[3'-[(4-ethyl-1-piperazinyl)methyl]-6-(methyloxy)-3-biphenylyl]methyl}-2,6-pyridinedicarboxamide | 774 | 1.31 |
| 186 | OMe | | N-{[1,6-diethyl-4-(tetrahydro-2H-pyran-4-ylamino)-1H-pyrazolo[3,4-b]pyridin-5-yl]methyl}-N'-{[3'-{[[2-(dimethylamino)ethyl](methyl)amino]methyl}-6-(methyloxy)-3-biphenylyl]methyl}-2,6-pyridinedicarboxamide | 762 | 1.24 |
| 187 | OMe | | N-{[1,6-diethyl-4-(tetrahydro-2H-pyran-4-ylamino)-1H-pyrazolo[3,4-b]pyridin-5-yl]methyl}-N'-{[6-(methyloxy)-3'-(1-piperidinylmethyl)-3-biphenylyl]methyl}-2,6-pyridinedicarboxamide | 745 | 1.46 |
| 188 | Me | | N-({3'-[(4-acetyl-1-piperazinyl)methyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 772 | 1.41 |

Example 189

N-{[1,6-Diethyl-4-(tetrahydro-2H-pyran-4-ylamino)-1H-pyrazolo[3,4-b]pyridin-5-yl]methyl}-N'-[(6-methyl-3'-{[(2S)-2-methyl-1-piperazinyl]methyl}-3-biphenylyl)methyl]-2,6-pyridinedicarboxamide

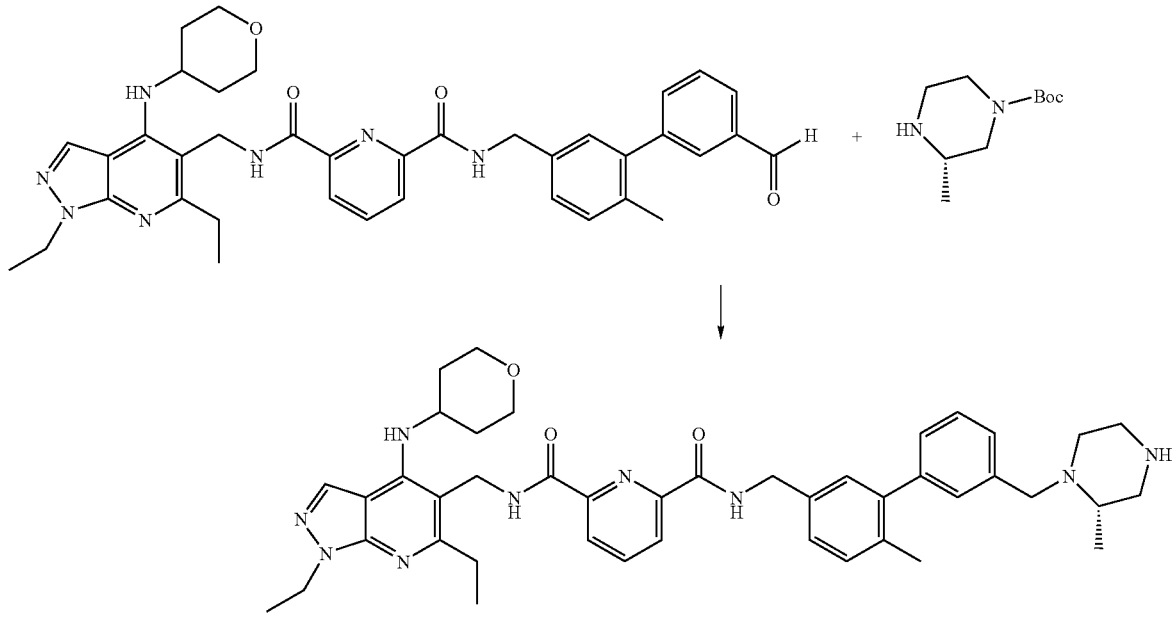

N-{[1,6-Diethyl-4-(tetrahydro-2H-pyran-4-ylamino)-1H-pyrazolo[3,4-b]pyridin-5-yl]methyl}-N'-[(3'-formyl-6-methyl-3-biphenylyl)methyl]-2,6-pyridinedicarboxamide (39.0 mg, 0.059 mmol) was diluted in DMSO (1.5 mL) and dispensed into a 1 dram vial containing 1,1-dimethylethyl (3S)-3-methyl-1-piperazinecarboxylate (0.177 mmol, 3.0 eq) and acetic acid (3.55 mg, 0.059 mmol) and fitted magnetic stir bar. The result solution was stirring at room temperature for 4 h. MP-B(OAc)$_3$H (0.591 mmol, 138 mg, 10.0 eq) was added and the solution was stirred for another 12 h. The polymer reagent was filtered off and MeOH (2.0 mL) and 1 drop of concentrated HCl was added to the solution. The solution was heated at 60° C.° for 12 h. Purification was completed via a Gilson HPLC (acidic conditions). The product was dissolved in 3 mL of MeOH and passed through 0.5 g amine columns (washed with 8 mL MeOH) to afford 14.5 mg (33.03%) of the title compound. LC-MS m/z 744 (M+H)$^+$, 1.43 min (ret time).

Examples 190-210

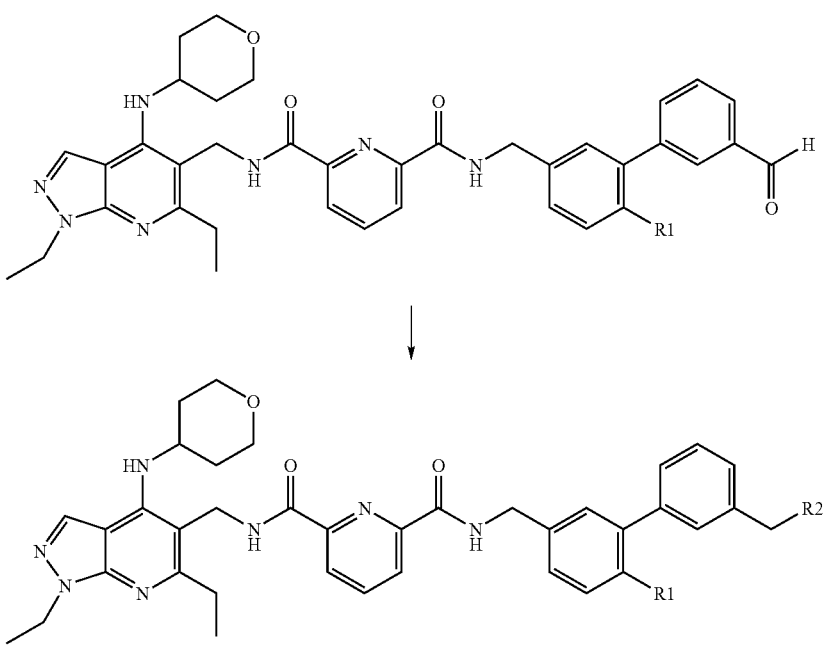

Using array chemistry, following the procedure as described above in the preparation of N-{[1,6-diethyl-4-(tetrahydro-2H-pyran-4-ylamino)-1H-pyrazolo[3,4-b]pyridin-5-yl]methyl}-N'-[(6-methyl-3'-{[(2S)-2-methyl-1-piperazinyl]methyl}-3-biphenylyl)methyl]-2,6-pyridinedicarboxamide (Example 189), an appropriate aldehyde was reacted with an appropriate amine to give the Examples 190-210 listed in Table 3.

TABLE 3

Examples 190-210.

| Example | R1 | R2 | Name | LC-MS m/z (M + H)+ | RT (min) |
|---------|----|----|------|--------------------|----------|
| 190 | Me | | N-{[1,6-diethyl-4-(tetrahydro-2H-pyran-4-ylamino)-1H-pyrazolo[3,4-b]pyridin-5-yl]methyl}-N'-[(6-methyl-3'-{[(3R)-3-methyl-1-piperazinyl]methyl}-3-biphenylyl)methyl]-2,6-pyridinedicarboxamide | 745 | 0.82 |
| 191 | Me | | N-{[1,6-diethyl-4-(tetrahydro-2H-pyran-4-ylamino)-1H-pyrazolo[3,4-b]pyridin-5-yl]methyl}-N'-[(6-methyl-3'-{[(3S)-3-methyl-1-piperazinyl]methyl}-3-biphenylyl)methyl]-2,6-pyridinedicarboxamide | 745 | 0.83 |
| 192 | F | | N-{[1,6-diethyl-4-(tetrahydro-2H-pyran-4-ylamino)-1H-pyrazolo[3,4-b]pyridin-5-y]methyl}-N'-[(6-fluoro-3'-{[(3R)-3-methyl-1-piperazinyl]methyl}-3-biphenylyl)methyl]-2,6-pyridinedicarboxamide | 749 | 1.32 |
| 193 | F | | N-{[1,6-diethyl-4-(tetrahydro-2H-pyran-4-ylamino)-1H-pyrazolo[3,4-b]pyridin-5-yl]methyl}-N'-[(6-fluoro-3'-{[(2S)-2-methyl-1-piperazinyl]methyl}-3-biphenylyl)methyl]-2,6-pyridinedicarboxamide | 749 | 1.25 |
| 194 | OMe | | N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3R)-3-methyl-1-piperazinyl]methyl}-3-biphenylyl)methyl]-2,6-pyridinedicarboxamide | 761 | 1.22 |
| 195 | OMe | | N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide | 761 | 1.37 |

TABLE 3-continued

Examples 190-210.

| Example | R1 | R2 | Name | LC-MS m/z (M + H)+ | RT (min) |
|---|---|---|---|---|---|
| 196 | Cl | | N-[(6-chloro-3'-{[(3R)-3-methyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 764 | 1.31 |
| 197 | Cl | | N-({6-chloro-3'-[(1R,2S)-2,5-diazabicyclo[2.2.1]hept-2-ylmethyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 762 | 1.22 |
| 198 | Cl | | N-[(6-chloro-3'-{[(2S)-2-methyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 764 | 1.31 |
| 199 | Cl | | N-[(6-chloro-3'-{[(3S)-3-methyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarobxamide | 764 | 1.31 |
| 200 | F | | N-[(3'-{[(3S)-3-amino-1-pyrrolidinyl]methyl}-6-fluoro-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 735 | 1.26 |
| 201 | Cl | | N-{[6-chloro-3'-(hexahydro-1H-1,4-diazepin-1-ylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide | 764 | 1.25 |
| 202 | Cl | | N-[(3'-{[(3S)-3-amino-1-pyrrolidinyl]methyl}-6-chloro-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 750 | 1.37 |

TABLE 3-continued

Examples 190-210.

| Example | R1 | R2 | Name | LC-MS m/z (M + H)+ | RT (min) |
|---|---|---|---|---|---|
| 203 | F | 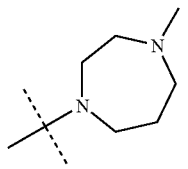 | N-{[1,6-diethyl-4-(tetrahydro-2H-pyran-4-ylamino)-1H-pyrazolo[3,4-b]pyridin-5-yl]methyl}-N'-({6-fluoro-3'-[(4-methylhexahydro-1H-1,4-diazepin-1-yl)methyl]-3-biphenylyl}methyl)-2,6-pyridinedicarboxamide | 763 | 1.22 |
| 204 | Me | 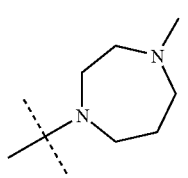 | N-{[1,6-diethyl-4-(tetrahydro-2H-pyran-4-ylamino)-1H-pyrazolo[3,4-b]pyridin-5-yl]methyl}-N'-({6-methyl-3'-[(4-methylhexahydro-1H-1,4-diazepin-1-yl)methyl]-3-biphenylyl}methyl)-2,6-pyridinedicarboxamide | 759 | 1.25 |
| 205 | Me | 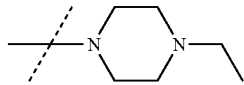 | N-{[1,6-diethyl-4-(tetrahydro-2H-pyran-4-ylamino)-1H-pyrazolo[3,4-b]pyridin-5-yl]methyl}-N'-({3'-[(4-ethyl-1-piperazinyl)methyl]-6-methyl-3-biphenylyl}methyl)-2,6-pyridinedicarboxamide | 759 | 1.38 |
| 206 | Cl | 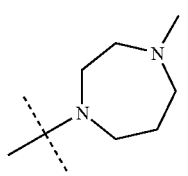 | N-({6-chloro-3'-[(4-methylhexahydro-1H-1,4-diazepin-1-yl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 778 | 1.32 |
| 207 | Cl | 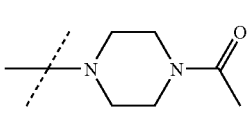 | N-({3'-[(4-acetyl-1-piperazinyl)methyl]-6-chloro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 792 | 1.41 |
| 208 | Cl | 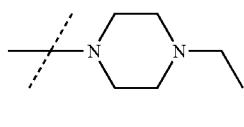 | N-({6-chloro-3'-[(4-ethyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 778 | 1.36 |
| 209 | Cl | 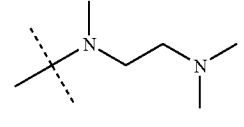 | N-[(6-chloro-3'-{[[2-(dimethylamino)ethyl](methyl)amino]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 766 | 1.27 |

TABLE 3-continued

Examples 190-210.

| Example | R1 | R2 | Name | LC-MS m/z (M + H)+ | RT (min) |
|---|---|---|---|---|---|
| 210 | Cl | piperidinylmethyl | N-{[6-chloro-3'-(1-piperidinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide | 749 | 1.48 |

Example 211

N-{[1,6-Diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-6-fluoro-3-biphenylyl)methyl]-2,6-pyridinedicarboxamide

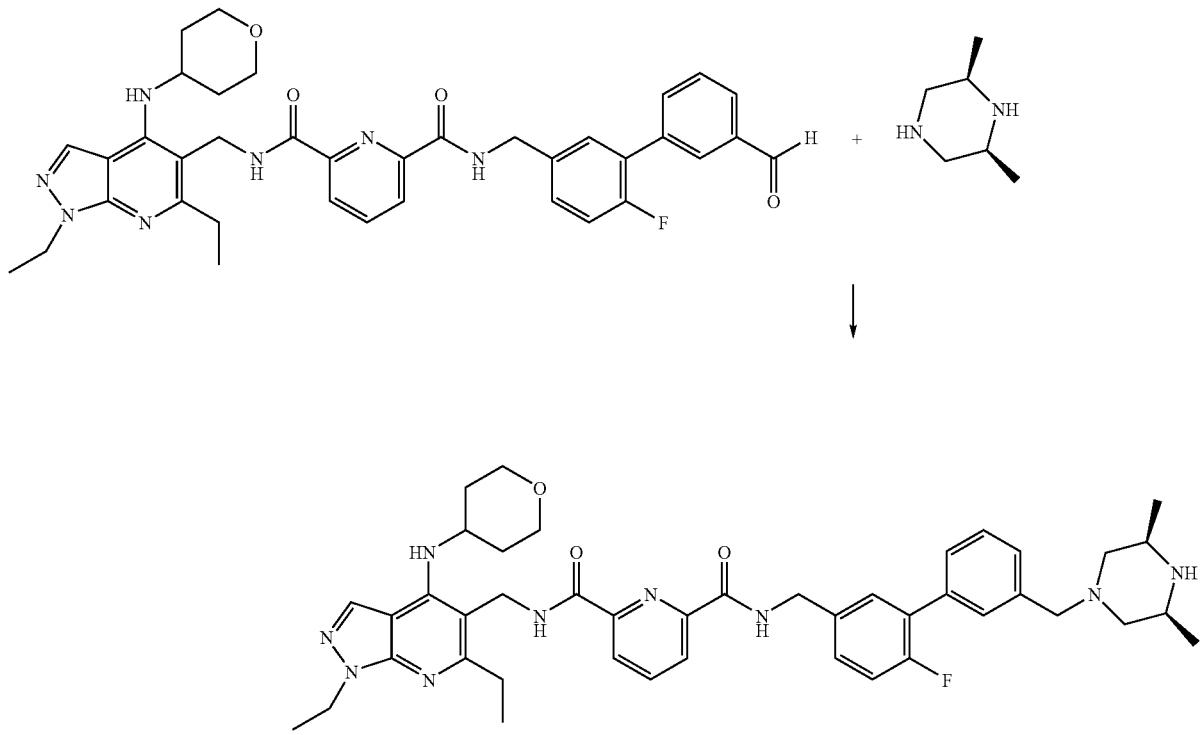

N-{[1,6-Diethyl-4-(tetrahydro-2H-pyran-4-ylamino)-1H-pyrazolo[3,4-b]pyridin-5-yl]methyl}-N'-[(6-fluoro-3'-formyl-3-biphenylyl)methyl]-2,6-pyridinedicarboxamide (0.059 mmol) was diluted in DMSO (1.5 mL) and dispensed into a 1 dram vial containing (2R,6S)-2,6-dimethylpiperazine (0.177 mmol, 3.0 eq) and acetic acid (3.55 mg, 0.059 mmol) and fitted a magnetic stir bar. The resulting solution was stirred at room temperature for 4 h. MP-B(OAc)$_3$H (0.591 mmol, 138 mg, 10.0 eq) was added and the solution was stirred for another 12 h. The polymer reagent was filtered. Purification was completed via a Gilson HPLC (acidic conditions). The product was dissolved in 3 mL of MeOH and passed through 0.5 g amine columns (washed with 8 mL of MeOH) to afford 29.9 mg of the title compound (66.5%). LC-MS m/z 763 (M+H)+, 1.31 min (ret time).

Examples 212-217

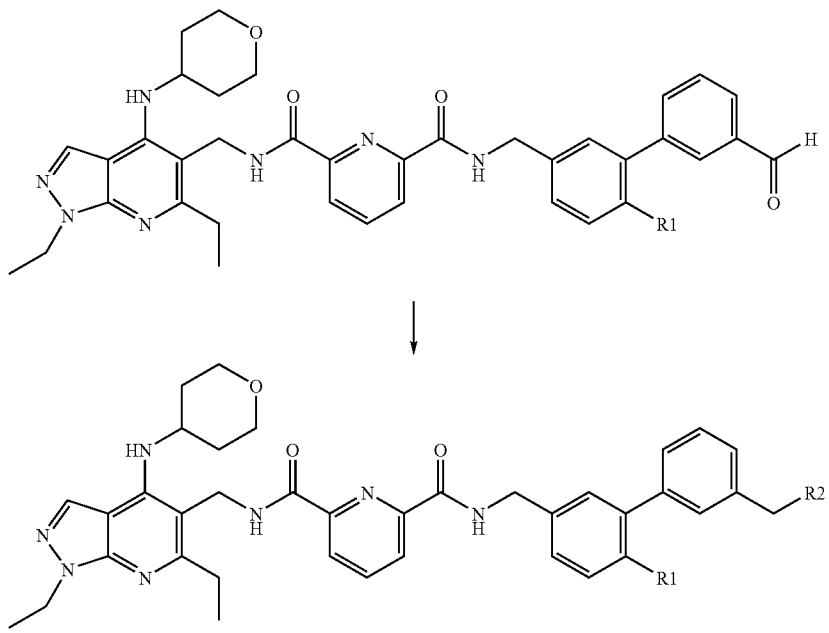

Using array chemistry, following the procedure as described for the preparation of N-{[1,6-diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-6-fluoro-3-biphenylyl)methyl]-2,6-pyridinedicarboxamide (Example 211), an appropriate aldehyde was reacted with an appropriate amine to give Examples 212-217 listed in Table 4.

TABLE 4

Example 212-217.

| Example | R1 | R2 | Name | LC-MS m/z (M + H)+ | RT (min) |
|---|---|---|---|---|---|
| 212 | F | piperazine-NH (tert-butyl linker) | N-{[1,6-diethyl-4-(tetrahydro-2H-pyran-4-ylamino)-1H-pyrazolo[3,4-b]pyridin-5-yl]methyl}-N'-{[6-fluoro-3'-(1-piperazinylmethyl)-3-biphenylyl]methyl}-2,6-pyridinedicarboxamide | 735 | 1.26 |
| 213 | Cl | piperazine-NH | N-{[6-chloro-3'-(1-piperazinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide | 751 | 1.28 |
| 214 | Cl | (3R,5S)-3,5-dimethylpiperazine-NH | N-[(6-chloro-3'-{[(3R,5S)-3,5-dimethyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide | 778 | 1.35 |
| 215 | Cl | 4-methylpiperazine | N-({6-chloro-3'-[(4-methyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide | 764 | 1.38 |

TABLE 4-continued

Example 212-217.

| Example | R1 | R2 | Name | LC-MS m/z (M + H)+ | RT (min) |
|---|---|---|---|---|---|
| 216 | Me | (structure) | N-{[1,6-diethyl-4-(tetrahydro-2H-pyran-4-ylamino)-1H-pyrazolo[3,4-b]pyridin-5-yl]methyl}-N'-[(3'-{[[2-(dimethylamino)ethyl](methyl)amino]methyl}-6-methyl-3-biphenylyl)methyl]-2,6-pyridinedicarboxamide | 749 | 1.30 |
| 217 | Me | (structure) | N-{[1,6-diethyl-4-(tetrahydro-2H-pyran-4-ylamino)-1H-pyrazolo[3,4-b]pyridin-5-yl]methyl}-N'-{[6-methyl-3'-(1-piperidinylmethyl)-3-biphenylyl]methyl}-2,6-pyridinedicarboxamide | 729 | 1.50 |

What is claimed is:

1. A compound which is selected from the group consisting of:

N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-3,4-bis(methyloxy)-2,5-furandicarboxamide;

N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,3-dihydro-6H-[1,4]dioxino[2,3-c]pyrrole-5,7-dicarboxamide;

N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-2,5-thiophenedicarboxamide;

N-{[1,6-diethyl-4-(tetrahydro-2H-pyran-4-ylamino)-1H-pyrazolo[3,4-b]pyridin-5-yl]methyl}-N'-[(6-fluoro-3'-{[(3S)-3-methyl-1-piperazinyl]methyl}-3-biphenylyl)methyl]-3,5-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-(4-piperidinylmethyl)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-fluoro-3'-(4-piperidinylmethyl)-3-biphenylyl]methyl}-2,6-pyridinedicarboxamide;

N-{[6-Chloro-3'-(4-piperidinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-methyl-3'-(4-piperidinylmethyl)-3-biphenylyl]methyl}-2,6-pyridinedicarboxamide;

N-({3'-[(1S,4S)-2,5-diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-methyl-3'-{[(3S)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-(1-piperazinylmethyl)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[(3R)-3-methyl-1-piperazinyl]methyl}-3-biphenylyl)methyl]-2,6-pyridinedicarboxamide;

N-({3'-[(1S,4S)-2,5-Diazabicyclo[2.2.1]hept-2-ylmethyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[(3S)-3-methyl-1-piperazinyl]methyl}-3-biphenylyl)methyl]-2,6-pyridinedicarboxamide;

$N^2$-{[1,6-diethyl-4-(tetrahydro-2H-pyran-4-ylamino)-1H-pyrazolo[3,4-b]pyridin-5-yl]methyl}-$N^4$-[(6-fluoro-3'-{[(3S)-3-methyl-1-piperazinyl]methyl}-3-biphenylyl)methyl]-2,4-pyridinedicarboxamide;

N-({6-chloro-3'-[(4-methyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({3'-[(4-methyl-1-piperazinyl)methyl]-3-biphenylyl}methyl)-2,6-pyridinedicarboxamide;

$N^4$-{[1,6-diethyl-4-(tetrahydro-2H-pyran-4-ylamino)-1H-pyrazolo[3,4-b]pyridin-5-yl]methyl}-$N^2$-[(6-fluoro-3'-{[(3S)-3-methyl-1-piperazinyl]methyl}-3-biphenylyl)methyl]-2,4-pyridinedicarboxamide;

N-{[1,6-diethyl-4-(tetrahydro-2H-pyran-4-ylamino)-1H-pyrazolo[3,4-b]pyridin-5-yl]methyl}-N'-({6-fluoro-3'-[(1-methyl-4-piperidinyl)methyl]-3-biphenylyl}methyl)-2,6-pyridinedicarboxamide;

N-({6-Chloro-3'-[(1-methyl-4-piperidinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-methyl-3'-[(1-methyl-4-piperidinyl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-(methyloxy)-3'-[(1-methyl-4-piperidinyl)methyl]-3-biphenylyl}methyl)-2,6-pyridinedicarboxamide;

N-({3'-[(1S,4S)-2,5-Diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide hydrochloride;

N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-(4-piperidinylmethyl)-3-biphenylyl]methyl}-3,5-pyridinedicarboxamide;

N-{[1,6-diethyl-4-(tetrahydro-2H-pyran-4-ylamino)-1H-pyrazolo[3,4-b]pyridin-5-yl]methyl}-N'-({3'-[(1-methyl-4-piperidinyl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[2-(3-{[(3S)-3-methyl-1-piperazinyl]methyl}phenyl)-4-pyridinyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({3'-[(4-methylhexahydro-1H-1,4-diazepin-1-yl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({2-[3-(4-piperidinylmethyl)phenyl]-4-pyridinyl}methyl)-2,6-pyridinedicarboxamide;

N-({3'-[(1S,4S)-2,5-diazabicyclo[2.2.1]hept-2-ylmethyl]-6-fluoro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[3'-[(1R,4R)-2,5-diazabicyclo[2.2.1]hept-2-ylmethyl]-6-(methyloxy)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]4yridine-5-yl]methyl}-N'-[(6-(methyloxy)-3'-{[(2S)-2-methyl-1-piperazinyl]methyl}-3-biphenylyl)methyl]-2,6-pyridinedicarboxamide;

N-({3'-[(1R,4R)-2,5-diazabicyclo[2.2.1]hept-2-ylmethyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-(methyloxy)-3'-(1-piperazinylmethyl)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-{[(3R,5S)-3,5-dimethyl-1-piperazinyl]methyl}-6-(methyloxy)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-6-methyl-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-fluoro-3'-[(4-methyl-1-piperazinyl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-(methyloxy)-3'-[(4-methyl-1-piperazinyl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-methyl-3'-[(4-methyl-1-piperazinyl)methyl]-3-biphenylyl}methyl)-2,6-pyridinedicarboxamide;

N-({3'-[(4-acetyl-1-piperazinyl)methyl]-6-fluoro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({3'-[(4-ethyl-1-piperazinyl)methyl]-6-fluoro-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[[2-(dimethylamino)ethyl](methyl)amino]methyl}-6-fluoro-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-fluoro-3'-(1-piperidinylmethyl)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-[(4-methylhexahydro-1H-1,4-diazepin-1-yl)methyl]-6-(methyloxy)-3-biphenylyl]methyl}-2,6-pyridinedicarboxamide;

N-{[3'-[(4-acetyl-1-piperazinyl)methyl]-6-(methyloxy)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-[(4-ethyl-1-piperazinyl)methyl]-6-(methyloxy)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[3'-{[[2-(dimethylamino)ethyl](methyl)amino]methyl}-6-(methyloxy)-3-biphenylyl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-(methyloxy)-3'-(1-piperidinylmethyl)-3-biphenylyl]methyl}-2,6-pyridinedicarboxamide;

N-({3'-[(4-acetyl-1-piperazinyl)methyl]-6-methyl-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-methyl-3'-{[(2S)-2-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-methyl-3'-{[(3R)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-methyl-3'-{[(3S)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-fluoro-3'-{[(3R)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-fluoro-3'-{[(2S)-2-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3R)-3-methyl-1-piperazinyl]methyl}-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(6-(methyloxy)-3'-{[(3S)-3-methyl-1-piperazinyl]methyl}-3-biphenylyl)methyl]-2,6-pyridinedicarboxamide;

N-[(6-chloro-3'-{[(3R)-3-methyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-({6-chloro-3'-[(1R,4S)-2,5-diazabicyclo[2.2.1]hept-2-ylmethyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-[(6-chloro-3'-{[(2S)-2-methyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-[(6-chloro-3'-{[(3S)-3-methyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-[(3'-{[(3S)-3-amino-1-pyrrolidinyl]methyl}-6-fluoro-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[6-chloro-3'-(hexahydro-1H-1,4-diazepin-1-ylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-[(3'-{[(3S)-3-amino-1-pyrrolidinyl]methyl}-6-chloro-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-fluoro-3'-[(4-methylhexahydro-1H-1,4-diazepin-1-yl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({6-methyl-3'-[(4-methylhexahydro-1H-1,4-diazepin-1-yl)methyl]-3-biphenylyl}methyl)-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-({3'-[(4-ethyl-1-piperazinyl)methyl]-6-methyl-3-biphenylyl}methyl)-2,6-pyridinedicarboxamide;

N-({6-chloro-3'-[(4-methylhexahydro-1H-1,4-diazepin-1-yl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-({3'-[(4-acetyl-1-piperazinyl)methyl]-6-chloro-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-({6-chloro-3'-[(4-ethyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-[(6-chloro-3'-{[[2-(dimethylamino)ethyl](methyl)amino]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[6-chloro-3'-(1-piperidinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[(3R,5S)-3,5-dimethyl-1-piperazinyl]methyl}-6-fluoro-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-fluoro-3'-(1-piperazinylmethyl)-3-biphenylyl]methyl}-2,6-pyridinedicarboxamide;

N-{[6-chloro-3'-(1-piperazinylmethyl)-3-biphenylyl]methyl}-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-[(6-chloro-3'-{[(3R,5S)-3,5-dimethyl-1-piperazinyl]methyl}-3-biphenylyl)methyl]-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-({6-chloro-3'-[(4-methyl-1-piperazinyl)methyl]-3-biphenylyl}methyl)-N'-{[1,6-diethyl-4-(tetrahydro-2H-pyran-4-ylamino)-1H-pyrazolo[3,4-b]pyridin-5-yl]methyl}-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-[(3'-{[[2-(dimethylamino)ethyl](methyl)amino]methyl}-6-methyl-3-biphenylyl)methyl]-2,6-pyridinedicarboxamide;

N-{[1,6-diethyl-4-(tetrahydro-2H-pyran-4-ylamino)-1H-pyrazolo[3,4-b]pyridin-5-yl]methyl}-N'-{[6-methyl-3'-(1-piperidinylmethyl)-3-biphenylyl]methyl}-2,6-pyridinedicarboxamide; and a pharmaceutically acceptable salt thereof.

2. A compound which is N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide, or a salt thereof.

3. A compound according to claim 2 which is N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide.

4. A compound according to claim 2 which is N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide or a pharmaceutically acceptable salt thereof.

5. A compound according to claim 2 which is N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide hydrochloride.

6. A compound which is N-{[1,6-diethyl-4-(tetrahydro-2H-pyran-4-ylamino)-1H-pyrazolo[3,4-b]pyridin-5-yl]methyl}-N'-{[6-(methyloxy)-3'-(4-piperidinylmethyl)-3-biphenylyl]methyl}-2,6-pyridinedicarboxamide or a salt thereof.

7. A compound according to claim 6 which is N-{[1,6-diethyl-4-(tetrahydro-2H-pyran-4-ylamino)-1H-pyrazolo[3,4-b]pyridin-5-yl]methyl}-N'-{[6-(methyloxy)-3'-(4-piperidinylmethyl)-3-biphenylyl]methyl}-2,6-pyridinedicarboxamide.

8. A compound according to claim 6 which is N-{[1,6-diethyl-4-(tetrahydro-2H-pyran-4-ylamino)-1H-pyrazolo[3,4-b]pyridin-5-yl]methyl}-N'-{[6-(methyloxy)-3'-(4-piperidinylmethyl)-3-biphenylyl]methyl}-2,6-pyridinedicarboxamide or a pharmaceutically acceptable salt thereof.

9. A pharmaceutical composition comprising a compound which is N-{[1,6-diethyl-4-(tetrahydro-2H-pyran-4-ylamino)-1H-pyrazolo[3,4-b]pyridin-5-yl]methyl}-N'-{[6-methyl-3'-(1-piperazinylmethyl)-3-biphenylyl]methyl}-2,6-pyridinedicarboxamide, or a pharmaceutically acceptable salt thereof, and a pharmaceutically acceptable carrier or diluent.

10. A pharmaceutical composition comprising a compound which is N-{[1,6-diethyl-4-(tetrahydro-2H-pyran-4-ylamino)-1H-pyrazolo[3,4-b]pyridin-5-yl]methyl}-N'-{[6-(methyloxy)-3'-(4-piperidinylmethyl)-3-biphenylyl]methyl}-2,6-pyridinedicarboxamide, or a pharmaceutically acceptable salt thereof, and a pharmaceutically acceptable carrier or diluent.

11. A method of treating asthma, chronic obstructive pulmonary disease or rhinitis in a patient in need thereof, comprising administering to said patient an effective amount of a compound according to claim 1.

12. A method of treating asthma, chronic obstructive pulmonary disease or rhinitis in a patient in need thereof, comprising administering to said patient an effective amount of a compound according to claim 2.

13. A method of treating asthma, chronic obstructive pulmonary disease or rhinitis in a patient in need thereof, comprising administering to said patient an effective amount of a compound according to claim 6.

* * * * *